US011161869B2

(12) United States Patent
Crosby et al.

(10) Patent No.: US 11,161,869 B2
(45) Date of Patent: Nov. 2, 2021

(54) THERMALLY-CLEAVABLE PROTECTING AND LINKER GROUPS

(71) Applicant: EVONETIX LTD, Cambridge (GB)

(72) Inventors: Stuart Richard Crosby, Essex (GB); Mathew Jennison, Essex (GB); Joseph Brennan, Essex (GB)

(73) Assignee: Evonetix Ltd., Cambridge (GB)

( * ) Notice: Subject to any disclaimer, the term of this patent is extended or adjusted under 35 U.S.C. 154(b) by 92 days.

(21) Appl. No.: 16/604,329

(22) PCT Filed: Apr. 12, 2018

(86) PCT No.: PCT/GB2018/050975
§ 371 (c)(1),
(2) Date: Oct. 10, 2019

(87) PCT Pub. No.: WO2018/189546
PCT Pub. Date: Oct. 18, 2018

(65) Prior Publication Data
US 2021/0107934 A1  Apr. 15, 2021

(30) Foreign Application Priority Data

Apr. 12, 2017  (GB) .................................... 1705925

(51) Int. Cl.
*C07H 19/073* (2006.01)
*C07H 1/00* (2006.01)
*C07D 211/26* (2006.01)

(52) U.S. Cl.
CPC ......... *C07H 19/073* (2013.01); *C07D 211/26* (2013.01); *C07H 1/00* (2013.01)

(58) Field of Classification Search
None
See application file for complete search history.

(56) References Cited

U.S. PATENT DOCUMENTS

| 7,612,197 | B2 | 11/2009 | Beaucage et al. |
| 8,252,581 | B2 | 8/2012 | Joseph et al. |
| 8,575,113 | B2 | 11/2013 | Jarvis et al. |
| 9,527,083 | B2 | 12/2016 | Hasson et al. |
| 10,125,393 | B2 | 11/2018 | Esfandyarpour et al. |
| 2004/0209921 | A1 | 10/2004 | Bridger et al. |
| 2013/0085272 | A1 | 4/2013 | Chmielewski |

FOREIGN PATENT DOCUMENTS

| WO | WO 1991/017981 A1 | 11/1991 |
| WO | WO 2004/101582 A2 | 11/2004 |
| WO | WO 2006/122408 A1 | 11/2006 |
| WO | WO 2009/084737 A1 | 7/2009 |

OTHER PUBLICATIONS

International Patent Application No. PCT/GB2018/050975; Int'l Preliminary Report on Patentability; dated Oct. 24, 2019; 12 pages.
Nahm et al.; "N-methoxy-n-methylamides as effective acylating agents"; Tetrahedron Letters; vol. 22; 1981; p. 3815-3818.
Rostovtsev et al.; "A Stepwise Huisgen Cycloaddition Process: Copper(I)-Catalyzed Regioselective "Ligation" of Azides and Terminal Alkynes"; Angewandte Chemie Int'l Edition; vol. 41(14); 2002; p. 2596-2599.
Mino et al.; "Amination of N-Aryl Prolinol via Ring Expansion and Contraction: Application to the Chiral Ligand for the Catalytic Asymmetric Reaction"; The Journal of Organic Chemistry; vol. 70; 2005; p. 1937-1940.
M. Chmielewski; "Novel thermolabile protecting groups with higher stability at ambient temperature"; Tetrahedron Letters; vol. 53; 2012; p. 666-669.
Chmielewski et al.; "Thermolytic Carbonates for Potential 5'-Hydroxyl Protection of Deoxyribonucleosides"; The Journal of Organic Chemistry; vol. 68; 2003; p. 10003-10012.
International Patent Application No. PCT/GB2018/050975; Int'l Written Opinion and Search Report; dated Jul. 13, 2018; 16 pages.
Chmielewski M K; "Protection of a Thermolabile Protecting Group: "Click-Clack" Approach"; Organic Letter; 2009; vol. 11, No. 16; p. 3742-3745.
Cieslak et al.; "Thermolytic Properties of 3-(2-Pyridyl)-1-propyl and 2-[N-Methyl-N-(2-pyridyl)] aminoethyl Phosphate/Thiophosphate Protecting Groups in Solid-Phase Synthesis of Oligodeoxyribonucleotides"; J Org Chem; 2003; vol. 68; p. 10123-10129.
Cieslak et al.; "Thermolytic 4-Methylthio-1-butyl Group for Phosphate/Thiophosphate Protection in Solid-Phase Synthesis of DNA Oligonucleotides"; J Org Chem; 2004; vol. 69; p. 2509-2515.
Patek et al.; "Safety-Catch and Multiply Cleavable Linkers in Solid-Phase Synthesis"; Biopolymers (Peptide Science); 1998; vol. 47, p. 353-363.
Witkowska et al.; "Modulating the Stability of 2-Pyridinyl Thermolabile Hydroxyl Protecting Groups via the "Chemical Switch" Approach"; Journal of Organic Chemistry; 2015; vol. 80; p. 12129-12136.
Kenner et al.; "The safety catch principle in solid phase peptide synthesis"; J. Chem. Soc. D: Chem. Comm.; Mar. 1971; p. 636-637.
Rostovtsev et al.; "A Stepwise Huisgen Cycloaddition Process Catalyzed by Copper(I): Regioselective Ligation of Azides and Terminal Alkynes"; Angewandte Chemie Int'l Ed.; Z19191; 2002; Supporting Information; 5 pages.

*Primary Examiner* — Traviss C McIntosh, III
(74) *Attorney, Agent, or Firm* — BakerHostetler

(57) ABSTRACT

The present invention relates to chemical linkers and protecting groups, compounds and compositions containing the chemical linkers or protecting groups, and intermediates and processes that can be used to prepare them. The chemical linkers and protecting groups are based on pyrrolidine and piperidine activating groups, which undergo intramolecular cyclisation upon heating with release of carbon dioxide, thereby releasing the organic compound from a substrate. In particular, those chemical linkers and protecting groups are useful in the solid phase synthesis of oligonucleotides according to the following representative schemes.

32 Claims, 14 Drawing Sheets

Figure 1: Time course study results for cleavage of deprotected linker of Example 1C at 90 °C and at 20 °C
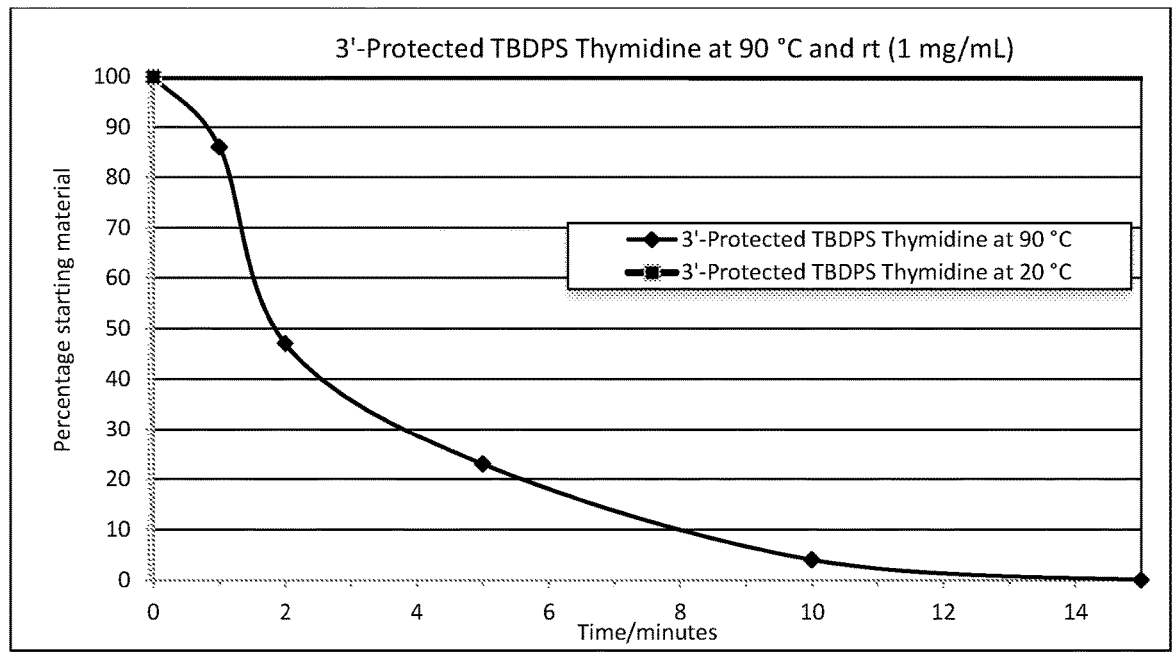
Figure 2: Time course study results for deprotected linker of Example 1C using different solvent systems at pH 7.4 PBS and acetonitrile and pH 5 buffer (TEEA)
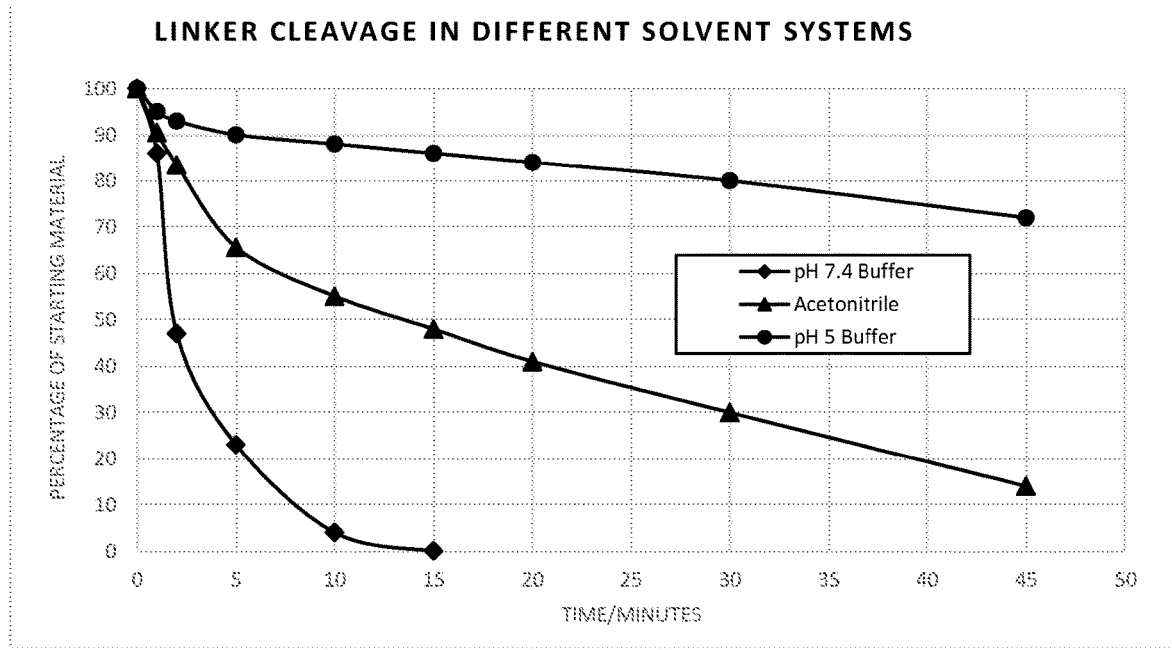

Figure 3: Time course study results for deprotected linker of Example 1C using different ratios of PBS:MeCN (acetonitrile) at 90 °C
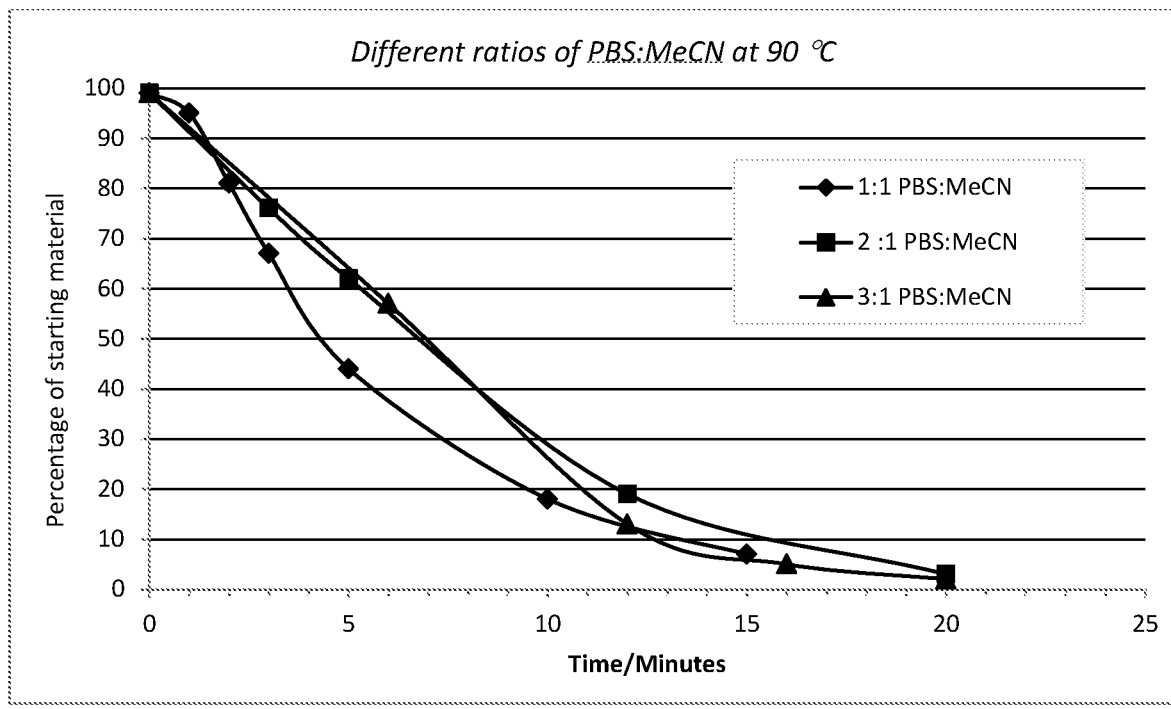
Figure 4A: Time course study results for deprotection and cleavage of Bsmoc-protected linker of Example 2
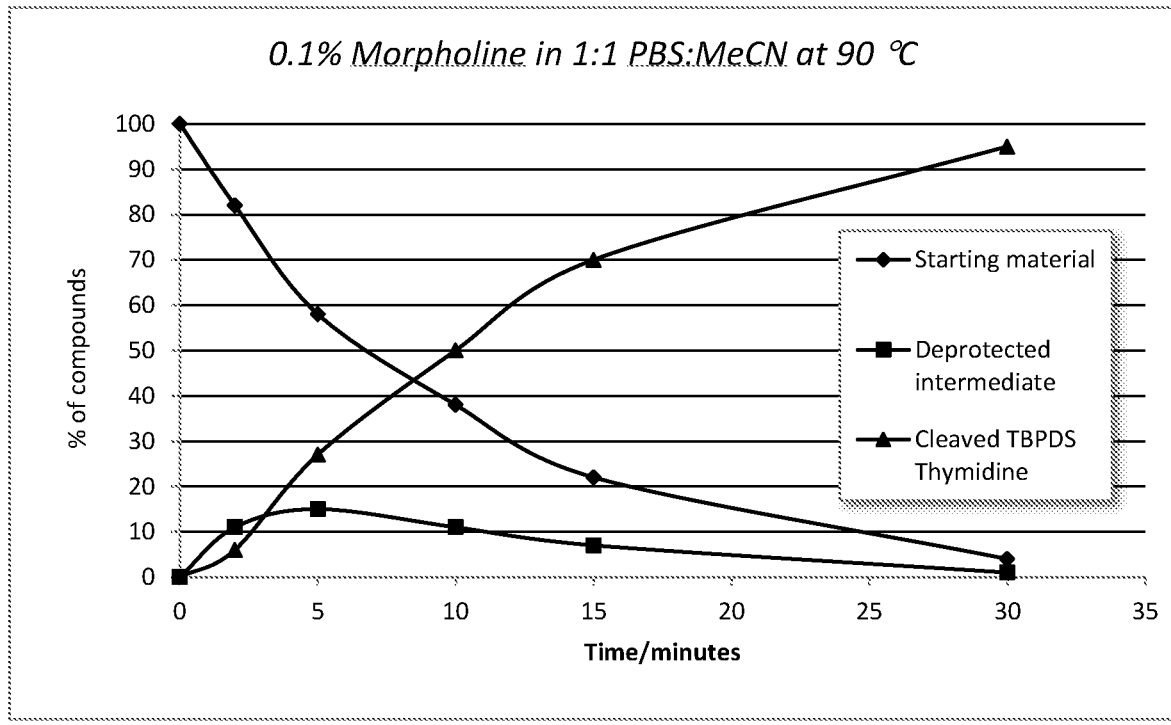

Figure 4B: Time course study results for deprotection of Bsmoc-protected linker of Example 2 at room temperature and 90 °C
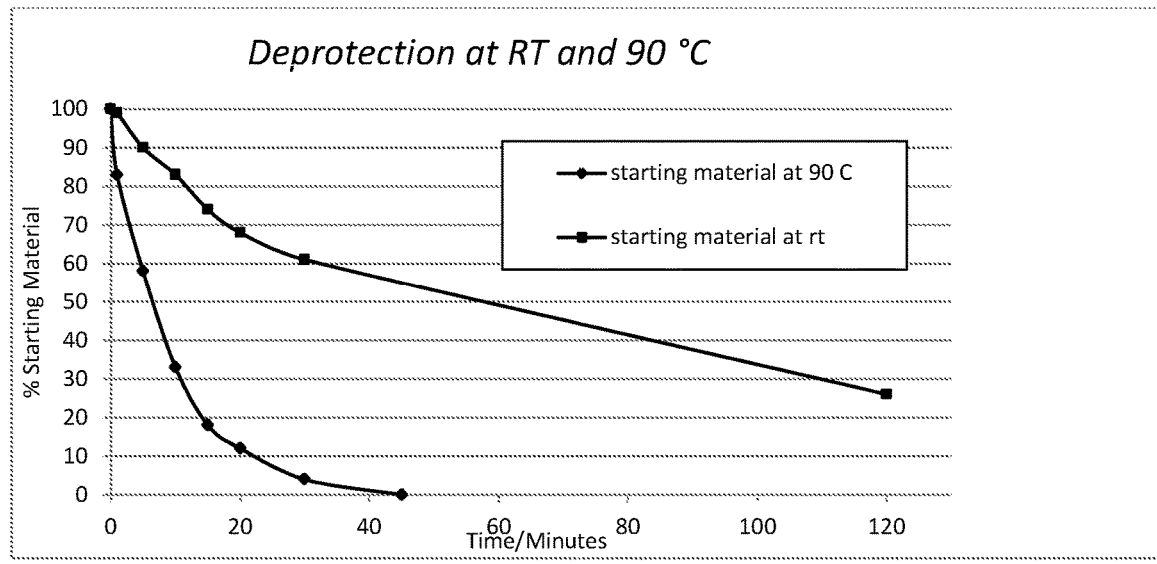
Figure 4C: Cleavage of TBPDS-Thymidine from Bsmoc-protected linker with Morpholine (0.1% in acetonitrile) at 90 °C and at RT (formation and cleavage of deprotected intermediate not shown)
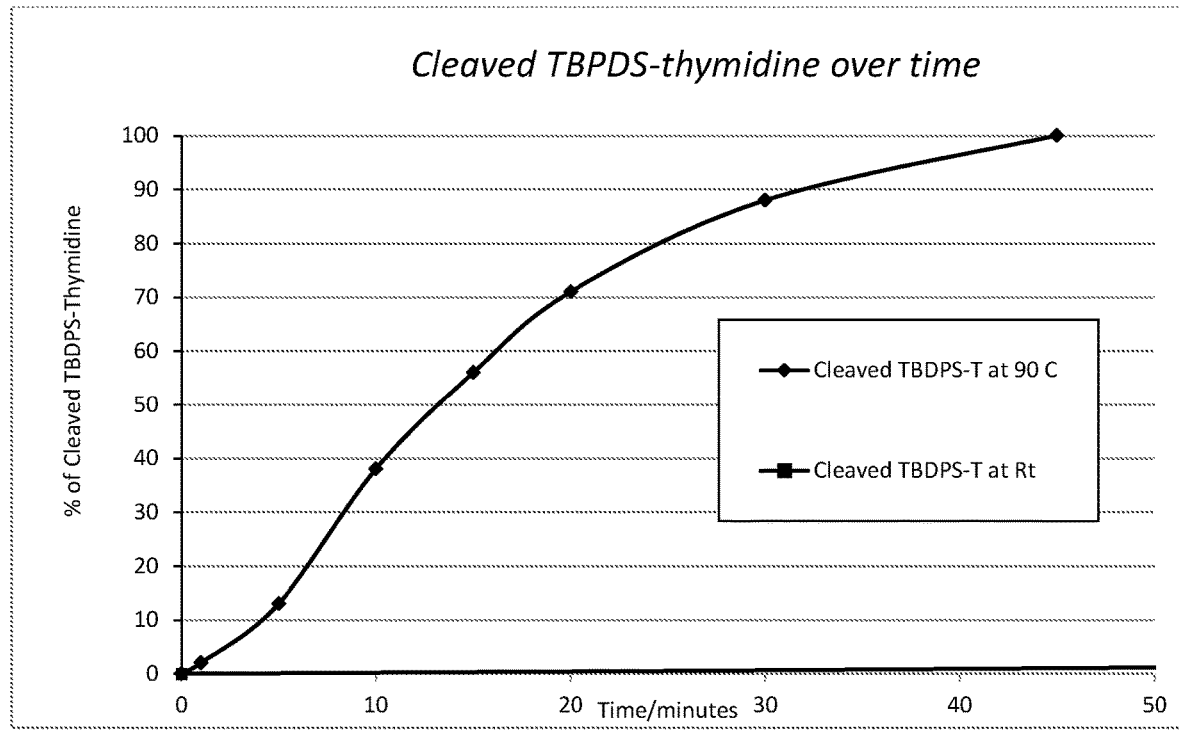

Figure 5:  Stability study results for Bsmoc protected linker of Example 2 under different pH conditions at 80°C
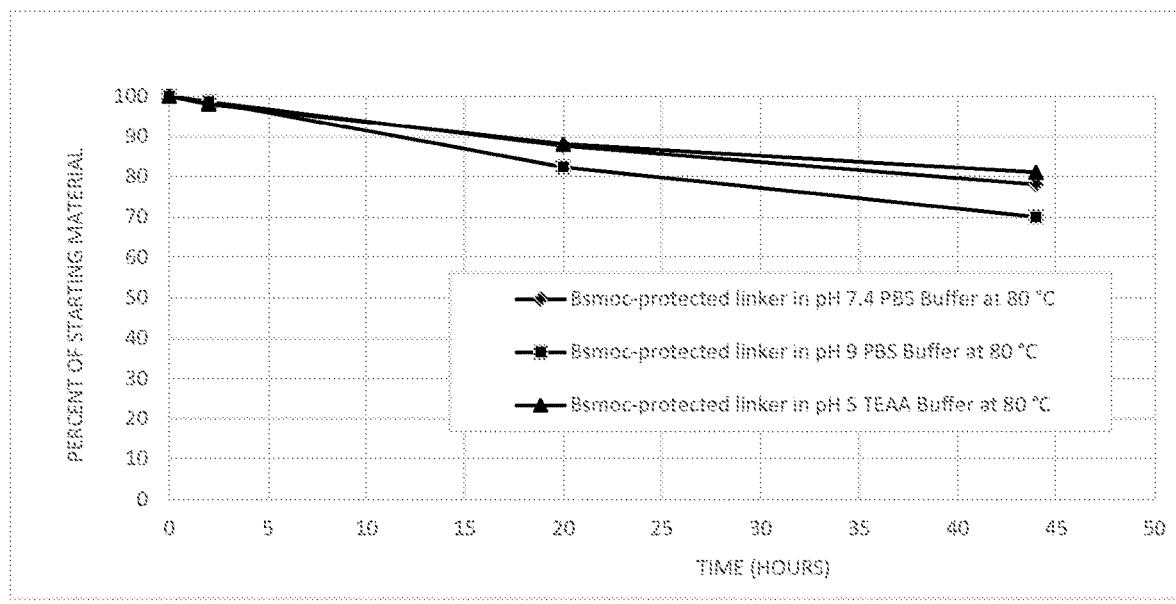
Figure 6:  Stability study results for Fmoc-protected linker of Example 3 using 0.1% piperidine under different temperature conditions (room temperature vs 90°C)
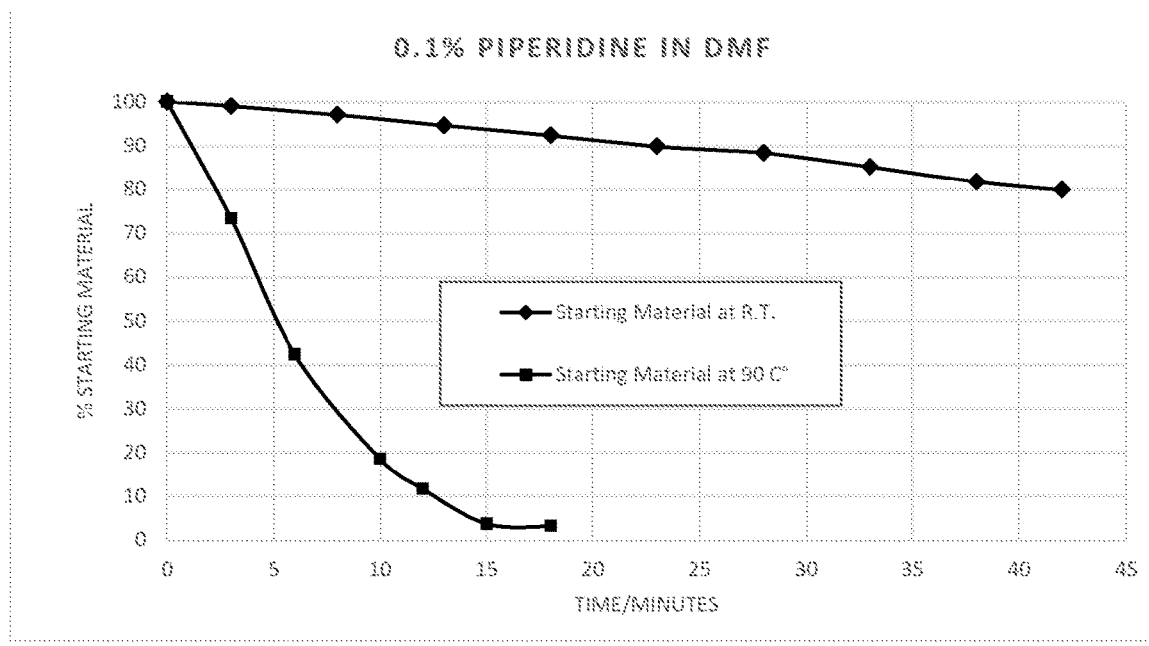

Figure 7: Stability study results for Fmoc-protected linker of Example 3 using 10% diisopropylamine under different temperature conditions (room temperature vs 90 °C)
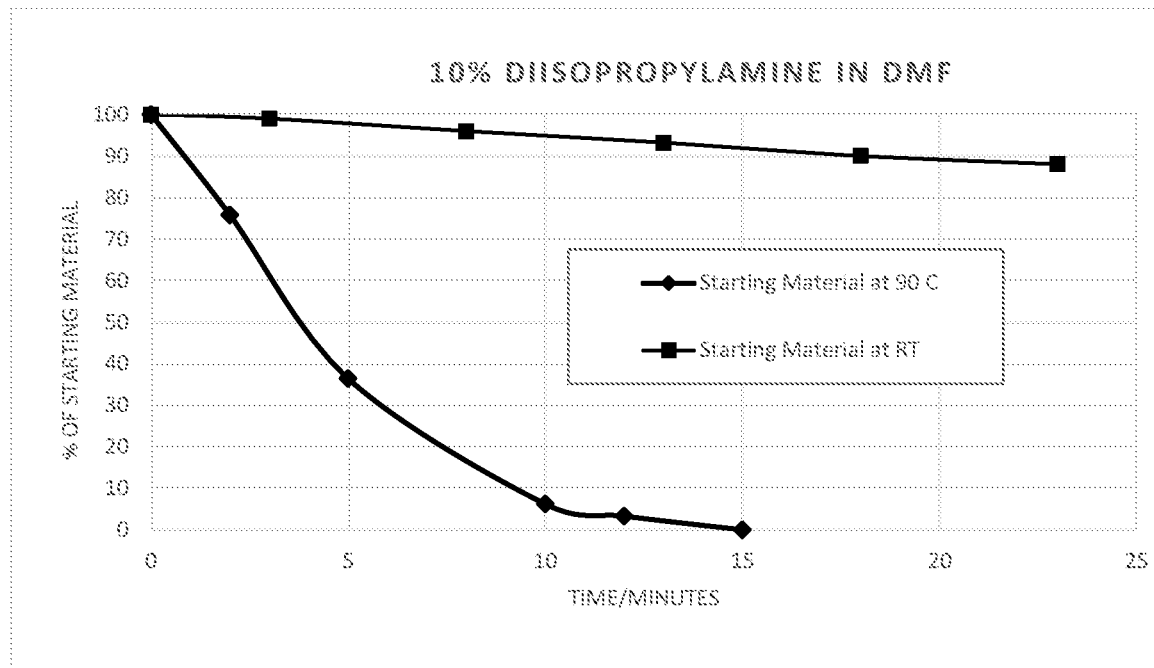
Figure 8: Stability study results for Fmoc-protected linker of Example 3 using 10% diisopropylamine at 90 °C using different solvents (DMF vs acetonitrile)
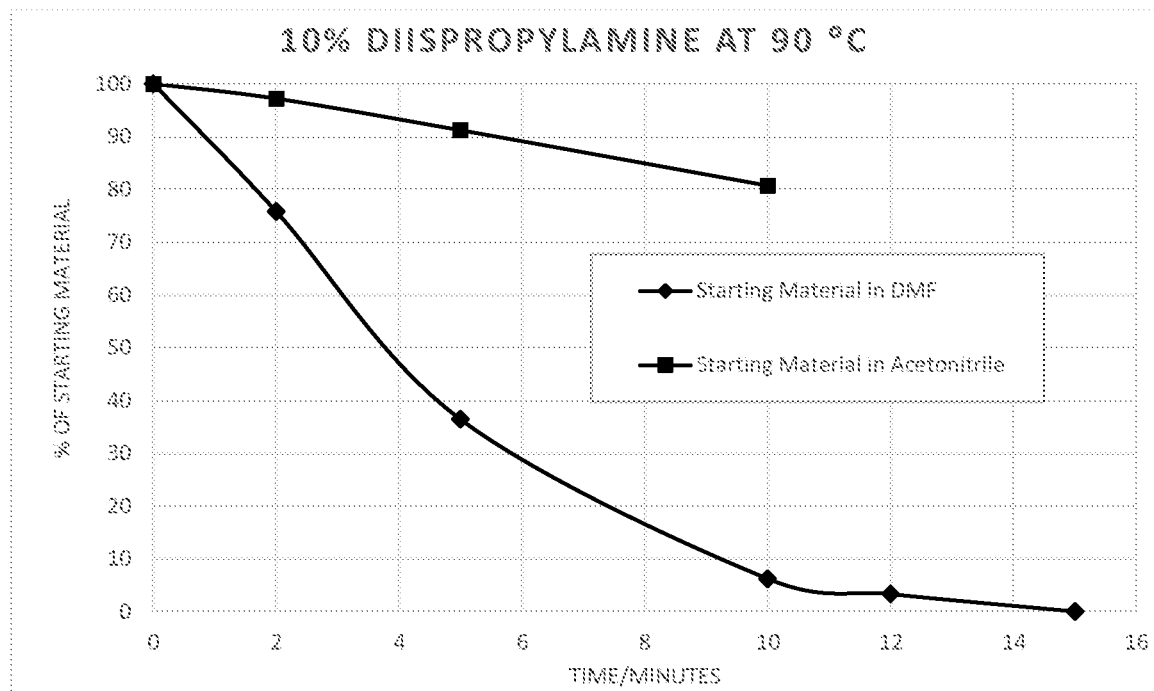

Figure 9: Stability study results for Fmoc-protected linker of Example 3 using 20% diisopropylamine in 2:1 DMF:CAPS buffer at different temperatures 10°C vs 90°C
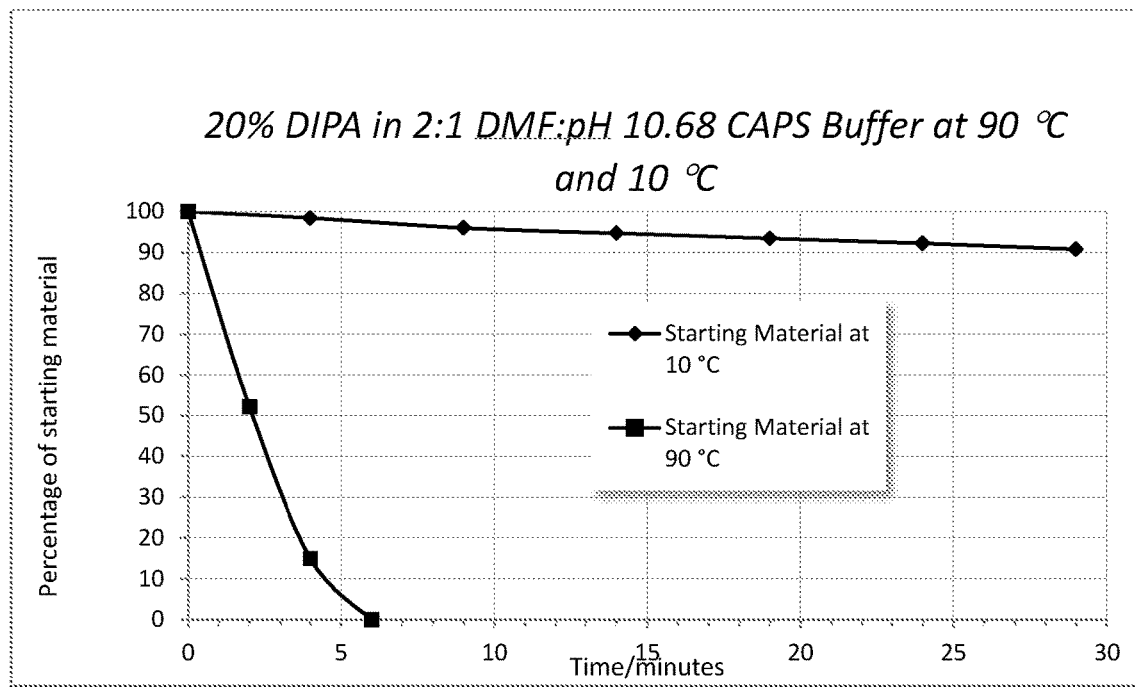
Figure 10: Cleavage of deprotected linkers of Examples 1C and Example 4C
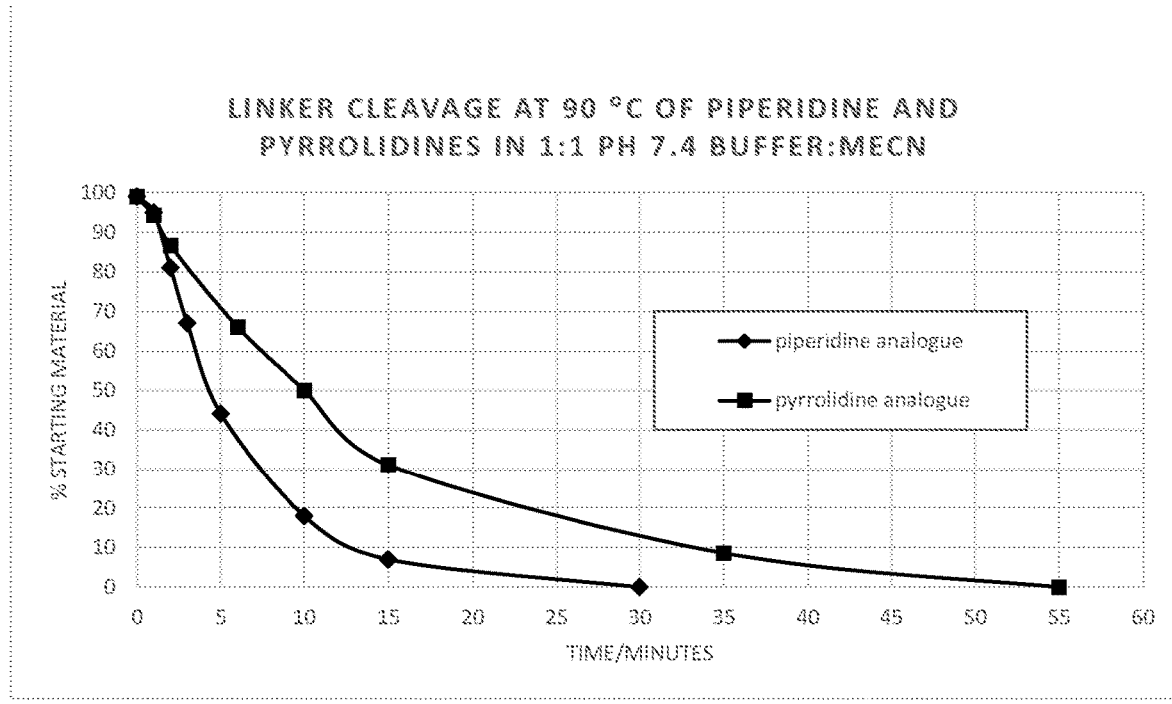

Figure 11: Stability study results for Example 4C at 90 °C in different solvent systems
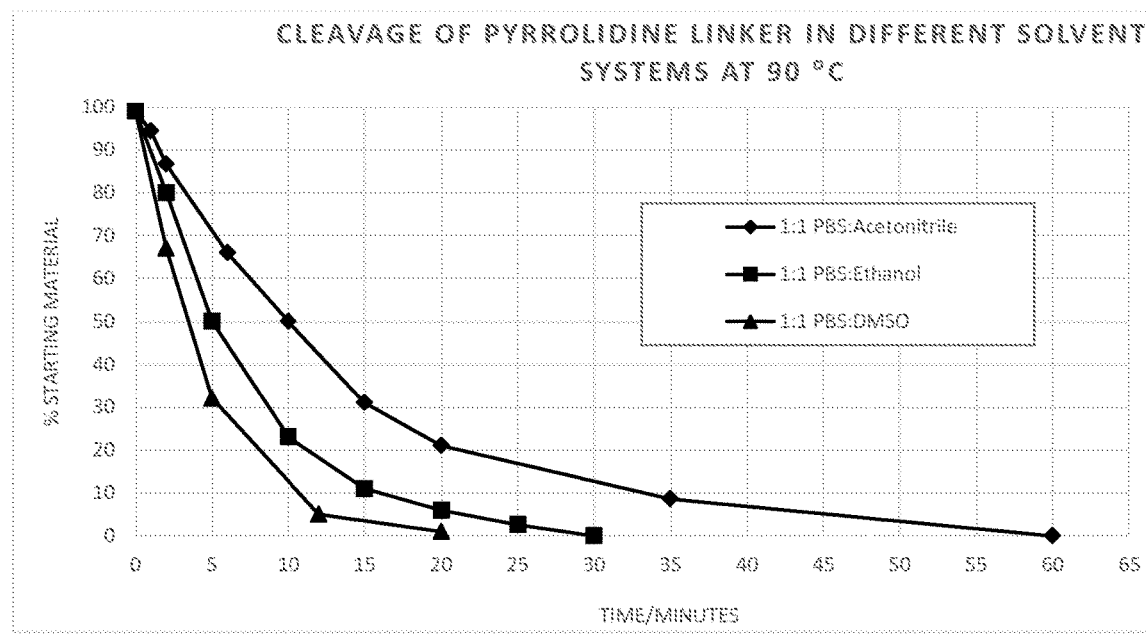
Figure 12: Time course study results for deprotection of Boc-protected linker (Compound of Example 1B)
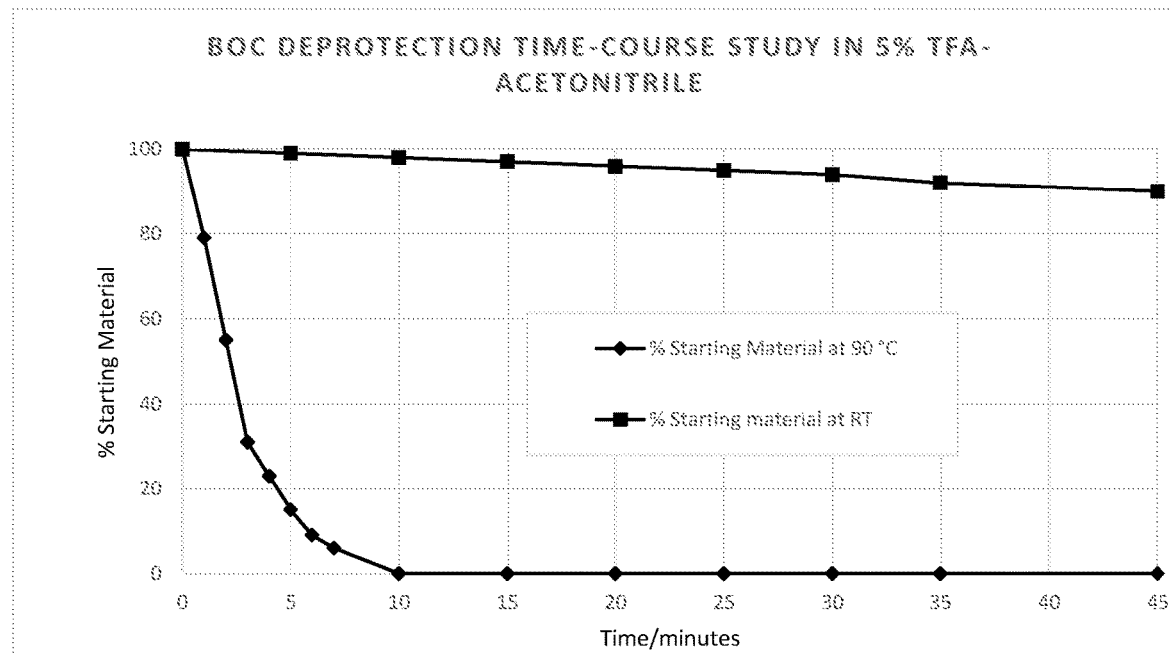

Figure 13: Time-course study on the non-protected α-Phenyl Safety-Catch Linker (compound of Example 6D)
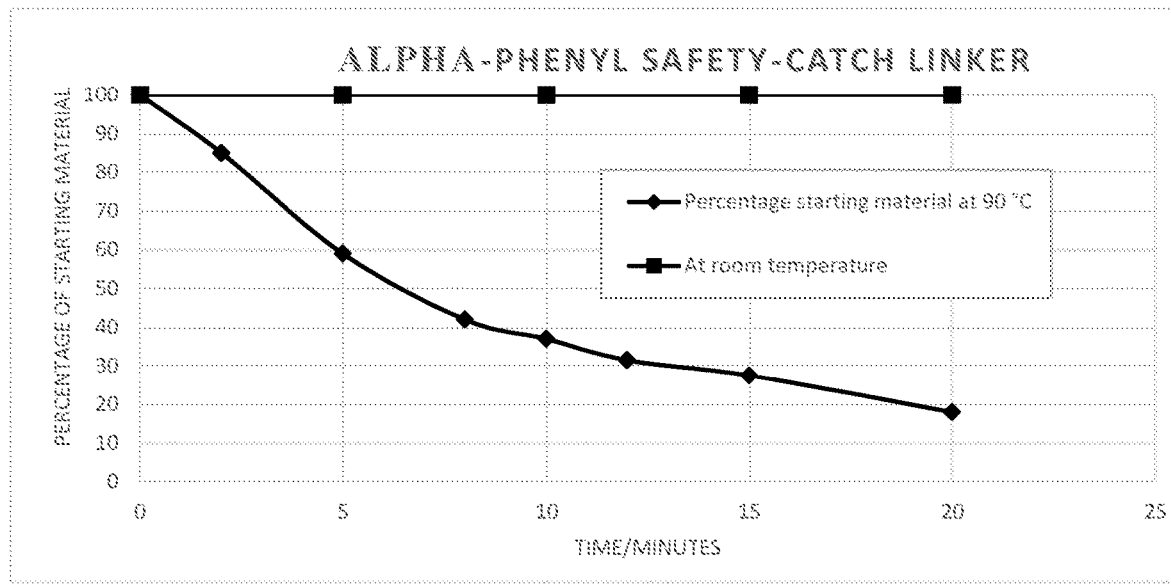
Figure 14: Time-course study on cleavage of non-protected Double Safety-Catch Linker (Compound of Example 8C) vs Single Safety-Catch Linker (Compound of Example 1C)
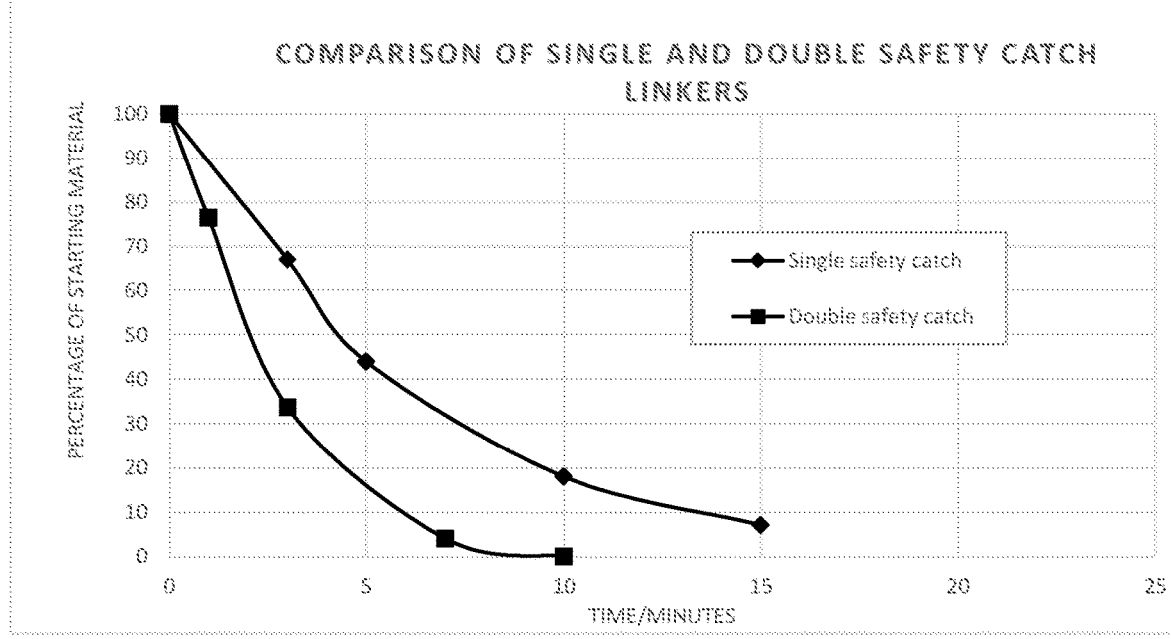

Figure 15: Time-course Study on the non-protected 5'-linked 3' O-Acetyl-Thymidine (Compound of Example 13B)
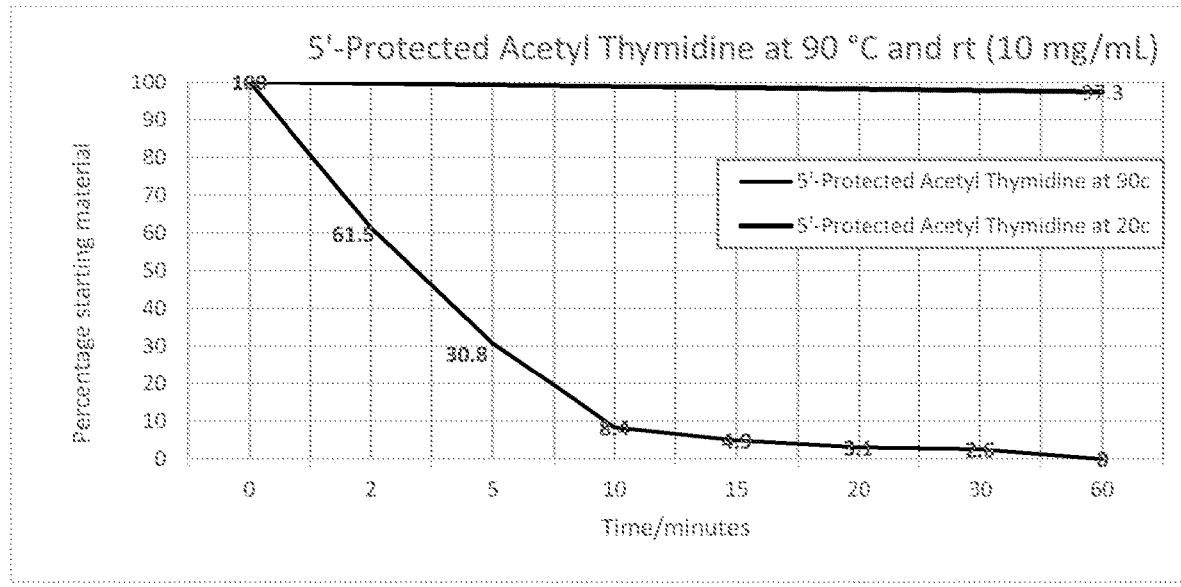
Figure 16: Time course study results for cleavage of unlocked linker of Example 16C at 90°C and at 20°C from 3'-derivatised guanosine in 0.01M Triethylamine in Acetonitrile
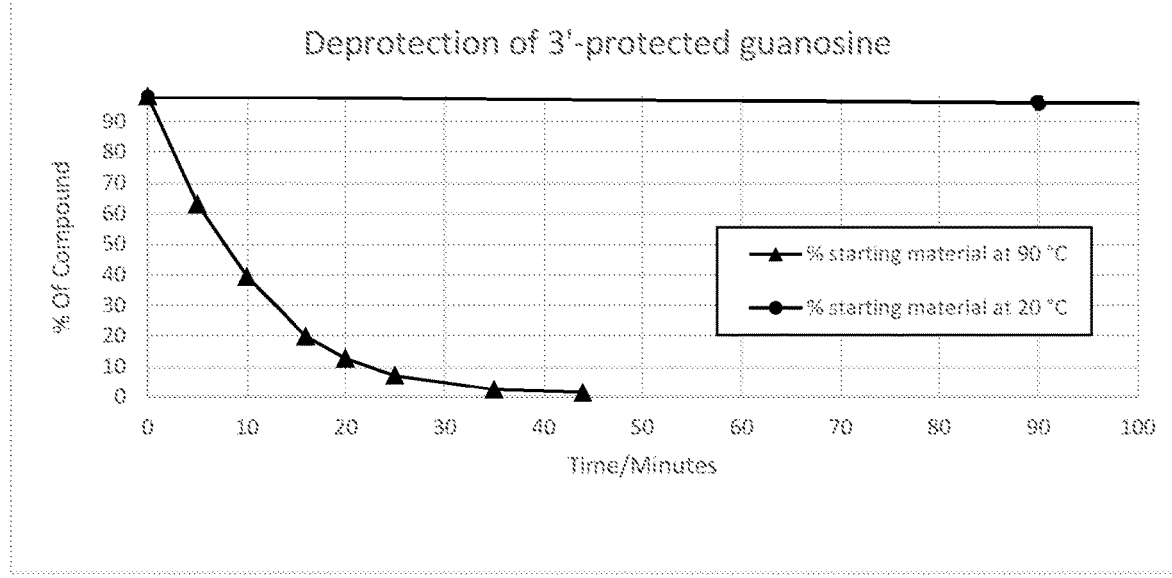

Figure 17  Time course study results for cleavage of unlocked linker of Example 16E at 90°C and at 20°C from 5'-derivatised guanosine in 0.01M Triethylamine in Acetonitrile
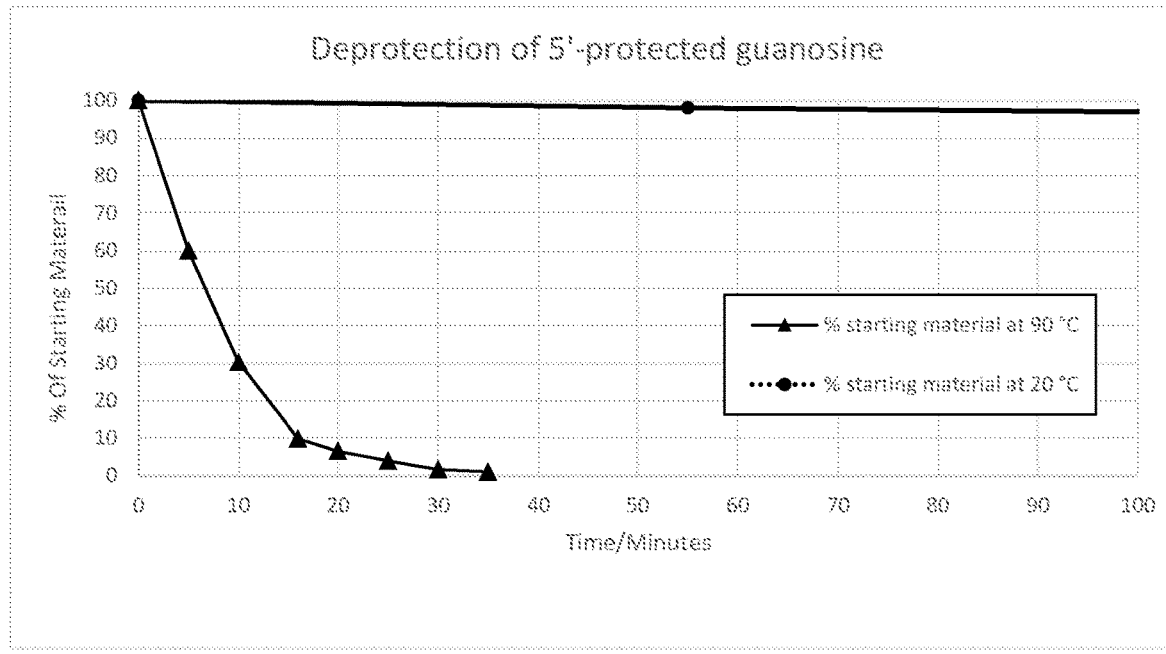
Figure 18 - Time Course studies on the cleavage of the unprotected linker of 5'-protected deoxyadenosine analogue of Example 17I
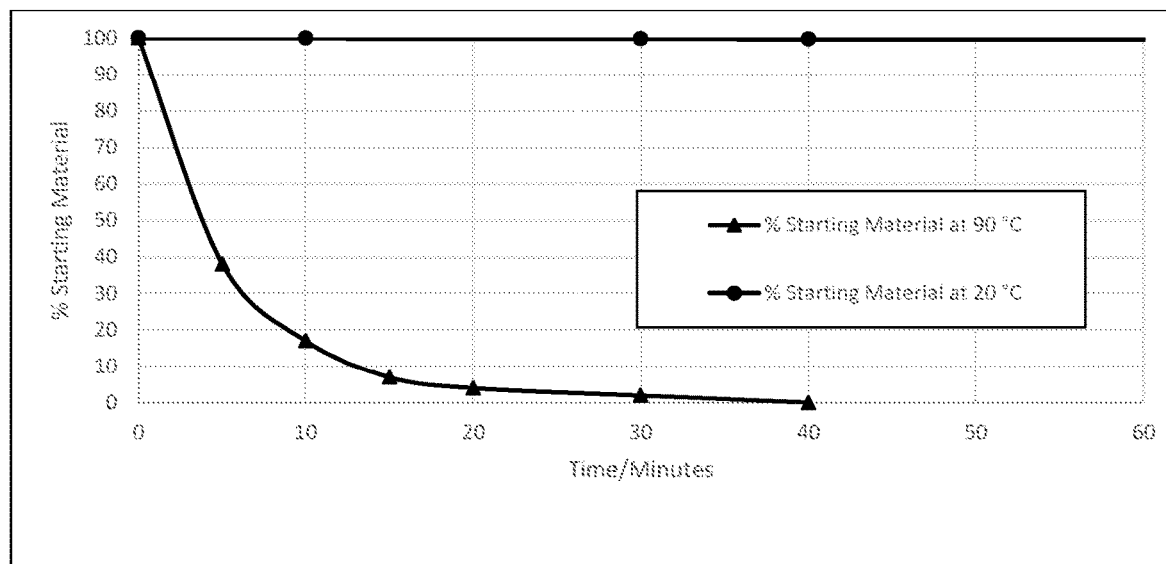

Figure 19 - Time Course studies on the cleavage of the unprotected linker of 3'-protected deoxyadenosine analogue of Example 17G with triethylamine
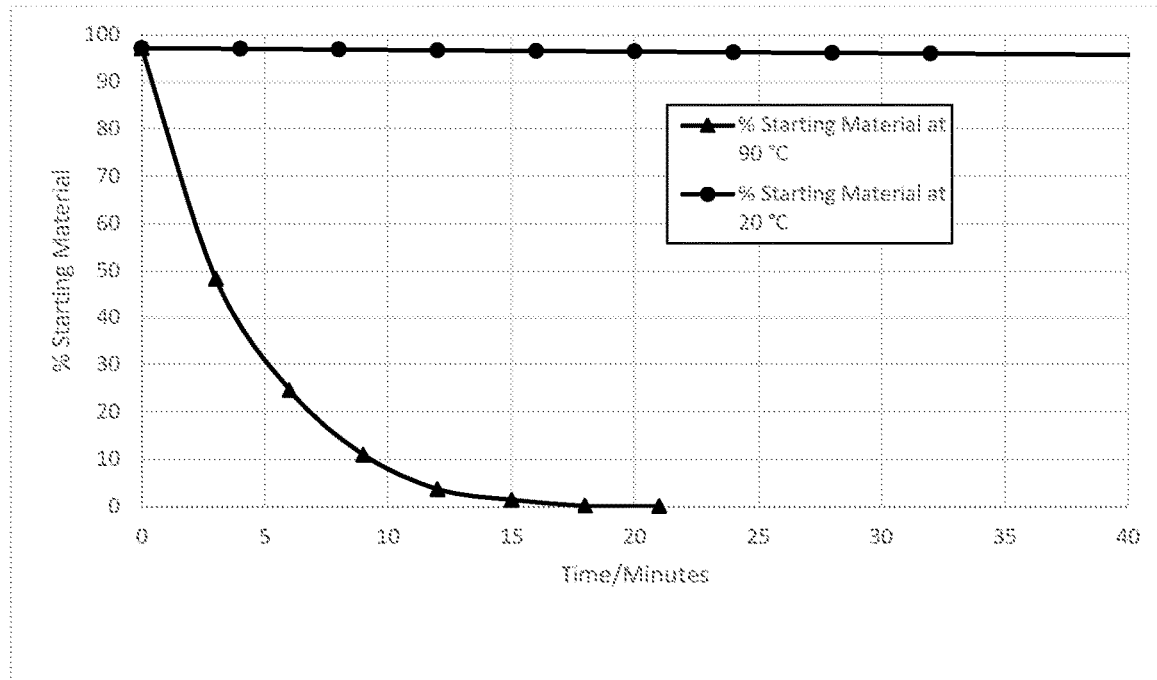
Figure 20: Time course study results for acidic unlocking of Adpoc- locked linker of Example 18I at 90°C and at 20°C
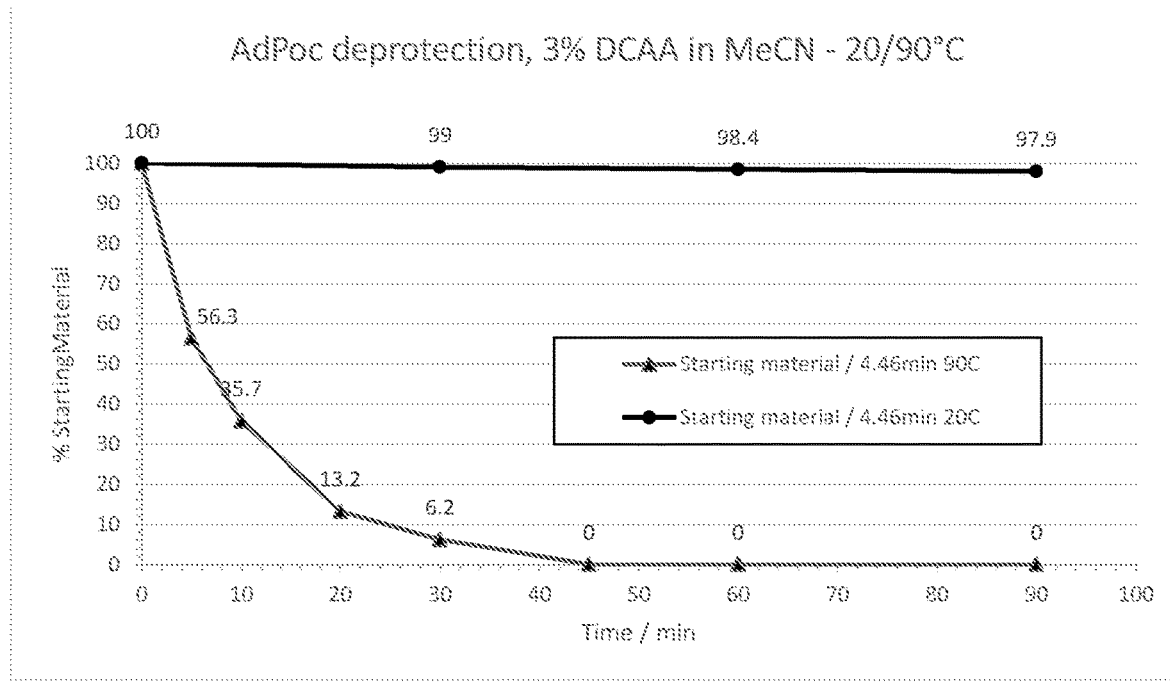

Figure 21: Time course study results for cleavage of unlocked linker of Example 19B at 90°C and at 20°C from 5'-derivatised cytosine in 0.01M Triethylamine in Acetonitrile
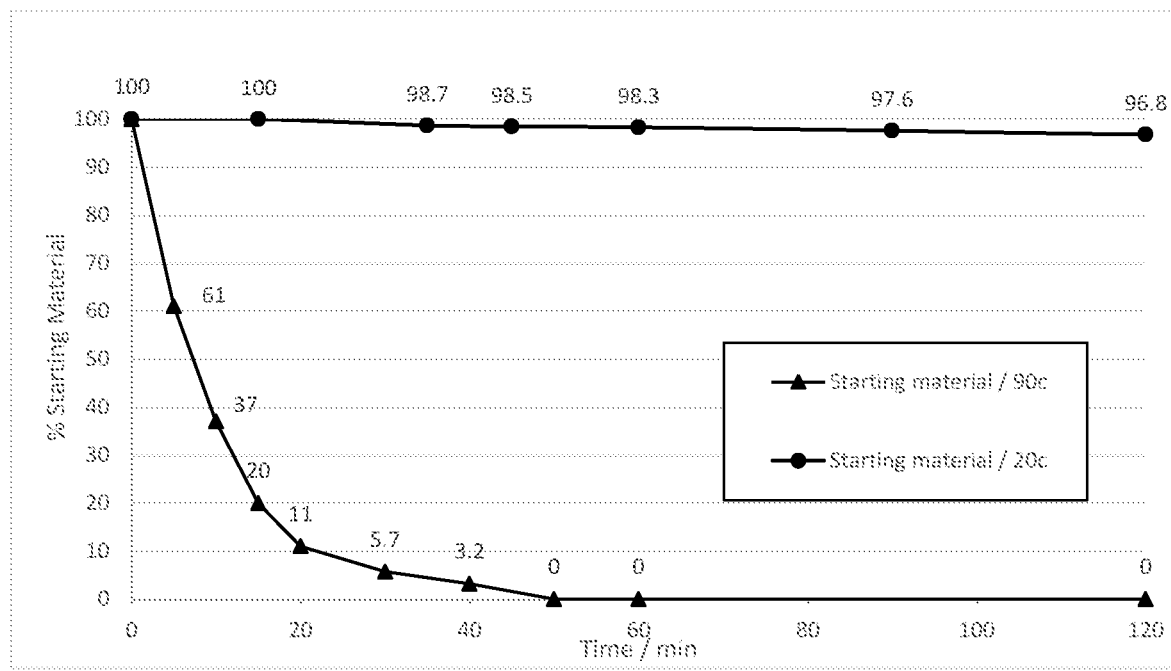
Figure 22: Time course study results for cleavage of unlocked linker of Example 1C at 90°C, 60°C, 40°C and 20°C in 1:1 0.01 M PBS Buffer:acetonitrile
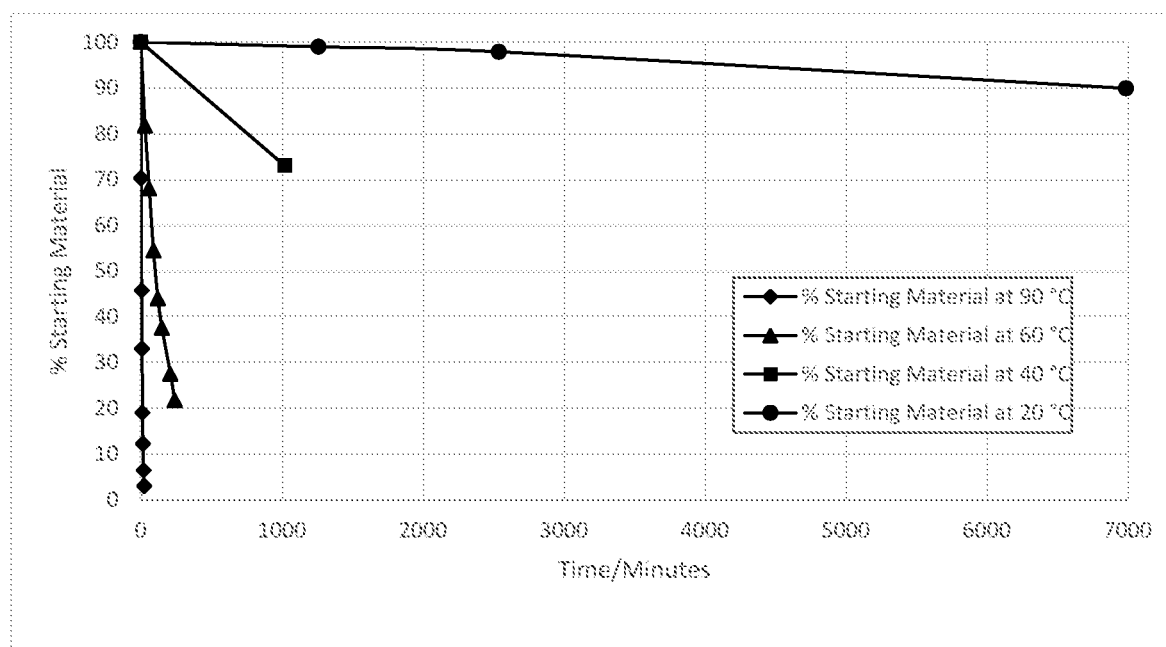

Figure 23: Time course experiments for cleavage of the 3'-protected 5' O-TBDPS-Thymidine (Compound of Example 20B) at 20°C, 40°C, 60°C and 90°C in 0.01M Hunig's Base in acetonitrile
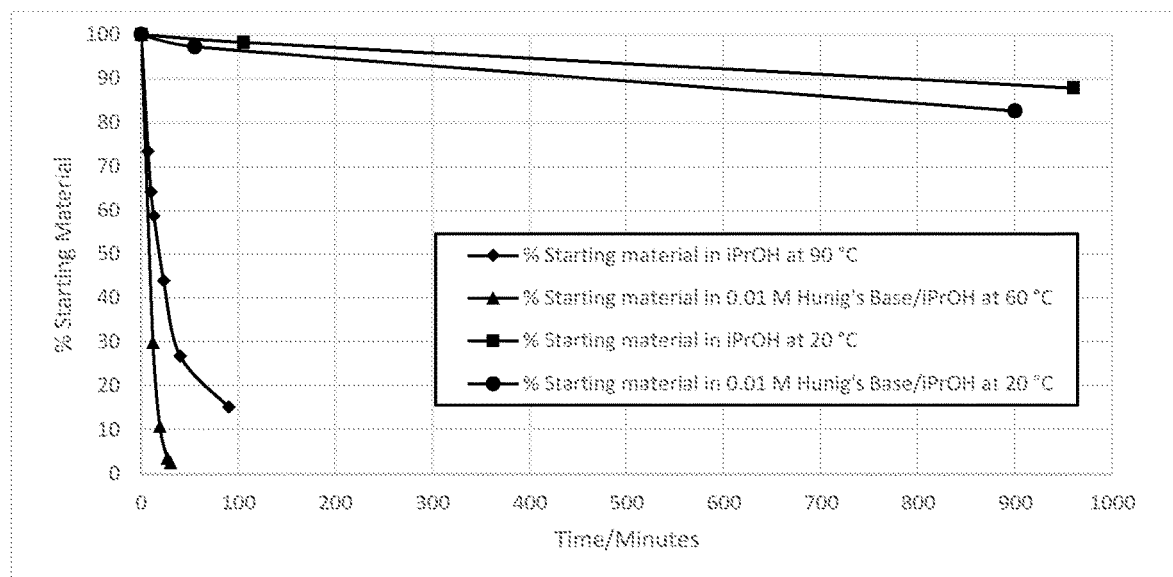
Figure 24: Time course experiments for cleavage of the 3'-protected 5' O-TBDPS-Thymidine (Compound of Example 4C) at 20°C, 40°C, 60°C and 90°C in 1:1 0.01 M PBS Buffer:acetonitrile
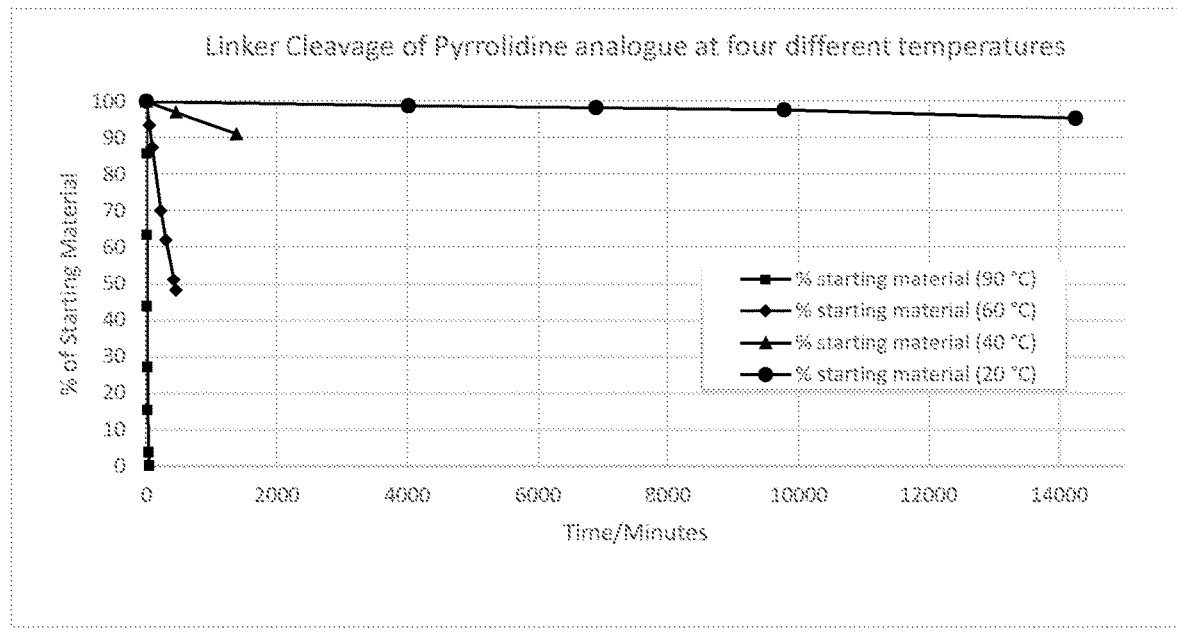

Figure 25: Time course experiments for cleavage of the 3'-protected 5' O-TBDPS-Cytidine (Compound of Example 24B) at 20°C, 40°C, 60°C and 90°C in 1:1 0.01 M PBS Buffer:acetonitrile
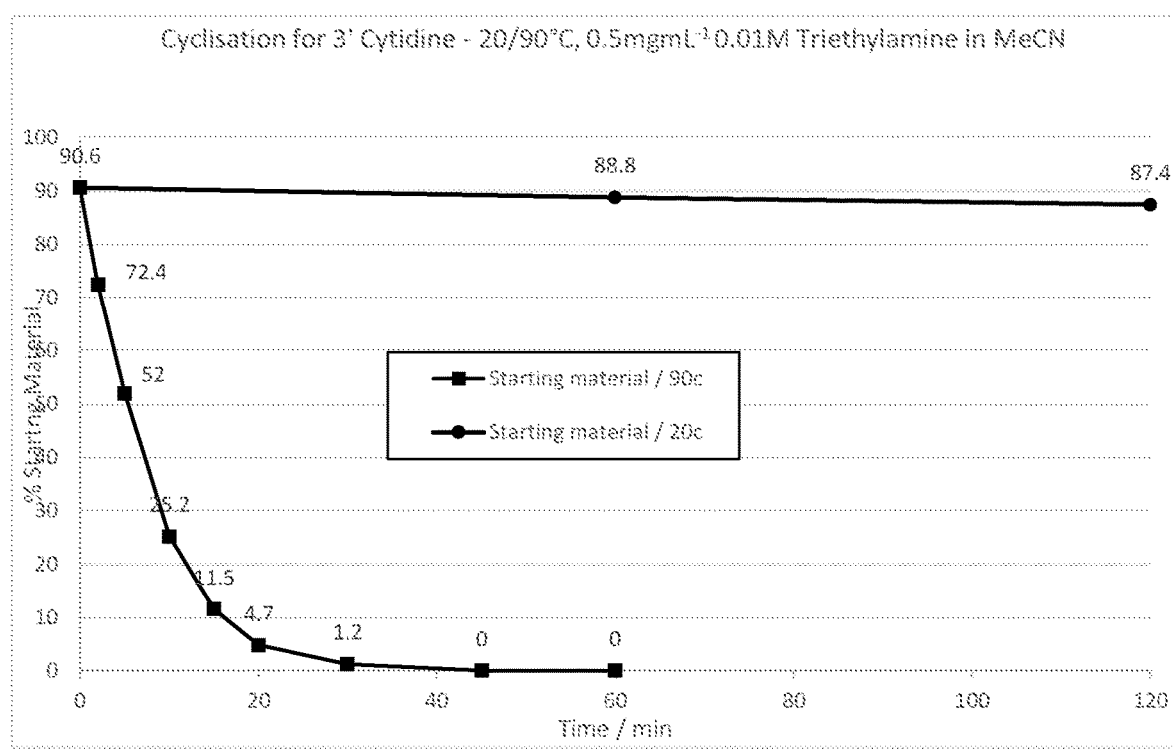

THERMALLY-CLEAVABLE PROTECTING AND LINKER GROUPS

CROSS-REFERENCE TO RELATED APPLICATIONS

This application is the National Stage of International Patent Application No. PCT/GB2018/050975, filed Apr. 12, 2018, which claims the benefit of Great Britain Patent Application No. 1705925.4, filed Apr. 12, 2017, both disclosures of which are incorporated herein by reference in their entireties.

FIELD OF THE INVENTION

The present invention relates to chemical linkers and protecting groups, compounds and compositions containing the chemical linkers or protecting groups, and intermediates and processes that can be used to prepare them. The chemical linkers and protecting groups may be used in synthetic procedures, or in a wide range of applications wherein a substance is to be released from a substrate.

BACKGROUND OF THE INVENTION

Chemical protecting groups and chemical linker groups are widely used in organic synthesis. The use of protecting groups to selectively prevent a particular reaction of a functional group, such as hydroxyl and amino groups, etc, under particular reaction conditions is ubiquitous in organic synthesis. In particular, protecting groups are widely used in the synthesis of peptides, proteins and biopolymers peptide synthesis oligonucleotide synthesis, and in the PCR (polymerase chain reaction) amplification of DNA fragments.

In solid phase synthesis, linker groups are used to attach an organic molecule to a solid support whilst reaction steps are carried out on the intermediates to the target molecule. When the final reaction step is complete, the linker must be cleaved from the solid support in order to release the product. For example, in the solid phase synthesis of oligonucleotides protected nucleoside phosphoramidites are widely used. In this method, a 5'-protected nucleoside is first covalently attached to a solid support, for example a polymer support. The 5'-protecting group is removed and a nucleoside-3'-phosphoramidite is coupled to the 5'-hydroxyl group to form a support-bound phosphite triester. Optionally, the resulting product is treated with a capping agent, in order remove failed sequences/unreacted nucleoside, typically by acetylation. The phosphite triester is then oxidised to the corresponding phosphotriester. The deprotection, coupling and oxidation steps are repeated until the desired oligonucleotide has been prepared. The resulting product is a support-bound oligonucleotide, which is then treated in order to release the oligonucleotide from the support, and subsequently separation of the oligonucleotide from the support, e.g. by filtration. Thus, the chemical linker between the support and the oligonucleotide must be stable to the oligonucleotide synthesis procedure, whilst being capable of facile release when required, at the end of the synthesis.

A key requirement of a linker or protecting group is the ability for it be inert and also to withstand cleavage during the reaction steps. A linker or protecting group is generally cleavable under different conditions (e.g. pH, temperature, UV light), from those used in the reaction steps (i.e. orthogonality). However, the linker or protecting group should also be readily cleavable under mild conditions in order to avoid exposing the target organic molecule or intermediate molecule to harsh conditions, and hence forming side products. This is particularly important in the case of biopolymers and peptides, which are common target molecules in solid state syntheses. The properties of the linker, such as stability, can have a profound effect on the synthetic procedure, and the purity of the final product.

In peptide synthesis, the use of "safety catch" linkers is known, for example, J. Chem. Soc. Chem. Comm. (1971), 636-637 and Biopolymers (Peptide Science) (1998), 47, 353-363. Such safety catch linkers involve a modification of the linker group in order to allow the linker to remain stable until it is activated by a first condition, e.g. a chemical modification, temperature changes, radiation, or by a reagent. A second condition provides for the activated linker to be cleaved. Thus, in a typical linker or protecting group with no safety catch, a single reaction step is required to cleave the linker or protecting group, whereas a safety catch linker requires a first reaction condition to activate the linker, and a second reaction condition in which the activated linker is cleaved. The safety catch therefore confers additional stability, and potentially allows a greater control of the timing and speed of the cleavage.

Chemical linker groups have widespread applications in a range of technologies, for example, process chemistry such as solid state synthesis, sensors, diagnostics and drug delivery. The use of chemical linker groups can enable the controlled release of a molecule in response to a stimulus, such as a change in temperature, pH or a reactant. A safety catch linker can additionally offer more precise control over the timing of the release. For example, in drug delivery it may be desirable to target the release of a drug at a specific site in the body in order to ensure delivery at the desired site of action, and/or to reduce drug degradation during transport to the site of action. For example, pH-dependent drug release systems, which take advantage of the pH differences at various sites of the gastrointestinal tract, e.g. stomach (pH about 1.5-3.5), small intestine (pH about 5.4-6.8) and colon (pH about 6.4-7.0) are well known. Linker chemistry also has broad applicability in other controlled drug-release applications such large or small-molecule drug conjugates, drug-eluting stents, and in the activation of prodrugs. However, a cleavable linker that attaches a drug or therapeutic entity to a delivery substrate may enable precise control of the site of release of the drug or therapeutic entity together with rapid and complete release at the target site.

Another example of the use of chemical linker groups in pharmacology is in the field of antibody-drug conjugates (ADCs) in the treatment of cancer. ADCs are complexes comprising a monoclonal antibody linked to a cytotoxic moiety, such as a cytotoxic drug. The ADCs discriminate between the healthy and diseased cells and provide targeted attack of the cancer cell in order to minimise the effect of the cytotoxic drug on the healthy cells. ADCs typically comprise an antibody that targets a tumour marker that is specific to tumour cells, whereupon the antibody attaches itself to the tumour cell, causing the ADC to be absorbed into the cell, which enables the cytotoxic component to be released to kill the tumour cell. A key aspect of ADCs is the provision of a stable linker between the antibody component and the cytotoxic agent. In such applications, linkers may be cleavable or non-cleavable. For non-cleavable linkers, the antibody, linker and cytotoxic unit is incorporated into the tumour cell. The nature of the linker typically determines the release profile of the cytotoxic agent. For example, cleavable linkers between the antibody and the cytotoxic agent are typically catalysed by enzymes in the tumour cell, wherein the antibody and the cytotoxic agents are cleaved to release the cytotoxic agent. The cytotoxic agent will then attack the tumour cell, and in some cases, will advantageously attack neighbouring tumour cells. Presently, only limited classes of chemical linkers have been developed for ADCs—hydrazones, thioethers, disulfides and peptides. These linkers respond to differences in pH, enzymes or reduction potential in order to release the cytotoxic agent in to the target cell.

The requirement for the linker to be stable to cleavage and/or degradation in the circulation, and to be readily and rapidly cleaved in the specific environment of the target cell is an onerous one, and the complexities in chemical linker technology have hampered the development of ADCs as therapeutic agents, since optimal stability and prevention or fine control of linker cleavage must be achieved in order to ensure that the cytotoxic agent is only released when the ADC reaches the tumour cell.

Linker chemistry development is also of high importance in proteomics, in particular for their applications in chemical probes used for detection and isolation of proteins. Chemical probes are designed based on small molecule interaction with proteins. The probes typically comprise a covalent binding motif in order for the probe to interact with the target protein, a detection/purification tag for visualisation/purification of the protein target and a linker group. The study of metabolically labelled proteins in chemical proteomics requires isolation and purification of the protein targets. The biotin-streptavidin system is widely used, but harsh conditions required to release the proteins may result in the release of non-selectively bound proteins, and hence poor protein recovery yields, protein destruction and release of background proteins. Cleavable linker strategies can be incorporated in order to reduce the background protein to enable the target protein to be purified.

Therefore, the development of linker groups and protecting groups having different stabilities and release characteristics to different stimuli such as reagents, temperature, pH, and other conditions, provides important tools for a whole host of technical applications.

SUMMARY OF THE INVENTION

The present invention relates to chemical linker and protecting groups that may be removed under specific, controlled conditions. The present invention further encompasses intermediates for preparing the chemical linker and protecting groups, and to compositions comprising the groups.

Thus in a first aspect, the present invention is directed to a compound of formula (I), or an acid addition salt thereof:

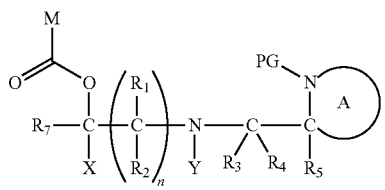

(I)

wherein:
  M represents an organic fragment;
  X represents hydrogen or hydrocarbyl;
  Y represents hydrocarbyl or

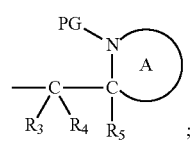

each of $R_1$, $R_2$, $R_3$, $R_4$, $R_5$ and $R_7$ are the same or different and each independently represents hydrogen or hydrocarbyl;
  PG represents a cleavable protecting group for nitrogen;
  n represents 0, 1, 2 or 3; and
  ring A represents a nitrogen-containing heterocyclic group;
  wherein at each occurrence, $R_1$, $R_2$, $R_3$, $R_4$, $R_5$, PG, A, Y, n may be the same or different.

The present invention further encompasses compositions comprising the above compound or acid addition salt thereof, wherein the compound is covalently bound to a substrate, such as a solid phase or a solid support, an antibody, a metal surface, a conductive surface, a polymeric support, a pharmaceutically inert support, a chip, a resin, a sensor, a glass support or a polystyrene support. The compound may optionally be bound to the substrate via a linker moiety.

In a further aspect, the present invention relates to a cleavable protecting group or cleavable linker of formula (L-I):

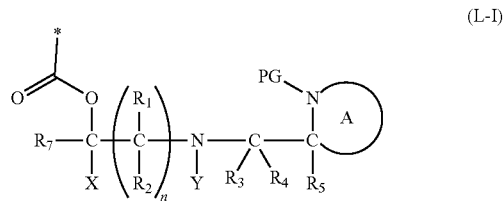

(L-I)

wherein:
  * represents a point of attachment to an organic moiety to be protected or to be released from the cleavable linker or protecting group;
  X represents hydrogen or hydrocarbyl;
  Y represents hydrocarbyl or

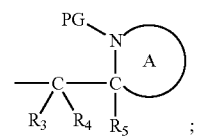

each of $R_1$, $R_2$, $R_3$, $R_4$, $R_5$ and $R_7$ are the same or different and each independently represents hydrogen or hydrocarbyl;
  PG represents a cleavable protecting group for nitrogen;
  n represents 0, 1, 2 or 3; and
  ring A represents a nitrogen-containing heterocyclic group;
  wherein at each occurrence $R_1$, $R_2$, $R_3$, $R_4$, $R_5$, PG, A, Y, n may be the same or different.

The cleavable protecting group or cleavable linker of formula (L-1) preferably has the formula (L-IA) or (L-IB):

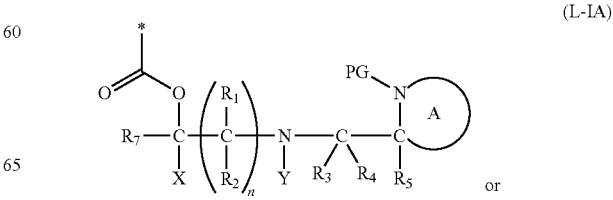

(L-IA)

or

-continued $$\text{(L-IB)}$$

The cleavable linker of formula (L-1), (L-IA) and (L-IB) may be covalently bound to a substrate.

The cleavable linker of the present application can be used in solid phase synthesis. Thus, solid phase synthesis of an organic compound can be carried on a starting material which is covalently bound to a solid substrate via the cleavable linker. Thus, for example, the cleavable linker can be used in the solid phase synthesis of peptide, oligonucleotides and the like. At the end of the synthesis, the cleavable linker together with the substrate can be quickly and selectively removed in order to isolate the synthesised organic compound.

The cleavable linker and protecting groups of the present invention can be readily, rapidly and cleanly removed when required under specific conditions. The removal step comprises a two step activation and cleavage process. In a first step, i.e. the activation step, a protecting group PG is removed under a specific reaction condition to form the deprotected linker intermediate. Subsequently, the second step, i.e. a cleavage step, involves a second reaction condition whereby the deprotected linker intermediate is reacted in order to cause intramolecular cyclisation with concomitant release of carbon dioxide.

The invention is useful for the manufacture of reagents, compositions and devices for use in a wide number of applications, including chemical synthesis, biochemical applications, pharmacology (e.g. drug delivery), molecular biology applications and medical diagnostics and medical screening.

DESCRIPTION OF THE FIGURES

FIG. 1: Time course study results for cleavage of deprotected linker of Example 1C at 90° C. and at 20° C.

FIG. 2: Time course study results for cleavage of deprotected linker of Example 1C using different solvent systems at pH 7.4 PBS and acetonitrile and pH 5 buffer (TEEA)

FIG. 3: Time course study results for cleavage of deprotected linker of Example 1C using different ratios of PBS:MeCN (acetonitrile) at 90° C.

FIG. 4A: Time course study results for deprotection (removal of Bsmoc) and cleavage of Bsmoc protected linker of Example 2 at 90° C.

FIG. 4B: Time course study results for deprotection of Bsmoc-protected linker (i.e. removal of Bsmoc) of Example 2 at room temperature and 90° C.

FIG. 4C: Time course study results showing cleavage of Bsmoc protected linker of Example 2 to give free TBDPS-thymidine at 90° C. and at 20° C. (formation and cleavage of deprotected intermediate not shown) FIG. 5: Stability study results for the Bsmoc protected linker of Example 2 under different pH conditions at 80° C.

FIG. 6: Stability study results for deprotected linker of Example 3 under different temperature conditions (room temperature vs 90° C.) FIG. 7: Stability study results for Fmoc-protected linker of Example 3 using 10% diisopropylamine under different temperature conditions (room temperature vs 90° C.

FIG. 8: Stability study results for Fmoc-protected linker of Example 3 using 10% diisopropylamine at 90° C. using different solvents (DMF vs acetonitrile)

FIG. 9: Stability study results for Fmoc-protected linker of Example 3 using 20% diisopropylamine in 2:1 DMF (dimethylformamide):CAPs (N-cyclohexyl-3-aminopropanesulfonic acid) buffer at different temperatures (10° C. vs 90° C.)

FIG. 10: Cleavage of deprotected linker of Example 1C and Example 4C at 90° C.

FIG. 11: Stability study results for Example 4C at 90° C. in different solvent systems FIG. 12: Time course study results for deprotection of Boc-protected linker (Compound of Example 1B)

FIG. 13: Time-course study on the non-protected α-Phenyl Safety-Catch Linker (compound of Example 6D)

FIG. 14: Time-course study on cleavage of non-protected Double Safety-Catch Linker (Compound of Example 8C) vs Single Safety-Catch Linker (Compound of Example 1C)

FIG. 15: Time-course study on the non-protected 5'-linked protected 3' O-Acetyl-Thymidine (Compound of Example 13B)

FIG. 16: Time course study results for cleavage of unlocked linker of Example 16C at 90° C. and at 20° C. from 3'-derivatised guanosine in 0.01M Triethylamine in Acetonitrile FIG. 17: Time course study results for cleavage of unlocked linker of Example 16E at 90° C. and at 20° C. from 5'-derivatised guanosine in 0.01M Triethylamine in Acetonitrile FIG. 18: Time Course studies on the cleavage of the unprotected linker of 5'-protected deoxyadenosine analogue of Example 17I FIG. 19: Time Course studies on the cleavage of the unprotected linker of 3'-protected deoxyadenosine analogue of Example 17G with triethylamine FIG. 20: Time course study results for acidic unlocking of Adpoc-locked linker of Example 18I at 90° C. and at 20° C.

FIG. 21: Time course study results for cleavage of unlocked linker of Example 19B at 90° C. and at 20° C. from 5'-derivatised cytosine in 0.01M Triethylamine in acetonitrile FIG. 22: Time course study results for cleavage of unlocked linker of Example 1C at 90° C., 60° C., 40° C. and 20° C. in 1:1 0.01 M PBS buffer:acetonitrile FIG. 23: Time course study results for cleavage of the 3'-protected 5' O-TBDPS-Thymidine (Compound of Example 20B) at 20° C., 40° C., 60° C. and 90° C. in different solvents FIG. 24: Time course study results for cleavage of the 3'-protected 5' O-TBDPS-Thymidine (Compound of Example 4C) at 20° C., 40° C., 60° C. and 90° C. in 1:1 0.01 M PBS buffer:acetonitrile FIG. 25: Time course experiments for cleavage of the 3'-protected 5' O-TBDPS Bz-Cytosine at 20° C. and 90° C.

DETAILED DESCRIPTION OF THE INVENTION

Definitions

The terms used herein have their normal meanings in the art unless otherwise indicated.

The term "nucleotide" refers to a nucleic acid (e.g. RNA, or DNA or analogues thereof) subunit that includes a sugar group, a heterocyclic base and a phosphate group.

The term "nucleoside" refers to a compound comprising a sugar group covalently coupled to a heterocyclic base. The heterocyclic base of a nucleoside or nucleotide is also known as a nucleobase.

In all cases, unless otherwise indicated, references to nucleosides, nucleotides and oligonucleotides include those having activating or protecting groups as appropriate.

In all cases, unless otherwise indicated, references to nucleoside(s), nucleotide(s) and oligonucleotide(s) include naturally occurring purine and pyrimidine bases, in particular, adenine, thymine, cytosine, guanine and uracil, as well as modified purine and pyrimidine analogues, such as alkylated, acylated, or protected purines and pyrimidines.

The term "hydrocarbyl" as used in herein refers to a monovalent group formed by removing a hydrogen atom from a hydrocarbon. The term hydrocarbyl encompasses alkyl, aryl, alkaryl and arylalkyl, alkenyl, or alkynyl groups as defined below. The alkyl groups and alkyl portions of the hydrocarbyl groups can include straight chain, branched, or cyclic alkyl. The term hydrocarbyl includes alkyl, aryl or arylalkyl, more preferably $C_{1-6}$ alkyl, $C_{6-10}$ aryl or $C_{7-12}$ arylalkyl. Even more preferably, hydrocarbyl refers to $C_{6-10}$ aryl, or $C_{7-12}$ arylalkyl, and most preferably phenyl or benzyl. The term hydrocarbyl (especially for the group Y) can also include alkyl, alkenyl, aryl, aralkyl or alkaryl groups (as defined below) which are substituted with a terminal alkynyl group. For example, hydrocarbyl may include: an alkyl, alkenyl, aryl, aralkyl or alkaryl which is substituted with a terminal alkynyl group, preferably wherein the terminal alkyne group is a $C_2$ to $C_6$ alkynyl group, more preferably a $C_2$ to $C_4$ alkynyl group, and most preferably ethynyl. In this respect, a preferred hydrocarbyl group includes —$CH_2$—($C_6H_4$)CH≡CH.

Alkyl groups relates to saturated, straight, branched, primary, secondary or tertiary or cyclic hydrocarbons. Alkyl groups can contain from 1-20 carbon atoms, 1-15 carbon atoms, or 1-6 carbon atoms. Particularly preferred alkyl groups are $C_{1-6}$ straight or branched alkyl groups, or $C_{3-6}$ cycloalkyl groups. Preferred alkyl groups are methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. More preferably alkyl groups can contain from 1-6 carbon atoms, particularly methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Alkyl also encompasses cycloalkyl groups which can contain 3 to 10 carbon atoms having single or multiple fused rings. Preferred cycloalkyl groups include adamantyl, cyclopropyl, cyclobutyl, cyclopentyl, cyclohexyl, cycloheptyl, cyclooctyl, cyclopropyl, cyclobutyl, cyclopentyl or hexyl.

Aryl groups relate to aromatic rings containing from 6-20, preferably 6-15 and more preferably 6-10 carbon atoms, and include monocyclic, bicyclic and polycyclic, fused or branched aryl groups. Preferred aryl groups are phenyl, biphenyl and naphthyl. A particularly preferred aryl group is phenyl.

Alkaryl groups can contain from 7-21 carbon atoms, preferably 7-16 carbon atoms and more preferably 7-11 carbon atoms, and include alkaryl group containing monocyclic, bicyclic and polycyclic or branched aryl groups, as well as straight, branched or cyclic alkyl groups. Preferred alkaryl groups are tolyl and xylyl.

Arylalkyl groups can contain from 7-21 carbon atoms, preferably 7-16 carbon atoms and more preferably 7-11 carbon atoms, and include aryalkyl groups containing monocyclic, bicyclic and polycyclic or branched aryl groups, as well as straight, branched or cyclic alkyl groups. Preferred arylalkyl groups are benzyl, phenethyl, phenpropyl, phenbutyl, naphthylmethyl and naphthylmethyl.

Alkenyl refers to straight, branched and cyclic hydrocarbons having at least one carbon-carbon double bond. Preferably, alkenyl groups contain from 2-12, 2-8, 2-6 or 2-4 carbon atoms. Preferably, alkenyl refers 1-3 double bonds, and more preferably one double bond. Alkenyl groups preferably include: ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, and cyclopenten-4-yl.

Alkynyl relates to straight, branched or cyclic hydrocarbons having at least one carbon-carbon triple bond, preferably having 1-2 triple bonds, and more preferably one triple bond. Preferably, alkynyl groups include from 2 to 12 carbon atoms, preferably 2-8 or more preferably 2-4 carbon atoms. Preferred alkynyl groups are: ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl.

In any aspect or embodiment of the present invention, hydrocarbyl preferably refers to alkyl, aryl or arylalkyl, more preferably $C_{1-6}$ alkyl, $C_{6-10}$ aryl or $C_{7-12}$ arylalkyl. Even more preferably, hydrocarbyl refers to $C_{6-10}$ aryl, or $C_{7-12}$ arylalkyl, and most preferably phenyl or benzyl.

A heterocyclic group, for example, in the context of the ring A, refers to a non-aromatic cyclic group containing at least one ring nitrogen atom, i.e. the nitrogen atom which is part of the

moiety. The ring A heterocyclic group, which is represented by:

may be monocyclic, bicyclic or tricyclic, and preferably is monocyclic or bicyclic, more preferably monocyclic.

The heterocyclic group may contain unsaturated ring carbon atoms, but is preferably saturated. Preferably, the heterocyclic group of ring A is a 4-12 membered heterocyclic ring containing at least one ring nitrogen atom.

Suitable ring A heterocyclic groups for include: azetidinyl, pyrrolidinyl, 2,5-dihydropyrrole, pyrazolinyl, imidazolyl, imidazolinyl, oxazolidinyl, thiazolidinyl, isothiazolyl, isothiazolidinyl, piperidinyl, piperazinyl, 2-oxopiperazinyl, 2-oxopiperidinyl, 2-oxoazepinyl, azepinyl, 4-piperidonyl, morpholinyl, thiamorpholinyl and triazolyl. Bicyclic heterocyclic groups include, but are not limited to tetra-hydroisoquinolinyl and tetrahydroquinolinyl Preferred heterocyclic groups are those at least one ring nitrogen atom, and most preferably a 5 or 6-membered heterocyclic ring containing one ring nitrogen atom. Particularly, the ring A is a heterocyclic group selected from the group consisting of piperidinyl, pyrrolidinyl, azepanyl (homopiperidinyl) and azocanyl, and more preferably ring A is a heterocyclic group selected from the group consisting of piperidinyl, pyrrolidinyl and azepanyl, and most preferably ring A is piperidinyl or pyrrolidinyl. The ring A heterocyclic group can be unsubstituted or substituted at one or more ring atoms (preferably with inert substituents, such as alkyl, aryl, arylalkyl, or alkyaryl). Thus references to ring A and specific ring A groups include those having substituents on one or more ring atoms. Preferably, Ring A is unsubstituted.

The term "protecting group" refers to a moiety which is used to temporarily mask a reactive group on a molecule, in order to enable chemical transformation on another part of the molecule, and which can be subsequently removed. Protecting groups for different functional groups and reaction conditions are well known, e.g. from Greene's "Protective Groups in Organic Synthesis", Fifth edition (2014), Peter G. M. Wuts, Wiley.

The terms "fragment", "moiety", "group", "substituent" and "radical" are used herein interchangeably to refer to a portion of a molecule, for example having a particular functional group.

It will be appreciated that certain compounds of the present invention may contain one or more chiral centres. Unless otherwise indicated, references to a compound of unspecified stereochemistry are intended to include the single isomers or single enantiomers, or mixtures including racemates thereof.

The present invention provides, in a first aspect, a compound of formula (I), or an acid addition salt thereof:

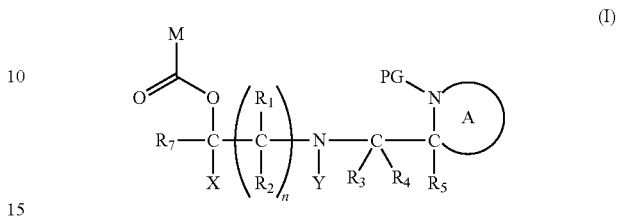

wherein:
M represents an organic fragment;
X represents hydrogen or hydrocarbyl;
Y represents hydrocarbyl or

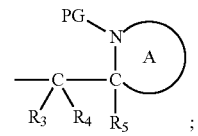

;

each of $R_1$, $R_2$, $R_3$, $R_4$, $R_5$ and $R_7$ are the same or different and each independently represents hydrogen or hydrocarbyl;
PG represents a cleavable protecting group for nitrogen;
n represents 0, 1, 2 or 3; and
ring A represents a nitrogen-containing heterocyclic group;
wherein at each occurrence, $R_1$, $R_2$, $R_3$, $R_4$, $R_5$, PG, and A may be the same or different. For example, each occurrence of $R_1$ and $R_2$ in the fragment —[C($R_1$)($R_2$)]$_n$ where n is 2 or more, can be the same or different. Similarly the $R_3$, $R_4$, $R_5$, PG, and A groups in the fragment Y when Y is:

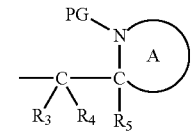

may be the same or different from the other $R_3$, $R_4$, $R_5$, PG, and A groups in the compound of Formula (I).

Preferably, each $R_1$, $R_1$, $R_2$, $R_3$, $R_4$, $R_5$, PG and A in the compound of formula (I) is the same.

In the compounds, compositions, linker and protecting groups of the present invention, the moiety M represents a fragment of a biological molecule, a drug, a therapeutic entity, a nucleotide, an oligonucleotide, a polynucleotide, an amino acid, a peptide, a peptide fragment, an antibody, an antibody conjugate, an engineered receptor such as an artificial T-cell receptor, a B-cell an antigen, a reporter molecule such as a dye or a dye conjugate, a chemotherapeutic sensitizer, a protein, a saccharide, an oligosaccharide, a polysaccharide. Typically, the attachment of the M fragment is via a —O—, —N($R_8$)— or —C($R_9$)($R_{10}$)—, or preferably a —O— or —C($R_9$)($R_{10}$)— on the M group, for example, a hydroxyl group on a nucleotide, or an amine group on a drug, etc.

In the above compounds of the present invention, the linker part of the compound can be cleaved from the fragment M. Thus, in the compounds of formula (I) above, one or both of the protecting groups PG is cleavable under a first reaction condition to produce a compound of formula (I*):

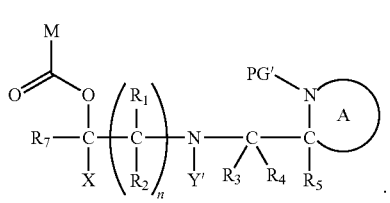

wherein:
PG' is hydrogen or a cleavable protecting group for nitrogen, provided that at least one PG' is hydrogen;
Y' represents hydrocarbyl, or

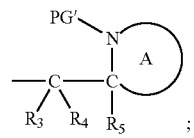

and
wherein X, $R_1$-$R_5$, $R_7$, A, M and n are as defined above for Formula (I)
Preferably in the compounds of formula (I) wherein Y represents:

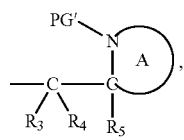

both PG groups are cleaved, thereby forming a compound of formula (I*), wherein each PG' represents H. The compound of formula (I*) represents an activated linker group, i.e. the first step of the safety catch linker removal process.

In accordance with the second step, i.e. linker/protecting group cleavage the compound of Formula (I*) is subjected to a different reaction condition, whereupon the compound can undergo intramolecular cyclisation (i.e. via intramolecular nucleophilic attack by nitrogen), resulting in cleavage and release of carbon dioxide, to produce a compound of formula (II):

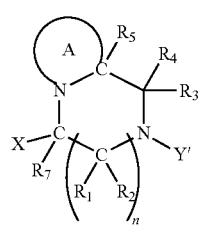

thereby releasing M or an organic compound comprising M. The fragment M may be released as an anion (i.e. M), or may be released as a neutral species, e.g. M–H or as a salt (i.e. an organic compound comprising M), depending on the reaction conditions.

In one embodiment, the compound of formula (I) can have the formula (IA):

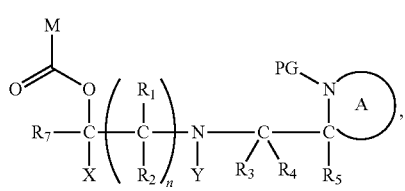

wherein:
Y represents hydrocarbyl; and
wherein X, $R_1$-$R_5$, $R_7$, PG, A, M and n are as defined for formula (I). In this embodiment, the fragment M can be released by the two step activation-cleavage process as described above. Thus, the PG protecting group is cleavable under a first reaction condition to produce a compound of formula (IA*):

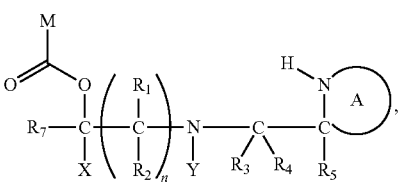

wherein:
Y represents hydrocarbyl; and
wherein X, $R_1$-$R_5$, $R_7$, A, M and n are as defined for Formula (I). Subsequently, when required, the compound of Formula (IA*) is subjected to a second, different reaction condition, to effect intramolecular cyclisation and cleavage with release of carbon dioxide, to produce a compound of formula (IIA):

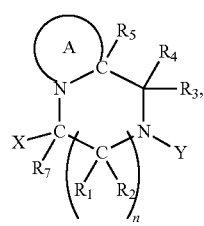

thereby releasing M or an organic compound comprising M.

In another embodiment of the present invention, there is provided a compound of formula (I), which contains two activating groups. Thus, the present invention provides a compound according to formula (I) having the formula (IB):

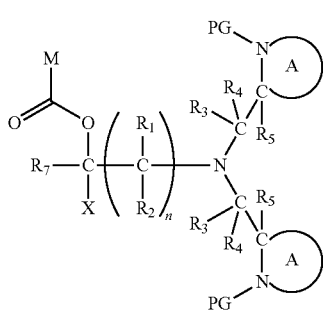

(IB)

wherein X, $R_1$-$R_5$, $R_7$, PG, A, M and n are as defined for Formula (I). In the compounds of Formula (IB), preferably the two moieties:

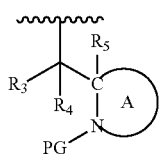

are the same, i.e. each $R_3$, $R_4$, $R_5$, PG, N and A are the same.

Preferably, each $R_1$, $R_1$, $R_2$, $R_3$, $R_4$, $R_5$, PG and A in the compound of formula (I) is the same.

In this embodiment, the fragment M can be released from the compound of Formula (IB) by an analogous two step activation-cleavage process as described above. Thus, at least one of the PG protecting groups, preferably both PG groups, is cleavable under a first reaction condition to produce a compound of formula (IB*):

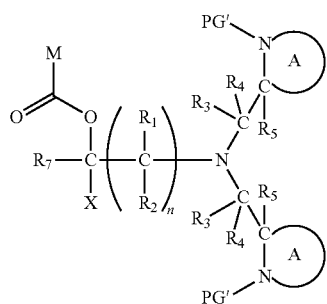

(IB*)

wherein

PG' is hydrogen or a cleavable protecting group for nitrogen, provided that at least one PG' (preferably both PG') is hydrogen; and wherein X, $R_1$-$R_5$, $R_7$, A, M and n are as defined in for Formula (I). Subsequently, when required, the compound of Formula (IB*) is subjected to a second, different reaction condition, to effect intramolecular cyclisation and cleavage with release of carbon dioxide, to produce a compound of formula (IIB):

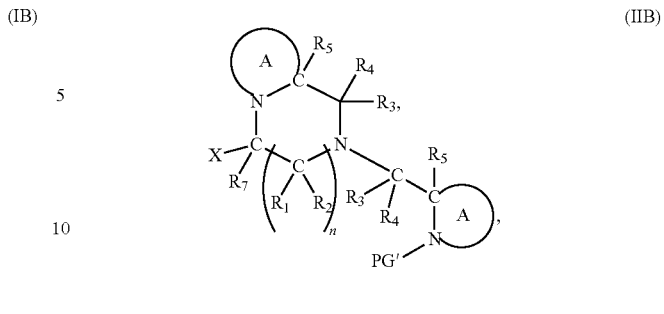

(IIB)

thereby releasing M or an organic compound comprising M. Preferably in the compounds of formula (IB), both PG groups are the same, and the activation step preferably results in both PG groups being removed. An advantage of having both nitrogen groups being activated is that the resulting compound of formula (IB*) has two nucleophilic sites available for the subsequent cleavage step, result in a significantly faster cleavage reaction.

In any aspect or embodiment of the present invention, ring A can be the same or different at each occurrence, and each represents a heterocyclic group as defined above. More preferably, ring A represents a 4-12 membered mono-, bi- or tri-cyclic, preferably mono- or bicyclic nitrogen-containing heterocyclic group, and which may contain, in addition to the nitrogen, one or more other heteroatoms selected from N, O or S, preferably O or N. Preferably, ring A represents a 4 to 8-membered monocyclic heterocyclic group. More preferably, ring A represents a 5, 6, or 7-membered monocyclic heterocyclic group. In other preferred embodiments, ring A represents a heterocycle selected from: piperidyl, morpholinyl, pyrrolidinyl, thiomorpholinyl, and imidazolyl. Even more preferably, ring A represents piperidyl, pyrrolidinyl or imidazolyl. In especially preferred embodiments of the present invention, ring A represents piperidyl, or pyrrolidinyl.

In any aspect or embodiment of the present invention, at each occurrence of —C($R_3$)($R_4$), both of $R_3$ or $R_4$ is hydrocarbyl, or one of $R_3$ or $R_4$ is hydrocarbyl, and the other is H, or both $R_3$ and $R_4$, represent H. Preferably, one of $R_3$ or $R_4$ is hydrocarbyl, and the other is H, or both $R_3$ and $R_4$, represent H.

In any aspect or embodiment of the present invention, n represents 0, 1 or 2; and preferably 0 or 1. Most preferably, n represents 1.

In any aspect or embodiment of the present invention, the group X is H or hydrocarbyl, wherein the hydrocarbyl is selected from the group consisting of alkyl, aryl or arylalkyl as defined above. Preferably X is H or aryl, and more preferably X is H or phenyl.

In any aspect or embodiment of the present invention, preferably the group $R_7$ is H.

In any aspect or embodiment of the present invention, preferable the groups $R_1$ and $R_2$ are preferably H.

In any aspect or embodiment of the present invention, preferably the groups $R_3$ and $R_4$ are H.

In any aspect or embodiment of the present invention, preferably the group $R_5$ is H.

In any aspect or embodiment of the present invention, the activation step, whereby at least one of the protecting groups PG is cleaved, is preferably effected by a change in pH, temperature, radiation, or by a chemical activating agent, or by a combination thereof.

Preferably, the cleavage of at least one protecting group PG can be activated by pH, temperature, a chemical activation agent, or by a combination thereof.

In a preferred embodiment, at least one protecting group PG is thermally cleavable in the presence of an activating agent. Typically, at least one protecting group PG is not thermally cleavable in the absence of an activating agent. Preferably, the activating agent is an acid or a base. In accordance with any aspect or embodiment of the present invention, the conditions whereby the PG group can be cleaved are different from the conditions that effect intramolecular cyclisation to release M or an organic compound comprising M form the compound or composition of the invention. The protecting groups can be selected in order to enable the two different conditions for activation and release.

In one embodiment, at least one protecting group PG is thermally cleavable in the presence of an acid, and the intramolecular cyclisation and cleavage of the linker is effected by heating in the presence of a base. In this embodiment, an acid-cleavable protecting group PG leads to deprotection of the PG group(s) resulting in a N-protonated intermediate. The N-protonated intermediate is then unable to effect linker cleavage until the deprotonation occurs, i.e. by reaction with a base. In a solution phase process deprotonation can be carried out with, for example, a cold aqueous basic work-up, before carrying out the second step of the process in a mild buffer or in an organic solvent. The deprotonation and the second step of linker cleavage may be carried out in a non-aqueous system/solution, e.g. in an organic solvent. Alternatively the base used for the second step of the process can be basic enough to both effect the deprotonation and to facilitate the intramolecular cyclisation and cleavage of the linker. In a solid phase process an excess of organic base strong enough to deprotonate the N-protonated intermediate can be added to the buffer solution or to the organic solvent (in the latter case, a non-aqueous system is used, and the N-protonated intermediate is added to the organic solvent) used for the second step, or a more basic buffer or a more basic non-aqueous system can be used.

Thus the use of an acid-cleavable protecting group offers a different level of orthogonality in each of the deprotection (i.e. PG removal) and cleavage (intramolecular cyclisation) steps.

Preferably, pH at which the acid-cleavable protecting group PG is removed ($pH_1$, wherein $pH_1$ is <7) and the pH at which the base-mediated intramolecular cyclisation is effected ($pH_2$, wherein $pH_2$ is >7) differs by: at least about 1, at least about 2, at least about 3, at least about 4, at least about 5, at least about 6, at least about 7, at least about 8, at least about 9, or at least about 10 pH units. Preferably, the difference in pH at which the protecting group PG and the intramolecular cyclisation/cleavage of the linker is: about 2 to about 10, about 3 to about 7, about 3 to about 7 or about 4 to about 7 or about 5 to about 6 pH units.

Preferred PG groups that are cleavable in the presence of acid are selected from: tert-butyloxycarbonyl (Boc), trityl (Trt), benzyloxycarbonyl, α,α-dimethyl-3,5-dimethoxybenzyloxycarbonyl (Ddz), 2-(4-biphenyl)isopropoxycarbonyl (Bpoc), 2-nitrophenylsulfenyl (Nps), tosyl (Ts). More preferably acid cleavable protecting groups are selected from Boc and Trt.

Alternatively, in another embodiment, at least one protecting group PG is thermally cleavable in the presence of a base (e.g. at a temperature $T_1$), and the intramolecular cyclisation and cleavage of the linker is effected by further heating (e.g. at a temperature $T_2$). The difference in temperatures (i.e. $T_2-T_1$), may be: at least about 20° C., at least about 25° C., at least about 30° C., at least about 35° C., at least about 40° C., at least about 45° C., at least about 50° C., at least about 55° C., at least about 60° C., at least about 65° C., at least about 70° C. or at least about 75° C. Preferably, the difference in temperatures at which the protecting group PG and the intramolecular cyclisation/cleavage of the linker occurs is from: about 30° C. to about 100° C., about 40° C. to about 90° C., about 50° C. to about 80° C. or about 55° C. to about 75° C.

Preferred PG groups that are cleavable in the presence of a base are selected from: (1,1-dioxobenzo[b]thiophene-2-yl)methyloxycarbonyl (Bsmoc), 9-fluorenylmethoxycarbonyl (Fmoc), (1,1-dioxonaphtho[1,2-b]thiophene-2-yl)methyloxycarbonyl (α-Nsmoc), 2-(4-nitrophenylsulfonyl)ethoxycarbonyl (Nsc), 2,7-di-tert-butyl-Fmoc, 2-fluoro-Fmoc, 2-monoisooctyl-Fmoc (mio-Fmoc) and 2,7-diisooctyl-Fmoc (dio-Fmoc), 2-[phenyl(methyl)sulfonio]ethyloxycarbonyl tetrafluoroborate (Pms), ethanesulfonylethoxycarbonyl (Esc), 2-(4-sulfophenylsulfonyl)ethoxycarbonyl (Sps), acetyl (Ac), benzoyl (Bz), $CF_3C(=O)$—trifluoroacetamido, and preferably wherein the base cleavable protecting group is selected from Bsmoc, Fmoc, α-Nsmoc, mio-Fmoc, dio-Fmoc, and more preferably Bsmoc.

In any aspect or embodiment of the present invention, PG is preferably selected from the group consisting of Boc, Fmoc or Bsmoc.

In another embodiment of the present invention, PG can be a cleavable protecting group, which is preferably cleavable in the presence of a palladium catalyst and an allyl scavenger, preferably wherein PG is Alloc (allyloxycarbonyl).

In accordance with any aspect or embodiment of the present invention, the group Y is preferably hydrocarbyl as described above. Preferably, the invention encompasses compounds wherein at least one Y group is hydrocarbyl, wherein at least one Y is alkyl, alkenyl, aryl, aralkyl, alkaryl, wherein said alkyl, alkenyl, aryl, aralkyl or alkaryl group is substituted with a terminal alkynyl group. The terms alkyl, alkenyl, aryl, aralkyl, alkaryl, and alkynyl are as defined. Particularly, in this embodiment, at least one Y group is alkyl, alkenyl, aryl, aralkyl, alkaryl, which is substituted with a terminal alkynyl group, wherein the terminal alkyne group is a $C_2$ to $C_6$ alkynyl group, more preferably a $C_2$ to $C_4$ alkynyl group, and most preferably ethynyl. In another embodiment, at least one Y group is aralkyl which is substituted with an alkynyl group and more preferably wherein one Y group is $CH_2-(C_6H_4)CH\equiv CH$.

With regards to the organic fragment to which the linker group is attached, i.e. M, this fragment contains a moiety which is covalently bound to the carbon atom of the $C(=O)$O— group of the compound. Thus, preferably, in any aspect or embodiment of the present invention, M represents —W—$R_6$, wherein W represents —N($R_8$)—, —O—, —S—, —C($R_9$)($R_{10}$)— or —P($R_{11}$)($R_{12}$)($R_{13}$)—, and preferably wherein W represents —O—, —($R_8$)— or —C($R_9$)($R_{10}$)—, or particularly —O— or —C($R_9$)($R_{10}$)—. Preferably each $R_8$, $R_9$, $R_{10}$, $R_{11}$, $R_{12}$ and $R_{13}$ independently represents: hydrogen, alkyl, aryl, alkaryl or aralkyl as described above; and $R_6$ represents an organic fragment. Following activation and cleavage from the linker, the fragment M may be released as H—W—$R_6$ or M can be released as an anion, i.e. $R_6$—W, or a salt, depending on the reaction conditions. The group $R_8$ in —N($R_8$)— is preferably selected from alkyl, aryl, alkaryl or aralkyl, more preferably, $R_8$ is alkyl or aryl, and more preferably wherein $R_8$ is alkyl, wherein alkyl, aryl, alkaryl or aralkyl are as described above. The groups $R_9$ and $R_{10}$ in —C($R_9$)($R_{10}$)— preferably each independently represents hydrogen, alkyl, aryl, alkaryl or aralkyl; preferably wherein $R_9$ and $R_{10}$ independently represents alkyl or aryl, more preferably wherein $R_9$ and $R_{10}$ independently represents H or alkyl and most preferably wherein $R_9$ and $R_{10}$ each represents H. The groups $R_{11}$, $R_{12}$ and $R_{13}$ in P($R_{11}$)($R_{12}$)($R_{13}$)— each independently represents alkyl, aryl, alkaryl or aralkyl, preferably wherein $R_{11}$, $R_{12}$ and $R_{13}$ each independently represents alkyl or aryl, and more preferably wherein $R_{11}$, $R_{12}$ and $R_{13}$ each independently represents alkyl, wherein alkyl, aryl, alkaryl or aralkyl are as described above. More preferably, W represents O.

According to any aspect or embodiment of the present invention, the compounds comprise a group M wherein M represents W—$R_6$, wherein $R_6$ is a residue of: a biological molecule, a drug, a therapeutic entity, a nucleotide, an oligonucleotide, a polynucleotide, an amino acid, a peptide, a peptide fragment, an antibody, an antibody conjugate, an engineered receptor such as an artificial T-cell receptor, a B-cell an antigen, a reporter molecule such as a dye or a dye conjugate, a chemotherapeutic sensitizer, a protein, a saccharide, an oligosaccharide, a polysaccharide. Preferably, $R_6$ is a residue of: an oligonucleotide, a polynucleotide, an amino acid, a peptide or peptide fragment, a protein, a saccharide, an oligosaccharide or a polysaccharide. More preferably, $R_6$ is a residue of a nucleotide, an oligonucleotide or a polynucleotide, which is preferably attached via an ether bond at the 3' or 5' position of a nucleotide.

In another embodiment of the present invention, there is provided a compound or formula (I) as described above, wherein:

M represents —W—$R_6$, wherein W represents —O— and $R_6$ represents an organic fragment which is covalently bound to W;

X represents hydrogen or phenyl;

Y represents hydrocarbyl, or the group

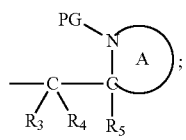

each of $R_1$, $R_2$, $R_3$, $R_4$ and $R_5$ represents hydrogen;
$R_7$ represents hydrogen or hydrocarbyl;
PG represents a cleavable protecting group for nitrogen;
n represents 0 or 1; and
ring A represents an unsubstituted nitrogen-containing heterocyclic group.

In this embodiment, $R_6$ is a residue of: a biological molecule, a drug, a therapeutic entity, a nucleotide, an oligonucleotide, a polynucleotide, an amino acid, a peptide, a peptide fragment, an antibody, an antibody conjugate, an engineered receptor such as an artificial T-cell receptor, a B-cell an antigen, a reporter molecule such as a dye or a dye conjugate, a chemotherapeutic sensitizer, a protein, a saccharide, an oligosaccharide, a polysaccharide. Preferably $R_6$ is a residue of: an oligonucleotide, a polynucleotide, an amino acid, a peptide or peptide fragment, a protein, a saccharide, an oligosaccharide or a polysaccharide. More preferably, $R_6$ is a residue of a nucleotide, an oligonucleotide or a polynucleotide, which is preferably attached via an ether bond at the 3' or 5' position of a nucleotide.

Also in this embodiment, the group PG is as defined above for the compounds of formulae (I), (IA) and (IB). Preferably n is 1. Also preferred are compounds wherein Y is benzyl. Alternatively, Y is:

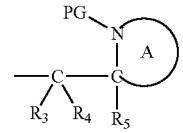

wherein each $R_3$, $R_4$ and $R_5$ represents hydrogen, both protecting groups PG are the same and both ring A are the same. The ring A in these compounds is defined as above, but is preferably piperidyl or pyrrolidinyl.

The present invention further encompasses a composition comprising a compound as described in any aspect or embodiment as defined herein, wherein the compound is covalently bound to a substrate, preferably via a linker group. The compound can be bound to a substrate at any suitable position, for example at one of the $R_1$, $R_2$, $R_3$, $R_4$, $R_5$, $R_7$, X, Y or A groups. Preferably, the compound is covalently bound to a substrate at $R_7$ or Y, and more preferably at Y. In particular, the composition comprises a compound as described in any aspect or embodiment as described herein, which is covalently bound to a substrate at Y wherein Y is:

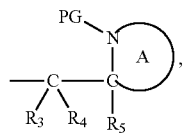

preferably via a linker group.

The substrate in the compositions of the present invention is a solid phase or a solid support, an antibody, a metal surface, a conductive surface, a polymeric support, a pharmaceutically inert support, a chip, a resin, a sensor, a glass support, or a polystyrene support. A solid phase substrate is preferably selected from a solid phase comprising an electrically conducive material, such as gold, colloidal metal, silicon or a polymer, or a solid phase which is a pharmaceutically inert support, a solid resin, a ceramic, a glass or silica gel. In a preferred embodiment, the substrate is a solid support comprising particles selected from gold or silicon.

The present invention further provides a cleavable protecting group or cleavable linker of formula (L-I):

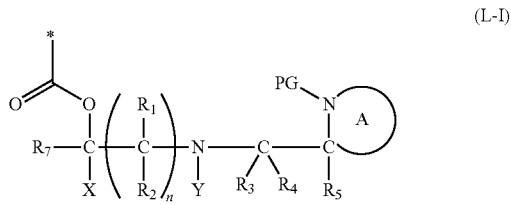

wherein:
* represents a point of attachment to an organic moiety to be protected or to be released from the cleavable linker or protecting group;
X represents hydrogen or hydrocarbyl;

Y represents hydrocarbyl or

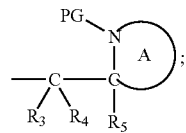

each of $R_1$, $R_2$, $R_3$, $R_4$, $R_5$ and $R_7$ are the same or different and each independently represents hydrogen or hydrocarbyl;

PG represents a cleavable protecting group for nitrogen;

n represents 0, 1, 2 or 3; and ring A represents a nitrogen-containing heterocyclic group;

wherein at each occurrence $R_1$, $R_2$, $R_3$, $R_4$, $R_5$, PG, A, Y, n may be the same or different.

The cleavable protecting group or cleavable linker according to the above aspect of the invention comprises at least one of the protecting groups PG which is cleavable under a first reaction condition to produce a deprotected linker, wherein the deprotected linker can undergo intramolecular cyclisation and cleavage with release of carbon dioxide under a second, different, reaction condition, to produce a compound of formula (II):

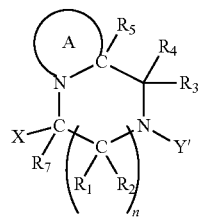

(II)

thereby releasing the organic moiety from the cleavable linker.

Preferably, in the cleavable protecting group or cleavable linker of the invention, X is H or hydrocarbyl selected from the group consisting of alkyl, aryl or arylalkyl, preferably wherein X is aryl, and more preferably wherein X is phenyl, wherein alkyl, aryl or arylakyl are as defined above. Preferably, Y is benzyl. Alternatively Y may be

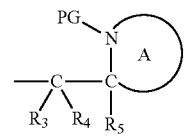

wherein each $R_3$, $R_4$ and $R_5$ represents hydrogen, both protecting groups PG are the same and both ring A are the same.

In a preferred embodiment the ring A of the cleavable protecting group or cleavable linker, represents piperidinyl or pyrrolidinyl.

Preferred cleavable linkers are selected from the group consisting of: (L-IA) or (L-IB):

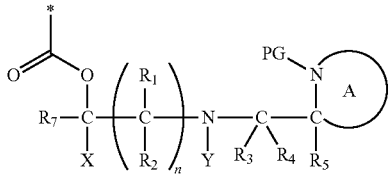

(L-IA)

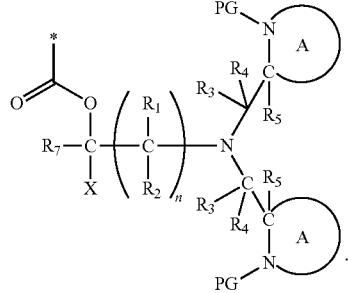

(L-IB)

Preferably, in the above cleavable protecting group or cleavable linker, at least one of the protecting groups PG is cleavable under a first reaction condition to produce a deprotected linker, wherein the deprotected linker can undergo intramolecular cyclisation and cleavage with release of carbon dioxide under a second, different, reaction condition, to produce a corresponding compound of formula (IIA) and (IIB) respectively:

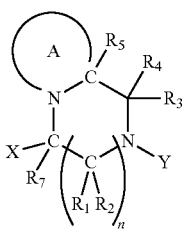

(IIA)

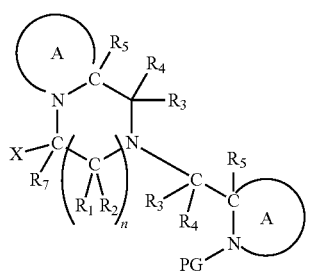

(IIB)

wherein PG' in (IIB) is hydrogen or a cleavable protecting group for nitrogen, thereby releasing the organic fragment M or an organic compound comprising M.

Preferably PG' in compound (IIB) is hydrogen.

Preferably, ring A represents a 4-12 membered mono-, bi- or tri-cyclic, preferably mono- or bicyclic nitrogen-containing heterocyclic group, and which may contain, in addition to the nitrogen, one or more other heteroatoms selected from N, O or S, preferably O or N. More preferably, ring A represents a 4 to 8-membered monocyclic heterocyclic group. Particularly, ring A represents a 5, 6, or 7-membered monocyclic heterocyclic group.

Specifically preferred groups for ring A are heterocyclic groups selected from the group consisting of piperidyl, morpholinyl, pyrrolidinyl, thiomorpholinyl, and imidazolyl.

Alternatively ring A is selected from the group consisting of: piperidyl, morpholinyl, pyrrolidinyl and thiomorpholinyl. In a further preferred embodiment, ring A represents piperidyl, pyrrolidinyl or imidazolyl. Most preferably, ring A represents piperidyl, or pyrrolidinyl.

In a preferred embodiment, the above cleavable protecting group or cleavable linker comprises $R_3$ and $R_4$ groups which are all H.

Preferably, n in the cleavable protecting group or cleavable linker according to any aspect of the present invention, n is 0, 1 or 2, preferably n is 0 or 1, and most preferably n is 1.

In a preferred embodiment of the cleavable protecting group or cleavable linker X is H or hydrocarbyl, wherein the hydrocarbyl is selected from the group consisting of alkyl, aryl or arylalkyl, wherein alkyl, aryl and arylkyl are described above. Preferably X is aryl, and more preferably X is phenyl.

The PG group in the cleavable protecting group or cleavable linker is preferably as described above for the compounds and compositions of the present invention. Similarly, the Y group is preferably as described above for the compounds and compositions of the invention.

In a preferred embodiment of the cleavable protecting group or cleavable linker $R_5$ is preferably hydrogen.

In a preferred embodiment of the cleavable protecting group or cleavable linker, X is: H or hydrocarbyl, wherein the hydrocarbyl is selected from the group consisting of alkyl, aryl or arylalkyl, as defined above, preferably wherein X is aryl, and more preferably wherein X is phenyl.

In a preferred embodiment of the cleavable protecting group or cleavable linker $R_7$ is H.

In a preferred embodiment of the cleavable protecting group or cleavable linker of this aspect of the present invention, $R_1$ and $R_2$ are H.

In a preferred embodiment of the cleavable protecting group or cleavable linker of this aspect of the present invention, $R_3$ and $R_4$ are both hydrogen.

In a further aspect of the present invention, there is provided a cleavable linker as described in accordance with any aspect or embodiment as described above, which is covalently bonded to a substrate at one of $R_1$, $R_2$, $R_3$, $R_4$, $R_5$, $R_7$, X, Y or A, preferably $R_7$ or Y. Preferably, the cleavable linker is covalently bonded to the substrate at $R_7$ when Y is

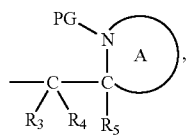, or wherein the cleavable linker is covalently bound to the substrate at Y when Y is hydrocarbyl.

Suitable substrates are those listed above for the compositions of the present invention. Hence, the substrate is preferably a solid phase or a solid support, a metal surface, a conductive surface, a polymeric support, a pharmaceutically inert support, a chip, a resin, a sensor, a glass support, or a polystyrene support. Particularly, the substrate is a solid phase comprising particles selected from the group consisting of gold, colloidal metal, silicon, a polymer, a pharmaceutically inert support, solid resin, ceramic, glass, and silica gel, preferably wherein the substrate is a solid support comprising particles selected from gold or silicon.

The compounds and compositions of the present invention can be prepared by the processes described below. The processes enable an efficient and facile preparation of compounds having a wide variety of different protecting groups PG. As discussed above, the use of different protecting groups enables fine control of the activation and cleavage step, ensuring that the linker group is only activated and subsequently released under specific reaction conditions.

As set out below, processes for the preparation of the compounds, compositions and linker/protecting groups of the present invention has been developed to enable the convenient modification of the protecting group PG from a common intermediate. The processes start from a heterocyclic compound containing a ketone or protected alcohol (see following Schemes 1-3). Use of a ketone substituted heterocyclic compound enables the preparation of compounds, compositions, and linker/protecting groups according to the invention wherein one of the $R_3$ or $R_4$ substituents is hydrocarbyl and the other is hydrogen, or wherein both $R_3$ and $R_4$ are hydrogen. Compounds wherein both $R_3$ and $R_4$ are hydrocarbyl can be prepared from the heterocyclic starting material containing a protected tertiary alcohol.

The starting heterocyclic compounds containing a ketone can be prepared in two steps by Grignard reaction of the corresponding Weinreb amide. The Weinreb amide can be prepared by reaction of the corresponding carboxylic acid with N,O-dimethylhydroxylamine hydrochloride in the presence of a peptide coupling reagent such as BOP [benzotriazol-1-yloxy)tris(dimethylamino)phosphonium hexafluorophosphate] or EDCI [1-Ethyl-3-(3-dimethylaminopropyl)carbodiimide] [see Nahm, S.; Weinreb, S. M. (1981), "N-methoxy-n-methylamides as effective acylating agents", Tetrahedron Letters, 22: 3815, doi:10.1016/s0040-4039(01)91316-41, followed by reaction with a suitable Grignard reagent, such as an alkyl magnesium bromide (e.g. methyl magnesium bromide), as depicted in the scheme below:

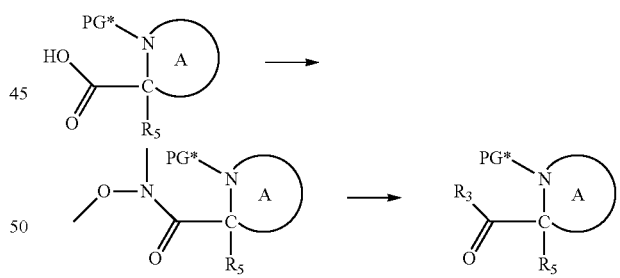

The starting material is protected at the ring nitrogen with a suitable protecting group PG*. The protecting group PG* can correspond to the PG protecting group in the final compound if appropriate. However, typically the protecting group PG* is selected such that it can be removed and replaced with the desired protecting group PG in the final compound or composition as shown in Schemes 1-3 below.

In particular, the PG* protecting group should be stable to the subsequent coupling reaction wherein the M fragment is coupled to the cleavable linker. The PG* protecting group should not be labile to conditions employed in the subsequent coupling reaction. Typically the coupling reaction to form the compound comprising M bound to the cleavable linker are conducted in basic conditions. Hence, the PG* protecting group is preferably not labile to basic conditions. For example, the PG* protecting group may preferably be Boc or Alloc.

For compounds wherein $R_3$ and $R_4$ are both hydrocarbyl, heterocyclic starting material containing a tertiary alcohol is employed. The ring nitrogen is protected with the protecting group PG*, and subsequently, the hydroxyl group is derivatised to a suitable leaving group, for example tosylate or mesylate.

to a linker, in accordance with the invention. The M fragment is preferably appropriately protected with suitable protecting groups. For example in the case of M being a nucleoside, the nucleoside may be protected at the free hydroxyl groups by the usual protecting groups, such as alkylsilyl, etc, and may be protected at the free amine groups of the base moiety.

Scheme 1: Compounds of Formula (IA) wherein Y=hydrocarbyl

Scheme 1

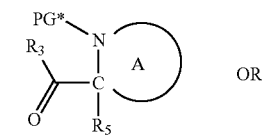

For compounds wherein $R_3$ and $R_4$ are both H or wherein one of $R_3/R_4$ is hydrocarbyl and the other is H

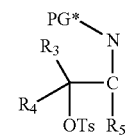

For compounds wherein $R_3$ and $R_4$ are both hydrocarbyl

PG* is preferably BOC or Alloc

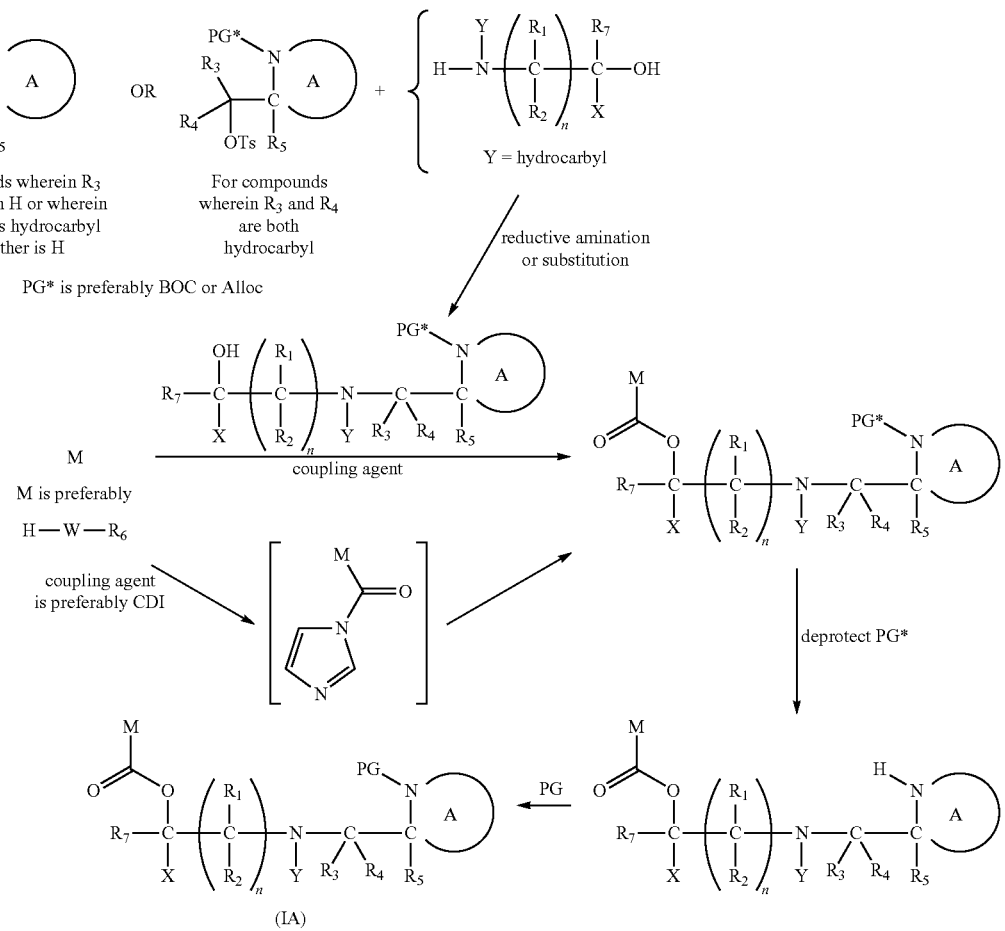

(IA)

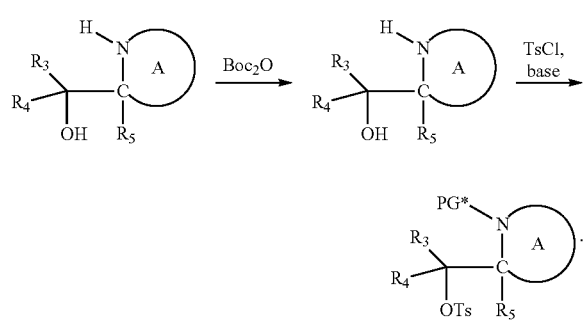

The following Schemes 1-3 describe preferred processes for preparing compounds comprising an M fragment bound Scheme 1 above illustrates the synthesis of compounds containing a single activating group (PG) wherein Y is hydrocarbyl. The synthesis comprises a reductive amination or substitution reaction of the heterocyclic starting material containing a ketone or protected alcohol (depending on the $R_3/R_4$ substituent in the final compound), with the amine alcohol.

The resulting compound from the reductive amination or substitution reaction is then coupled to the M fragment using a coupling agent [e.g. preferably using a 1,1'-carbonyldiimidazole (CDI)/1,8-diazabicyclo[5.4.0]undec-7-ene (DBU) coupling system].

The PG* groups may then be replaced as appropriate by deprotection and then re-protecting with the desired PG group in the final compound.

Scheme 2: Compounds of Formula (IB) wherein

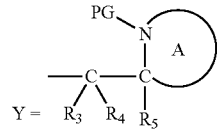

Y = and $R_{3-5}$, PG and A are the same

Scheme 2 above illustrates the synthesis of compounds of Formula IB, containing two activating groups (PG) wherein Y is

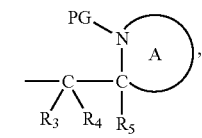

and $R_3$-$R_5$, PG and A are the same.

Scheme 2

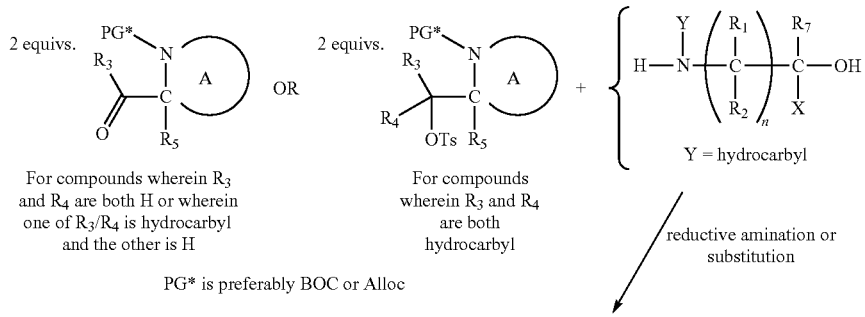

For compounds wherein $R_3$ and $R_4$ are both H or wherein one of $R_3$/$R_4$ is hydrocarbyl and the other is H For compounds wherein $R_3$ and $R_4$ are both hydrocarbyl Y = hydrocarbyl PG* is preferably BOC or Alloc reductive amination or substitution

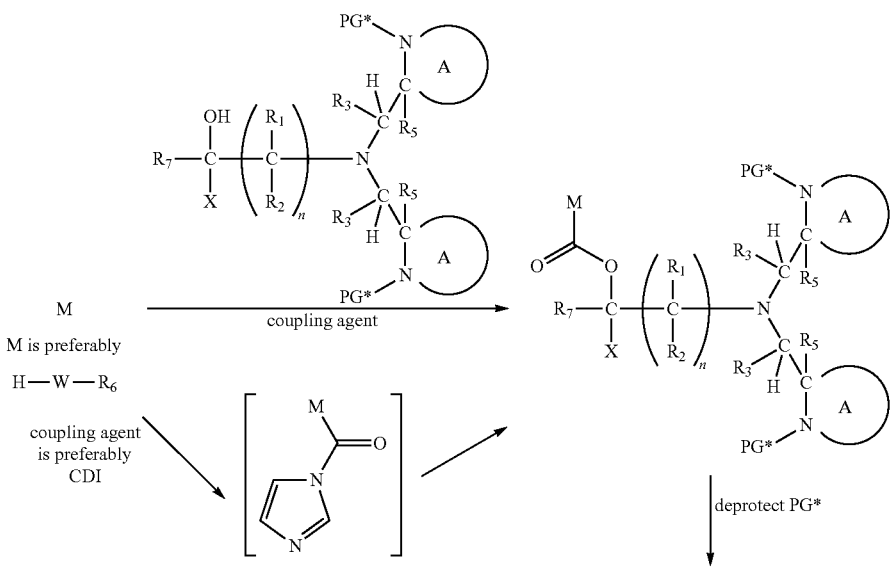

M

M is preferably

H—W—$R_6$ coupling agent is preferably CDI coupling agent deprotect PG*

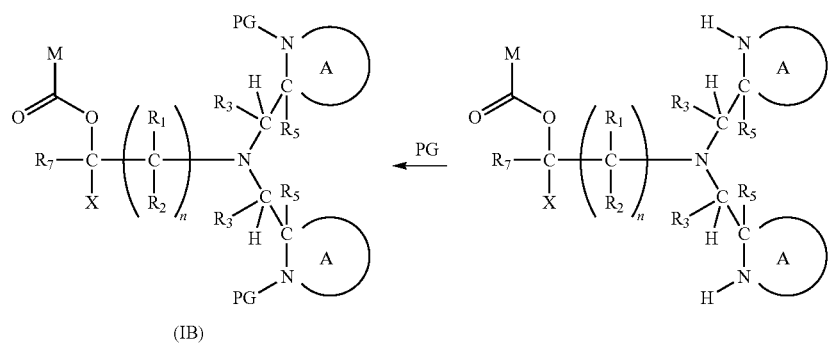

(IB)

PG

The synthesis comprises a reductive amination or substitution reaction of the heterocyclic starting material containing a ketone or protected alcohol (depending on the $R_3/R_4$ substituent in the final compound), with the amine alcohol. The reductive amination or substitution is carried out with two equivalents of the heterocyclic starting material.

The resulting compound from the reductive amination or substitution reaction is then coupled to the M fragment using a coupling agent [e.g. preferably using a 1,1'-carbonyldiimidazole (CDI)/1,8-diazabicyclo[5.4.0]undec-7-ene (DBU) coupling system].

The PG* groups may then be replaced as appropriate by deprotection and then re-protecting with the desired PG groups in the final compound.

Scheme 3: Compounds of Formula (IB) wherein

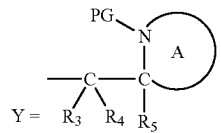

and $R_{3-5}$, and A are different

Scheme 3

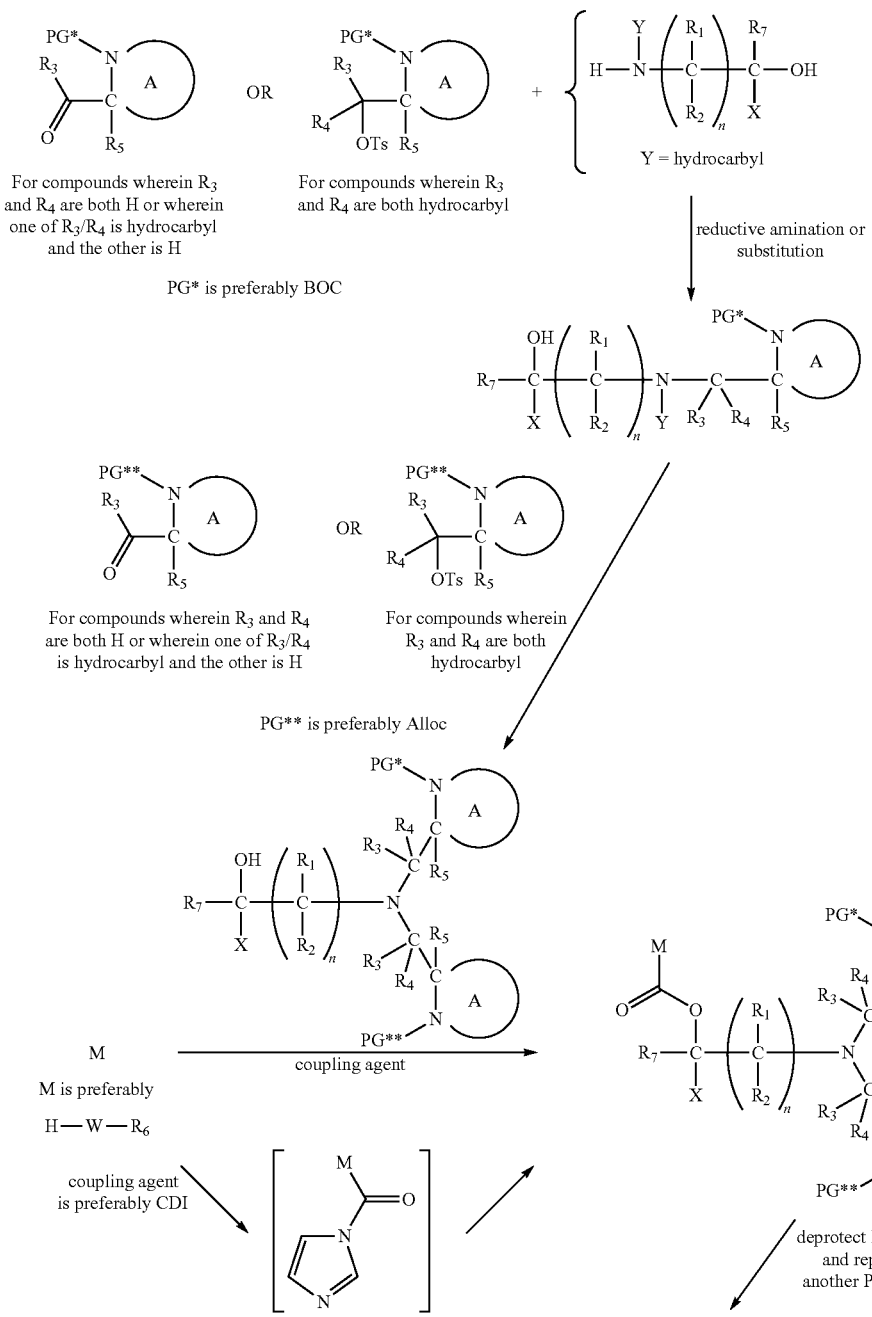

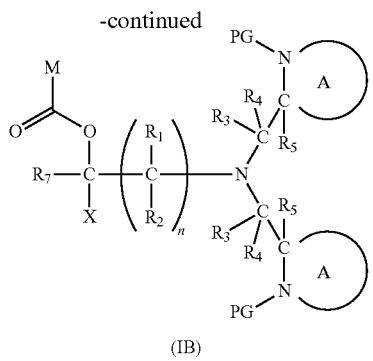

(IB)

Scheme 3 above illustrates the synthesis of compounds of Formula IB, containing two activating groups (PG) wherein Y is

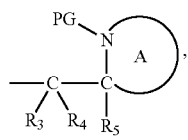

and $R_3$-$R_5$, PG and A are different.

The synthesis comprises a reductive amination or substitution reaction of the heterocyclic starting material containing a ketone or protected alcohol (depending on the $R_3$/$R_4$ substituent in the final compound), with the amine alcohol.

The heterocyclic starting material is protected at the ring nitrogen with a suitable protecting group PG* (preferably BOC or Alloc, which are stable to the subsequent coupling reaction).

The resulting compound is subjected to a second reductive amination or substitution step using a heterocyclic starting material containing a ketone or protected alcohol as in the first step, but wherein the protecting group PG* is different (e.g. the other of BOC or Alloc).

Coupling of the resulting compound with the fragment M results in a compound containing two different PG* protecting groups which can be selectively removed and re-protected in order to prepare the desired product.

The above processes can be modified by the appropriate derivatisation and incorporation of suitable functional groups in order to enable attachment of the compounds to the substrates in order to prepare compositions according to the present invention. In addition, the substrates may be derivatized with suitable functional groups in order to enable their attachment to the linker.

Attachment of the M-linker compound to a substrate in order to prepare the compositions of the present invention can be carried out by any suitable process. Suitable M-linker compounds for substrate attachment can be prepared starting from a compound comprising a suitable functionality to enable reaction with a functionality of the linker. For example, the linkage to a substrate can be carried out by click chemistry, whereby an ethynyl substituted M-linker compound is coupled to a substrate modified with a 1,2,3-triazole group.

For the linker attachment, the appropriate M-linker compound is prepared, wherein the linker fragment is provided with an alkynyl substituent at an appropriate position by use of an appropriately substituted starting material in accordance with the above reaction schemes. As stated above, the substrate can be attached to the linker via any of the substituent groups. For example the substrate may be attached at any one of the $R_1$, $R_2$, $R_3$, $R_4$, $R_5$, $R_7$, X, Y or A positions. The following reaction scheme (Scheme 4) illustrates a process for the preparation of a composition according to the present invention comprising a compound of the present invention (comprising the M-cleavable linker moieties) attached to a substrate at the Y group. In this example, Y is an alkynyl substituted benzyl group. It will be appreciated that modification of the reaction can be readily made, for example by using analogously substituted intermediates having a terminal alkynyl functionality at other substituent positions of the cleavable linker moiety, in order to achieve alternative substrate attachments.

Scheme 4

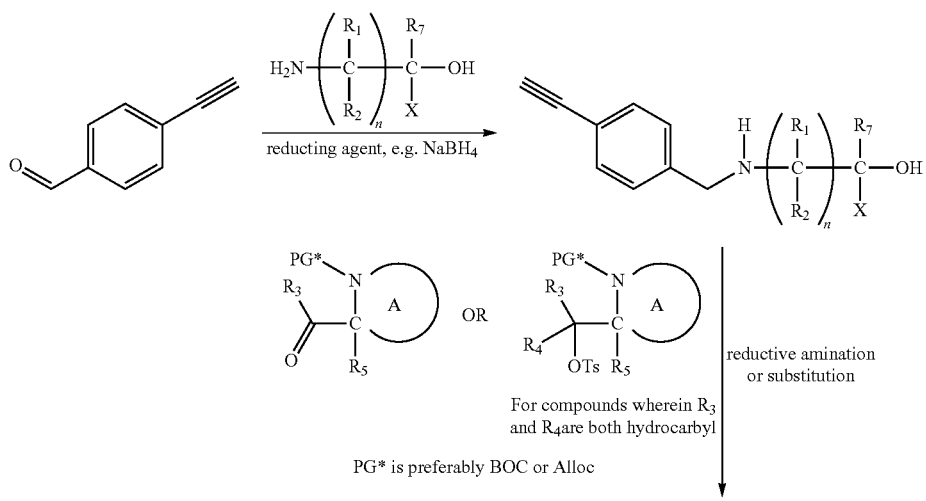

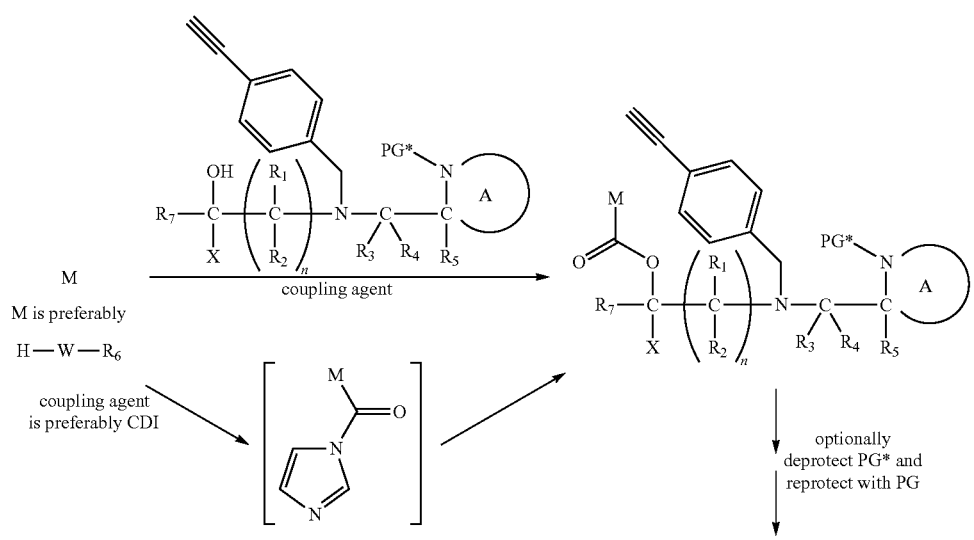

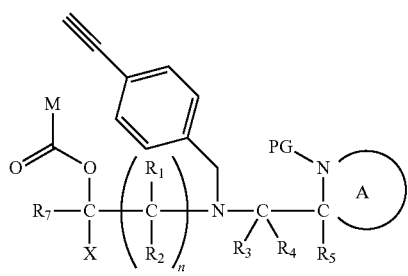

The instalment of a terminal acetylene functionality enables a facile attachment to an appropriately modified substrate, e.g., via well-known click chemistry using a copper (I) catalysed 1,2,3-triazole modified substrate formed form the corresponding azide as shown in Scheme 5 [see. e.g. Rostovtsev, Vsevolod V., Green, Luke Fokin, Valery V., Sharpless, K. Barry, A Stepwise Huisgen Cycloaddition Process: Copper(I)-Catalyzed Regioselective "Ligation" of Azides and Terminal Alkynes. Angewandte Chemie International Edition (2002), 41 (14), pages 2596-2599]:

Scheme 5

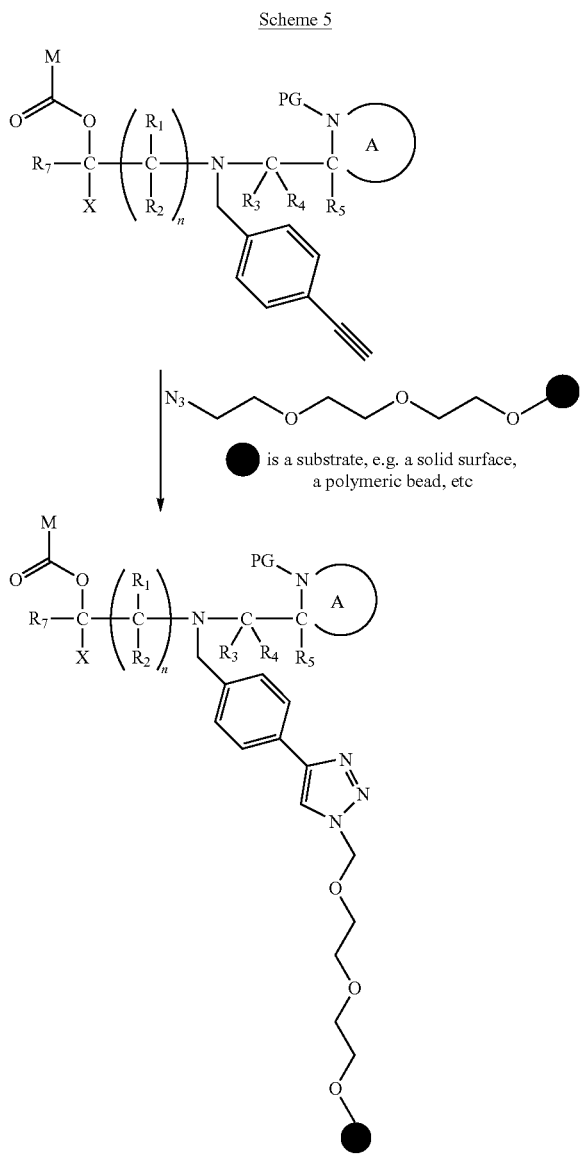

● is a substrate, e.g. a solid surface, a polymeric bead, etc

Azide modified substrates, such as polymeric beads are commercially available, or can be prepared as appropriate.

In a further aspect of the present invention, there is provided a process for the solid state synthesis of an organic compound comprising an organic fragment M, the process comprising:
(a) synthesis of the organic compound on a solid substrate which is covalently bound to the cleavable linker as described herein;
(b) cleaving the organic fragment M from the cleavable linker and substrate to form the organic compound, and
(c) optionally isolating the organic compound.

As discussed above, linker cleavage occurs by a controlled two stage process: i.e. firstly cleavage of the at least one protecting group PG on the cleavable linker to activate the linker, and at the appropriate time, subsequent intramolecular cyclisation with release of carbon dioxide, thereby releasing the organic compound from the substrate.

The organic compound may have the formula H—W—$R_6$, wherein $R_6$ is as defined in any embodiment discussed above.

In a particularly preferred embodiment of the invention, the organic compound is an oligonucleotide or polynucleotide.

In order to produce a double stranded oligonucleotide or double stranded polynucleotide, the process further comprises the step of annealing a complementary oligonucleotide or a complementary polynucleotide before step (b), and optionally isolating the double stranded oligonucleotide or double stranded polynucleotide. Alternatively, the process can comprise a step of annealing a complementary oligonucleotide or a complementary polynucleotide after step (b) or step (c), and optionally isolating the double stranded oligonucleotide or double stranded polynucleotide.

In one embodiment, step (b) comprises:
(i) heating in the presence of an activating agent to remove the protecting group;
(ii) heating, optionally in the presence of an activating agent, to effect intramolecular cyclisation and cleavage of the linker and solid substrate from the compound.

Preferably, in one embodiment, the activating agent in step (i) is an acid, and step (ii) comprises heating in the presence of a base.

Alternatively, the activating agent in step (i) is a base, and step (ii) comprises heating.

In another embodiment, step (i) comprises heating to a first temperature in the presence of a base, and wherein the intramolecular cyclisation and cleavage in step (ii) is effected by heating to a second temperature, wherein the second temperature is higher than the first temperature.

Preferably, the protecting group PG is selected from: tert-butyloxycarbonyl (Boc), trityl (Trt), benzyloxycarbonyl, α,α-dimethyl-3,5-dimethoxybenzyloxycarbonyl (Ddz), 2-(4-Biphenyl)isopropoxycarbonyl (Bpoc), 2-Nitrophenylsulfenyl (Nps), tosyl (Ts), and more preferably the protecting group is selected from Boc, or Trt. Particularly, the protecting group is Boc and the activating agent in step (i) is an acid, preferably selected from trifluoroacetic acid.

Alternatively, the activating agent in step (ii) or step (ii) is a base, preferably wherein the base is selected from a basic buffer, preferably phosphate buffer, preferably a phosphate buffer having a pH of about 7.1 to about 8.5, more preferably a pH of about 7.2 to about 8.0, and most preferably a pH of about 7.2 to about 7.6.

Alternatively, the activating agent in step (i) and/or step (ii) is a base in an organic solvent, particularly the activating agent in step (i) and/or step (ii) is an organic non-nucleophilic base, such as a trialkylamine (e.g. triethylamine or Hunig's base). The organic non-nucleophilic base can be employed in any suitable concentration, e.g. about 0.002 M to about 0.1 M, preferably about 0.005 M to about 0.05 M, more preferably about 0.0075 M to about 0.025 M, and most preferably about 0.01 M. The organic solvent is preferably inert, such as acetonitrile, DMF, THF or dioxane. The base may be suitably employed in excess.

As a further alternative, the activating conditions comprise a first neutralisation step, if an acid has been used to remove the protecting group, followed by heating in an inert solvent such as acetonitrile, DMF, THF and dioxane.

In one embodiment, the protecting group is selected from: (1,1-dioxobenzo[b]thiophene-2-yl)methyloxycarbonyl (Bsmoc), 9-fluorenylmethoxycarbonyl (Fmoc), (1,1-dioxonaphtho[1,2-b]thiophene-2-yl)methyloxycarbonyl (α-Nsmoc), 2-(4-nitrophenylsulfonyl)ethoxycarbonyl (Nsc), 2,7-di-tert-butyl-Fmoc, 2-fluoro-Fmoc, 2-monoisooctyl-Fmoc (mio-Fmoc) and 2,7-diisooctyl-Fmoc (dio-Fmoc), 2-[phenyl(methyl)sulfonio]ethyloxycarbonyl tetrafluoroborate (Pms), ethanesulfonylethoxycarbonyl (Esc), 2-(4-sulfophenylsulfonyl)ethoxycarbonyl (Sps), acetyl (Ac), benzoyl (Bz), CF$_3$C(=O)— trifluoroacetamido, and preferably the protecting group is selected from Bsmoc, Fmoc, α-Nsmoc, mio-Fmoc, dio-Fmoc, and more preferably the protecting group is Bsmoc, and wherein the activating agent in step (i) is a base, preferably selected from morpholine, piperidine.

Preferably, step (ii) is carried out in the presence of at least one polar solvent, preferably wherein the polar solvent comprises acetonitrile, or dimethylsulfoxide.

The present invention further provides the use of the compounds and compositions as described herein for the controlled release of a therapeutic entity; as a diagnostic; or for the purification of proteins and peptides. The invention further provides the use of a compound, a composition, a cleavable protecting group or a cleavable linker as defined in any aspect or embodiment as described herein, in solid state synthesis, preferably in the solid state synthesis of saccharides, oligosaccharides, polysaccharides, peptides, proteins, oligonucleotides, or polynucleotides, preferably in the solid state synthesis of peptides, proteins, oligonucleotides, or polynucleotides. Preferably, the compounds and compositions described herein are for use in the solid state synthesis of oligonucleotides or polynucleotides.

In a preferred embodiment, the invention provides a process for the preparation of one or more oligonucleotides or polynucleotides comprising:
  (i) providing a composition comprising a compound as described in any aspect or embodiment, wherein M represents —W—R$_6$, wherein R$_6$ represents a first optionally protected nucleotide, wherein the compound is covalently bound to a solid support; and
  (ii) conducting solid phase synthesis by the phosphoramidite method to produce the oligonucleotide or polynucleotide;
  (ii) cleaving the oligonucleotide or polynucleotide from the solid support.

Typically, the process comprises:
  (i) providing a composition comprising a compound as described herein, wherein M represents —W—R$_6$, wherein R$_6$ represents a first 5'-protected nucleotide, wherein the compound is covalently bound to a solid support;
  (ii) removing the 5'-protecting group from the 5'-protected nucleoside; (iii) coupling at the 5'-OH of the nucleoside with a nucleoside phosphoramidite monomer to form a support-bound phosphite triester;
  (iv) optionally capping the 5'-hydroxyl groups on the unreacted nucleoside; phosphoramidite monomer by acetylation;
  (v) oxidising the phosphite triester to a phosphotriester;
  (vi) repeating steps (ii) to (v) in order to produce the oligonucleotide or polynucleotide;
  (vii) cleaving the oligonucleotide or polynucleotide from the solid support; and
  (viii) optionally isolating the oligonucleotide.

The process may further comprise a step of annealing a complementary oligonucleotide or a complementary polynucleotide before step (vii), and optionally isolating the double stranded oligonucleotide or double stranded polynucleotide.

Alternatively, the process may comprise a step of annealing a complementary oligonucleotide or a complementary polynucleotide after step (vii) or step (viii), and optionally isolating the double stranded oligonucleotide or double stranded polynucleotide.

Preferably, step (vii) comprises:
  (vii-a) heating in the presence of an activating agent to remove the protecting group PG from the cleavable linker; and
  (vii-b) heating, optionally in the presence of an activating agent, to effect intramolecular cyclisation and cleavage of the linker and solid substrate from the compound.

The activating agent in step (vii-a) may be an acid, and step (vii-b) may comprise heating in the presence of a base. Alternatively, the activating agent in step (vii-a) may be a base, and step (vii-b) may comprise heating.

Step (vii-a) may comprise heating to a first temperature in the presence of a base, and wherein the intramolecular cyclisation and cleavage in step (vii-b) is effected by heating to a second temperature, wherein the second temperature is higher than the first temperature.

In this process, the protecting group PG is selected from: tert-butyloxycarbonyl (Boc), trityl (Trt), benzyloxycarbonyl, and α,α-dimethyl-3,5-dimethoxybenzyloxycarbonyl (Ddz), 2-(4-biphenyl)isopropoxycarbonyl (Bpoc), 2-nitrophenylsulfenyl (Nps), tosyl (Ts), and preferably wherein protecting group is selected from Boc, or Trt, and more preferably Boc, and wherein the activating agent in step (vii-a) is an acid, preferably selected from trifluoroacetic acid.

The activating agent in step (vii-b) is preferably a base, more preferably wherein the base is selected from a basic buffer, preferably a buffer having a pH of about 7.1 to about 8.5, more preferably a pH of about 7.2 to about 8.0, and most preferably a pH of about 7.2 to about 7.6.

Alternatively, the protecting group PG may be selected from: (1,1-dioxobenzo[b]thiophene-2-yl)methyloxycarbonyl (Bsmoc), 9-fluorenylmethoxycarbonyl (Fmoc), (1,1-dioxonaphtho[1,2-b]thiophene-2-yl)methyloxycarbonyl (α-Nsmoc), 2-(4-nitrophenylsulfonyl)ethoxycarbonyl (Nsc), 2,7-di-tert-butyl-Fmoc, 2-fluoro-Fmoc, 2-monoisooctyl-Fmoc (mio-Fmoc) and 2,7-diisooctyl-Fmoc (dio-Fmoc), 2-[phenyl(methyl)sulfonio]ethyloxycarbonyl tetrafluoroborate (Pms), ethanesulfonylethoxycarbonyl (Esc), 2-(4-sulfophenylsulfonyl)ethoxycarbonyl (Sps), acetyl (Ac), benzoyl (Bz), CF$_3$C(=O)— trifluoroacetamido, and preferably wherein the protecting group is selected from Bsmoc, Fmoc, α-Nsmoc, mio-Fmoc, dio-Fmoc, and more preferably wherein the protecting group is Bsmoc, and wherein the activating agent in step (vii-a) is a base, preferably selected from morpholine, and piperidine.

Preferably, step (vii-b) is carried out in the presence of at least one polar solvent, preferably wherein the polar solvent comprises acetonitrile and dimethylsulfoxide.

The following examples are provided to further illustrate the invention.

The results of the time course studies show that it is possible to devise cleavable linkers or protecting groups according to the invention, having a wide range of properties under different cleavage conditions. Thus, the linkers and protecting groups of the present invention can be fine tuned to enable controlled cleavage depending on the desired use, e.g. as protecting groups, or to provide controlled drug release.

EXAMPLES

Analytical Methods
LC-MS Methods

The time-course studies discussed below and analysis of reactions were carried out using LC-MS, which is described generally below:

Acquity Arc system; 2498 UV/Vis detector, QDa Detector Column; XSelect CSH C18 XP Column, 130 Å, 2.5 μm, 2.1 mm×50 mm Method A (acidic)

Component 1: H₂O+0.1% formic acid

Component 2: MeCN (acetonitrile)

| Time/seconds | Component 1 | Component 2 |
|---|---|---|
| 0 | 95 | 5 |
| 120 | 5 | 95 |
| 150 | 5 | 95 |
| 156 | 95 | 5 |
| 240 | 95 | 5 |

Method B (basic)

Component 1: H₂O+0.1%-25% ammonium formate in H₂O

Component 2: MeCN

| Time/seconds | Component 1 | Component 2 |
|---|---|---|
| 0 | 95 | 5 |
| 120 | 5 | 95 |
| 150 | 5 | 95 |
| 156 | 95 | 5 |
| 240 | 95 | 5 |

Method C (long acidic)

Component 1: H₂O+0.1% formic acid

Component 2: MeCN

| Time/seconds | Component 1 | Component 2 |
|---|---|---|
| 0 | 95 | 5 |
| 180 | 5 | 95 |
| 225 | 5 | 95 |
| 234 | 95 | 5 |
| 360 | 95 | 5 |

Route to compounds with protected activating group:

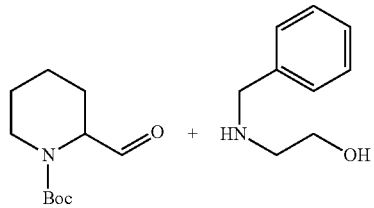

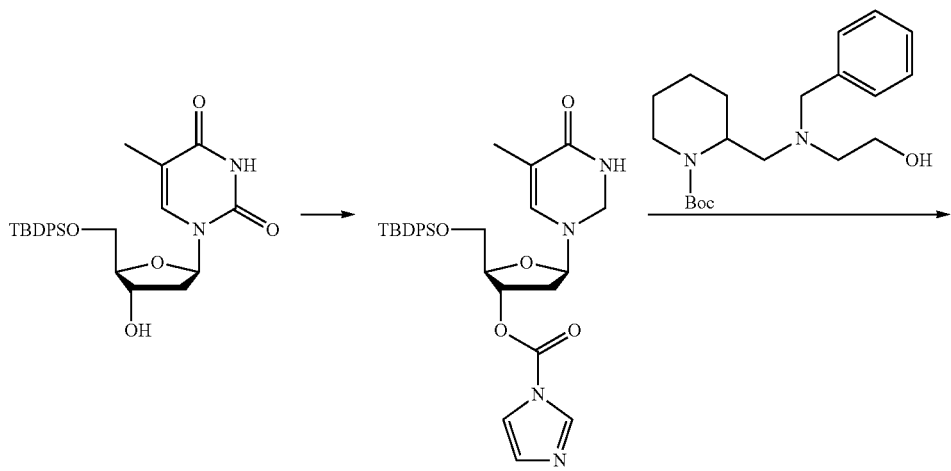

-continued
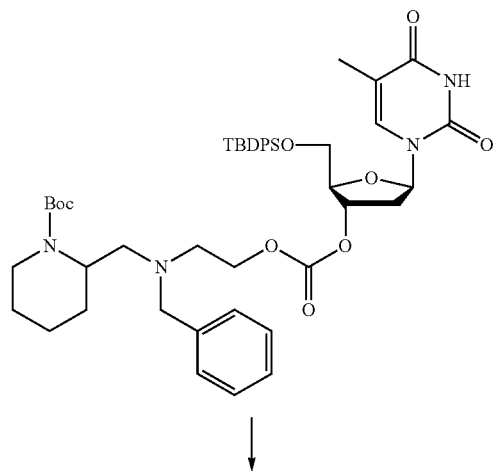
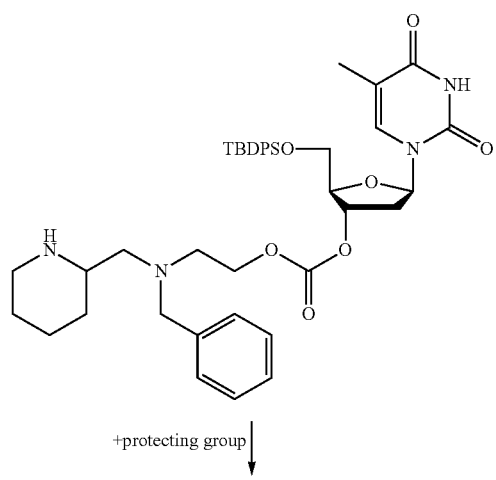
+protecting group
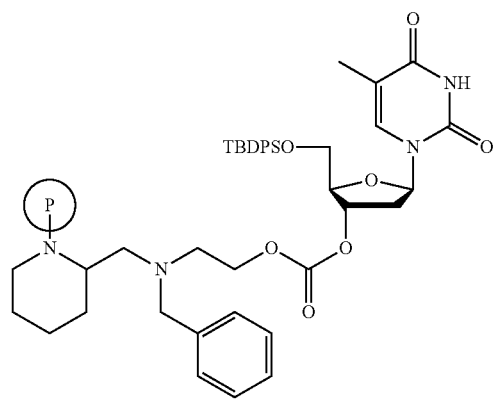

Example 1

Example 1A: tert-Butyl 2-((benzyl(2-hydroxyethyl)amino)methyl)piperidine-1-carboxylate (1)

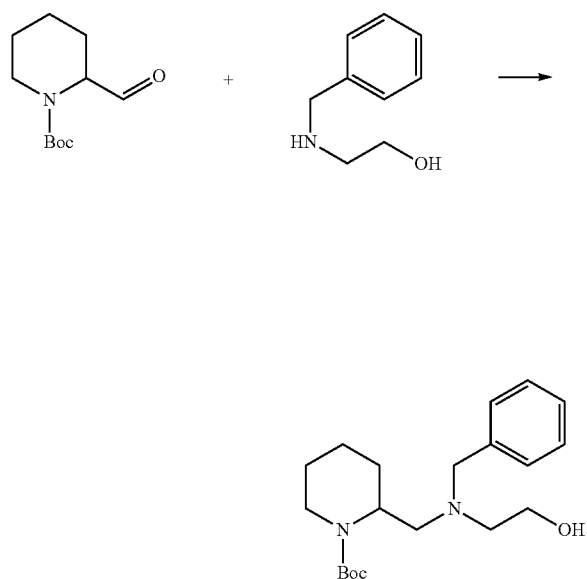

1-N-Boc-2-Piperidinecarbaldehyde (2 g, 9.3 mmol) was dissolved in THF (200 mL), and acetic acid (2.4 mL), and 2-benzylaminoethanol (1.6 g, 10 mmol, 1.2 eq.) were added. After 10 minutes at room temperature, sodium triacetoxyborohydride was added and the solution was stirred overnight. Saturated aqueous $NaHCO_3$ (300 mL) and ethyl acetate (500 mL) were added and the layers were separated. The organic layer was dried ($MgSO_4$) and the solvent was removed under reduced pressure. The residue was purified by silica chromatography (0-10% MeOH-DCM) to give the product as a colourless oil (2.33 g, 71%. LC-MS Method B (Basic); Rt=1.60, m/z 349.2 ($MH^+$).

Example 1B: tert-Butyl 2-((benzyl(2-(((((2R,3S,5R)-2-(((tert-butyldiphenylsilyl)oxy)methyl)-5-(5-methyl-2,4-dioxo-3,4-dihydropyrimidin-1(2H)-yl)tetrahydrofuran-3-yl)oxy)carbonyl)oxy)ethyl)amino)methyl)piperidine-1-carboxylate (2)

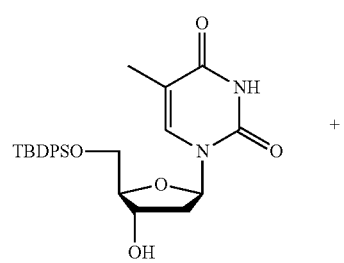

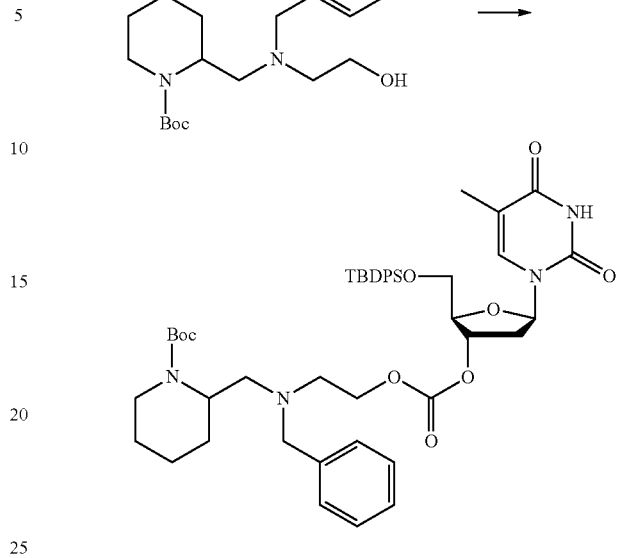

5'-O-TBDPS-Thymidine (1.3 g, 2.9 mmol, 1.0 eq) and CDI (534 mg, 3.5 mmol, 1.2 eq) were dissolved in anhydrous acetonitrile (40 mL) and the solution was stirred at room temperature under $N_2$ overnight. After this time the reaction was complete by tlc (10% MeOH-DCM, uv). tert-Butyl 2-((benzyl(2-hydroxyethyl)amino)methyl)piperidine-1-carboxylate (1) (1 g, 2.29 mmol) and 1,1,3,3-tetramethylguanidine (0.72 mL, 5.8 mmol, 2 eq.) were then added and the solution was stirred for a further two hours. Water (200 mL) and EtOAc (200 mL) were added and the layers were separated. The organic layer was dried ($MgSO_4$) and the solvent was removed. The resulting oil was purified by silica chromatography, eluting with 0-50% EtOAc-petrol to give the product as a colourless oil, 890 mg, 37%. LC-MS; Method B (Basic); Rt=3.47, m/z 855.46 ($MH^+$).

Example 1C: 2-(Benzyl(piperidin-2-ylmethyl)amino)ethyl ((2R,3S,5R)-2-(((tert-butyldiphenylsilyl)oxy)methyl)-5-(5-methyl-2,4-dioxo-3,4-dihydropyrimidin-1(2H)-yl)tetrahydrofuran-3-yl) carbonate (3)

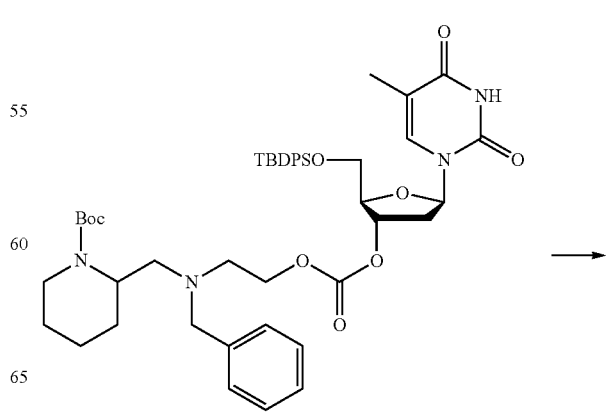

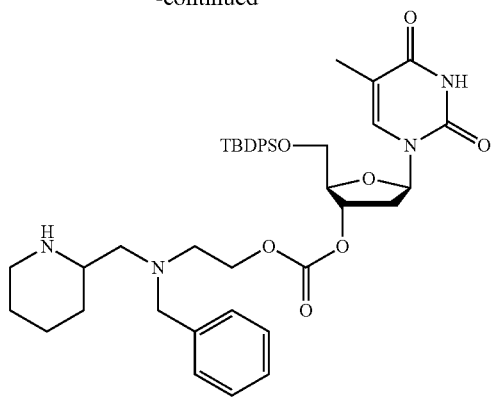

tert-Butyl 2-((benzyl(2-(((((2R,3S,5R)-2-(((tert-butyldiphenylsilyl)oxy)methyl)-5-(5-methyl-2,4-dioxo-3,4-dihydropyrimidin-1(2H)-yl)tetrahydrofuran-3-yl)oxy)carbonyl)oxy)ethyl)amino)methyl)piperidine-1-carboxylate (2) (100 mg, 0.12 mmol) was dissolved in dichloromethane (2 mL) and trifluoroacetic acid (2 mL) and the solution was stirred at room temperature for 1 h. After this time the reaction was complete by LC-MS. The solvent was removed and dichloromethane (100 mL) and saturated aqueous NaHCO₃ (100 mL) were added and the layers were separated. The organic layer was dried (MgSO₄) and the solvent was removed under reduced pressure at 20° C. The residue was purified by silica chromatography (0-10% MeOH-DCM) to give the product as a colourless oil (63 mg, 71%). LC-MS; Method B (Basic); Rt=2.20, m/z 755.46 (MH⁺).

Example 2

(1,1-Dioxidobenzo[b]thiophen-2-yl)methyl 2-((benzyl(2-(((((2R,3S,5R)-2-(((tert-butyldiphenylsilyl)oxy)methyl)-5-(5-methyl-2,4-dioxo-3,4-dihydropyrimidin-1(2H)-yl)tetrahydrofuran-3-yl)oxy)carbonyl)oxy)ethyl)amino)methyl)piperidine-1-carboxylate (4)

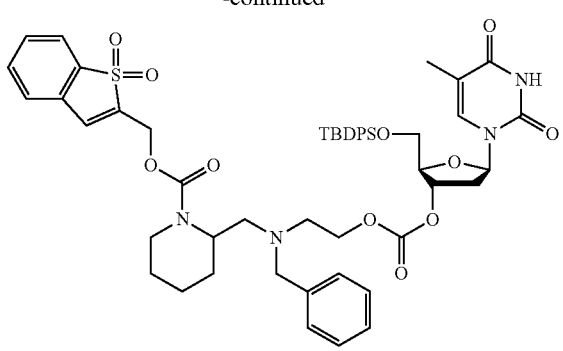

tert-Butyl 2-((benzyl(2-(((((2R,3S,5R)-2-(((tert-butyldiphenylsilyl)oxy)methyl)-5-(5-methyl-2,4-dioxo-3,4-dihydropyrimidin-1(2H)-yl)tetrahydrofuran-3-yl)oxy)carbonyl)oxy)ethyl)amino)methyl)piperidine-1-carboxylate (2) (290 mg, 0.38 mmol) was dissolved in 1:1 TFA-DCM (10 mL) at rt. After 1 h the reaction was complete by tlc (10% MeOH-DCM, uv). The excess TFA was removed under reduced pressure and sat. aq. NaHCO₃ (50 mL) and DCM (50 mL) were added. The layers were separated and the organic layer was washed with brine (50 mL), dried (MgSO₄) and the solvent removed to give the free amine as a colourless oil. This oil was dissolved in DCM (20 mL) and Hunig's base (0.13 mL, 0.76 mmol, 2 eq.) was added, followed by 1,1-dioxobenzo[b]thiophen-2-ylmethyl chloride (100 mg, 0.46 mmol, 1.2 eq.). After 1 h the reaction was complete by tlc, (10% MeOH-DCM). Water (50 mL) and DCM (50 mL) were added, the layers were separated and the organic layer was dried (MgSO₄). The solvent was removed under reduced pressure and the crude product was purified by silica chromatography (0-60% EtOAC-petrol) to give the product as a colourless oil (250 mg, 67%). LC-MS; Method B (Basic); Rt=2.85, m/z 977.40 (MH⁺).

Example 3

(9H-fluoren-9-yl)methyl 2-((benzyl(2-(((((2R,3S,5R)-2-(((tert-butyldiphenysilyl)oxy)methy)-5-(5-methy-2,4-dioxo-3,4-dihydropyrimidin-1(2H)-yl)tetrahydrofuran-3-yl)oxy)carbonyl)oxy)ethyl)amino)methyl)piperidine-1-carboxylate (5)

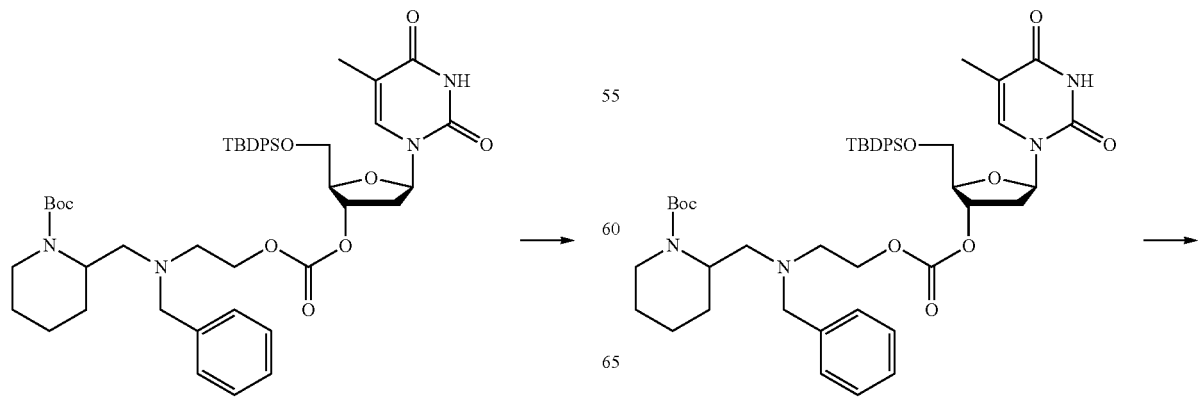

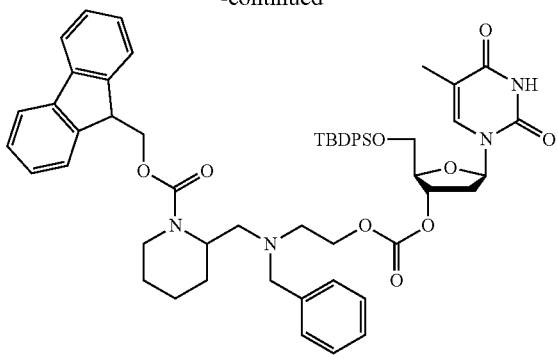

tert-Butyl 2-((benzyl(2-(((((2R,3S,5R)-2-(((tert-butyldiphenylsilyl)oxy)methyl)-5-(5-methyl-2,4-dioxo-3,4-dihydropyrimidin-1(2H)-yl)tetrahydrofuran-3-yl)oxy)carbonyl)oxy)ethyl)amino)-methyl)piperidine-1-carboxylate (2) (800 mg, 0.93 mmol) was dissolved in 1:1 TFA-DCM (20 mL) at rt. After 1 h the reaction was complete by tlc (10% MeOH-DCM, uv). The excess TFA was removed under reduced pressure and sat. aq. NaHCO₃ (50 mL) and DCM (50 mL) were added. The layers were separated and the organic layer was washed with brine (50 mL), dried (MgSO₄) and the solvent removed to give the free amine as a colourless oil. This oil was dissolved in DCM (60 mL) and Hunig's base (0.26 mL, 1.86 mmol, 2 eq.) was added, followed by 9-fluorenylmethoxycarbonyl chloride (342 mg, 1.1 mmol, 1.2 eq.). After 1 h the reaction was complete by tlc, (10% MeOH-DCM). Water (50 mL) and DCM (50 mL) were added, the layers were separated and the organic layer was dried (MgSO₄). The solvent was removed under reduced pressure and the crude product was purified by silica chromatography (0-60% EtOAC-petrol) to give the product as a colourless oil (250 mg, 67%). LC-MS; Method B (Basic); Rt=3.31, m/z 978.61.40 (MH⁺).

Example 4

Example 4A: tert-Butyl 2-((benzyl(2-hydroxyethyl)amino)methy)pyrrolidine-1-carboxylate (6)

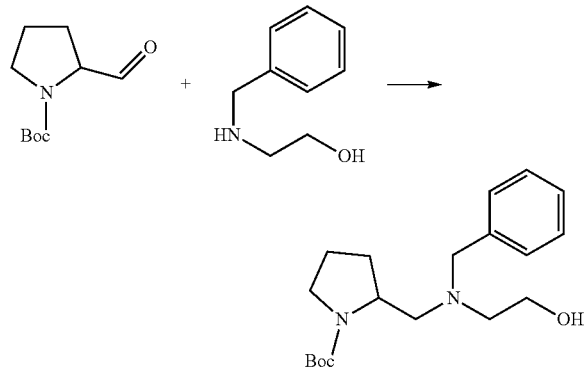

N-Boc-L-Prolinal (3 g, 15 mmol) was dissolved in THF (200 mL), and acetic acid (3 mL 75 mmol, 5 eq.) and 2-benzylaminoethanol (2.3 g, 16 mmol, 1.2 eq.) were added. After 10 minutes at rt, sodium triacetoxyborohydride was added and the solution was stirred for 3 h. Sat. aq. NaHCO₃ was added and the layers were separated. The organic layer was dried (MgSO₄) and the solvent was removed under reduced pressure. The residue was purified by silica chromatography (0-10% MeOH-DCM) to give the product as a colourless oil (3.1 g mg, 63%). LC-MS; Method B (Basic); Rt=1.53, m/z 335.3 (MH⁺).

Example 4B: tert-Butyl (S)-2-((benzyl(2-(((((2R,3S,5R)-2-(((tert-butyldiphenylsilyl)oxy)methyl)-5-(5-methyl-2,4-dioxo-3,4-dihydropyrimidin-1(2H)-yl)tetrahydrofuran-3-yl)oxy)carbonyl)oxy)ethyl)amino)methyl)pyrrolidine-1-carboxylate (7)

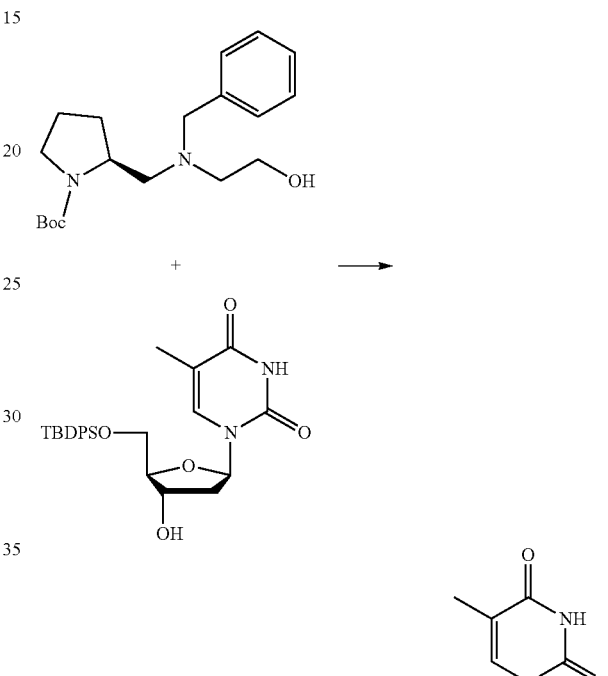

5'-O-TBDPS-Thymidine (1.4 g, 3 mmol, 1.0 eq.) and CDI (530 mg, 3.3 mmol, 1.2 eq.) were dissolved in anhydrous acetonitrile (40 mL) and the solution was heated at 40° C. under N₂ for 2 hours. tert-Butyl 2-((benzyl(2-hydroxyethyl)amino)methyl) pyrrolidine-1-carboxylate (6) (1 g, 3 mmol) and 1,1,3,3-tetramethylguanidine (1 mL, 8.4 mmol, 3 eq.) were added and the solution was stirred at rt for 2 h. Water (200 mL) and EtOAc (200 mL) were added and the layers were separated. The organic layer was dried (MgSO₄) and the solvent was removed. The resulting oil was purified by silica chromatography, eluting with 0-50% EtOAc-petrol to give the product as a colourless oil, 1 g, 40%. LC-MS; Method B (Basic); Rt=3.30, m/z 841.09 (MH⁺).

Example 4C: 2-(Benzyl(((S)-pyrrolidin-2-yl)methyl) amino)ethyl ((2R,3S,5R)-2-(((tert-butyldiphenylsilyl)oxy)methyl)-5-(5-methyl-2,4-dioxo-3,4-dihydropyrimidin-1(2H)-yl)tetrahydrofuran-3-yl)carbonate

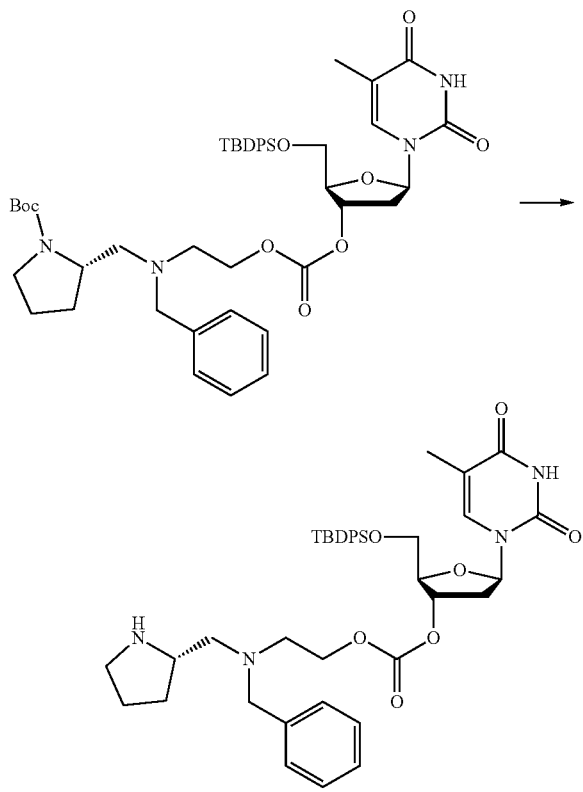

tert-Butyl (S)-2-((benzyl(2-(((((2R,3S,5R)-2-(((tert-butyldiphenylsilyl)oxy)methyl)-5-(5-methyl-2,4-dioxo-3,4-dihydropyrimidin-1(2H)-yl)tetrahydrofuran-3-yl)oxy)carbonyl)oxy)ethyl)amino)methyl)pyrrolidine-1-carboxylate (7) (100 mg, 0.12 mmol) was dissolved in dichloromethane (2 mL) and trifluoroacetic acid (2 mL) and the solution was stirred at room temperature for 1 h. After this time the reaction was complete by LC-MS. The solvent was removed and dichloromethane (100 mL) and saturated aqueous NaHCO₃ (100 mL) were added and the layers were separated. The organic layer was dried (MgSO₄) and the solvent was removed under reduced pressure. The residue was purified by silica chromatography (0-10% MeOH-DCM) to give the product as a colourless oil (60 mg, 69%).

Example 5

Time-Course Experiments

General Procedure—Reactions at High Temperature

The compound to be tested was dissolved in the required solution at a concentration of 0.5 mg/mL at room temperature. This solution was divided (0.5-0.75 mL per vial) between enough LC-MS vials to measure the reaction course at the required number of time-points as well as one for the room temperature measurements. The vials for the heated experiment were immediately placed in a hot water bath set at 90° C. (±0.1° C.), such that the level of liquid in the vial was below the surface of the hot water. At each time-point in the experiment an LC-MS vial was removed and then immediately cooled in a brine ice-bath at a temperature of 3° C. The LC-MS experiment was then carried out within ten minutes of the reaction being quenched by cooling. The ratio of starting material to cleaved TBDPS-Thymidine was measured by integrating the corresponding peaks in the UV trace of the LC-MS.

General Procedure—Reactions at Various High Temperatures

The compound to be tested was dissolved in the required solution at a concentration of 0.5 mg/mL at room temperature. This solution was divided (0.5-0.75 mL per vial) between enough LC-MS vials to measure the reaction course at the required number of time-points as well as one for the room temperature measurements. The vials for the heated experiments were immediately placed in a hot water bath set at either 40° C., 60° C. or 90° C. (±0.1° C.), such that the level of liquid in the vial was below the surface of the hot water. At each time-point in the experiment an LC-MS vial was removed and then immediately cooled in a brine ice-bath at a temperature of 3° C. The LC-MS experiment was then carried out within ten minutes of the reaction being quenched by cooling. The ratio of starting material to cleaved nucleoside was measured by integrating the corresponding peaks in the UV trace of the LC-MS.

General Procedure—Reactions at Room Temperature

An LC-MS vial containing the same solution as used for the high-temperature experiment was kept at room temperature i.e. 20±3° C. and the solution was analysed by LC-MS at suitable time-points.

General Procedure—Reactions at the Low Temperature

An LC-MS vial containing the same solution as used for the high-temperature experiment was placed in the pre-chilled auto sampler chamber of the LC-MS machine set at the low temperature, for example, 200.1° C. or 10±0.1° C. and the solution was analysed by LC-MS at suitable time-points.

Reactions at 10° C.

An LC-MS vial containing the same solution as used for the high-temperature experiment was place in the pre-chilled auto sampler chamber of the LC-MS machine set at 10° C. and the solution was repeatedly analysed by LC-MS at suitable time-points.

Example 5A: Time Course Studies on the Cleavage of the Unprotected Linker of Example 1C

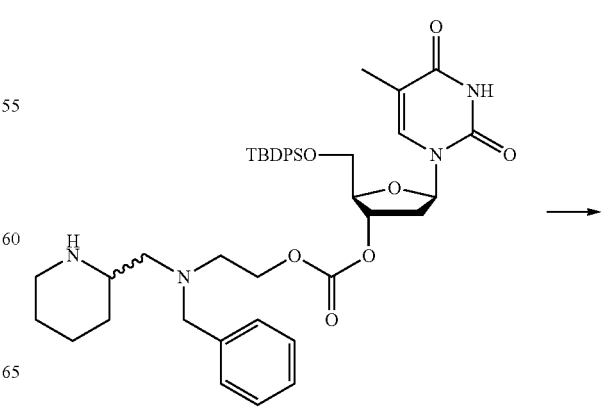

Example 5B: Studies on Deprotection of Bsmoc-Protected Activating Group Followed by Linker-Cleavage (Compound of Example 2)

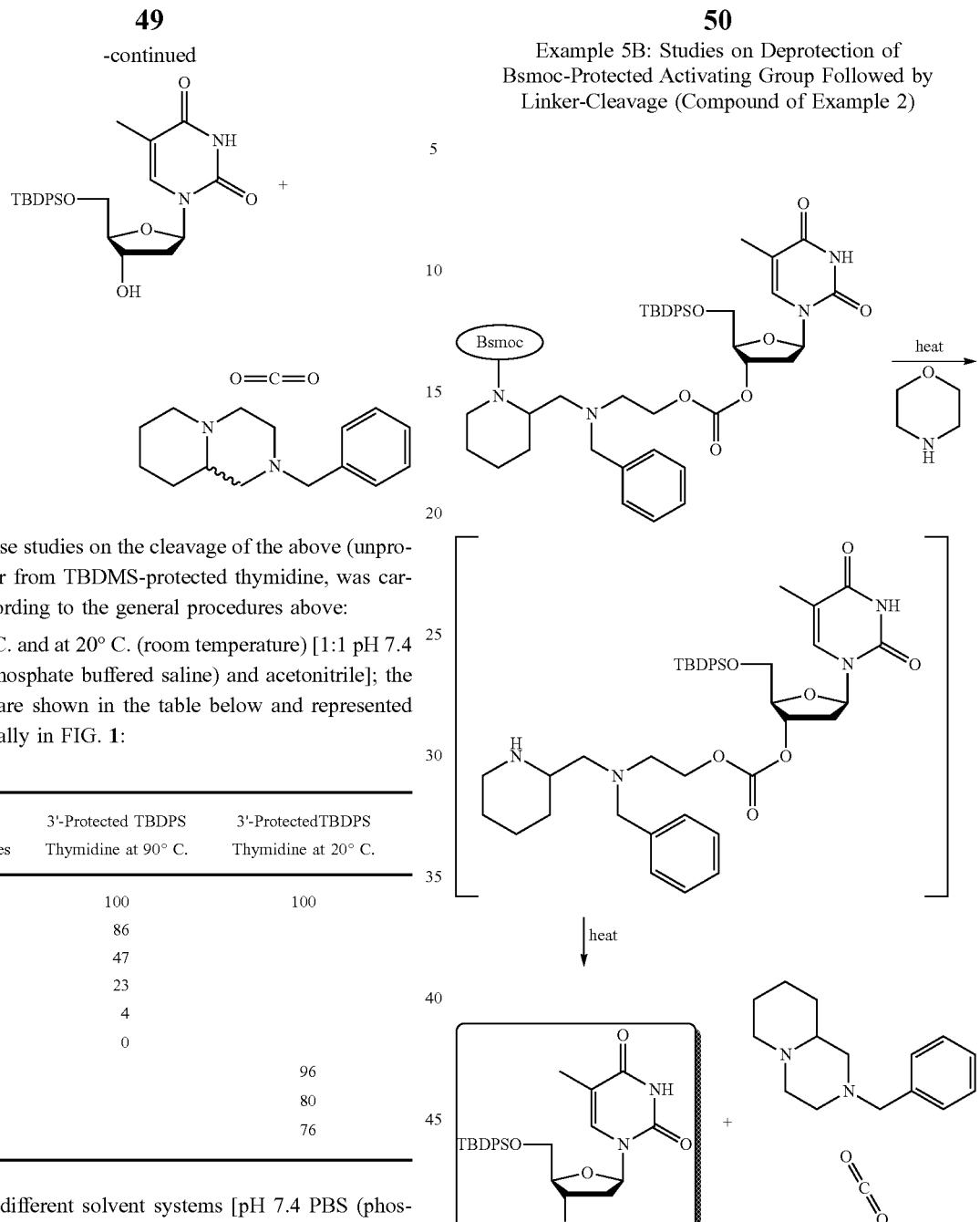

Time course studies on the cleavage of the above (unprotected) linker from TBDMS-protected thymidine, was carried out according to the general procedures above:

(i) at 90° C. and at 20° C. (room temperature) [1:1 pH 7.4 PBS (phosphate buffered saline) and acetonitrile]; the results are shown in the table below and represented graphically in FIG. 1:

| Time/minutes | 3'-Protected TBDPS Thymidine at 90° C. | 3'-Protected TBDPS Thymidine at 20° C. |
|---|---|---|
| 0 | 100 | 100 |
| 1 | 86 | |
| 2 | 47 | |
| 5 | 23 | |
| 10 | 4 | |
| 15 | 0 | |
| 1260 | | 96 |
| 5760 | | 80 |
| 10080 | | 76 |

(ii) using different solvent systems [pH 7.4 PBS (phosphate buffered saline)]; acetonitrile and pH 5 buffer (TEEA (triethylammonium acetate) buffer] (FIG. 2)

(iii) using different ratios of PBS:MeCN (acetonitrile) at 90° C. (FIG. 3)

The results of the time course studies on the above compound in PBS (phosphate buffered saline) and MeCN (acetonitrile) at 90° C. and at room temperature (20° C.) are shown in FIG. 1.

As shown in FIG. 1, the unprotected linker shows a clear differentiation of cleavage at 20° C. vs 90° C. Thus, at 20° C., only starting material was detected, whereas at 90° C., the linker was cleaved from the nucleotide. Further, at 90° C., the cleavage was rapid, with no starting material remaining after about 13 minutes.

Time course studies on the cleavage of the above Bsmoc-protected linker from TBDMS-protected thymidine (i.e. the compound of Example 2), was carried out according to the general procedures above.

The Bsmoc protecting group was heated at 90° C. and the concentrations of the starting material, Bsmoc-deprotected intermediate and the cleaved thymidine were measured (FIG. 4A). FIG. 4B shows the extent of deprotection of the Bsmoc-group over time at 20° C. and at 90° C.

FIG. 4C shows that when the Bsmoc-protected linker is treated with base at room temperature this does not lead to immediate cleavage of the linker, because although the deprotection step occurs reasonably quickly at RT, the second step (i.e. cleavage) requires heating.

Example 5C: Stability Studies on Bsmoc-Protected Linker of Example 2

Stability studies were conducted under different pH conditions at 80° C.:
(i) pH 7.4 phosphate buffered saline;
(ii) pH 9 phosphate buffered saline
(iii) pH 5 TEEA (triethylammonium acetate) buffer The results are shown in FIG. 5. The results show that minimal cleavage of the Bsmoc-protected linker was observed under heated (80° C.) conditions over several hours. Furthermore, minimal side-product formation was observed under these conditions. By comparison, as shown in the previous study (FIGS. 4A, 4B and 4C), conditions of 0.1% morpholine at 90° C. enabled a facile and rapid two step deprotection and linker cleavage.

Example 5D: Studies on Deprotection of Fmoc-Protected Activating Group Followed by Linker-Cleavage (Compound of Example 3)

Studies with the Fmoc protecting group of the compound of Example 3 demonstrated a similar level of control to the Bsmoc protecting group. A key difference was that, as well as piperidine, non-nucleophilic bases such as diisopropylamine can also be used to remove the Fmoc group (FIGS. 6, 7 and 9). A significant deceleration of the reaction rate was observed when changing the solvent from DMF to acetonitrile (FIG. 8). Hence, it can be seen that the incorporation of different protecting groups offers further control of the deprotection-cleavage conditions. In addition, adjustment of the reaction conditions enables a simple way of fine tuning the deprotection and cleavage of the linker.

Example 5E: Comparative Studies Between the Pyrrolidine (Compound of Example 4C) and Piperidine (Compound of Example 1C) Activating Groups Studies with a pyrrolidine activating group showed that there was a deceleration of reaction speed compared to the piperidine activating, in spite of the increased nucleophilic-

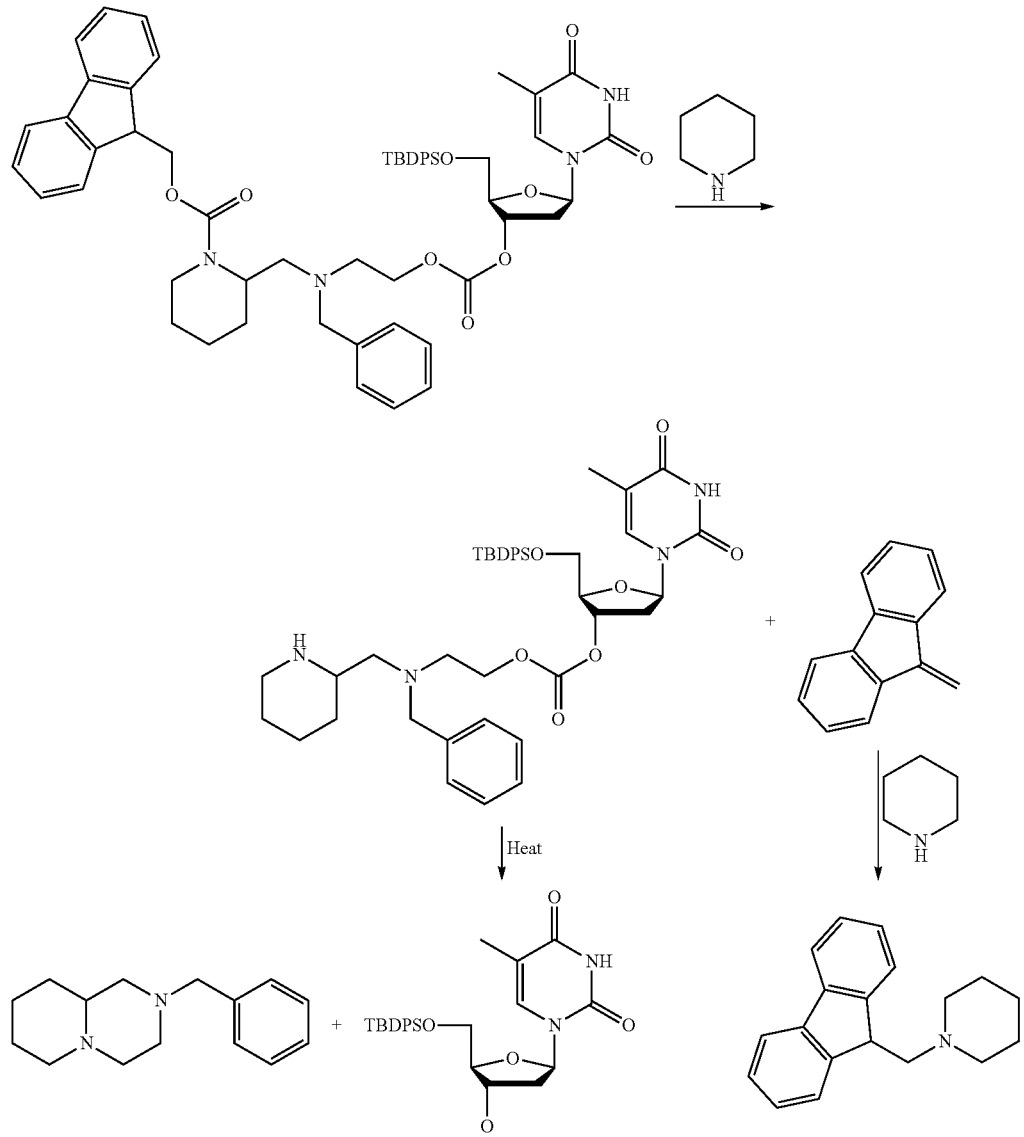

ity of the pyrrolidine nitrogen (FIG. 10). These studies indicate that the conformation of the cyclised product is likely to be more important in determining reaction speed, and thus provides a further method by which fine control of the linker deprotection-cleavage can be achieved.

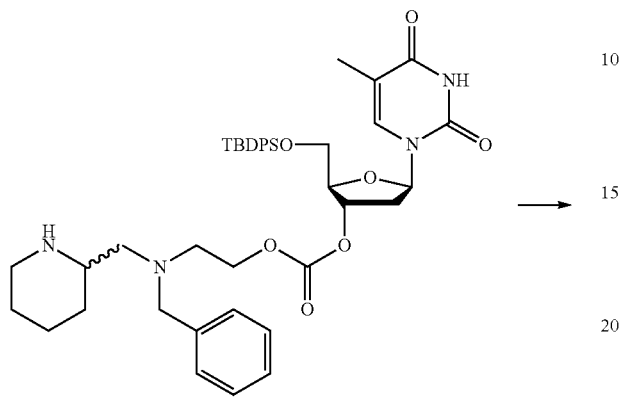

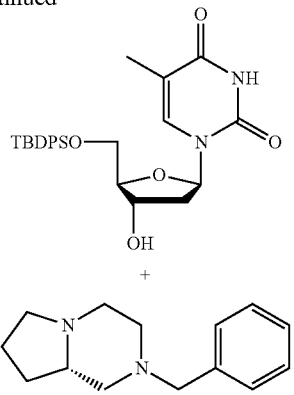

Example 5F: Co-Solvent Study with Pyrrolidine Linker (Compound of Example 4C)

The effect of co-solvents on reaction speed was explored. As shown in FIG. 11, it was found that DMSO gave the fastest reaction speed in this system.

Example 5G: Time-Course Study for Deprotection of Boc-Protected Linker (Compound of Example 1B3)

The general procedure for carrying out the time-course experiments at 20° C. and at 90° C. was used, at with the modification that the reaction at each time-point was quenched by cooling the LC-MS vial in a brine-ice bath, and then adding an excess of triethylamine (50 μL, ~3 eq.)

The aim of using an acid-cleaved protecting group was to demonstrate a two step deprotection-cleavage process with a different level of orthogonality in each step, since deprotection of the activating group with acids leads to a protonated activating group which is unable to effect linker cleavage until deprotonation occurs (known as proton-blocking).

The study demonstrated that no linker-cleavage was observed under these conditions despite 100% deprotection of the activating group occurring (FIG. 12).

Example 6

Synthesis of α-Carbon Substituted Compounds

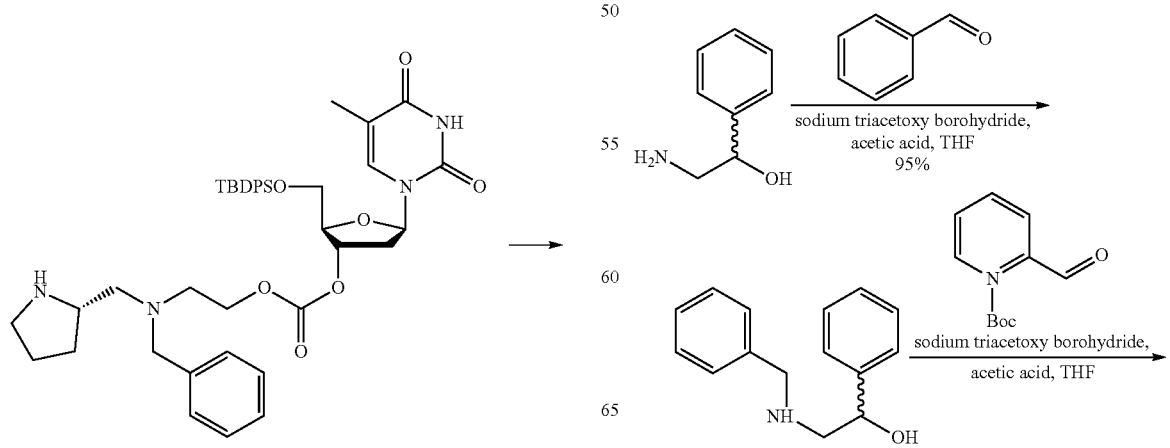

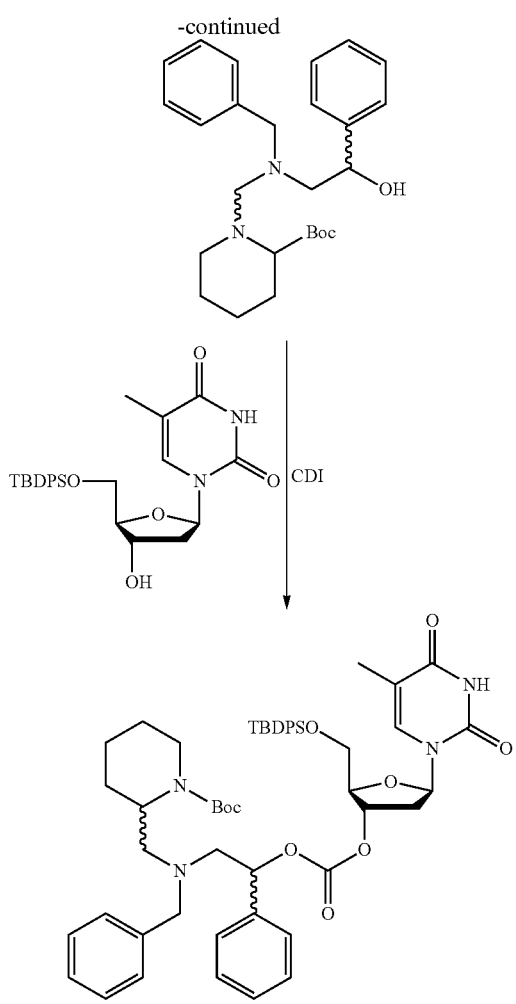

Example 6A: 2-(Benzylamino)-1-phenylethan-1-ol

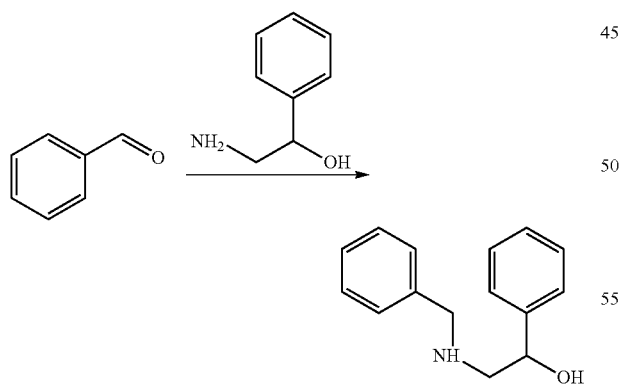

2-Hydroxy-2-phenylethylamine (4.7 g, 34 mmol, 1.2 eq) and benzaldehyde (3.6 g, 34 mmol) were dissolved in methanol (100 ml) and stirred at rt for 10 minutes. After this time the solution was cooled to 0° C. and sodium borohydride (1.6 g, 34 mmol) was added. The solution was warmed to rt and stirred for 2 h, after which time the reaction was complete by LC-MS and tlc. An ethyl acetate-water workup was carried out and the organic layer was dried (MgSO₄) and the solvent was removed under reduced pressure to give an off-white crystalline solid. This was triturated with petrol and ethyl acetate to give a white solid, 5 g, 65%. LC-MS; Method B (Basic); Rt=1.94, m/z 228.2 (MH⁺).

Example 6B: tert-Butyl 2-((benzyl(2-hydroxy-2-phenylethyl)amino)methyl) piperidine-1-carboxylate

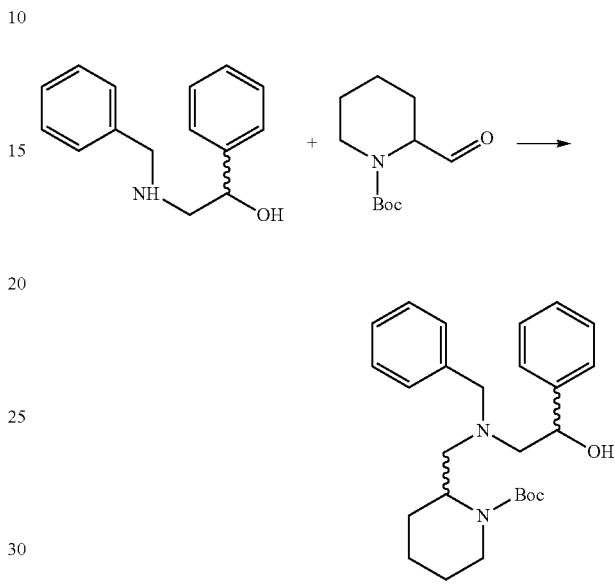

2-(Benzylamino)-1-phenylethan-1-ol (1.96, 8.6 mmol) and 1-N-boc-2-piperidinecarbaldehyde (1.8 g, 8.6 mmol) were dissolved in 1,2-dichloroethane (100 mL) and acetic acid was added (3 mL). After 10 minutes sodium triacetoxyborohydride (2.7 g, 12 mmol, 1.5 eq) was added and the solution was stirred overnight. After this time there was clean conversion to the product by LC-MS. A dichloromethane/saturated aqueous NaHCO₃ workup was carried out and the organic solution was dried (MgSO₄) and the solvent removed to give the diastereomeric products as a colourless oil, 3.7 g, 100%. LC-MS; Method B (Basic); Rt=2.88 and 2.93, m/z 425.3 (MH⁺).

Example 6C: tert-Butyl 2-((benzyl(2-(((((2R,3S,5R)-2-(((tert-butyldiphenylsilyl)oxy)-methyl)-5-(5-methyl-2,4-dioxo-3,4-dihydropyrimidin-1(2H)-yl)tetrahydrofuran-3-yl)oxy)carbonyl)oxy)-2-phenylethyl)amino)methyl)piperidine-1-carboxylate

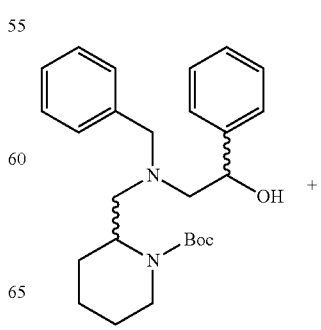

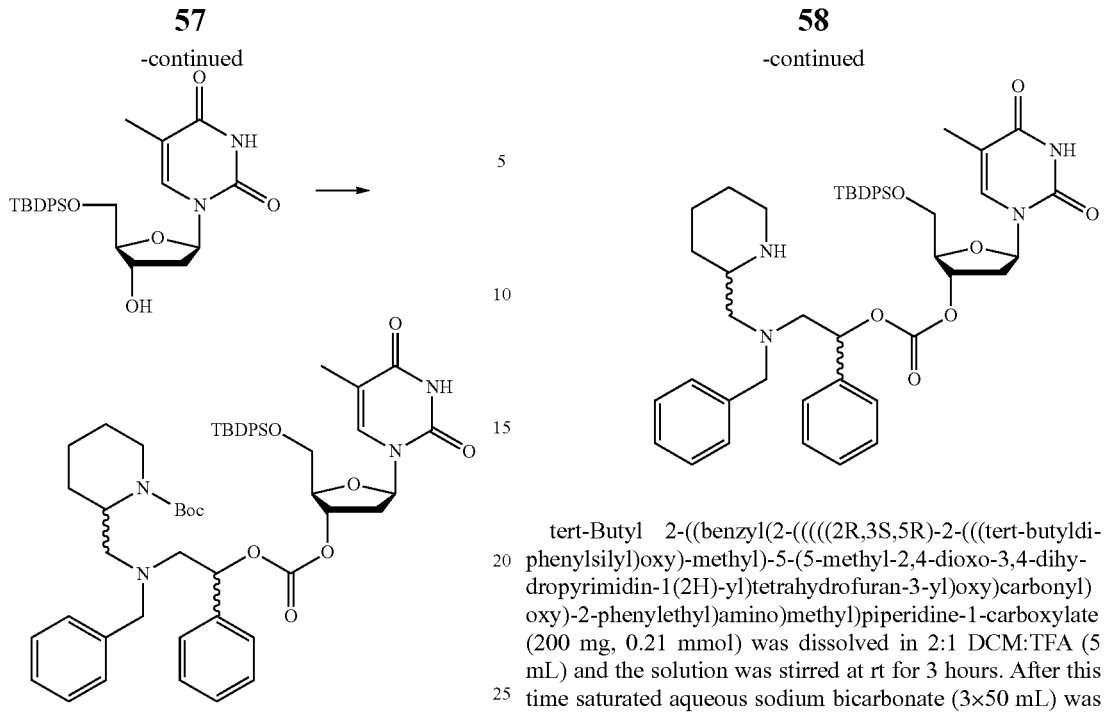

i) A mixture of tert-butyl 2-((benzyl(2-hydroxy-2-phenylethyl)amino)methyl)piperidine-1-carboxylate (500 mg, 1.2 mmol) and CDI (283 mg, 1.44 mmol, 1.2 eq.) were dissolved in anhydrous acetonitrile (60 mL) and the solution was heated at 50° C. for 1 h under $N_2$ to give clean conversion to the diastereomeric intermediates by LC-MS. ii) 5'-O-TBDPS-Thymidine (560 mg, 1.2 mmol) and DBU (0.44 mL, 2.92 mmol, 2 eq.) were then added and the solution was stirred overnight. A water/EtOAc/brine workup was carried out, the organic solution was dried ($MgSO_4$) and the solvent was removed under reduced pressure. The product was then purified by silica chromatography, eluting with 0-60% ethyl acetate-petrol to give the diastereomeric products as a white foam, 700 mg, 63%. LC-MS; Method C (Long Acidic); Rt=2.88 and 2.93, m/z 931.6 (MH+). $^1$H NMR (CDCl3) consistent with structure.

Example 6D: 2-(Benzyl(piperidin-2-ylmethyl)amino)-1-phenylethyl ((2R,3S,5R)-2-(((tert-butyldiphenylsilyl)oxy)methyl)-5-(5-methyl-2,4-dioxo-3,4-dihydropyrimidin-1(2H)-yl)tetrahydrofuran-3-yl) carbonate

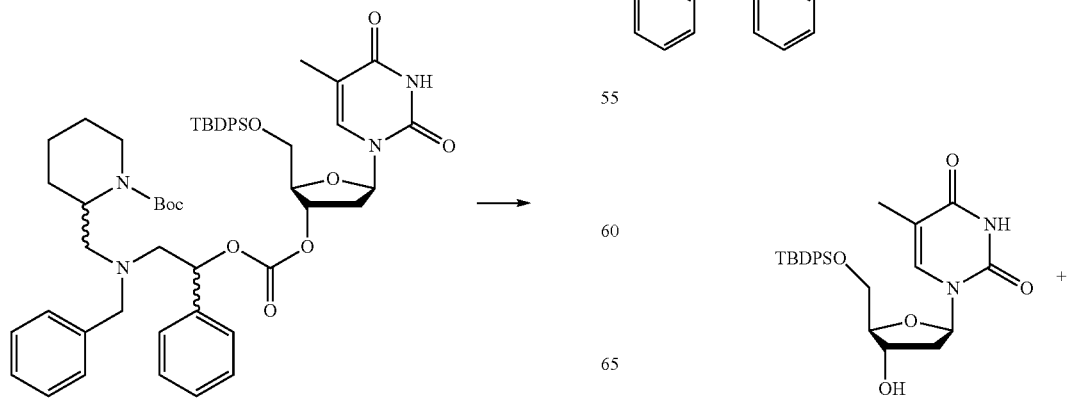

tert-Butyl 2-((benzyl(2-(((((2R,3S,5R)-2-(((tert-butyldiphenylsilyl)oxy)-methyl)-5-(5-methyl-2,4-dioxo-3,4-dihydropyrimidin-1(2H)-yl)tetrahydrofuran-3-yl)oxy)carbonyl)oxy)-2-phenylethyl)amino)methyl)piperidine-1-carboxylate (200 mg, 0.21 mmol) was dissolved in 2:1 DCM:TFA (5 mL) and the solution was stirred at rt for 3 hours. After this time saturated aqueous sodium bicarbonate (3×50 mL) was added and the layers were separated. The organic layer was dried ($MgSO_4$) and the solvent was removed under reduced pressure at 20° C. to give the diastereomeric products as a white foam, 160 mg, 88%. LC-MS; Method C (Long Acidic); Rt=2.31, 2.33 and 2.36, m/z 831.6 (MH+). $^1$H NMR (CDCl3) consistent with structure.

Example 7

Time-Course Study on Non-Protected α-Phenyl Safety-Catch Linker (Compound of Example 6D)

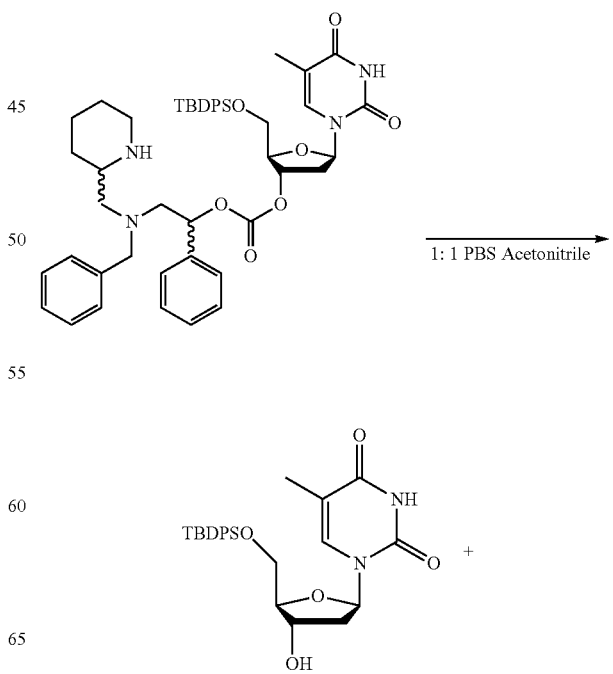

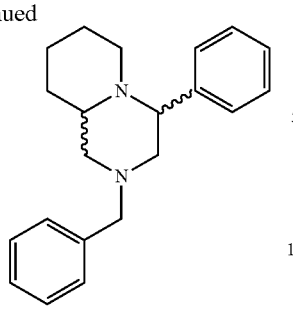

The aim of this study was to determine whether substitution at the α-carbon would be tolerated. It was observed that the reaction was slower than for the unsubstituted analogue, but proceeded cleanly (FIG. 13). Therefore the presence of substituents can be used to provide additional control of the rate of cleavage of the linkers/protecting groups.

Example 8

Double Safety-Catch Protecting Groups

Example 8A: di-Tert-butyl 2,2'-(((2-hydroxyethyl)azanediyl)bis(methylene))bis(piperidine-1-carboxylate)

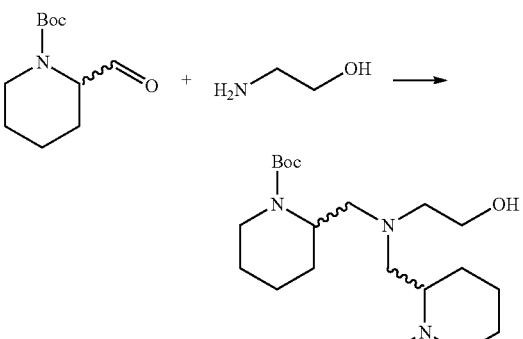

1-N-Boc-2-piperidinecarbaldehyde (1 g, 2.3 mmol) and ethanolamine (0.143 mL, 2.3 mmol) were dissolved in 1,2-dichloroethane (100 mL) and acetic acid (6 mL, 85 mmol, 5 eq.) was added. After 10 minutes sodium triacetoxyborohydride (2.7 g, 3.45 mmol, 1.5 eq.) was added. After 1 h, a mixture of both the intermediate and product were visible by LC-MS. Hence, the other equivalent of aldehyde was added, followed by another equivalent of

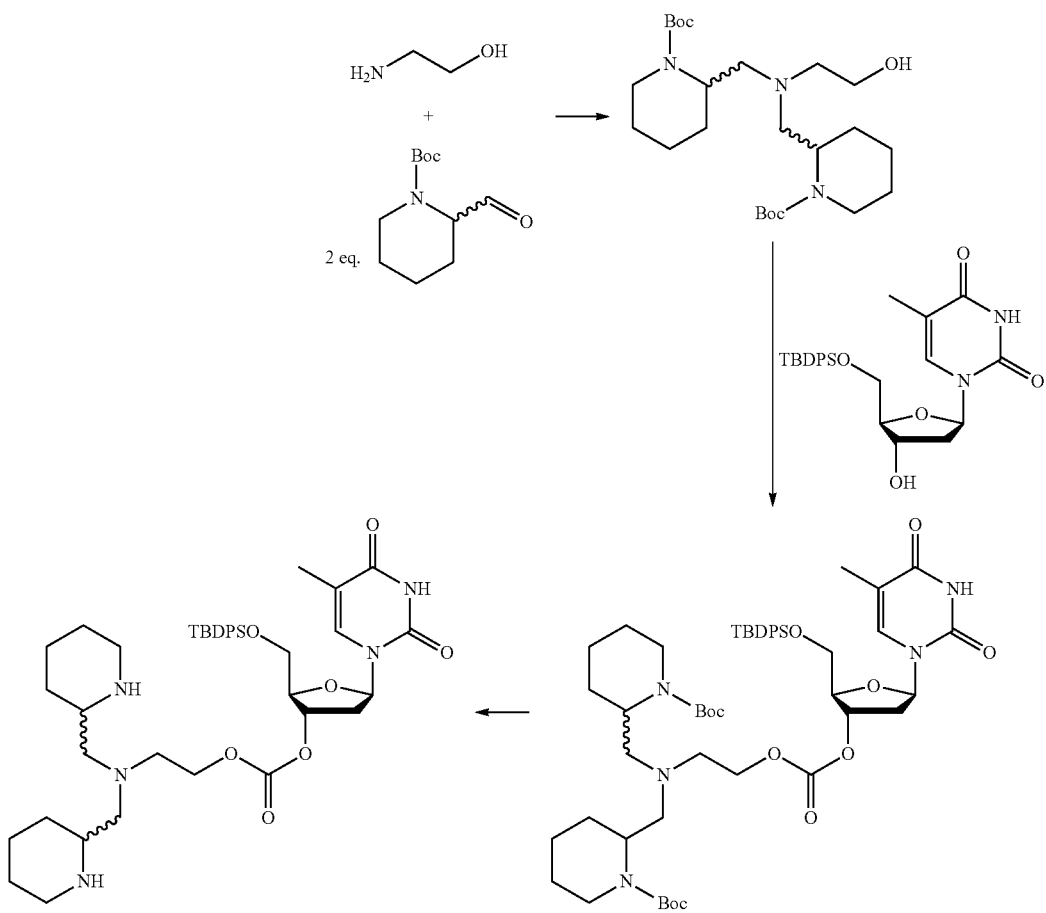

sodium triacetoxyborohydride and the solution was then stirred overnight. A saturated aqueous NaHCO₃/DCM workup was carried out, the organic solution was dried (MgSO₄) and the solvent was removed under reduced pressure. The crude product was then purified by silica chromatography, eluting with DCM-EtOAc (0-50%) to give the product as a pale yellow oil, 1 g, 95%. LC-MS; Method A (Acidic); Rt=1.84, m/z 456.4 (MH⁺).

Example 8B: di-Tert-butyl 2,2'-(((2-(((((2R,3S,5R)-2-(((tert-butyldiphenylsilyl)oxy)methyl)-5-(5-methyl-2,4-dioxo-3,4-dihydropyrimidin-1(2H)-yl)tetrahydrofuran-3-yl)oxy)carbonyl)oxy)ethyl)azanediyl)bis(methylene))-bis(piperidine-1-carboxylate)

due was purified by silica chromatography, eluting with 0-80% EtOAc in DCM to give the product as a white foam, 280 mg, 41%. LC-MS; Method C (long acidic) Rt=4.03, m/z 962.7 (MH⁺).

Example 8C: 2-(Bis(piperidin-2-ylmethyl)amino) ethyl ((2R,3S,5R)-2-(((tert-butyldiphenylsilyl)oxy) methyl)-5-(5-methyl-2,4-dioxo-3,4-dihydropyrimidin-1(2H)-yl)tetrahydrofuran-3-yl) carbonate

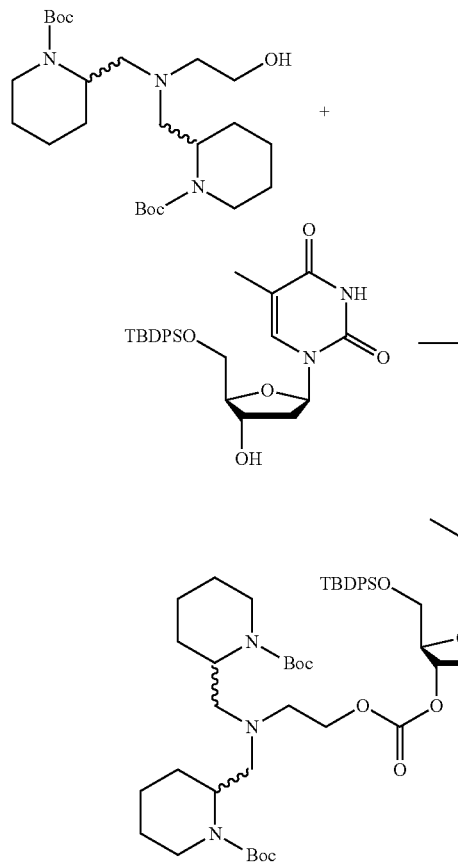

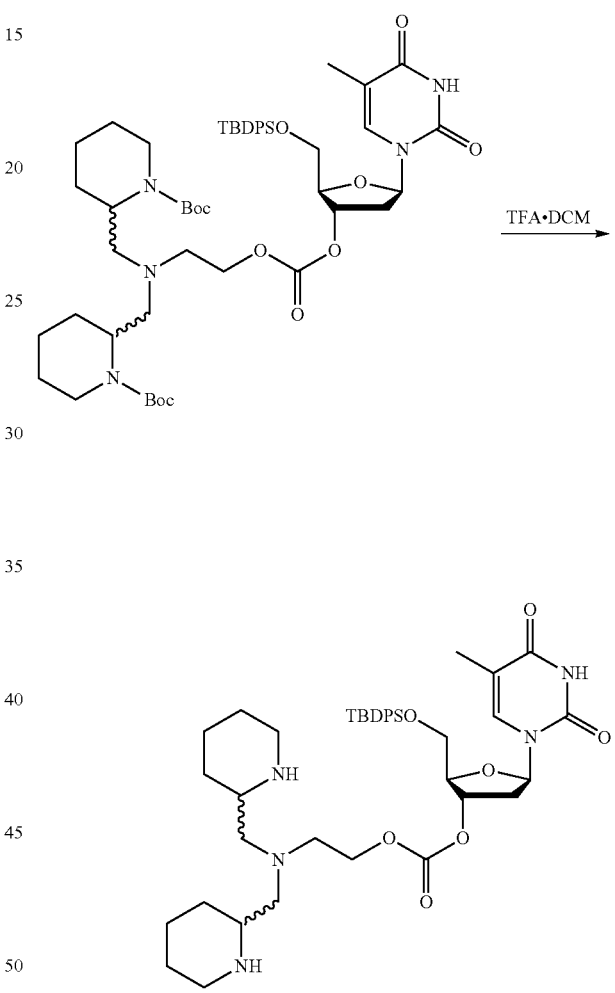

i) 5'-O-TBPDS-Thymidine (340 mg, 0.71 mmol) and CDI (130 mg, 0.85 mmol, 1.2 eq.) were dissolved in dry acetonitrile (60 mL) and the solution was heated at 50° C. for 4 hours and then left over the weekend. ii) di-Tert-butyl 2,2'-(((2-hydroxyethyl)azanediyl) bis(methylene))bis(piperidine-1-carboxylate) (323 mg, 0.71 mmol) and DBU (0.2 mL, 1.42 mmol, 2 eq.) were added and the solution was stirred at 40° C. for 2 h, after which time the reaction had gone to completion by LC-MS. A water/EtOAc workup was carried out and the organic solution was dried (MgSO₄) and the solvent was removed under reduced pressure. The residue di-Tert-butyl 2,2'-(((2-(((((2R,3S,5R)-2-(((tert-butyldiphenylsilyl)oxy)methyl)-5-(5-methyl-2,4-dioxo-3,4-dihydropyrimidin-1(2H)-yl)tetrahydrofuran-3-yl)oxy)carbonyl)oxy)ethyl) azanediyl)bis(methylene))bis(piperidine-1-carboxylate) (50 mg, 0.052 mmol) was dissolved in 1:1 TFA:DCM (2 mL) at rt. After 30 minutes the reaction was complete by LC-MS. DCM and saturated aqueous NaHCO₃ were added and the layers were separated. The DCM layer was dried (MgSO₄) and the solvent was removed under reduced pressure at 20° C. to give the product as a white foam, 30 mg, 76%. LC-MS; Method A (Acidic); Rt=1.73, m/z 762.4 (MH⁺).

Example 9

Time-Course Study of Double Safety-Catch Linker (Compound of Example 8C)

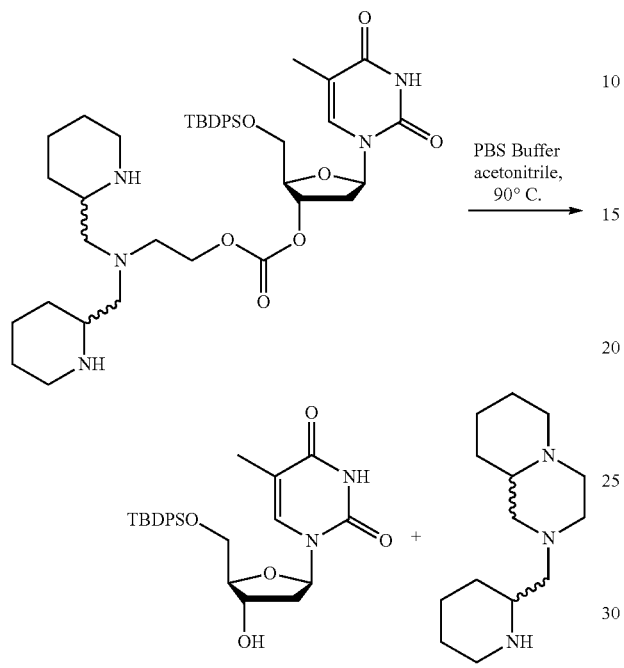

The aim of this study was to investigate whether a linker containing two activating groups (Compound of Example 8C) would have an accelerated linker cleavage time, compared to the linker cleavage of the mono-activating group compound (Compound of Example 1C). Furthermore, it is proposed that molecules containing two or more activating groups would give an increase in rate of cleavage without compromising the level of thermal control, since the effective concentration of the reacting nucleophile would be doubled but the activation energy of the reaction would not change significantly. The results of this study are shown in FIG. 14. It was found that the extra activating group considerably increased the speed of the linker cleavage. Furthermore the presence of two activating groups (i.e. Ring A) allows greater control of the two steps of the linker cleavage by either carrying out 100% deprotection of both protecting groups, or carrying out the deprotection step only until at least one activating group is deprotected per molecule.

Example 10

Synthesis of Linkers with Functionality to Attach to a Surface

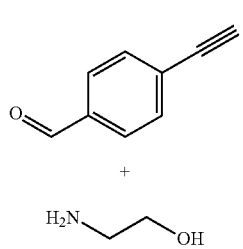

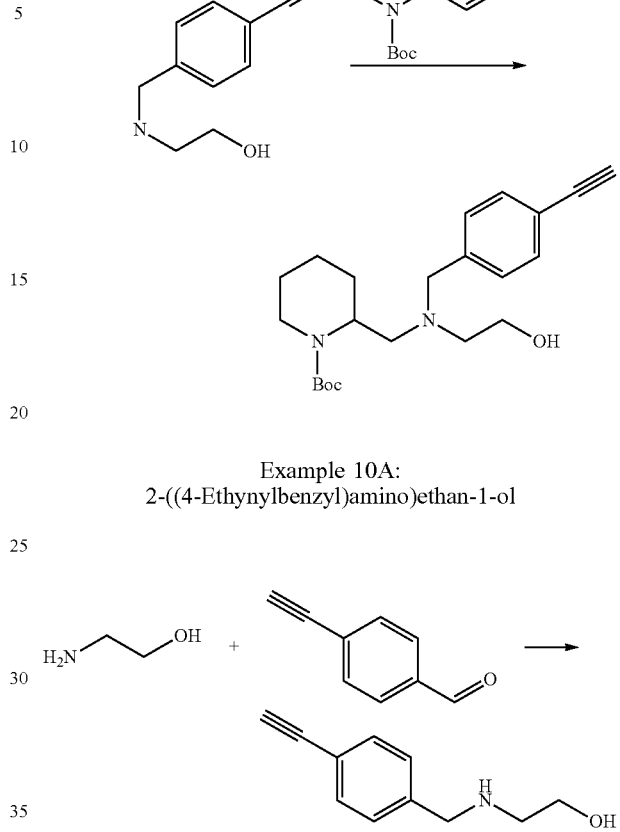

Example 10A: 2-((4-Ethynylbenzyl)amino)ethan-1-ol

4-Ethynylbenzaldehyde (5 g, 38 mmol) and ethanolamine (2.3 g, 38 mmol) were dissolved in methanol (200 mL), and sodium borohydride (1.4 g, 38 mmol) was added after 10 minutes. The reaction solution was stirred overnight. After this time a water/ethyl acetate workup was carried out, the organic solution was dried (MgSO$_4$) and the solvent was removed under reduced pressure. The crude product was purified by silica chromatography (0-10% MeOH-DCM) to give a colourless oil which crystallised on standing, 3 g, 45% overall. LC-MS; Method B (Basic); Rt=1.55, m/z 176.1 (MH$^+$). $^1$H NMR (400 MHz, CDCl$_3$) δ ppm: 2.77-2.83 (m, 2H) 3.06 (s, 1H) 3.63-3.69 (m, 2H) 3.82 (s, 2H) 7.25-7.31 (m, 2H) 7.46 (d, J=7.46 Hz, 2H).

Example 10B: tert-Butyl 2-(((4-ethynylbenzyl)(2-hydroxyethyl)amino)-methyl)piperidine-1-carboxylate

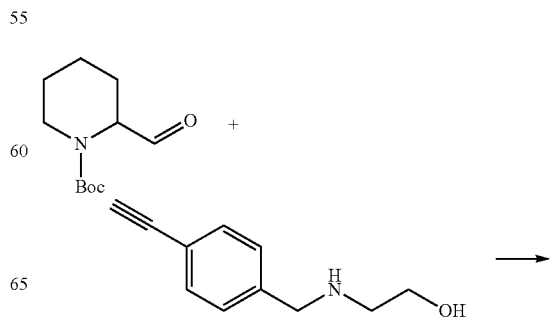

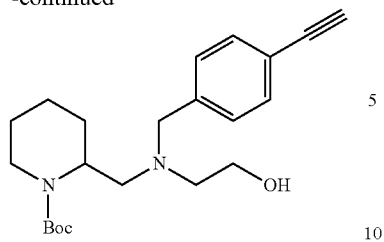

2-((4-Ethynylbenzyl)amino)ethan-1-ol (1.6 g, 8.5 mmol) and 1-N-Boc-2-piperidinecarbaldehyde (2 g, 9 mmol, 1.1 eq) were dissolved in 1,2-dichloroethane (80 mL) and acetic acid (3 mL, 85 mmol, 5 eq.) was added and the solution was stirred for 10 minutes at rt. Sodium triacetoxyborohydride was added and after 3 hours there was clean conversion to the product by LC-MS. A DCM/saturated aqueous NaHCO$_3$ workup was carried out and the organic layer was dried (MgSO$_4$) and the solvent was removed under reduced pressure to give a pale yellow oil, 3.4 g, 100%. LC-MS; Method A (Acidic); Rt=1.64, m/z 373.3 (MH$^+$). $^1$H NMR (400 MHz, CDCl$_3$) δ ppm: 1.09-1.31 (m, 4H) 1.46 (s, 9H) 2.02-2.22 (m, 2H) 2.55-2.92 (m, 4H) 3.07 (s, 1H) 3.30 (br s, 1H) 3.58-3.88 (m, 5H) 4.44 (br s, 1H) 7.21-7.31 (m, 2H) 7.43 (br d, J=7.91 Hz, 2H).

Example 10C: tert-Butyl 2-(((2-(((((2R,3S,5R)-2-(((tert-butyldiphenylsilyl)oxy)methyl)-5-(5-methyl-2,4-dioxo-3,4-dihydropyrimidin-1(2H)-yl)tetrahydrofuran-3-yl)oxy)carbonyl)oxy)ethyl)(4-ethynylbenzyl)amino)methyl)piperidine-1-carboxylate

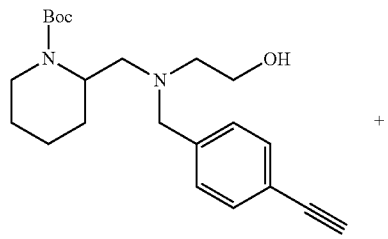

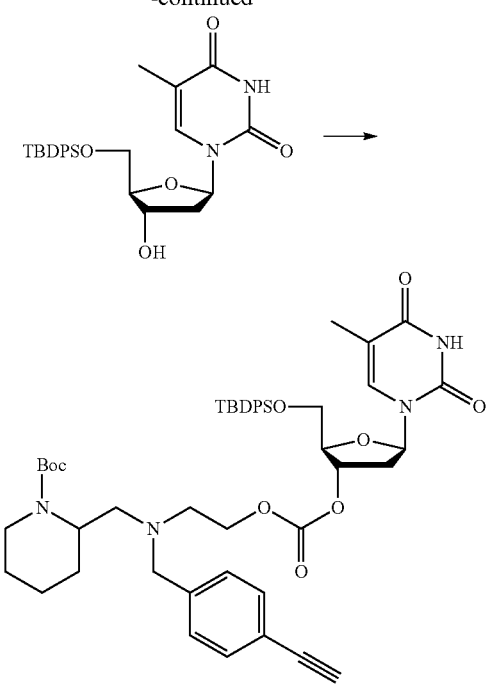

i) 5'-O-TBDPS-Thymidine (2 g, 4.1 mmol) and CDI (797 mg, 4.92 mmol, 1.2 eq.) were dissolved in dry acetonitrile (100 mL) under N$_2$. The solution was then stirred overnight at rt. After this time there was clean conversion to the active intermediate by LC-MS. tert-Butyl 2-(((4-ethynylbenzyl)(2-hydroxyethyl)amino)methyl)piperidine-1-carboxylate (1.55 g, 4.1 mmol) and DBU (1.2 mL, 8.1 mmol, 2 eq.) were added and the solution was stirred at rt. After 30 minutes the reaction had gone to completion. An ethyl acetate/water workup was carried out and the crude product was purified by silica chromatography (0-100% EtOAc-DCM) to give a pale yellow oil, 2.2 g, 61%. LC-MS; Method A (Acidic); Rt=3.29, m/z 879.6 (MH$^+$).

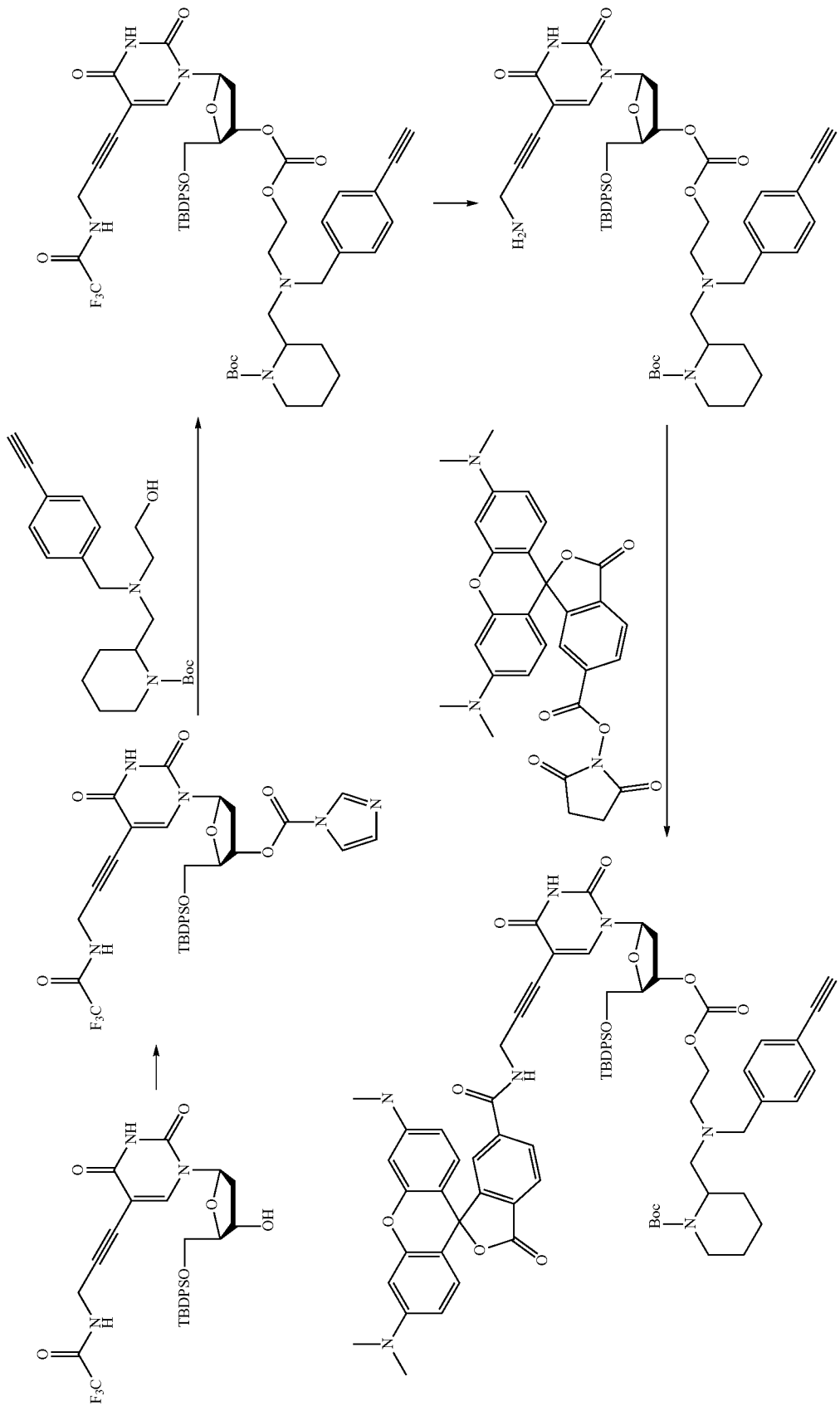

Example 11

Example 11A: 1-((2R,4S,5R)-5-(((tert-butyldiphenylsilyl)oxy)methyl)-4-hydroxytetrahydrofuran-2-yl)-5-iodopyrimidine-2,4(1H,3H)-dione

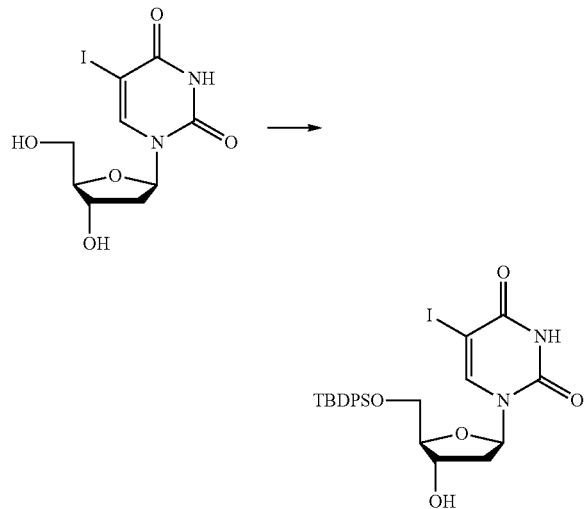

2'-Deoxy-5-iodouridine (5 g, 14 mmol) and imidazole (2.9 g, 42 mmol, 3 eq.) were dissolved in DMF (80 mL) and the solution was cooled in an ice-bath and TBDPSCl (4.2 g, 17 mmol, 1.2 eq.) was added. The solution was warmed to rt and stirred for 2 h after which time the reaction had gone to completion by LC-MS. A water/EtOAc/Brine workup was carried out, the organic layer was dried (MgSO₄) and the solvent was removed to give a pale yellow oil. EtOAc and petrol were added to induce crystallisation and the resulting solid was filtered off with petrol-EtOAc washing to give the product as a white crystalline solid, 5.5 g, 69%. 2016_06_01_012, rt. 2.54, found 593.0, 98% pure. LC-MS; Method A (Acidic); Rt=2.52, m/z 593.0 (MH⁺).

Example 11B: N-(3-(1-((2R,4S,5R)-5-(((tert-butyldiphenylsilyl)oxy)methyl)-4-hydroxytetrahydrofuran-2-yl)-2,4-dioxo-1,2,3,4-tetrahydropyrimidin-5-yl)prop-2-yn-1-yl)-2,2,2-trifluoroacetamide

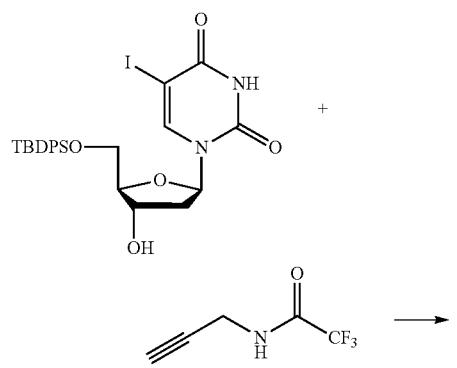

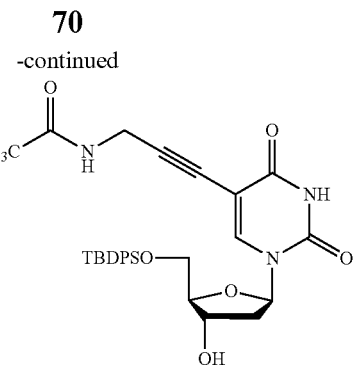

1-((2R,4S,5R)-5-(((tert-butyldiphenylsilyl)oxy)methyl)-4-hydroxytetrahydrofuran-2-yl)-5-iodopyrimidine-2,4(1H,3H)-dione (5 g, 8.4 mmol), 2,2,2-trifluoro-N-(prop-2-yn-1-yl)acetamide (3.8 g, 25.2 mmol, 3 eq.), tetrakis(triphenylphosphine)palladium(0) (1 g, 0.84 mmol, 0.1 eq.), triethylamine (2 mL, 16.8 mmol, 2 eq.) and copper iodide (325 mg, 1.7 mmol, 0.2 eq.) were dissolved in anhydrous DMF (80 mL) under $N_2$ and the reaction mixture was heated briefly in a hot water bath (40° C.), then stirred at rt for 30 minutes. After this time the reaction was complete by LC-MS. A water/EtOAc/brine workup was carried out, the organic solution was dried (MgSO₄) and the solvent was removed under reduced pressure. The resulting oil was purified by silica chromatography (0-100% EtOAc-petrol, then 0-5% DCM-Methanol) to give the product as an off-white solid, 3 g, 60%. LC-MS; Method A (Acidic); Rt=2.45, m/z 616.2 (MH⁺).

Example 11C: tert-Butyl 2-(((2-(((((2R,3S,5R)-2-(((tert-butyldiphenylsilyl)oxy)methyl)-5-(2,4-dioxo-5-(3-(2,2,2-trifluoroacetamido)prop-1-yn-1-yl)-3,4-dihydropyrimidin-1(2H)-yl)tetrahydrofuran-3-yl)oxy)carbonyl)oxy)ethyl)(4-ethynylbenzyl)amino)methyl)piperidine-1-carboxylate

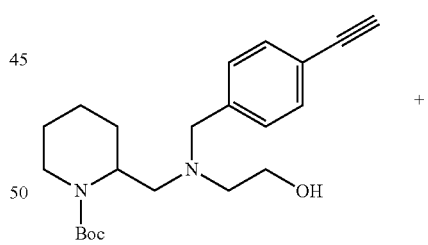

+

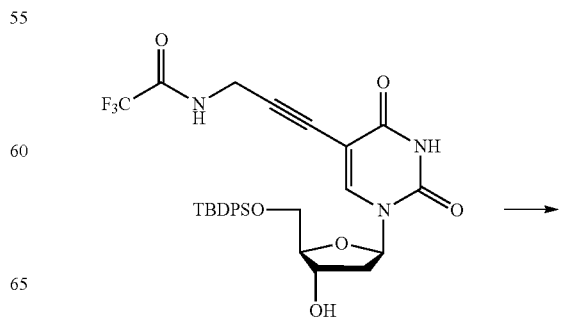

71

-continued

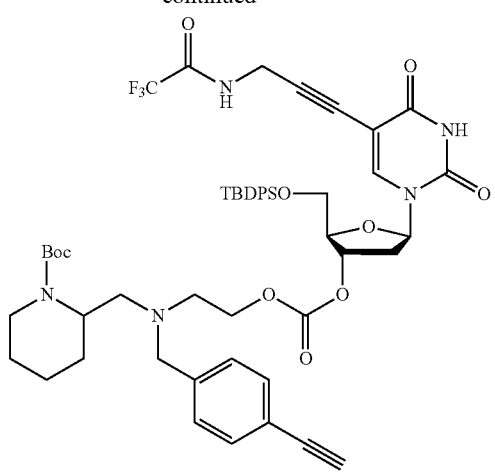

N-(3-(1-((2R,4S,5R)-5-(((tert-Butyldiphenylsilyl)oxy) methyl)-4-hydroxytetrahydrofuran-2-yl)-2,4-dioxo-1,2,3,4-tetrahydropyrimidin-5-yl)prop-2-yn-1-yl)-2,2,2-trifluoroacetamide (2.3 g, 3.7 mmol) and CDI (720 mg, 4.4 mmol, 1.2 eq.) were dissolved in acetonitrile (100 mL) and the solution was stirred under $N_2$ overnight. After this time tert-butyl 2-(((4-ethynylbenzyl)(2-hydroxyethyl)amino)methyl) piperidine-1-carboxylate (1.4 g, 3.7 mmol) and DBU (1.1 mL, 7.4 mmol, 2 eq.) were added and the solution was stirred at rt. After 30 minutes the reaction had gone to completion by LC-MS. An ethyl acetate/water workup was carried out and the crude product was purified by silica chromatography (0-100% EtOAc-DCM) to give a pale yellow foam, 900 mg, 23%. LC-MS; Method A (Acidic); Rt=3.22, m/z 1014.5 (MH⁺).

Example 11D: tert-Butyl 2-(((2-(((((2R,3S,5R)-5-(5-(3-aminoprop-1-yn-1-yl)-2,4-dioxo-3,4-dihydropyrimidin-1(2H)-yl)-2-(((tert-butyldiphenylsilyl)oxy) methyl)-tetrahydrofuran-3-yl) oxy)carbonyl)oxy) ethyl) (4-ethynylbenzyl)amino)methyl)piperidine-1-carboxylate

72

-continued

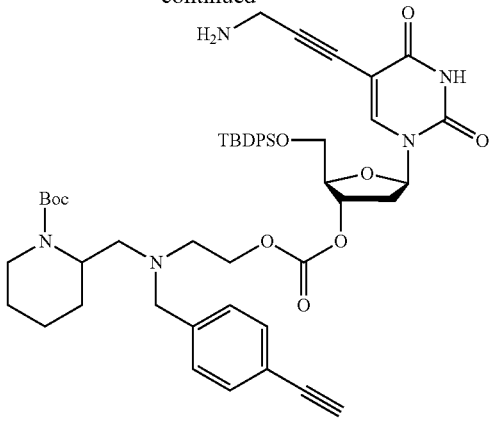

tert-Butyl 2-(((2-(((((2R,3S,5R)-2-((tert-butyldiphenylsilyl)oxy)methyl)-5-(2,4-dioxo-5-(3-(2,2,2-trifluoroacetamido) prop-1-yn-1-yl)-3,4-dihydropyrimidin-1(2H)-yl)tetrahydrofuran-3-yl)oxy)carbonyl)oxy)ethyl)(4-ethynylbenzyl) amino)methyl)piperidine-1-carboxylate (500 mg, 0.1 mmol) was dissolved in 1:1 25% aqueous ammonia:acetonitrile (20 mL). After 4 h at rt the solvent was removed under reduced pressure and the residue was purified by silica chromatography (0-70% EtOAc-DCM, then 0-10% MeOH-DCM) to give the product as a pale yellow foam, 280 mg, 62%. LC-MS; Method A (Acidic); Rt=2.32, m/z 918.6 (MH⁺).

Example 11E: tert-Butyl 2-(((2-(((((2R,3S,5R)-5-(5-(3-(3',6'-bis(dimethylamino)-3-oxo-3H-spiro[isobenzofuran-1,9'-xanthene]-6-carboxamido)prop-1-yn-1-yl)-2,4-dioxo-3,4-dihydropyrimidin-1(2H)-yl)-2-(((tert-butyldiphenylsilyl)oxy)methyl) tetrahydrofuran-3-yl)oxy)carbonyl)oxy)ethyl)(4-ethynylbenzyl)amino)methyl)piperidine-1-carboxylate

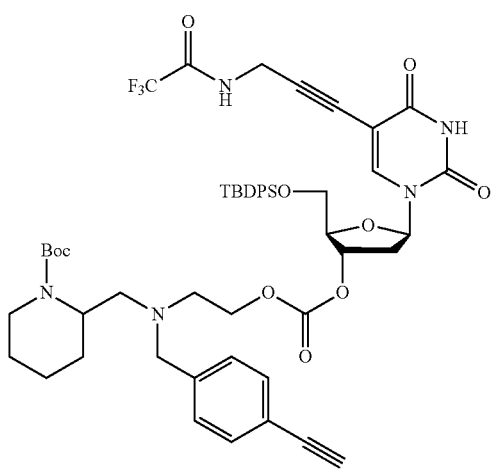

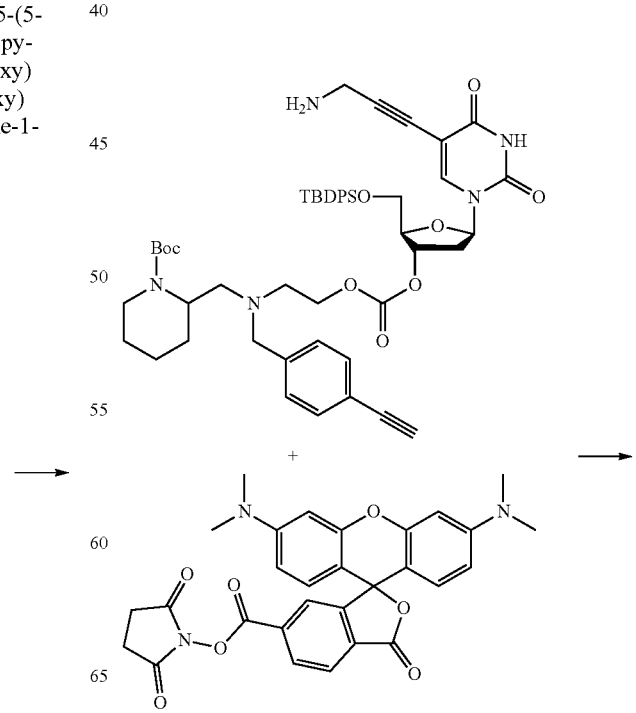

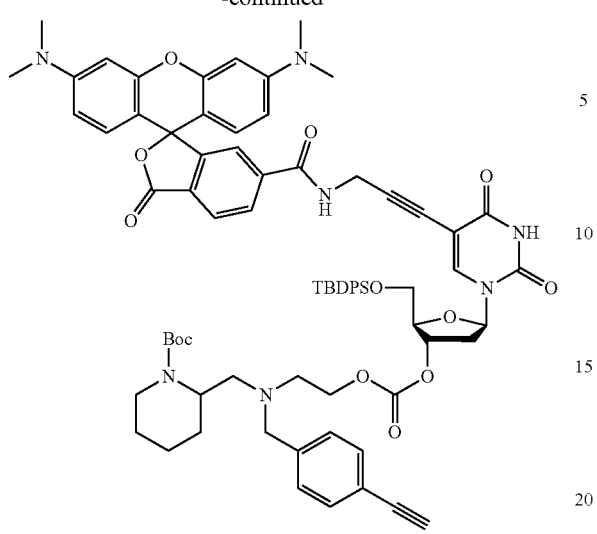

tert-Butyl 2-(((2-(((((2R,3S,5R)-5-(5-(3-aminoprop-1-yn-1-yl)-2,4-dioxo-3,4-dihydro pyrimidin-1(2H)-yl)-2-(((tert-butyldiphenylsilyl)oxy)methyl)tetrahydrofuran-3-yl)oxy)carbonyl)oxy)ethyl) (4-ethynylbenzyl)amino)methyl) piperidine-1-carboxylate (110 mg, 0.12 mmol) was dissolved in DMF (10 mL) and 6-TAMRA N-succinimidyl ester (63 mg, 0.120 mmol) and Hunig's Base (50 µL, 0.24 mmol, 2 eq.) were added. The solution was stirred overnight, after which time the reaction had gone cleanly to completion by LC-MS. The solvent was removed under reduced pressure and the residue was purified by silica chromatography (0-20% Methanol-DCM) to give the product as a purple solid, 146 mg, 91%. LC-MS; Method A (Acidic); Rt=2.57, m/z 666.2 (% M+).

Example 11F: TAMRA Dye-Tagged 5'-O-TBDPS-Thymidine Attached to Magnetic Beads Via Boc-Protected Linker

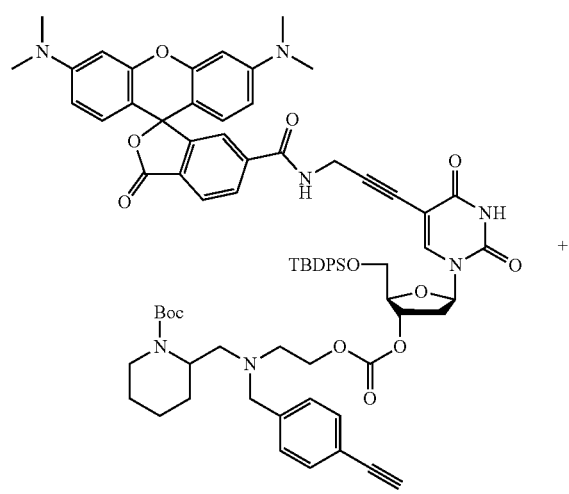

+

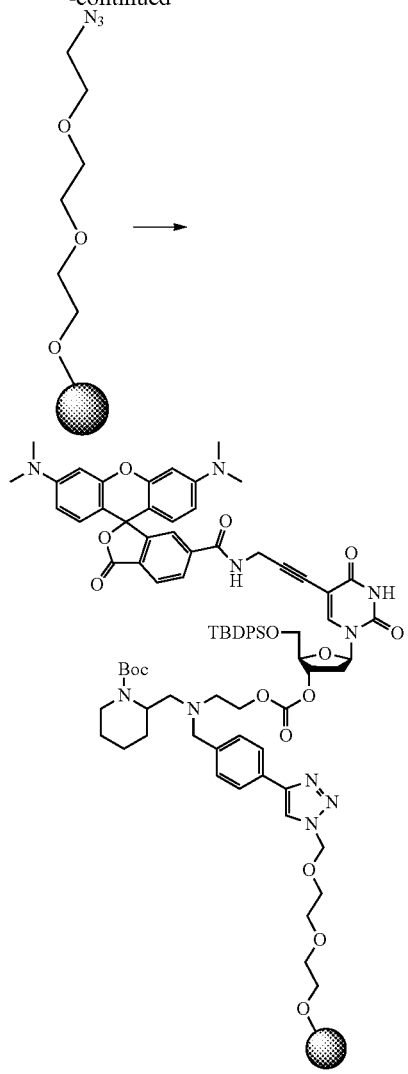

The beads (azide magnetic beads from Kerafast, 1 µm, 30-50 nmol azide groups per mg) were suspended in a solution of tert-Butyl 2-(((2-(((((2R,3S,5R)-5-(5-(3-(3',6'-bis(dimethylamino)-3-oxo-3H-spiro[isobenzofuran-1,9'-xanthene]-6-carboxamido)prop-1-yn-1-yl)-2,4-dioxo-3,4-dihydropyrimidin-1(2H)-yl)-2-(((tert-butyldiphenylsilyl)oxy)methyl)tetrahydrofuran-3-yl)oxy)carbonyl)oxy)ethyl) (4-ethynylbenzyl)amino)methyl)piperidine-1-carboxylate (6.6 mg, 5 µmol, 10 eq.) in THF (0.5 mL), and a portion was removed to use as a control reaction with no click reagents added. To the main reaction mixture was added aqueous copper sulfate solution (0.1 M, 25 µL, 2.5 µmol) and aqueous sodium ascorbate solution (0.1 M, 50 µL, 5 µmol) and this mixture was stirred vigorously for 3 days. After this time an identical series of washes were carried out on both sets of beads; 3×THF, 3×DCM, 3×MeOH, 2×THF, 2×MeOH and 2×DCM. Examination with a fluorescent microscope confirmed that the click reaction had successfully taken place in the presence of copper catalyst, but not without copper, and the reacted beads were therefore strongly fluorescent. Furthermore the beads treated with alkyne and catalyst were red, whereas the untreated beads remained brown.

Example 12

Thermally Mediated Cleavage of TAMRA Dye-Tagged 5'-O-TBDPS-Thymidine from Surface of Beads.

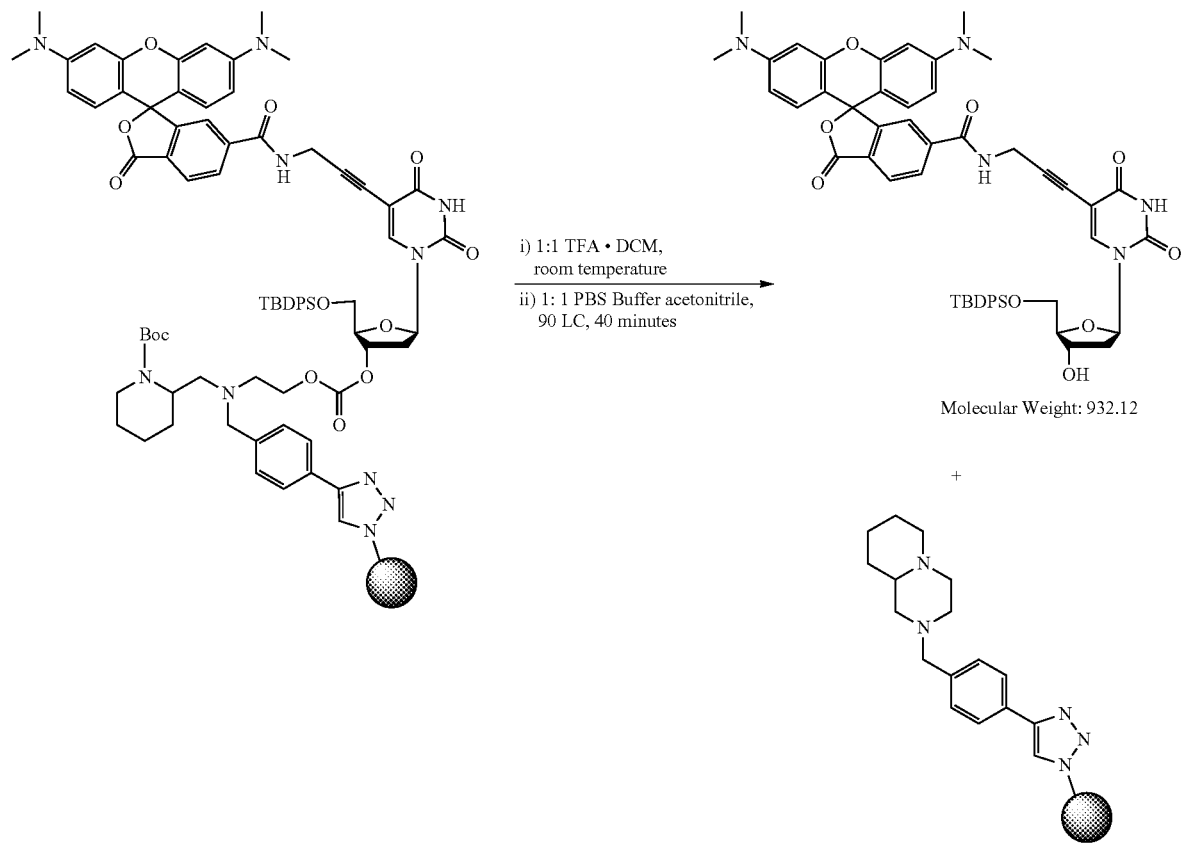

Molecular Weight: 932.12 i) The coated beads were stirred vigorously in TFAA: DCM (1:2) at rt for 2 h. After this time the beads were still red and no cleaved TAMRA-tagged TBPDS-Thymidine was detected in an LC-MS sample of the reaction solution. The beads were then washed with 3×DCM, 3×MeOH, and then 10% Hunig's Base-DCM in order to remove any excess TFAA.

ii) 1 mL of a 1:1 pH 7.4 solution of PBS Buffer and acetonitrile plus 2-3 drops of Hunig's Base was added to the beads and they were heated in a hot-water bath at 90° C. for 40 minutes. After this time an LC-MS of the reaction solution showed a clear signal for cleaved TAMRA-tagged TBPDS-Thymidine. The beads were washed (3×acetonitrile, 3×MeOH) and examined with a fluorescent microscope, which showed that the fluorescent signal was now much reduced. Furthermore, the beads had reverted to their original brown colour.

Example 13

Experiments on 5'-Protected Thymidine

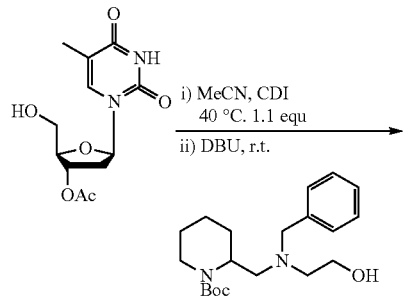

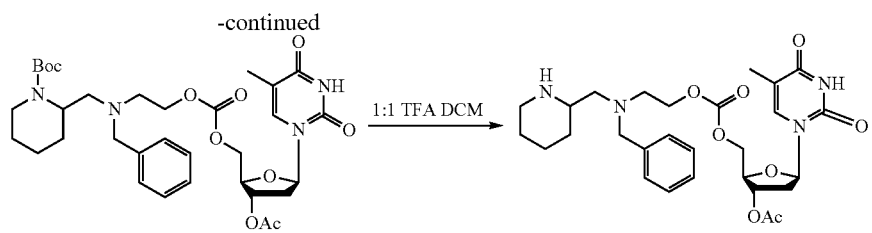

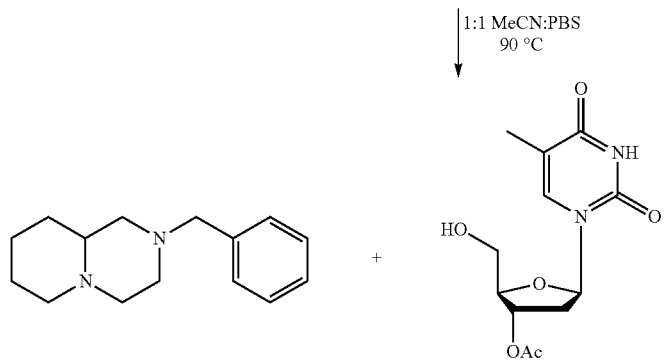

Example 13A: tert-Butyl 2-(((2-(((((2R,3S,5R)-3-acetoxy-5-(5-methyl-2,4-dioxo-3,4-dihydropyrimidin-1(2H)-yl)tetrahydrofuran-2-yl)methoxy)carbonyl)oxy)ethyl)-(benzyl)amino)methyl)piperidine-1-carboxylate

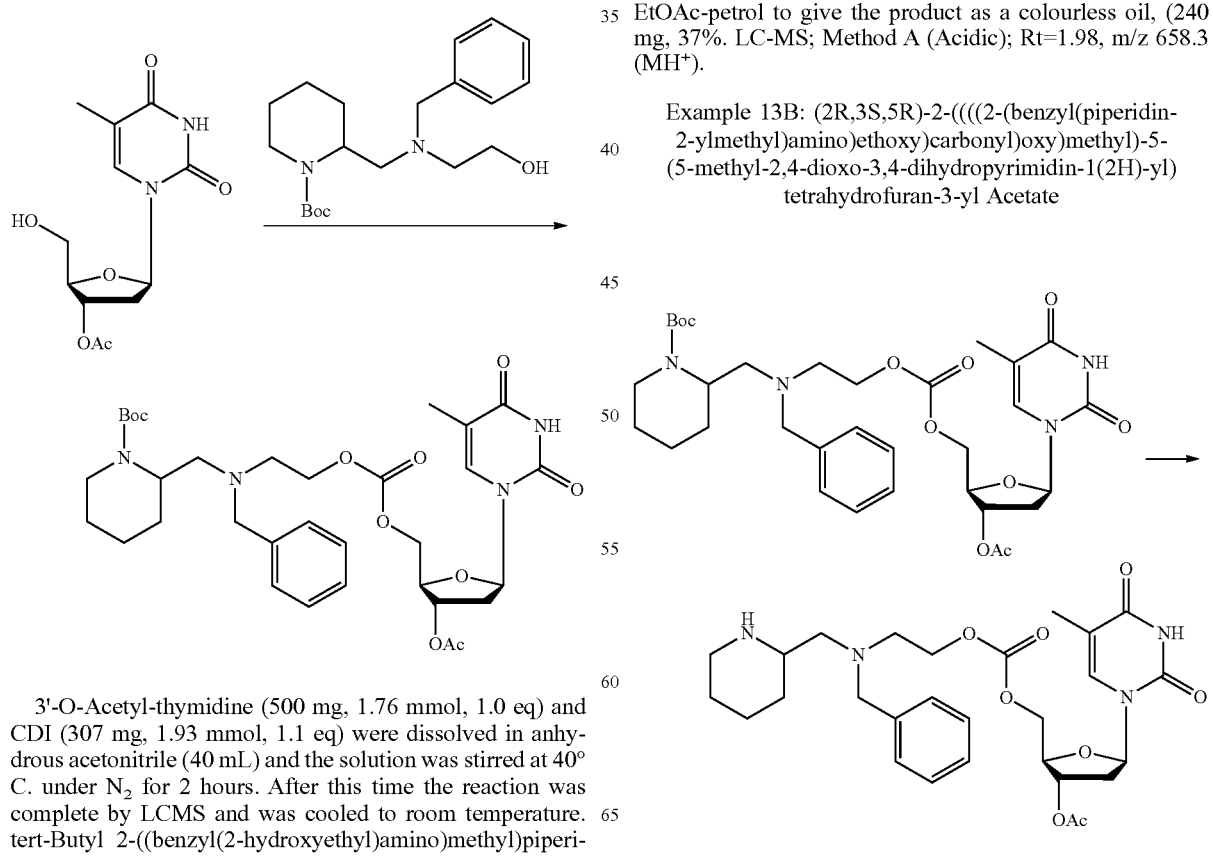

3'-O-Acetyl-thymidine (500 mg, 1.76 mmol, 1.0 eq) and CDI (307 mg, 1.93 mmol, 1.1 eq) were dissolved in anhydrous acetonitrile (40 mL) and the solution was stirred at 40° C. under $N_2$ for 2 hours. After this time the reaction was complete by LCMS and was cooled to room temperature. tert-Butyl 2-((benzyl(2-hydroxyethyl)amino)methyl)piperidine-1-carboxylate (673 mg, 1.93 mmol) and DBU (0.28 mL, 1.93 mmol, 1.1 eq.) were then added and the solution was stirred at room temperature for 18 hours. Solvent was removed in vacuo to give a brown oil which was partitioned between water (50 mL) and EtOAc (50 mL) and the layers were separated. The aqueous layer was back extracted with EtOAc (2×50 mL). The combined organic layers was dried (MgSO$_4$) and the solvent was removed. The resulting oil was purified by silica chromatography, eluting with 0-50% EtOAc-petrol to give the product as a colourless oil, (240 mg, 37%. LC-MS; Method A (Acidic); Rt=1.98, m/z 658.3 (MH$^+$).

Example 13B: (2R,3S,5R)-2-((((2-(benzyl(piperidin-2-ylmethyl)amino)ethoxy)carbonyl)oxy)methyl)-5-(5-methyl-2,4-dioxo-3,4-dihydropyrimidin-1(2H)-yl)tetrahydrofuran-3-yl Acetate tert-Butyl 2-(((2-(((((2R,3S,5R)-3-acetoxy-5-(5-methyl-2,4-dioxo-3,4-dihydropyrimidin-1(2H)-yl)tetrahydrofuran-2-yl)methoxy)carbonyl)oxy)ethyl)(benzyl)amino)methyl)piperidine-1-carboxylate (100 mg, 0.15 mmol) was dissolved in dichloromethane (2 mL) and trifluoroacetic acid (2 mL), and the solution was stirred at room temperature for 1 h. After this time the reaction was complete by LC-MS. The solvent was removed and dichloromethane (50 mL) and saturated aqueous NaHCO$_3$(50 mL) were added and the layers were separated. The organic layer was dried (MgSO$_4$) and the solvent was removed under reduced pressure at 20° C. to give a colourless oil which was co evaporated with diethyl ether to give the product as a white solid (40 mg, 47%. LC-MS; Method B (Basic); Rt=1.51, m/z 558 (MH$^+$).

Example 14

Time Course Experiments for Cleavage of the 5'-Protected 3' O-Acetyl-Thymidine (Compound of Example 131B)

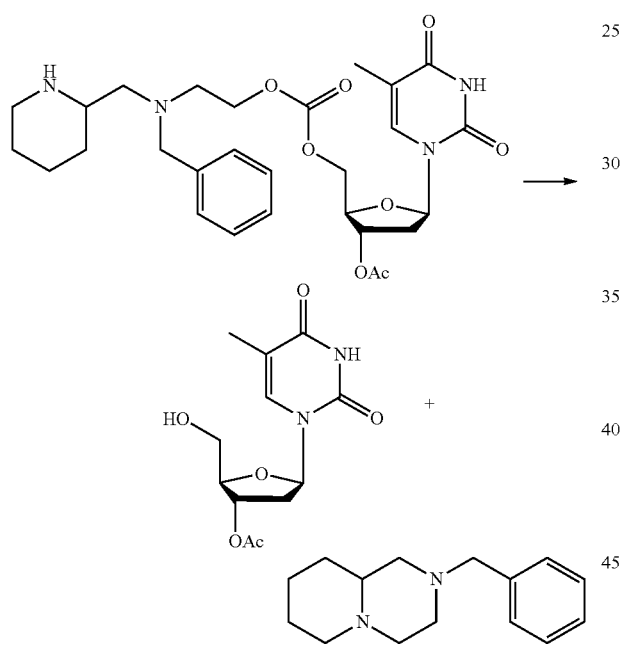

The standard conditions for time course experiments at high and low temperatures were adhered to with the exception of the concentration being 10 mg/ml of (2R,3S,5R)-2-(((((2-(benzyl(piperidin-2-ylmethyl)amino)ethoxy)carbonyl)oxy)methyl)-5-(5-methyl-2,4-dioxo-3,4-dihydropyrimidin-1(2H)-yl)tetrahydrofuran-3-yl acetate in MeCN.

The aim of this study was to demonstrate that the thermal and pH-controlled safety-catch molecule could be used as a protecting group for the 5'-position of a nucleoside. The study showed that the molecule is an effective safety-catch protecting group at this position and would therefore be suitable for use oligonucleotide synthesis. Thus, as shown in FIG. 15, the compound is stable at room temperature, with fast and clean cleavage to release 3'-O-acetyl-thymidine being readily effected at 90° C.

In a similar manner, the safety-catch compounds can be attached to functional groups in other compounds, e.g. as protecting groups, or release-modifying groups in other applications as discussed above.

Example 15

Synthesis of a Bsmoc-Locked 5'-Thymidine (Example 15A) and Removal of Bsmoc Under Cold Basic Conditions with Minimal Cyclisation-Mediated Deprotection (Example 15B)

Example 15A: (1,1-Dioxidobenzo[b]thiophen-2-yl) methyl 2-(((2-(((((2R,3S,5R)-3-acetoxy-5-(5-methyl-2,4-dioxo-3,4-dihydropyrimidin-1(2H)-yl) tetrahydrofuran-2-yl)methoxy)carbonyl)oxy)ethyl) (4-ethynylbenzyl)amino)methyl)piperidine-1-carboxylate

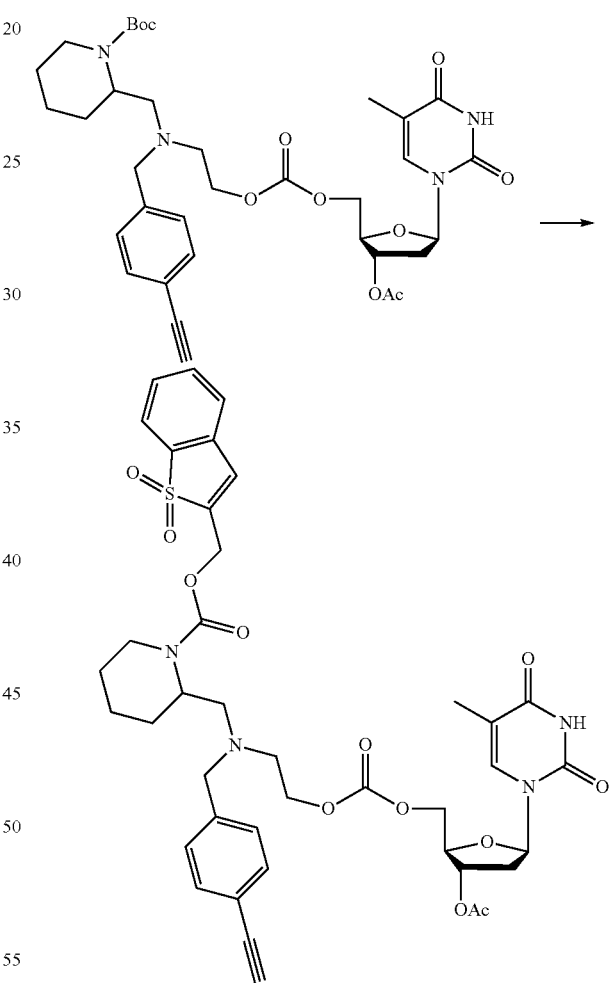

Tert-Butyl 2-(((2-(((((2R,3S,5R)-3-acetoxy-5-(5-methyl-2,4-dioxo-3,4-dihydropyrimidin-1(2H)-yl)tetrahydrofuran-2-yl)methoxy)carbonyl)oxy)ethyl)(4-ethynylbenzyl)amino) methyl)piperidine-1-carboxylate (80 mg, 0.12 mmol) was dissolved in 1:1 TFA-DCM (10 mL) at rt. After 1 h the reaction was complete by LC-MS. The excess TFA was removed under reduced pressure and sat. aq. NaHCO$_3$ (50 mL) and DCM (50 mL) were added. The layers were separated and the organic layer was washed with brine (50 mL), dried (MgSO$_4$) and the solvent removed to give the free amine as a colourless oil. This oil was dissolved in DCM (10 mL) and Hunig's base (62 µL, 0.35 mmol, 2 eq.) was added, followed by 1,1-dioxobenzo[b]thiophen-2-ylmethyl chloride (36 mg, 0.14 mmol, 1.2 eq.). After 1 h the reaction was complete by tlc, (10% MeOH-DCM). Water (50 mL) and DCM (50 mL) were added, the layers were separated and the organic layer was dried (MgSO$_4$). The solvent was removed under reduced pressure and the crude product was purified by silica chromatography (0-60% EtOAC-petrol) to give the product as a colourless oil (68 mg, 67%). LC-MS; Method A (Acidic); Rt=2.08, m/z 805 (MH$^+$).

Example 15B: (2R,3S,5R)-2-((((2-((4-Ethynylbenzyl)(piperidin-2-ylmethyl)amino)ethoxy)carbonyl)oxy)methyl)-5-(5-methyl-2,4-dioxo-3,4-dihydropyrimidin-1(2H)-yl)tetrahydrofuran-3-yl Acetate

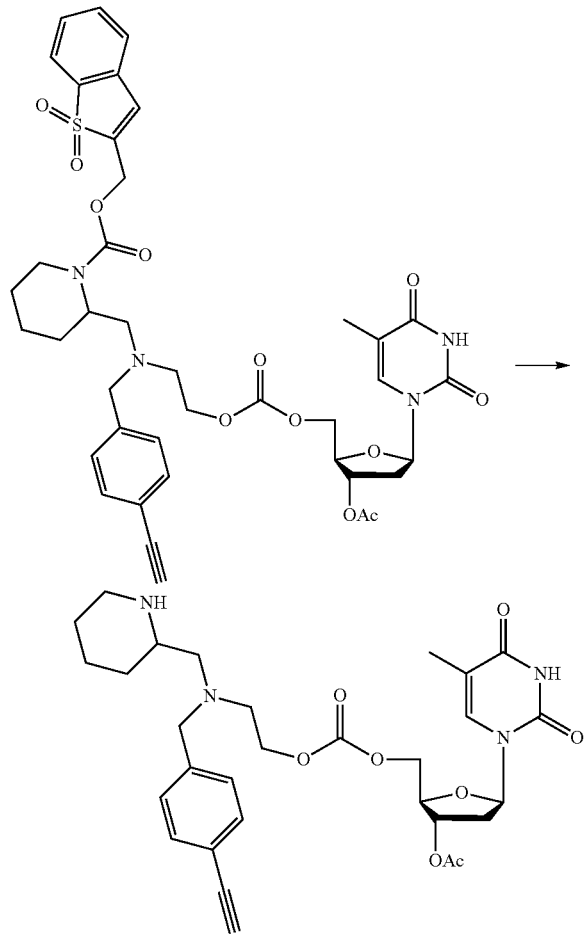

(1,1-Dioxidobenzo[b]thiophen-2-yl)methyl 2-(((2-(((((2R,3S,5R)-3-acetoxy-5-(5-methyl-2,4-dioxo-3,4-dihydropyrimidin-1(2H)-yl)tetrahydrofuran-2-yl)methoxy)carbonyl)oxy)ethyl)(4-ethynylbenzyl)amino)methyl)piperidine-1-carboxylate (0.5 mg, 6.2 µmol) was dissolved in 2% piperidine in acetonitrile (1 mL) at 20° C. After 5 minutes the reaction had gone cleanly to completion by LC-MS to give the deprotected product (LC-MS; Method A (Acidic); Rt=1.55, m/z 583 (MH$^+$)., with no cleavage of the carbonate ester observed. After 1 hour at 20° C. there was no change in the reaction mixture profile by LC-MS. After 19 h at 20° C. there was 17% conversion to the deprotected 3'-acetyl thymidine by cyclisation of the linker molecule (LC-MS; Method A (Acidic); Rt=1.28, m/z 307 (M+Na$^+$).

Example 16

Synthesis and Time-Course Studies on Deoxyguanosine

Example 16A: 2-Amino-9-((2R,4S,5R)-5-(((tert-butyldiphenylsilyl)oxy)methyl)-4-hydroxytetrahydrofuran-2-yl)-1,9-dihydro-6H-purin-6-one

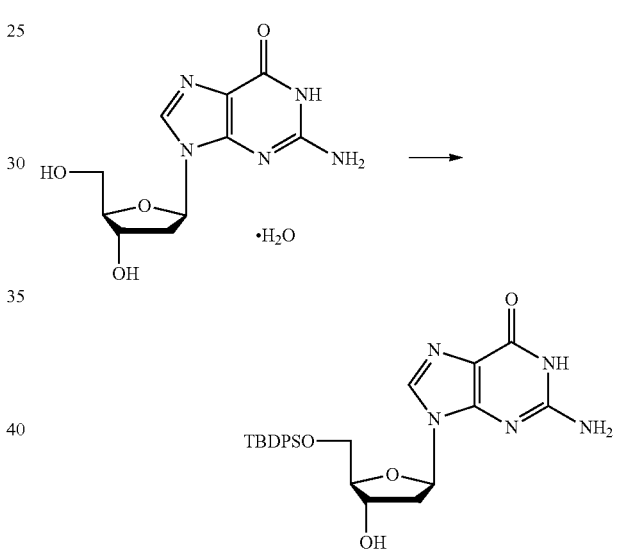

Deoxyguanosine monohydrate (2 g, 7.5 mmol), tert-butyldiphenylsilyl chloride (2.5 g, 9 mmol, 1.2 eq.), imidazole (952 mg, 14 mmol, 2 eq.) and DMAP (100 mg) were dissolved in DMF (80 mL) and the solution was stirred overnight. After this time there was still 30% starting material, hence another 0.5 eq. of tert-butyldiphenylsilyl chloride was added. After 30 minutes ethyl acetate (500 mL) and water (400 mL) were added and the layers were separated. The organic layer was washed with brine (300 mL) and the solvent was removed under reduced pressure. The resulting solid was triturated with ethyl acetate and methanol to give the product as a white crystalline solid (3.2 g, 84%). (LC-MS; Method A (Acidic); Rt=2.05, m/z 506 (MH$^+$). $^1$H NMR (400 MHz, CDCl$_3$) δ ppm: 7.70 (2H, m), 7.64-7.52 (5H, m), 7.42-7.35 (4H, m), 6.13 (1H, m), 4.60 (1H, m), 3.76 (1H, m), 2.99 (1H, s), 2.86 (1H, s), 1.82 (4H, m), 1.06 (2H, m), 1.01 (9H, s), 0.89 (2H, m)

Example 16B: Allyl 2-(((2-(((((2R,3S,5R)-5-(2-amino-6-oxo-1,6-dihydro-9H-purin-9-yl)-2-(((tert-butyldiphenylsilyl)oxy)methyl)tetrahydrofuran-3-yl)oxy)carbonyl)oxy)ethyl)(4-ethynylbenzyl)amino)methyl)piperidine-1-carboxylate

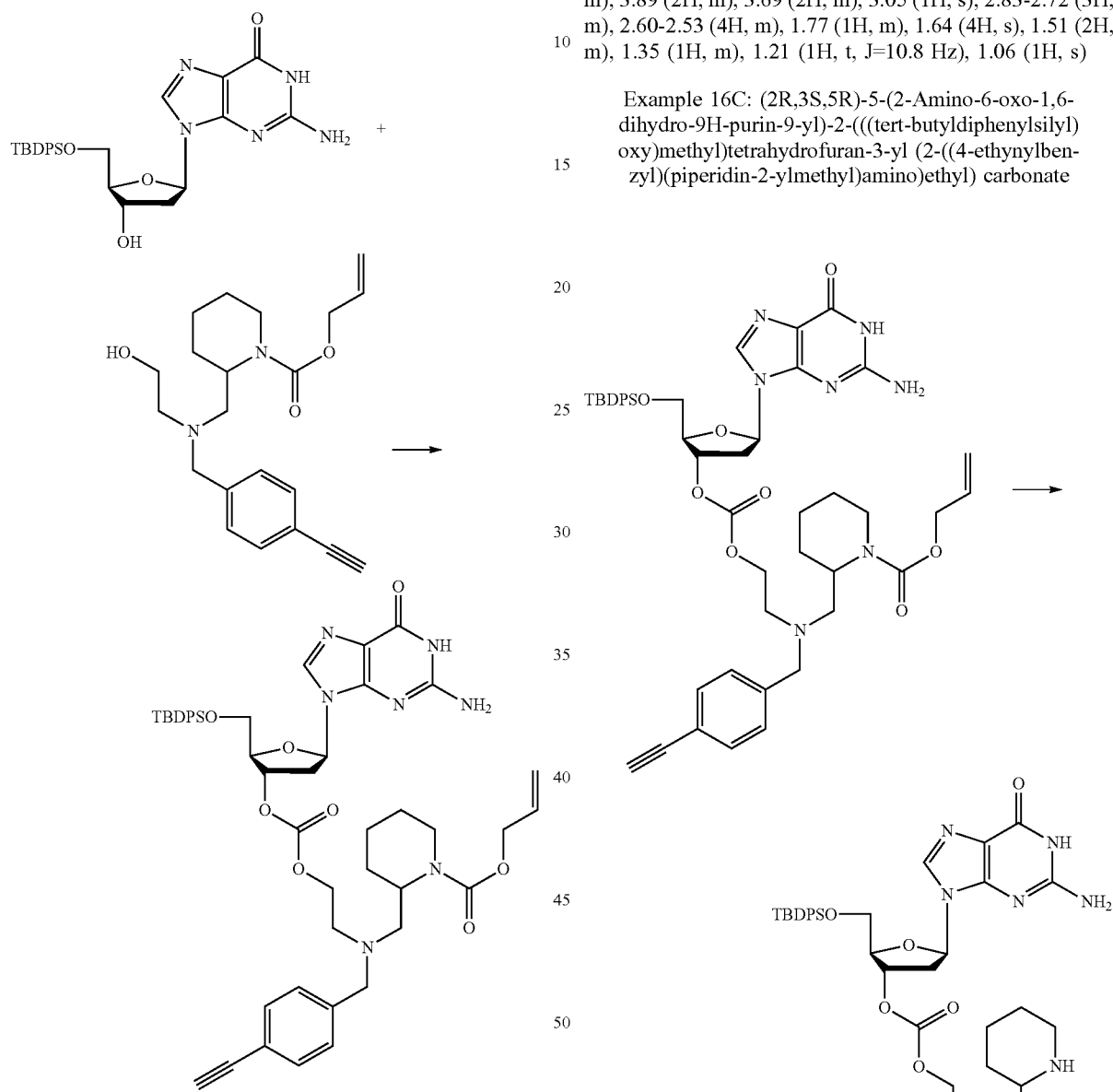

Allyl 2-(((4-ethynylbenzyl)(2-hydroxyethyl)amino)methyl)piperidine-1-carboxylate (352 mg, 0.28 mmol) was dissolved in anhydrous acetonitrile (60 mL0 and CDI (194 mg, 1.2 mmol, 1.2 eq.) was added under $N_2$. The reaction was stirred overnight, after which time the desired intermediate had formed by LC-MS. 2-Amino-9-((2R,4S,5R)-5-(((tert-butyldiphenylsilyl)oxy)methyl)-4-hydroxytetrahydrofuran-2-yl)-1,9-dihydro-6H-purin-6-one was added (500 mg, 1 mmol), followed by DBU (0.3 mL, 2 mmol, 2 eq.) and the solution was heated at 45° C. for 2 hours. After this time water (100 mL) and ethyl acetate (300 mL) were added and the layers were separated. The organic layer was dried ($MgSO_4$) and the solvent was removed under reduced pressure. The resulting oil was purified by silica chromatography, eluting with 0-10% methanol-DCM to give the product as a white foam, 200 mg, 25%. LC-MS; Method A (Acidic); Rt=2.84, m/z 878 ($MH^+$). $^1H$ NMR (400 MHz, $CDCl_3$) δ ppm: 7.65-7.62 (5H, m), 7.42-7.32 (9H, m), 7.26 (1H, s), 6.22 (1H, m), 5.86 (2H, m), 5.42 (1H, d, J=4.8 Hz), 5.28 (1H, m), 5.18 (1H, d, J=10.4 Hz), 4.57 (2H, m), 4.21 (3H, m), 3.89 (2H, m), 3.69 (2H, m), 3.05 (1H, s), 2.83-2.72 (3H, m), 2.60-2.53 (4H, m), 1.77 (1H, m), 1.64 (4H, s), 1.51 (2H, m), 1.35 (1H, m), 1.21 (1H, t, J=10.8 Hz), 1.06 (1H, s)

Example 16C: (2R,3S,5R)-5-(2-Amino-6-oxo-1,6-dihydro-9H-purin-9-yl)-2-(((tert-butyldiphenylsilyl)oxy)methyl)tetrahydrofuran-3-yl (2-((4-ethynylbenzyl)(piperidin-2-ylmethyl)amino)ethyl) carbonate Allyl 2-(((2-(((((2R,3S,5R)-5-(2-amino-6-oxo-1,6-dihydro-9H-purin-9-yl)-2-(((tert-butyldiphenylsilyl)oxy)methyl)tetrahydrofuran-3-yl)oxy)carbonyl)oxy)ethyl)(4-ethynylbenzyl)amino)methyl)piperidine-1-carboxylate (100 mg, 0.12 mmol) and dimedone (84 mg, 0.6 mmol, 5 eq.)

were dissolved in anhydrous THF (10 mL) and the solution was purged of oxygen by bubbling through nitrogen for 10 minutes. Tetrakis(triphenylphosphine)paladium(0) (13 mg, 0.012 mmol, 0.1 eq.) was added and the resulting yellow solution was re-purged of oxygen. After 1 h the reaction had gone cleanly to completion by LC-MS. Ethyl acetate (100 mL) and sat. aq. sodium bicarbonate (50 mL) were added and the layers were separated. The organic layer was dried (MgSO$_4$) and the solvent was removed under reduced pressure. The resulting oil was purified by silica chromatography, eluting with 0-20% methanol-DCM to give the product as a white foam, 46 mg, 50%. LC-MS; Method A (Acidic); Rt=2.03, m/z 805 (MH$^+$).

Example 16D: tert-Butyl 2-(((2-(((((2R,3S,5R)-3-acetoxy-5-(2-isobutyramido-6-oxo-1,6-dihydro-9H-purin-9-yl)tetrahydrofuran-2-yl)methoxy)carbonyl)oxy)ethyl)(4-ethynylbenzyl)amino)methyl)piperidine-1-carboxylate

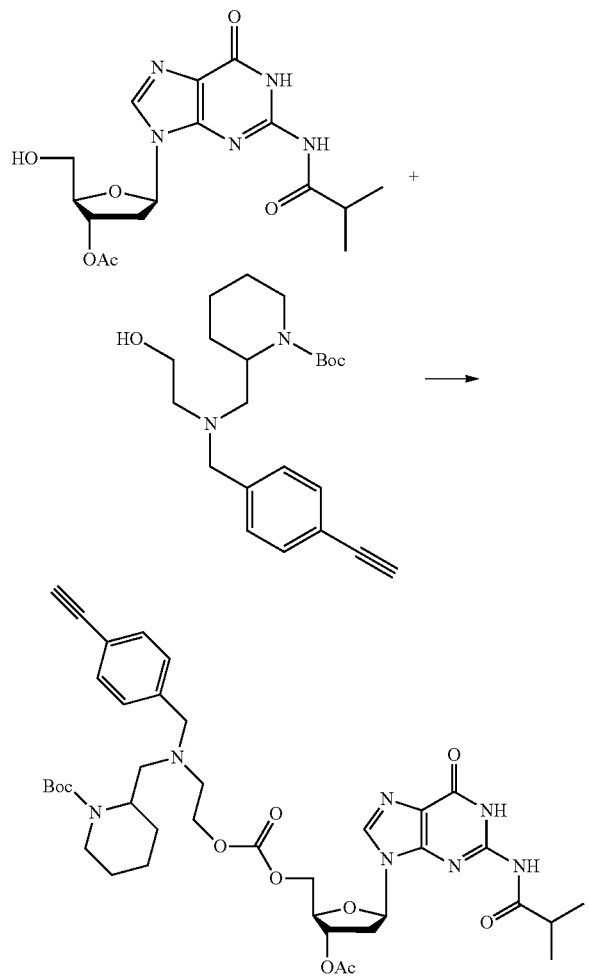

3'-(O-acetyl)-2'-deoxyguanosine (N-Bu) (500 mg, 1.3 mmol) was dissolved in anhydrous acetonitrile (60 mL) and CDI (256 mg, 1.6 mmol, 1.2 eq.) was added under N$_2$. The reaction was stirred for 1 hour, after which time the desired intermediate had formed by LC-MS. Allyl 2-(((4-ethynyl-benzyl)(2-hydroxyethyl)amino)methyl)piperidine-1-carboxylate (352 mg, 0.28 mmol) was added, followed by DBU (0.3 mL, 2 mmol, 2 eq.) and the solution was heated at 45° C. for 2 hours. After this time water (100 mL) and ethyl acetate (300 mL) were added and the layers were separated. The organic layer was dried (MgSO$_4$) and the solvent was removed under reduced pressure. The resulting oil was purified by silica chromatography, eluting with 0-10% methanol-DCM to give the product as a white foam, 200 mg, 25%. LC-MS; Method A (Acidic); Rt=2.84, m/z 778 (MH$^+$). $^1$H NMR (400 MHz, CDCl$_3$) δ ppm: 7.73 (1H, m), 7.40 (2H, d, J=8.4 Hz), 7.24 (d, J=8.0 Hz), 6.18 (1H, q, dd, J=6.0, 8.0 Hz), 5.44 (1H, d, J=5.6 Hz), 4.67 (1H, m), 4.40 (1H, quin), 4.34 (1H, m), 3.73 (1H, d, J=13.6 Hz), 3.57 (1H, d, J=14 Hz), 3.03 (2H, m), 2.85 (1H, m), 2.77 (1H, m), 2.60 (1H, m), 2.47 (2H, m), 2.12 (3H, s), 1.75 (1H, m), 1.58 (6H, s), 1.50-1.39 (12H, m), 1.24 (6H, t, J=6.8 Hz), 1.39 (1H, m)

Example 16E: (2R,3S,5R)-2-((((2-((4-Ethynylbenzyl)(piperidin-2-ylmethyl)amino)ethoxy)carbonyl)oxy)methyl)-5-(2-isobutyramido-6-oxo-1,6-dihydro-9H-purin-9-yl)tetrahydrofuran-3-yl Acetate

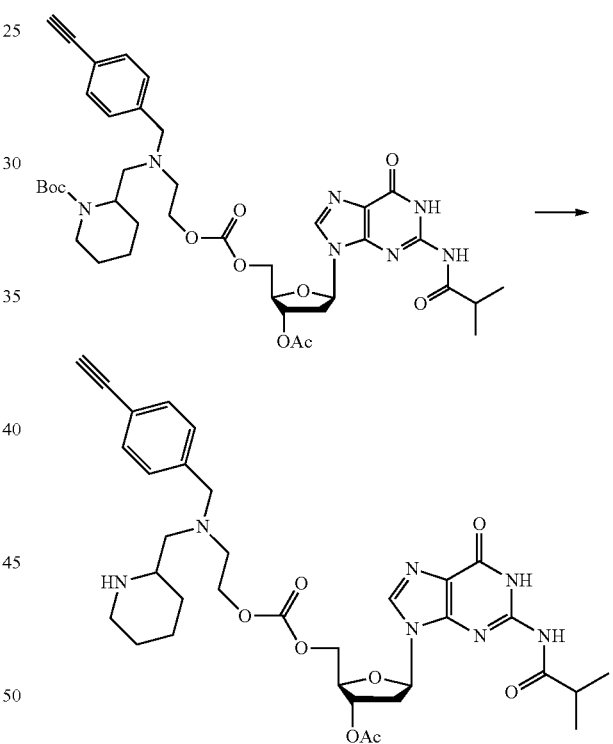

tert-Butyl 2-(((2-(((((2R,3S,5R)-3-acetoxy-5-(2-isobutyramido-6-oxo-1,6-dihydro-9H-purin-9-yl)tetrahydrofuran-2-yl)methoxy)carbonyl)oxy)ethyl)(4-ethynylbenzyl)amino)methyl)piperidine-1-carboxylate (50 mg, 0.06 mmol) was dissolved in 1:1 trifluoroacetic acid and dichloromethane (1 mL) at rt. After 1 hour clean conversion to the desired Boc-deprotected product was observed by LC-MS. The excess trifluoroacetic acid was removed under reduced pressure and dichloromethane (20 mL) and saturated aq. sodium bicarbonate were added. The layers were separated and the organic layer was dried (MgSO$_4$). The crude oil was purified by silica chromatography (0-10% MeOH-DCM) to give the product as a pale yellow foam, 20 mg, 50%. LC-MS; Method A (Acidic); Rt=1.67, m/z 678 (MH$^+$).

Example 16F: Time Course Study for Cleavage of Unlocked Linker of Example 16C at 90° C. and at 20° C. from 3'-Derivatised Guanosine in 0.01M Triethylamine in Acetonitrile

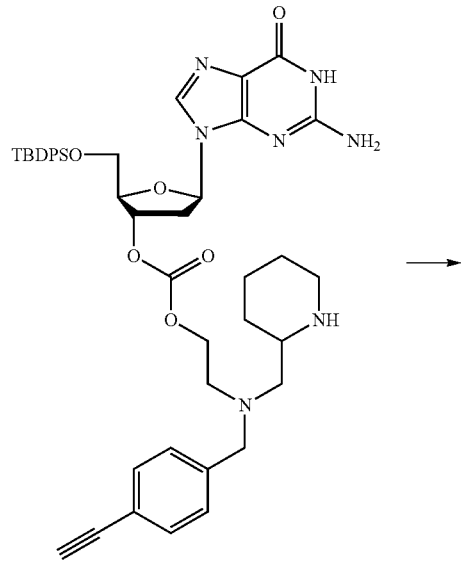

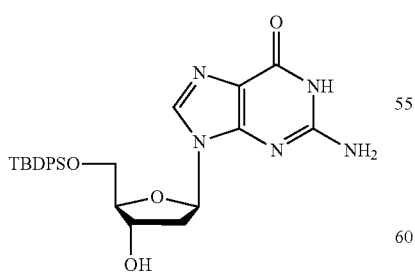

A time course study using the protocol as described above was carried out using 0.01M triethylamine in acetonitrile. The results of the time course study are represented graphically in FIG. 16.

Example 16G: Time Course Study for Cleavage of Unlocked Linker of Example 16E at 90° C. and at 20° C. from 5'-Derivatised Guanosine in 0.01M Triethylamine in Acetonitrile

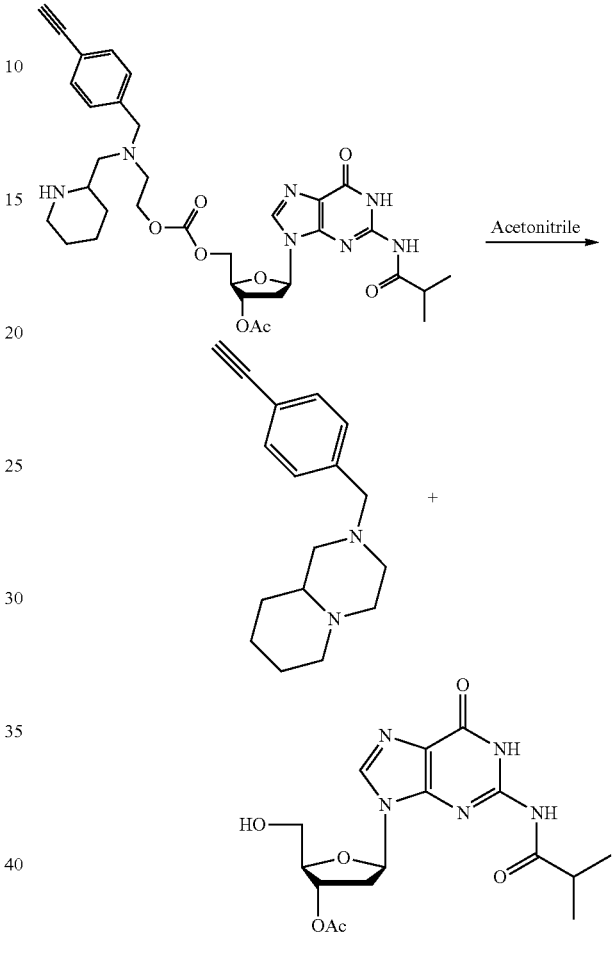

A time course study using the protocol as described above was carried out using 0.01M triethylamine in acetonitrile. The results of the time course study are represented graphically in FIG. 17

Example 17

Synthesis and Time-Course Studies on Deoxyadenosine

Example 17A: 2-((4-Ethynylbenzyl)amino)ethan-1-ol

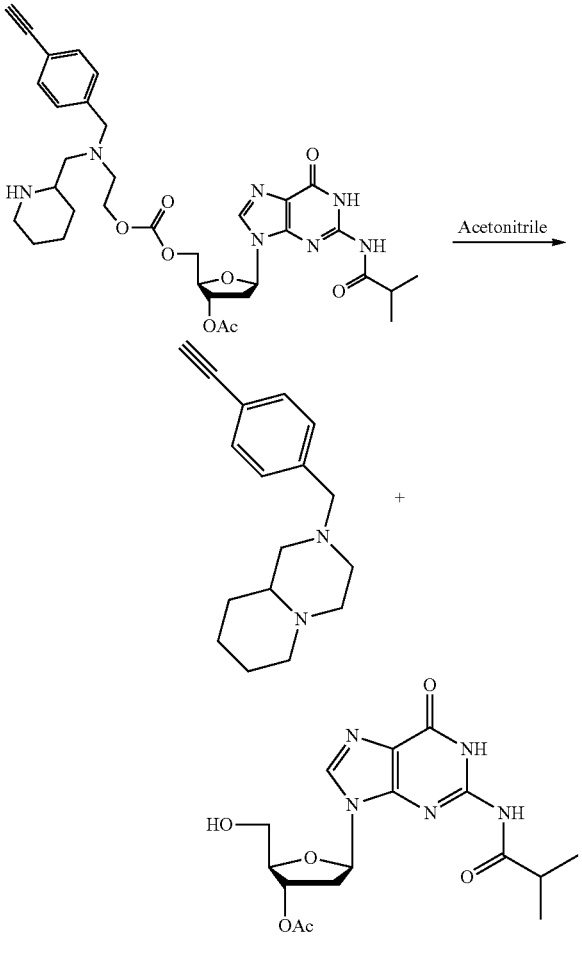

4-Ethynylbenzaldehyde (9.04 g, 69.5 mmol) and ethanolamine (4.2 mL, 69.5 mmol) were dissolved in MeOH (200 mL). Most solids dissolved after 20 minutes to give a dark brown solution. Sodium borohydride (2.63 g, 69.5 mmol) was added at portion wise over 30 minutes; effervescence and a small exotherm were observed. The resultant mixture was stirred at room temperature under a nitrogen atmosphere overnight. The mixture was chilled in an ice-water bath and water (100 mL) was added, then most of the MeOH removed by evaporation in vacuo. The reaction was extracted with EtOAc (3×300 mL). The combined organic extracts were washed with brine, dried ($Na_2SO_4$) and the solvent evaporated in vacuo to leave a yellow oil (10.4 g). This was purified by flash column chromatography using an increasing gradient from 0-15% MeOH/DCM to give the product (8.0 g, 45.7 mmol, 66%) as a pale yellow oil which solidified on standing.

UPLC-MS (Basic 2 min): rt 0.76 min, m/z 176 $[M+H]^+$ $^1$H NMR (400 MHz, $CDCl_3$) δ ppm: 2.77-2.83 (m, 2H) 3.06 (s, 1H) 3.63-3.69 (m, 2H) 3.82 (s, 2H) 7.25-7.31 (m, 2H) 7.46 (d, J=7.46 Hz, 2H).

Example 17B: tert-Butyl-2-(((4-ethynylbenzyl)(2-hydroxyethyl)amino)methyl)-piperidine-1-carboxylate

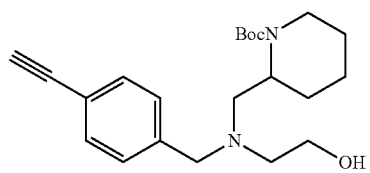 [SMILES: C#Cc1ccc(CN(CCO)CC2CCCCN2C(=O)OC(C)(C)C)cc1]

AcOH (13.1 mL, 228 mmol) was added slowly to a stirred suspension of 2-((4-ethynylbenzyl)amino)ethan-1-ol (8.0 g, 45.7 mmol) and 1-N-Boc-2-piperidinecarboxaldehyde (10.3 g, 48.4 mmol) in 1,2-DCE (200 mL). After 30 minutes all solids dissolved to give a yellow solution. $NaBH(OAc)_3$ (24.2 g, 114 mmol) was added portion wise over 20 minutes, producing some effervescence, and the mixture stirred at room temperature under a nitrogen atmosphere overnight. Saturated aqueous $NaHCO_3$ (800 mL) was added until pH 7. The separated aqueous layer was extracted with DCM (3×500 mL), the combined organic extracts were dried ($Na_2SO_4$) and the solvent evaporated in vacuo to leave a yellow oil (21 g). This was purified by flash column chromatography using an increasing gradient from 10-50% EtOAc/hexane to give the product (17.8 g, 47 mmol, quantitative) as a yellow oil.

UPLC-MS (Basic 2 min): rt 1.21 min, m/z 373 $[M+H]^+$ $^1$H NMR (400 MHz, $CDCl_3$) δ ppm: 1.09-1.31 (m, 4H) 1.46 (s, 9H) 2.02-2.22 (m, 2H) 2.55-2.92 (m, 4H) 3.07 (s, 1H) 3.30 (br s, 1H) 3.58-3.88 (m, 5H) 4.44 (br s, 1H) 7.21-7.31 (m, 2H) 7.43 (br d, J=7.91 Hz, 2H).

Example 17C: 2-((4-Ethynylbenzyl)(piperidin-2-ylmethyl)amino)ethan-1-ol trifluoroacetic Acid

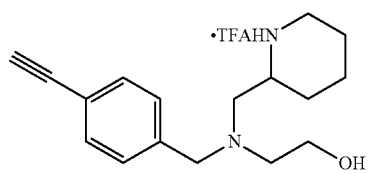

TFA (30 mL, 390 mmol) was added to a stirred solution of tert-butyl-2-(((4-ethynylbenzyl)(2-hydroxyethyl)amino)methyl)piperidine-1-carboxylate (12.55 g, 33.7 mmol) in DCM (60 mL). A small exotherm was observed and gas was evolved. The mixture was stirred at room temperature for 1.5 hours and then evaporated in vacuo, azeotroping with $CH_3CN$/PhMe (1:1, 2×100 mL) to leave a pale yellow oil. This was dissolved in DCM (300 mL) and washed with saturated aqueous $NaHCO_3$ (500 mL). The separated aqueous layer was re-extracted with DCM (5×150 mL), the combined organic extracts dried ($Na_2SO_4$) and the solvent evaporated in vacuo to give the product as a pale yellow oil (13.3 g, 34.5 mmol, quantitative).

UPLC-MS (Acidic 2 min): rt 0.64 min, m/z 273 $[M+H]^+$ $^1$H NMR (400 MHz, $CDCl_3$) δ ppm: $^1$H NMR (400 MHz, CHLOROFORM-d) δ ppm 1.31-1.42 (m, 1H) 1.43-1.59 (m, 1H) 1.62-1.80 (m, 4H) 2.61-2.89 (m, 6H) 3.06-3.09 (m, 1H) 3.15-3.28 (m, 1H) 3.52-3.69 (m, 2H) 3.70-3.76 (m, 2H) 7.22-7.29 (m, 2H) 7.42-7.48 (m, 2H)

Example 17D: Allyl 2-(((4-ethynylbenzyl)(2-hydroxyethyl)amino)methyl)-piperidine-1-carboxylate

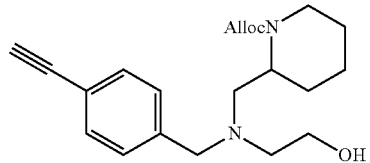

Allyl(2,5-dioxopyrrolidin-1-yl)carbonate (3.5 mL, 22.4 mmol) was added slowly to a stirred solution of 2-((4-ethynylbenzyl)(piperidin-2-ylmethyl)amino)ethan-1-ol trifluoroacetic acid (8.6 g, 22.4 mmol) in DCM (100 mL). DIPEA (4 mL, 23 mmol) was added and the mixture stirred at room temperature under a nitrogen atmosphere overnight. Further DIPEA (4 mL, 23 mmol) was added to ensure the solution was basic. Water (100 mL) was added and the separated aqueous layer extracted with DCM (3×100 mL). The combined organic extracts were dried ($Na_2SO_4$) and the solvent evaporated in vacuo to leave a yellow oil (11 g). This was purified by flash column chromatography using an increasing gradient from 10-70% EtOAc/hexane to give the product (7.13 g, 20.0 mmol, 89%) as a yellow oil.

UPLC-MS (Basic 2 min): rt 1.15 min, m/z 357 $[M+H]^+$ $^1$H NMR (400 MHz, $CDCl_3$) δ ppm: $^1$H NMR (400 MHz, CHLOROFORM-d) δ ppm 1.13-1.38 (m, 2H) 1.41-1.59 (m, 4H) 2.03-2.30 (m, 2H) 2.59-2.68 (m, 2H) 2.70-2.88 (m, 2H) 3.06 (s, 1H) 3.30-3.40 (m, 1H) 3.55-3.85 (m, 4H) 4.43 (br s, 1H) 4.52-4.68 (m, 2H) 5.16-5.39 (m, 2H) 5.97 (br s, 1H) 7.22 (d, J=7.66 Hz, 2H) 7.41 (br d, J=7.91 Hz, 2H)

Example 17E: (2R,3S,5R)-5-(6-Amino-9H-purin-9-yl)-2-(((tert-butyldiphenyl-silyl)oxy)methyl)tetrahydrofuran-3-ol

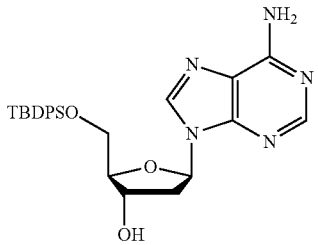

TBDPS-Cl (1.8 mL, 7.06 mmol) was added dropwise over 40 minutes to a stirred suspension of 2-deoxyadenosine monohydrate (2.0 g, 7.43 mmol) and imidazole (1.52 g, 22.3 mmol) in DCM (100 mL) under a nitrogen atmosphere. The resulting white suspension was stirred at room temperature for 2 days. Water (50 mL) was added and the mixture extracted with DCM (3×100 mL). The combined organic extracts were dried ($Na_2SO_4$) and the solvent evaporated in vacuo to leave a colourless oil. This was purified by flash column chromatography using an increasing gradient from 50-100% EtOAc/hexane then 2-10% MeOH/EtOAc to give the product (430 mg, 0.88 mmol, 12%) as a white foam.

UPLC-MS (Acidic 2 min): rt 1.00 min, m/z 490 [M+H]$^+$ $^1$H NMR (400 MHz, CDCl$_3$) δ ppm: $^1$H NMR (400 MHz, CHLOROFORM-d) δ ppm 1.06 (s, 9H) 2.49-2.57 (m, 1H) 2.75 (dd, J=13.30, 6.65 Hz, 1H) 3.82-3.95 (m, 2H) 4.04-4.15 (m, 1H) 4.71-4.75 (m, 1H) 5.73 (br s, 2H) 6.45 (t, J=6.46 Hz, 1H) 7.11 (s, 1H) 7.33-7.45 (m, 6H) 7.60-7.66 (m, 4H) 8.02 (s, 1H) 8.29 (s, 1H)

Example 17F: Allyl-2-(((2-(((((2R,3S,5R)-5-(6-amino-9H-purin-9-yl)-2-(((tert-butyldiphenylsilyl)oxy)methyl)tetrahydrofuran-3-yl)oxy)carbonyl)oxy)ethyl)(4-ethynylbenzyl)amino)methyl)piperidine-1-carboxylate

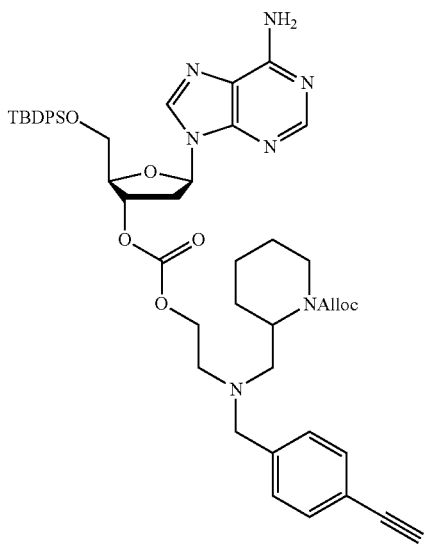

CDI (50 mg, 0.31 mmol) was added to a stirred solution of allyl 2-(((4-ethynylbenzyl)(2-hydroxyethyl)amino)methyl)piperidine-1-carboxylate (100 mg, 0.28 mmol) in anhydrous CH$_3$CN (3 mL) under a nitrogen atmosphere. The colourless solution was stirred at 40° C. overnight. The solution was allowed to cool to room temperature and (2R,3S,5R)-5-(6-amino-9H-purin-9-yl)-2-(((tert-butyldiphenylsilyl)oxy)methyl)tetrahydrofuran-3-ol (138 mg, 0.28 mmol) was added, followed by DBU (0.05 mL, 0.31 mmol), and the mixture stirred at room temperature for 4 hours. Water (20 mL) was added and the mixture extracted with EtOAc (2×50 mL). The combined organic extracts were dried (Na$_2$SO$_4$) and the solvent evaporated in vacuo to leave a pale yellow oil. This was purified by flash column chromatography using an increasing gradient from 20-100% EtOAc/hexane to give the product (170 mg, 0.19 mmol, 70%) as a white foam.

UPLC-MS (Acidic 2 min): rt 1.40 min, m/z 872 [M+H]$^+$ $^1$H NMR (400 MHz, CDCl$_3$) δ ppm: $^1$H NMR (400 MHz, CHLOROFORM-d) δ ppm 1.07 (s, 9H) 1.30-1.41 (m, 2H) 1.47-1.62 (m, 2H) 1.72-1.82 (m, 2H) 2.52-2.71 (m, 4H) 2.73-2.91 (m, 3H) 3.03 (s, 1H) 3.60-3.76 (m, 2H) 3.87-4.02 (m, 2H) 4.19-4.28 (m, 2H) 4.36 (br s, 1H) 4.52-4.61 (m, 2H) 5.14-5.30 (m, 2H) 5.44 (br d, J=5.52 Hz, 1H) 5.61 (br s, 2H) 5.92 (br d, J=5.27 Hz, 1H) 6.45 (dd, J=8.28, 5.65 Hz, 1H) 7.20-7.27 (m, 2H) 7.30-7.45 (m, 8H) 7.64 (td, J=7.81, 1.44 Hz, 4H) 8.00 (d, J=1.25 Hz, 1H) 8.30 (d, J=1.00 Hz, 1H)

Example 17G: (2R,3S,5R)-5-(6-Amino-9H-purin-9-yl)-2-(((tert-butyldiphenylsilyl)oxy)methyl)-tetrahydrofuran-3-yl (2-((4-ethynylbenzyl)(piperidin-2-ylmethyl)amino)ethyl) Carbonate

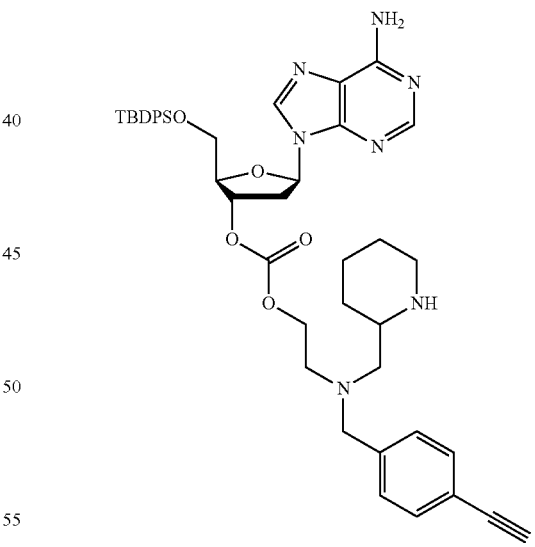

A stirred solution of allyl-2-(((2-(((((2R,3S,5R)-5-(6-amino-9H-purin-9-yl)-2-(((tert-butyldiphenylsilyl)oxy)methyl)tetrahydrofuran-3-yl)oxy)carbonyl)oxy)ethyl)(4-ethynylbenzyl)amino)methyl)piperidine-1-carboxylate (45 mg, 0.052 mmol) and dimedone (36 mg, 0.26 mmol) in THF (3 mL) was degassed by nitrogen bubbling for 5 minutes. Pd(PPh$_3$)$_4$ (6 mg, 0.005 mmol) was added and degassing continued for 2 minutes. The resulting yellow solution was stirred at room temperature for 1 hour. The mixture was diluted with EtOAc (30 mL) and washed with saturated aqueous NaHCO₃ (10 mL). The separated aqueous layer was extracted with EtOAc (20 mL) and the combined organic extracts were dried (Na₂SO₄) and the solvent evaporated in vacuo at 20° C. to leave a glassy yellow solid. This was purified by flash column chromatography using an increasing gradient from 0-10% MeOH/DCM then 0.1-1% Et₃N in 10% MeOH/DCM to leave an oily residue (55 mg) containing a mixture of the product and a triethylamine salt. This was suspended in EtOAc (10 mL) and washed with water (10 mL). The separated aqueous layer was extracted with EtOAc (10 mL) and the combined organic extracts were dried (Na₂SO₄) and the solvent evaporated in vacuo at 20° C. to give the product as an oily solid. This was suspended in Et₂O (5 mL) and evaporated in vacuo (repeated process twice) to give the product (30 mg, 0.038 mmol, 73%) as a white solid.

UPLC-MS (Acidic 2 min): rt 0.98 min, m/z 788 [M+H]⁺
¹H NMR (400 MHz, CDCl₃) δ ppm: ¹H NMR (400 MHz, CHLOROFORM-d) δ ppm 1.03 (s, 9H) 1.60-1.95 (m, 6H) 2.62-2.92 (m, 7H) 3.03 (d, J=1.51 Hz, 1H) 3.16 (br dd, J=13.11, 9.10 Hz, 1H) 3.39-3.49 (m, 1H) 3.69-4.00 (m, 4H) 4.15-4.30 (m, 3H) 5.43 (br t, J=5.08 Hz, 1H) 5.77 (br s, 2H) 6.45 (dt, J=8.91, 5.71 Hz, 1H) 7.29-7.43 (m, 10H) 7.58-7.64 (m, 4H) 7.99-8.00 (d, J=1.25 Hz, 1H) 8.26 (d, J=4.64 Hz, 1H)

Example 17H: Allyl-2-(((2-(((((2R,3S,5R)-3-acetoxy-5-(6-benzamido-9H-purin-9-yl)tetrahydrofuran-2-yl)methoxy)carbonyl)oxy)ethyl)(4-ethynylbenzyl)amino)methyl)piperidine-1-carboxylate

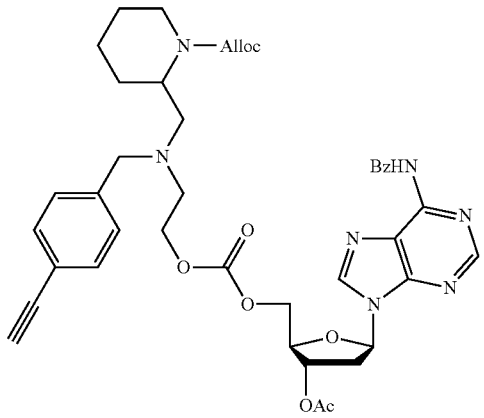

Allyl 2-(((4-ethynylbenzyl)(2-hydroxyethyl)amino) methyl)piperidine-1-carboxylate (0.1 g, 0.28 mmol) and carbonyldiimidazole (50 mg, 0.31 mmol) were dissolved in anhydrous acetonitrile (3 mL). The resultant mixture was stirred at 40° C. overnight. Then the reaction was cooled to room temperature and (2R,3S,5R)-5-(6-benzamido-9H-purin-9-yl)-2-(hydroxymethyl)tetrahydrofuran-3-yl acetate (0.11 g, 0.28 mmol) was added, followed by DBU (0.046 mL, 0.31 mmol). The reaction was stirred at room temperature for 3 hours. The mixture was partitioned between water (10 mL) and EtOAc (10 mL) and the layers were separated. The aqueous layer was back extracted with EtOAc (2×10 mL). Combined organics were dried (Na₂SO₄) and the solvent was removed in vacuo. The crude was purified by flash column chromatography (Silica 12 g, 30-100% EtOAc/hexane) to give the product (155 mg, 71%) as a white foam.

UPLC-MS (Acidic 2 min): rt 1.05 min, m/z 780.4 [M+H]⁺
¹H NMR (DMSO-d₆, 400 MHz) δ ppm: 1.26-1.50 (m, 4H), 1.65 (m, 2H), 2.33 (s, 3H), 2.59-2.82 (m, 4H), 3.17 (dt, J=14.5, 7.1 Hz, 2H), 3.72-3.85 (m, 2H), 4.09-4.25 (m, 4H), 4.29-4.35 (m, 3H), 4.37-4.41 (m, 2H), 4.47 (br s, 2H), 5.07-5.30 (m, 2H), 5.40-5.56 (m, 1H), 5.81-5.96 (m, 1H), 6.53 (dd, J=7.8, 6.5 Hz, 1H), 7.26 (d, J=7.0 Hz, 2H), 7.34-7.41 (m, 2H), 7.50-7.59 (m, 2H), 7.60-7.69 (m, 1H), 7.99-8.10 (m, 2H), 8.65 (s, 1H), 8.75 (s, 1H), 11.21 (br s, 1H).

Example 17I: (2R,3S,5R)-5-(6-Benzamido-9H-purin-9-yl)-2-((((2-((4-ethynylbenzyl)(piperidin-2-ylmethyl)amino)ethoxy)carbonyl)oxy)methyl)-tetrahydrofuran-3-yl Acetate

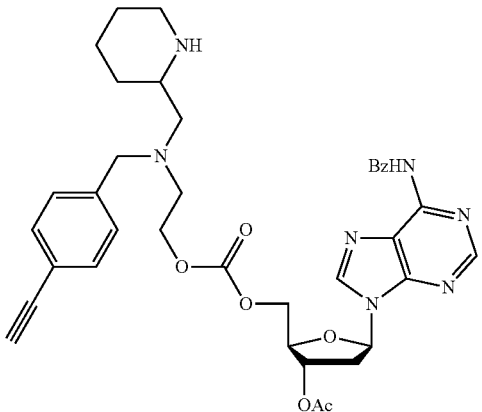

To a solution of allyl-2-(((2-(((((2R,3S,5R)-3-acetoxy-5-(6-benzamido-9H-purin-9-yl)tetrahydrofuran-2-yl) methoxy)carbonyl)oxy)ethyl)(4-ethynylbenzyl)amino) methyl)piperidine-1-carboxylate (115 mg, 0.15 mmol) in anhydrous THF (5.7 mL) was added dimedone (105 mg, 0.75 mmol). The solution was degassed by nitrogen bubbling for 5 minutes. Then Pd(PPh₃)₄ (35 mg, 0.03 mmol) was added and the solution was degassed by nitrogen bubbling again for 5 minutes. The resultant mixture was stirred at room temperature for 30 minutes. Saturated aqueous NaHCO₃ solution (50 mL) was added and the reaction was extracted with EtOAc (3×50 mL). Combined organics were dried (Na₂SO₄) and the solvent was removed in vacuo (temperature of water bath <20° C.). The crude was purified by flash column chromatography (Silica 20 g, 0-10% MeOH/DCM) to give to give the product as an oily solid. This was suspended in Et₂O (5 mL) and evaporated in vacuo (repeated process twice) to give the product (80 mg, 77%) as a white solid.

UPLC-MS (Acidic 2 min): rt 0.84 min, m/z 696.3 [M+H]⁺
¹H NMR (CDCl₃, 400 MHz) δ ppm: 1.22-1.34 (m, 2H), 1.47-1.61 (m, 2H), 1.74 (m, 2H), 2.17 (s, 3H), 2.40-2.72 (m, 6H), 2.74-2.92 (m, 2H), 3.02 (d, J=3.8 Hz, 3H), 3.56 (br d, J=14.1 Hz, 1H), 3.73 (brd, J=14.1 Hz, 1H), 4.10-4.23 (m, 2H), 4.34-4.45 (m, 4H), 5.31-5.55 (m, 1H), 6.59 (m, 1H), 7.21 (br s, 2H), 7.37 (br d, J=8.0 Hz, 2H), 7.47-7.57 (m, 2H), 7.57-7.70 (m, 1H), 7.91-8.04 (m, 2H), 8.29-8.45 (m, 1H), 8.80 (s, 1H).

Example 17J: Time Course Studies on the Cleavage of the Unprotected Linker of 5'-Protected Deoxyadenosine Analogue (Compound of Example 17I)

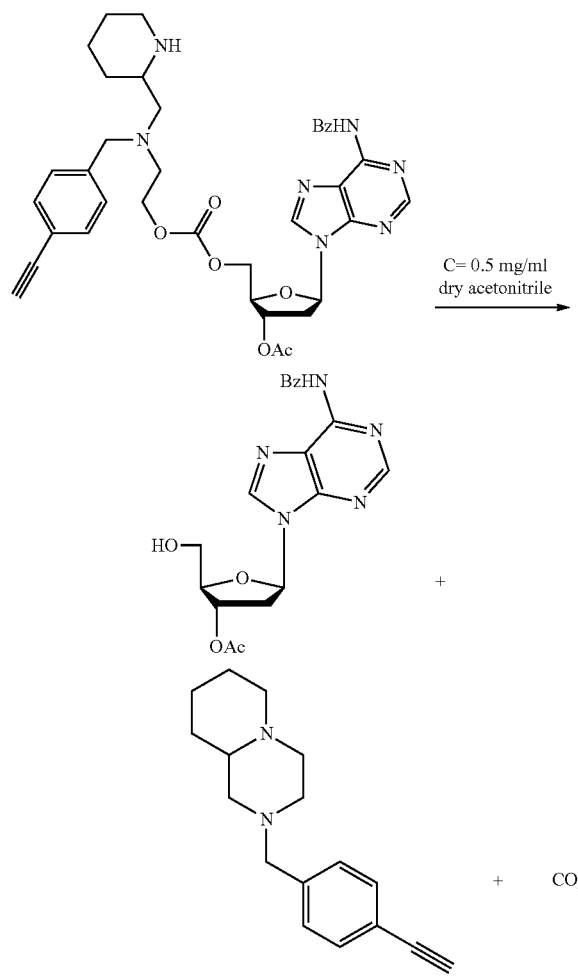

A time course study using the protocol as described above was carried out using acetonitrile. The results of the time course study are shown in the table below and are represented graphically in FIG. 18.

| Time | % Starting Material at 90° C. | % Starting Material at 20° C. |
|---|---|---|
| 0 | 100 | 100 |
| 5 | 38 | |
| 10 | 17 | 99.9 |
| 15 | 7 | |
| 20 | 4 | |
| 30 | 2 | 99.8 |
| 40 | 0 | 99.7 |
| 4320 | | 98.6 |
| 5760 | | 98.1 |
| 7200 | | 96.3 |
| 8640 | | 95.4 |
| 15840 | | 93.2 |
| 18720 | | 92 |

Example 17K: Time Course Studies on the Cleavage of the Unprotected Linker of 3'-Protected Deoxyadenosine Analogue of Example 17G with 0.01 M Triethylamine in Acetonitrile

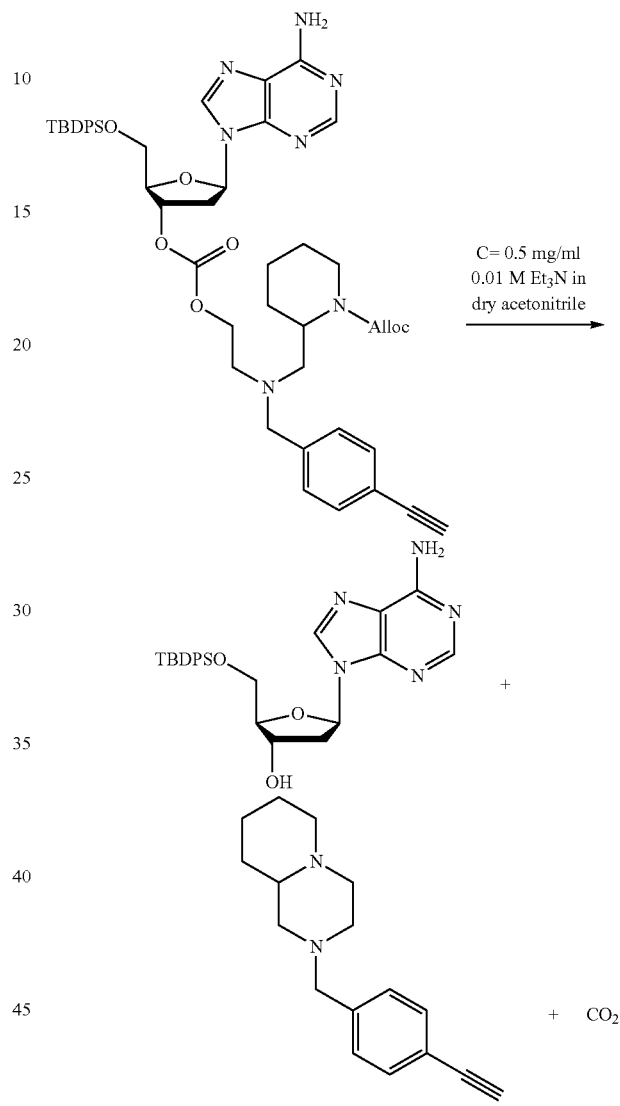

A time course study using the protocol as described above was carried out using 0.01 M triethylamine in acetonitrile. The results of the time course study are shown in the table below and are represented graphically in FIG. 19.

| Time | % Starting Material at 90° C. | % Starting Material at 20° C. |
|---|---|---|
| 0 | 97.08 | 97.08 |
| 3 | 48.29 | |
| 4 | | 96.96 |
| 6 | 24.6 | |
| 8 | | 96.79 |
| 9 | 10.9 | |
| 12 | 3.61 | 96.65 |
| 15 | 1.36 | |
| 16 | | 96.52 |
| 18 | 0.05 | |

-continued

| Time | % Starting Material at 90° C. | % Starting Material at 20° C. |
| --- | --- | --- |
| 20 | | 96.39 |
| 21 | 0 | |
| 24 | | 96.23 |
| 28 | | 96.12 |
| 32 | | 95.98 |
| 120 | | 93 |
| 240 | | 88 |
| 360 | | 84 |
| 1320 | | 55 |
| 1500 | | 51 |
| 1800 | | 44 |
| 2760 | | 28 |

Example 18

Synthesis of Adpoc Locked 3'-Protected Thymidine

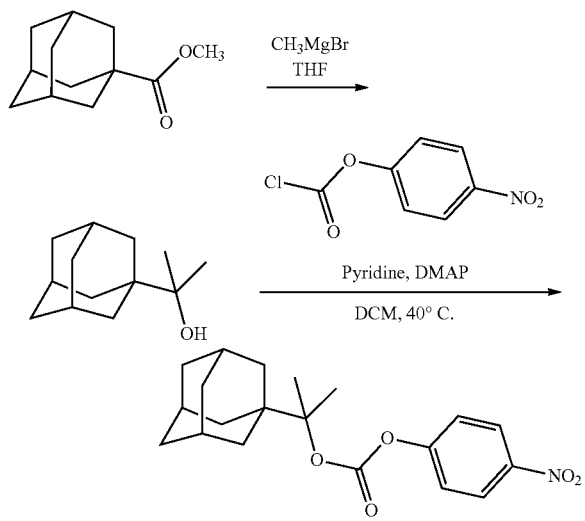

Example 18A:
2-((3R,5R,7R)-Adamantan-1-yl)propan-2-ol

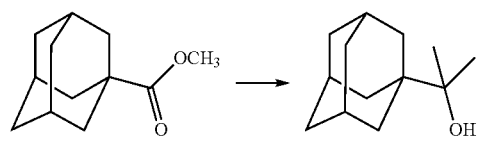

1-Adanamatane-methylester (5.0 g, 25.7 mmol, 1 equ) was dissolved in anhydrous THF (35 mL) and was cooled to 0° C. 3M Methylmagnesiumbromide in diethyl ether (21.51 mL, 64.4 mmol, 2.5 eq.) was added drop wise over 30 minutes at 0-5° C. After addition was complete the reaction mixture was warmed to ambient temperature and stirred for 2 hours. After this time the reaction was complete by TLC (3:1 Petroleum ether:EtOAc—visualised with anisaldehyde). The reaction mixture was cooled to 0° C., quenched with saturated $NH_4Cl$ solution (40 mL) and extracted with EtOAc (2×100 mL). The combined organic phases was washed with saturated $HNaCO_3$ solution (100 mL), saturated brine solution (100 mL), dried over $MgSO_4$ and the solvent removed under reduced pressure at 40° C. The crude product was purified by silica chromatography (0-10% Petroleum ether:EtOAc) to give the product as a white crystalline solid (3.96 g, 79%). 1H NMR (CDCl3, 400 MHz); 1.99 (3H, s), 1.69-1.59 (12H, m), 1.19 (1H, 2), 1.12 (6H, s)

Example 18B: 2-((3R,5R,7R)-adamantan-1-yl)propan-2-yl (4-nitrophenyl) carbonate

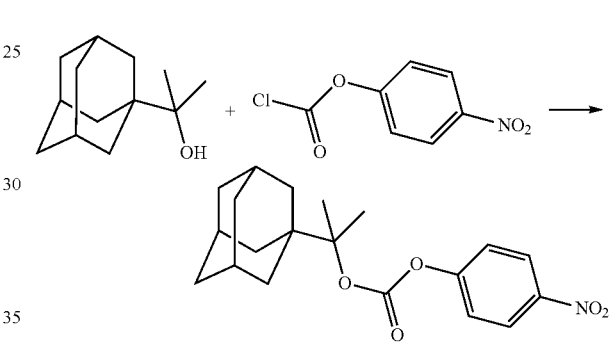

A solution of 2-((3R,5R,7R)-adamantan-1-yl)propan-2-ol (1 g, 5.15 mmol, 1 equ) in DCM (10 mL) was cooled to ~0° C. DMAP (63 mg, 0.515 mmol, 0.1 equ) in DCM (500 uL) and Pyridine (500 uL, 6.18 mmol, 1.2 equ) and were added and stirred for 10 minutes at 0° C. 4-Nitrochloroformate (1.25 g, 6.18 mmol, 1.2 equ) in DCM (10 mL) was added slowly over 15 minutes at 0° C. after which the reaction mixture was heated to 40° C. and stirred for 18 hours. After this time the reaction was complete by LC-MS and TLC (9:1 Petroleum ether:EtOAc stained with anisaldehyde). The reaction mixture cooled to room temperature, diluted with DCM (30 mL), washed with water (2×50 mL), saturated $HNaCO_3$ solution (50 mL), passed through a phase separator and the solvent removed under reduced pressure at 40° C. The crude product was purified by silica chromatography (Petroleum ether:NEt3 98:2) to give the product as a white crystalline solid (940 mg, 51%). LCMS Method B (Basic); Rt=3.09 min. $^1$H NMR (CDCl3, 400 MHz); 8.24 (2H, d, J=10 Hz), 7.33 (2H, d, J=9.7 Hz), 2.02 (3H, s), 1.71-1.61 (12H, m), 1.52 (6H, s)

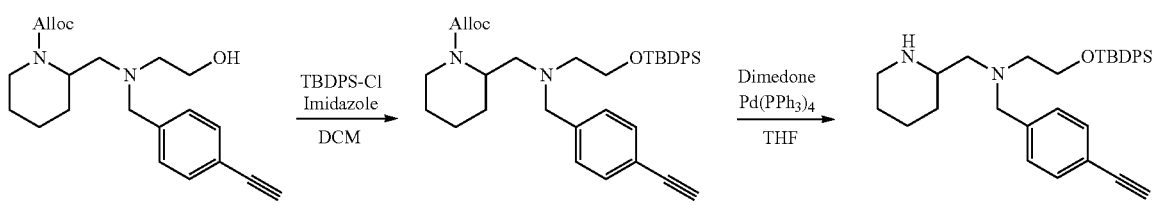

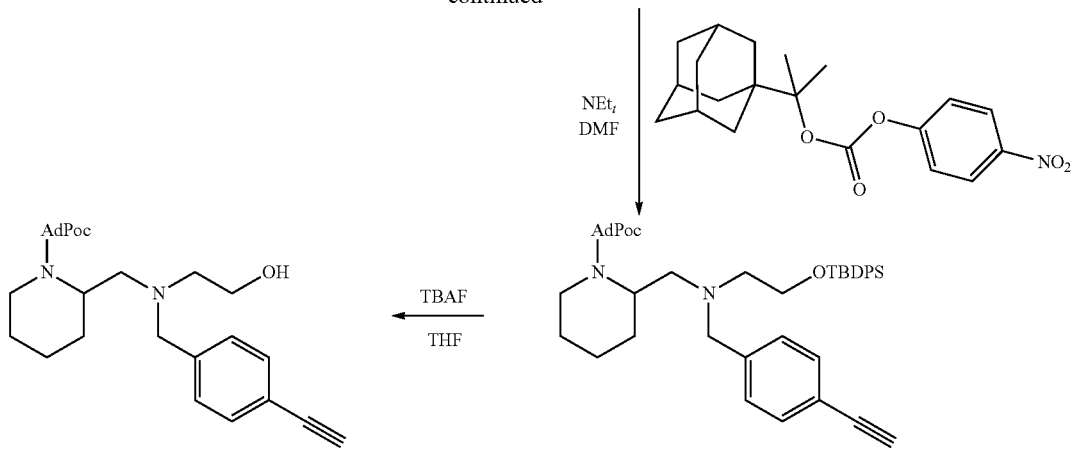

Example 18C: Allyl 2-(((2-((tert-butyldiphenylsilyl)oxy)ethyl)(4-ethynylbenzyl)-amino)methyl)piperidine-1-carboxylate

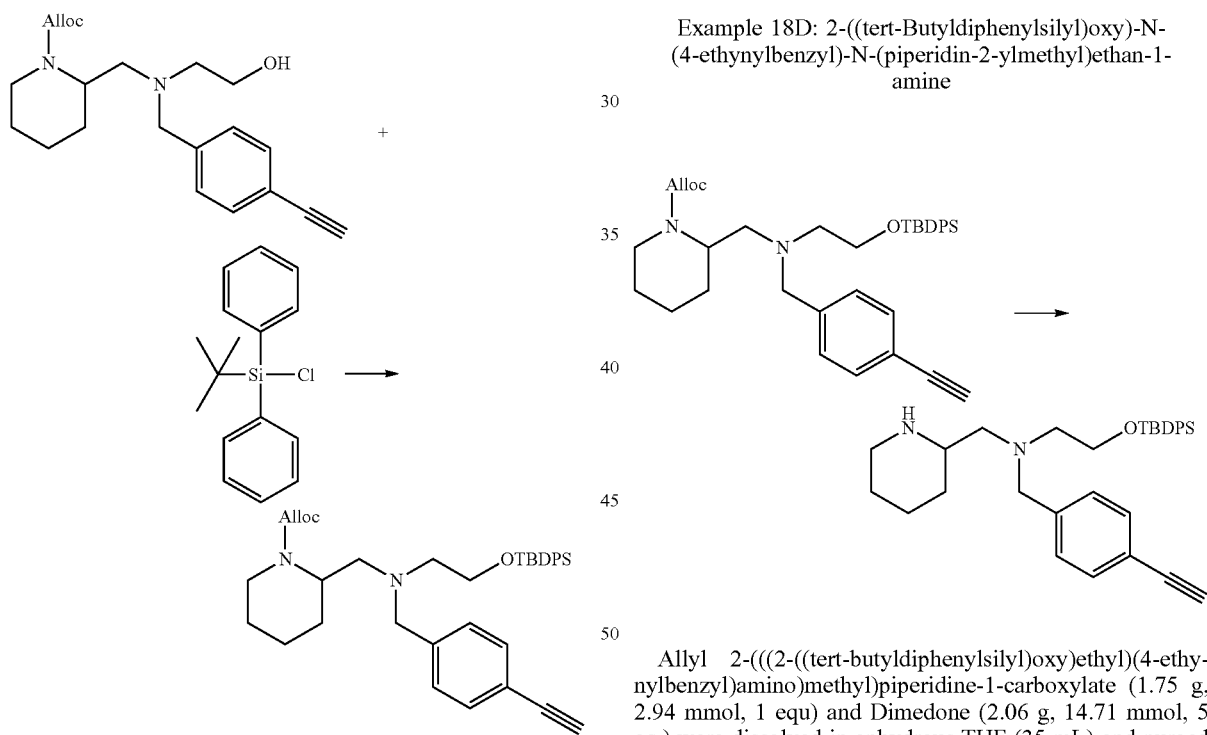

Allyl 2-(((4-ethynylbenzyl)(2-hydroxyethyl)amino)methyl)piperidine-1-carboxylate (1.67 g, 4.68 mmol, 1 equ) and imidazole (960 mg, 14.05 mmol, 3 equ) were dissolved in DCM (75 mL) and stirred for 5 minutes. TBDPS-Cl (1.46 mL, 5.62 mmol, 1.2 equ) was added and the reaction mixture stirred for 1 hour at room temperature. After this time the reaction was complete by LC-MS. Reaction mixture washed with water (2×50 mL), passed through a phase separator and the solvent removed under reduced pressure at 40° C. The crude product was purified by silica chromatography (0-10% Petroleum ether:EtOAc) to give the product as a colourless oil (1.75 g, 62%). LC-MS Method A (Adidic); Rt=3.29 min, m/z 595 (MH+). 1H NMR (CDCl3, 400 MHz); 7.63 (4H, d, J=9.2 Hz), 7.42-7.33 (9H, m), 7.20 (2H, d, J=7.6 Hz), 5.86 (1H, s), 5.29 (1H, s), 4.52 (1H, s), 3.71 (3H, m), 3.58 (2H, m), 3.01 (1H, s), 2.73 (2H, m), 2.62-2.45 (4H, m), 1.76 (1H, d), 1.44-1.23 (6H, m), 1.01 (9H, s).

Example 18D: 2-((tert-Butyldiphenylsilyl)oxy)-N-(4-ethynylbenzyl)-N-(piperidin-2-ylmethyl)ethan-1-amine Allyl 2-(((2-((tert-butyldiphenylsilyl)oxy)ethyl)(4-ethynylbenzyl)amino)methyl)piperidine-1-carboxylate (1.75 g, 2.94 mmol, 1 equ) and Dimedone (2.06 g, 14.71 mmol, 5 eq.) were dissolved in anhydrous THF (35 mL) and purged with N2(g) for 10 minutes. Tetrakis(triphenylphosphine)palladium(0) (340 mg, 0.29 mmol, 0.1 eq.) was added stirred for 20 minutes at room temperature. After this time the reaction was complete by LC-MS. EtOAc (50 mL) and H2O (50 mL) were added. The combined organic layers were washed with saturated HNaCO3 solution (50 mL), saturated brine solution (100 mL), dried over MgSO4 and the solvent removed under reduced pressure at 40° C. The crude product was purified by reverse phase chromatography (0-100% H2O:MeCN+0.1% formic acid) to give an orange oil which was taken up in methanol and passed through an SCX cartridge to give the product as an orange oil (990 mg, 66%). LC-MS Method A (Acidic); Rt=2.25 min, m/z 511 (MH+).

101

Example 18E: 2-((3R,5R,7R)-Adamantan-1-yl)propan-2-yl 2-(((2-((tert-butyldiphenylsilyl)oxy)ethyl)(4-ethynylbenzyl)amino)methyl)piperidine-1-carboxylate

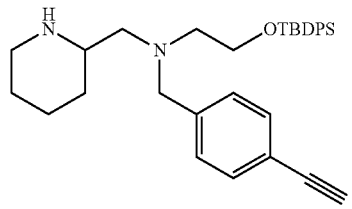

+

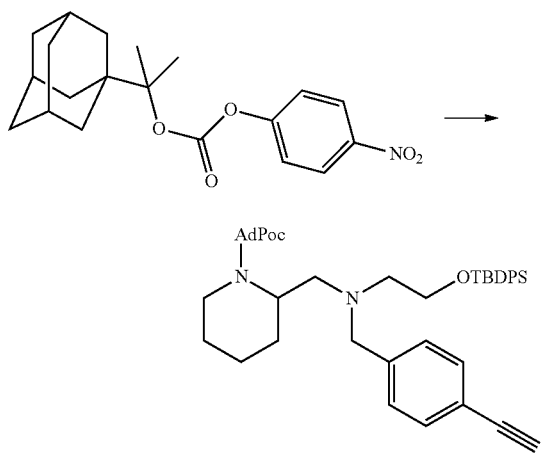

2-((tert-butyldiphenylsilyl)oxy)-N-(4-ethynylbenzyl)-N-(piperidin-2-ylmethyl)ethan-1-amine (520 mg, 1.02 mmol, 1 eq.) was dissolved in DMF (7 mL). Triethylamine (220 uL, 1.22 mmol, 1.2 eq.) and 2-((3R,5R,7R)-adamantan-1-yl)propan-2-yl (4-nitrophenyl) carbonate (440 mg, 1.55 mmol, 1.5 eq.) were added after which the reaction mixture was heated 100° C. for 2 hours. After this time the reaction was complete by LC-MS. The reaction mixture cooled to room temperature, diluted with EtOAc (50 mL), washed with saturated brine solution (3×50 mL), dried over MgSO₄ and the solvent removed under reduced pressure at 40° C. The crude product was purified by silica chromatography (0-10% Petroleum ether:EtOAc) to give the product as an colourless gum (216 mg, 29%). LC-MS Method D (Acidic lipophilic); Rt=5.02 min, m/z 732 (MH⁺).

102

Example 18F: 2-((3R,5R,7R)-Adamantan-1-yl)propan-2-yl 2-(((4-ethynylbenzyl)(2-hydroxyethyl)amino)methyl)piperidine-1-carboxylate

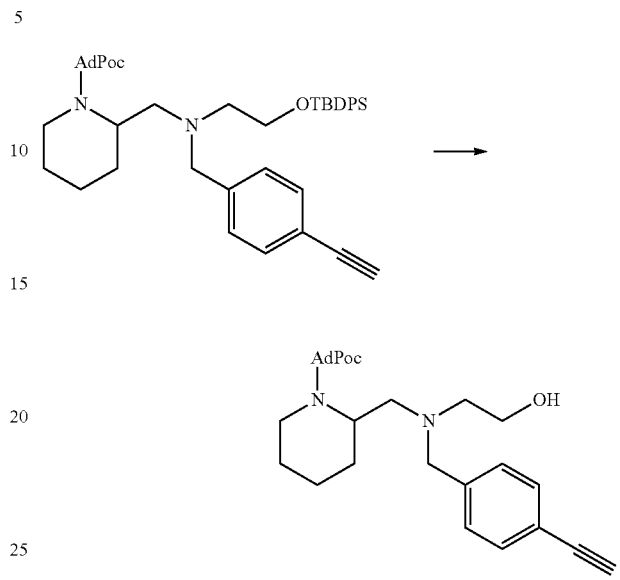

2-((3R,5R,7R)-Adamantan-1-yl)propan-2-yl 2-(((2-((tert-butyldiphenylsilyl)oxy)ethyl)(4-ethynylbenzyl)amino)methyl)piperidine-1-carboxylate (210 mg, 0.287 mmol, 1 eq.) was dissolved in anhydrous THF (5 mL) purged with nitrogen and cooled to 0° C. 1M Tetra-n-butylammonium fluoride in THF (430 μL, 0.430 mmol, 1.5 eq.) was added, reaction mixture warmed to ambient temperature and stirred for 1 hour. After this time the reaction was complete by LC-MS. Saturated NH₄Cl solution (10 mL) was added and the reaction mixture extracted with DCM (2×25 mL). The combined organic phases were washed with water (50 mL), saturated HNaCO₃ solution (50 mL) passed through a phase separator and the solvent removed under reduced pressure at 40° C. The crude product was purified by silica chromatography (Petroleum ether:EtOAc 3:1) to give the product as an colourless oil (100 mg, 71%). LC-MS Method A (Acidic); Rt=2.17 min, m/z 493 (MH).). ¹H NMR (CDCl₃, 400 MHz); 7.42 (2H, d, J=8.0 Hz), 7.29 (2H, d, J=8.0 Hz), 4.44 (1H, m), 3.81-3.60 (5H, m), 3.29 (1H, m), 3.04 (1H, s), 2.82 (1H, m), 2.57 (1H, m), 2.15-2.03 (6H, m), 1/71 (10H, m), 1.59-1.52 (6H, m), 1.46 (3H, s), 1.30-1.12 (4H, m), 0.95 (1H, sextet, J=6.8 Hz)

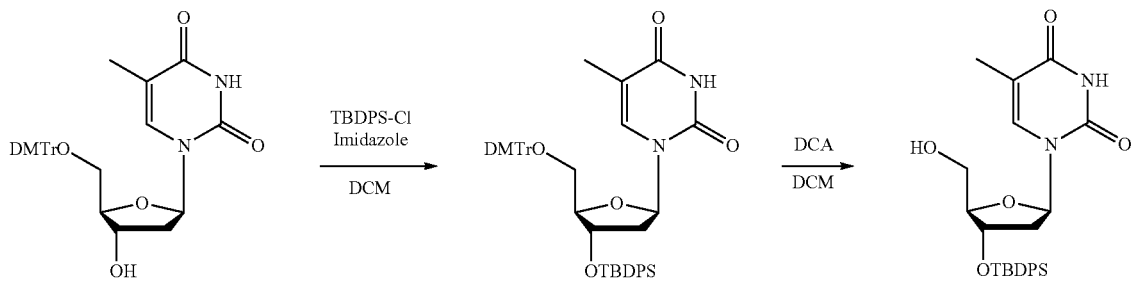

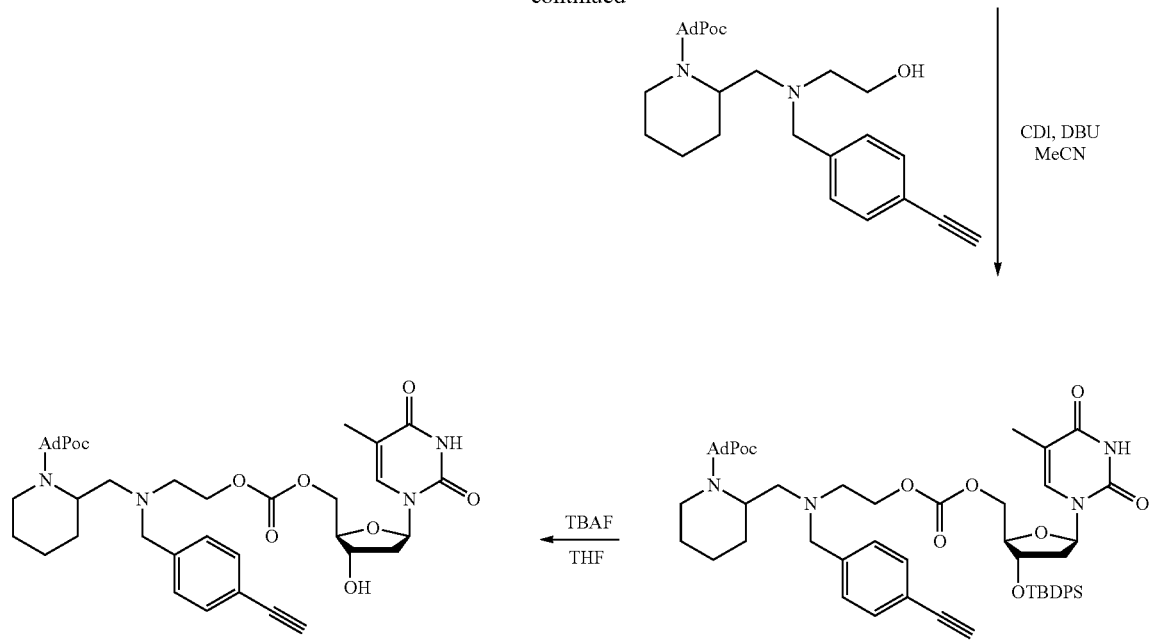

Example 18G: 1-((2R,4S,5R)-5-((Bis(4-methoxyphenyl)(phenyl)methoxy)methyl)-4-((tert-butyldiphenylsilyl)oxy)tetrahydrofuran-2-yl)-5-methylpyrimidine-2,4(1H,3H)-dione

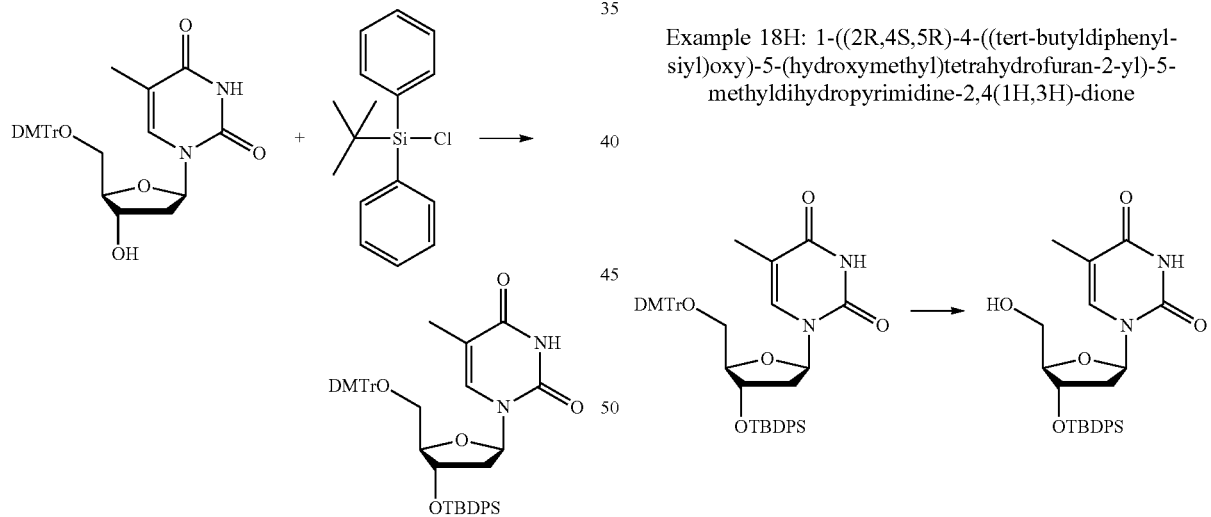

1-((2R,4S,5R)-5-((bis(4-methoxyphenyl)(phenyl)methoxy)methyl)-4-hydroxytetrahydrofuran-2-yl)-5-methylpyrimidine-2,4(1H,3H)-dione (3.00 g, 5.51 mmol, 1 equ) and Imidazole (1.13 g, 16.53 mmol, 3 equ), were dissolved in DCM (100 mL) and stirred for 5 minutes. TBDPS-Cl (1.72 mL, 6.61 mmol, 1.2 equ) added and the reaction mixture stirred for 3 hours at room temperature. After this time the reaction was complete by LC-MS. Reaction mixture washed with $H_2O$ (2×50 mL), saturated $HNaCO_3$ solution (100 mL), passed through a phase separator and the solvent removed under reduced pressure at 40° C. The crude product was purified by silica chromatography (25-50% Petroleum ether:EtOAc) to give the product as a white solid (4.3 g, 99%). LC-MS Method A (Acidic); Rt=3.26 min, m/z 806 (MNa$^+$).

Example 18H: 1-((2R,4S,5R)-4-((tert-butyldiphenylsilyl)oxy)-5-(hydroxymethyl)tetrahydrofuran-2-yl)-5-methyldihydropyrimidine-2,4(1H,3H)-dione 1-((2R,4S,5R)-5-((bis(4-methoxyphenyl)(phenyl) methoxy)methyl)-4-((tert-butyldiphenylsilyl) oxy)tetrahydrofuran-2-yl)-5-methylpyrimidine-2,4(1H,3H)-dione(4.3 g, 5.41 mmol, 1 equ) was dissolved in a solution of 5% DCA in DCM (100 mL) and stirred for 1 hour at room temperature. After this time the reaction was complete by LC-MS. The solvent was removed under reduced pressure at 40° C. The crude product was purified by silica chromatography (25-50% Petroleum ether:EtOAc) to give the product as a white solid (2.2 g, 79%). LC-MS Method A (Acidic); Rt=2.50 min, m/z 505 (MNa$^+$).

Example 18I: 2-((3R,5R,7R)-Adamantan-1-yl)pro-
pan-2-yl 2-(((2-(((((2R,3S,5R)-3-((tert-butyldiphe-
nylsilyl)oxy)-5-(5-methyl-2,4-dioxotetrahydropy-
rimidin-1(2H)-yl)tetrahydrofuran-2-yl)methoxy)
carbonyl)oxy)ethyl)(4-ethynylbenzyl)amino)
methyl)-piperidine-1-carboxylate

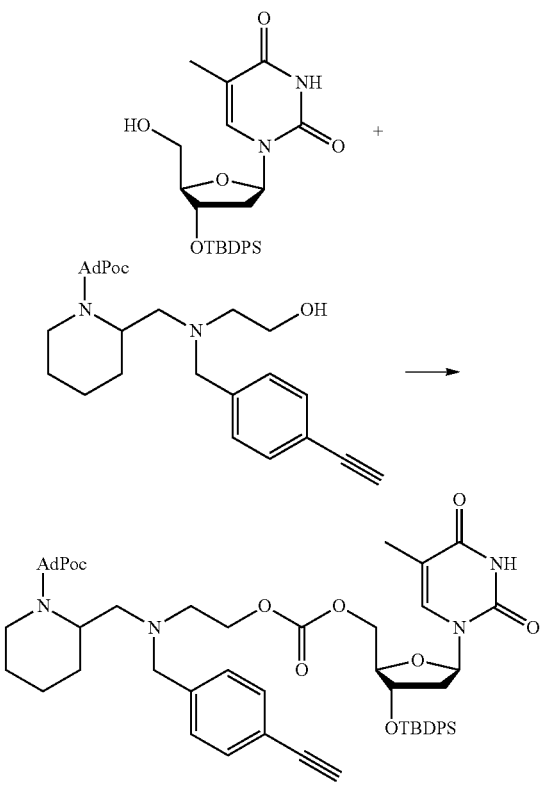

1-((2R,4S,5R)-4-((tert-butyldiphenylsilyl)oxy)-5-(hy-droxymethyl)tetrahydrofuran-2-yl)-5-methyldihydropyrimi-dine-2,4(1H,3H)-dione (135 mg, 0.28 mmol, 1 equ) was dissolved in anhydrous acetonitrile (5 mL) after which CDI (50 mg, 0.31 mmol, 1.1 equ) was added, reaction mixture stirred for 2 hours at room temperature. After this time the CDI intermediate formation was complete by LC-MS. 2-((3R,5R,7R)-adamantan-1-yl)propan-2-yl 2-(((4-ethynyl-benzyl)(2-hydroxyethyl)amino) methyl)piperidine-1-car-boxylate (165 mg, 0.33 mmol, 1.2 equ) in anhydrous acetonitrile (5 mL) and DBU (50 uL, 0.33 mmol, 1.2 equ) were added and the reaction mixture was stirred for 48 hours. After this time the reaction was complete by LC-MS. EtOAc (20 mL) was added and washed with H₂O (50 mL), saturated brine solution (50 mL), saturated HNaCO₃ solu-tion (50 mL), dried over Mg₂SO₄ and the solvent removed under reduced pressure at 40° C. The crude product was purified by silica chromatography (10-30% Petroleum ether: EtOAc) to give the product as a white solid (110 mg, 40%). LC-MS Method D (Acidic lipophilic); Rt=4.46 min, m/z 1022 (MNa⁺). 1H NMR (CDCl3, 400 MHz) 7.99 (1H, s), 7.61 (4H, m), 7.46-7.35 (8H, m), 7.21 (2H, d, J=7.6 Hz), 6.42 (1H, m), 4.32 (2H. m), 4.32 (2H, m) 4.20-4.05 (3H, m), 3.99 (1H, dt), 3.67 (1H, sept), 3.49 (1H, quart, J=6.8 Hz), 3.05 (1H, s), 2.79 (1H, m), 2.47 (2H, s), 2.33 (1H, m), 2.01-1.79 (6H, m), 1.65 (12H, m), 1.56 (12H, s), 1.21 (2H, m), 1.06 (9H, s)

Example 18J: 2-((3R,5R,7R)-adamantan-1-yl)pro-
pan-2-yl 2-(((4-ethynylbenzyl)(2-(((((2R,3S,5R)-3-
hydroxy-5-(5-methyl-2,4-dioxo-3,4-dihydropyrimi-
din-1(2H)-yl)tetrahydrofuran-2-yl)methoxy)
carbonyl)oxy)ethyl)amino)methyl)piperidine-1-
carboxylate

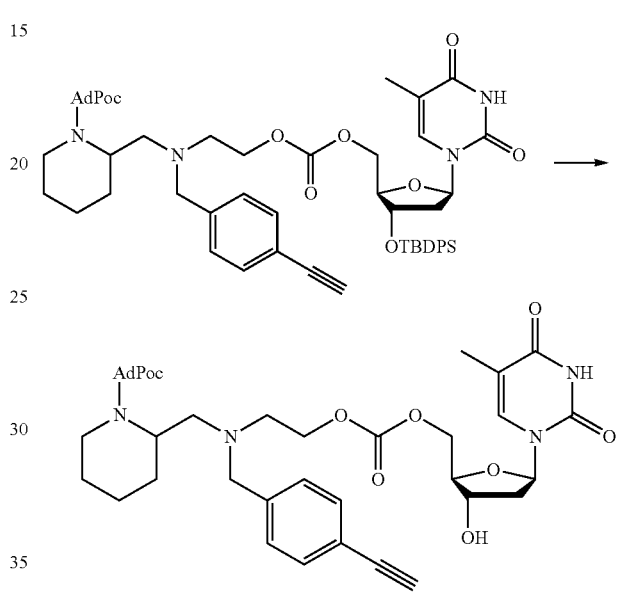

2-((3R,5R,7R)-adamantan-1-yl)propan-2-yl 2-(((2-(((((2R,3S,5R)-3-((tert-butyldiphenylsilyl)oxy)-5-(5-methyl-2,4-dioxotetrahydropyrimidin-1(2H)-yl)tetrahydro-furan-2-yl)methoxy)carbonyl)oxy)ethyl)(4-ethynylbenzyl) amino)methyl)piperidine-1-carboxylate (100 mg, 0.1 mmol, 1 equ) was dissolved in anhydrous THF (5 mL) and cooled to 0° C. 1M Tetra-n-butylammonium fluoride in THF (150 uL, 0.15 mmol, 1.5 equ) was then added, reaction mixture warmed to room temperature and the reaction mixture stirred for 1 hour. After this time the reaction was complete by LC-MS. Saturated NH₄C solution (10 mL) was added and the reaction mixture extracted with DCM (2×25 mL). Combined organic phases were washed with water (50 mL), saturated HNaCO₃ solution (50 mL) passed through a phase separator and the solvent removed under reduced pressure at 40° C. The crude product was purified by silica chromatog-raphy (75:25 Petroleum ether:EtOAc) to give the product as a white solid (56 mg, 75%). LC-MS Method D (Acidic lipophilic); Rt=2.71 min, m/z 761 (MH⁺). 1H NMR (CDCl3, 400 MHz) 8.08 (1H, s), 7.38 (3H, m), 7.23 (1H, m), 6.29 (1H, quart, J=6.4 Hz), 4.44-4.28 (5H, m), 4.15 (1H, m), 4.09 (1H, m), 3.88 (1H, m), 3.70 (1H, m), 3.58 (1H, m), 3.05 (1H, s), 2.76 (2H, m), 2.53 (2H, s), 2.39 (1H, m), 2.19 (1H, m), 1.98 (3H, s), 1.88 (3H, m), 1.65-1.58 (16H, m), 1.44 (7H, s), 1.23 (2H, s)

Example 18K: Kinetic Experiments on Acid-Catalysed Thermal Unlocking of Adpoc-Locked 5-Protected Thymidine of Example 181

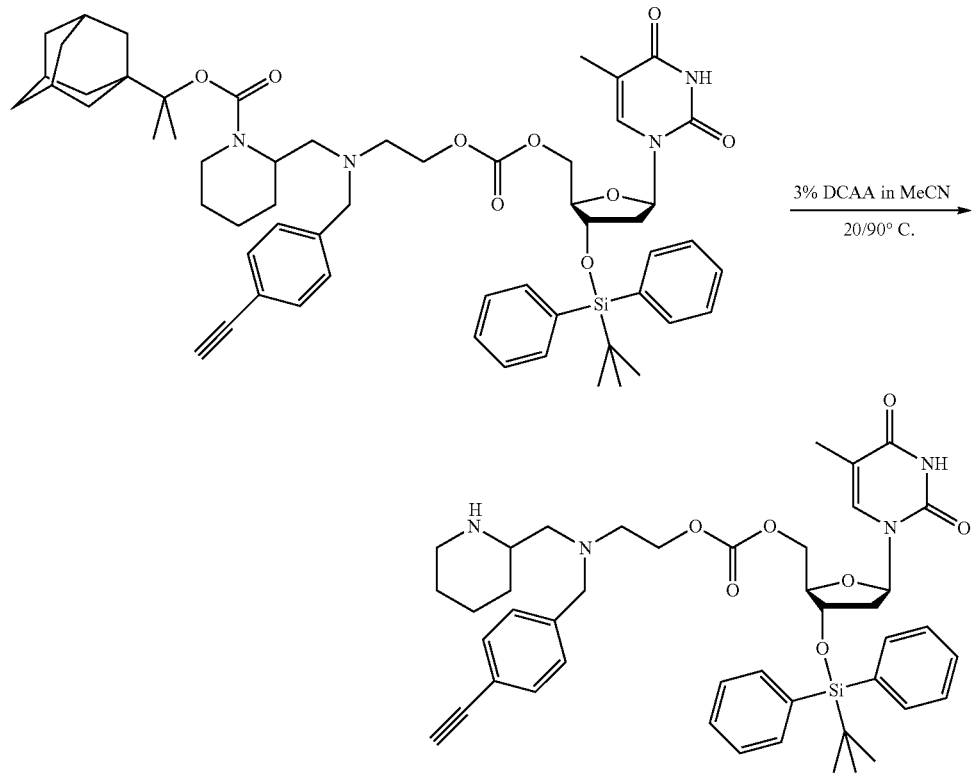

2-((3R,5R,7R)-adamantan-1-yl)propan-2-yl 2-(((2-(((((2R,3S,5R)-3-((tert-butyldiphenylsilyl)oxy)-5-(5-methyl-2,4-dioxotetrahydropyrimidin-1(2H)-yl)tetrahydrofuran-2-yl)methoxy)carbonyl)oxy)ethyl) (4-ethynylbenzyl)amino)methyl) piperidine-1-carboxylate (5.4 mg) was dissolved in a solution of Dichloroacetic acid (DCA) in acetonitrile (5.4 mL) (3% DCA v/v). 300 uL aqua-lots were dispensed into maximum recovery LC-MS vials, sealed and heated to 90° C. in a hot water bath for the designated time. After this time the vials were chilled in a nice bath and analyses by LCMS(Method D) within 10 minutes. The results are presented in the following tables, and are represented graphically in FIG. 20.

| Temp/ ° C. | Time/ min | Starting material/ 4.46 min, Mna+ 1022 | Deprotection product/ 2.26 min MH+ 779 |
|---|---|---|---|
| N/A | 0 | 100.0 | 0.0 |
| 90 | 5 | 56.3 | 43.7 |
| 90 | 10 | 35.7 | 64.3 |
| 90 | 20 | 13.2 | 86.8 |
| 90 | 30 | 6.2 | 93.8 |
| 90 | 45 | 0.0 | 100.0 |
| 90 | 60 | 0.0 | 100.0 |
| 90 | 90 | 0.0 | 100.0 |
| 90 | 1200 | 0.0 | 100.0 |
| 20 | 0 | 100.0 | 0.0 |
| 20 | 30 | 99.0 | 1.0 |
| 20 | 60 | 98.4 | 1.6 |
| 20 | 90 | 97.9 | 2.1 |
| 20 | 1200 | 83.4 | 16.6 |

| Temp/ ° C. | Time/ min | Starting material/ 4.46 min, Mna+ 1022 | Deprotection product/ 2.26 min MH+ 779 |
|---|---|---|---|
| 20 | 2580 | 69.2 | 30.8 |
| 20 | 6960 | 39.0 | 61.0 |
| N/A | 0 | 100.0 | 0.0 |
| 90 | 5 | 56.3 | 43.7 |
| 90 | 10 | 35.7 | 64.3 |
| 90 | 20 | 13.2 | 86.8 |
| 90 | 30 | 6.2 | 93.8 |
| 90 | 45 | 0.0 | 100.0 |
| 90 | 60 | 0.0 | 100.0 |
| 90 | 90 | 0.0 | 100.0 |
| 90 | 1200 | 0.0 | 100.0 |
| 20 | 0 | 100.0 | 0.0 |
| 20 | 30 | 99.0 | 1.0 |
| 20 | 60 | 98.4 | 1.6 |
| 20 | 90 | 97.9 | 2.1 |
| 20 | 1200 | 83.4 | 16.6 |
| 20 | 2580 | 69.2 | 30.8 |
| 20 | 6960 | 39.0 | 61.0 |

| Temp/ ° C. | Time/ min | Starting material/ 4.46 min, Mna+ 1022 | Deprotection product/ 2.26 min MH+ 779 |
|---|---|---|---|
| N/A | 0 | 100.0 | 0.0 |
| 90 | 5 | 56.3 | 43.7 |
| 90 | 10 | 35.7 | 64.3 |

109
-continued
| Temp/ °C. | Time/ min | Starting material/ 4.46 min, Mna+ 1022 | Deprotection product/ 2.26 min MH+ 779 |
|---|---|---|---|
| 90 | 20 | 13.2 | 86.8 |
| 90 | 30 | 6.2 | 93.8 |
| 90 | 45 | 0.0 | 100.0 |
| 90 | 60 | 0.0 | 100.0 |
| 90 | 90 | 0.0 | 100.0 |
| 90 | 1200 | 0.0 | 100.0 |
| 20 | 0 | 100.0 | 0.0 |
| 20 | 30 | 99.0 | 1.0 |
| 20 | 60 | 98.4 | 1.6 |
| 20 | 90 | 97.9 | 2.1 |
110
-continued
| Temp/ °C. | Time/ min | Starting material/ 4.46 min, Mna+ 1022 | Deprotection product/ 2.26 min MH+ 779 |
|---|---|---|---|
| 20 | 1200 | 83.4 | 16.6 |
| 20 | 2580 | 69.2 | 30.8 |
| 20 | 6960 | 39.0 | 61.0 |
Example 19
Synthesis and Kinetic Experiments on Acid-Catalysed Thermal Unlocking of Adpoc-Locked 5-Protected Bz-Cytosine
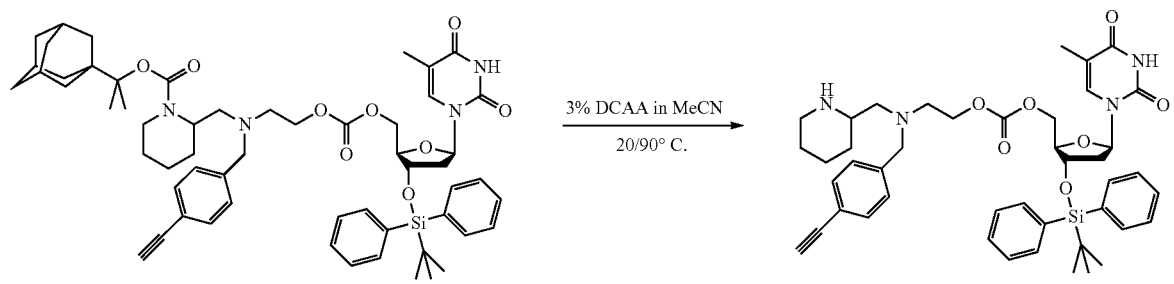
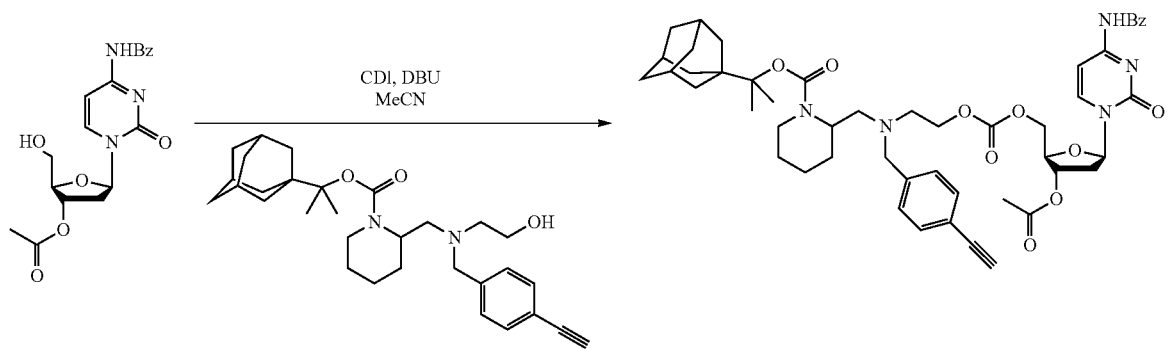
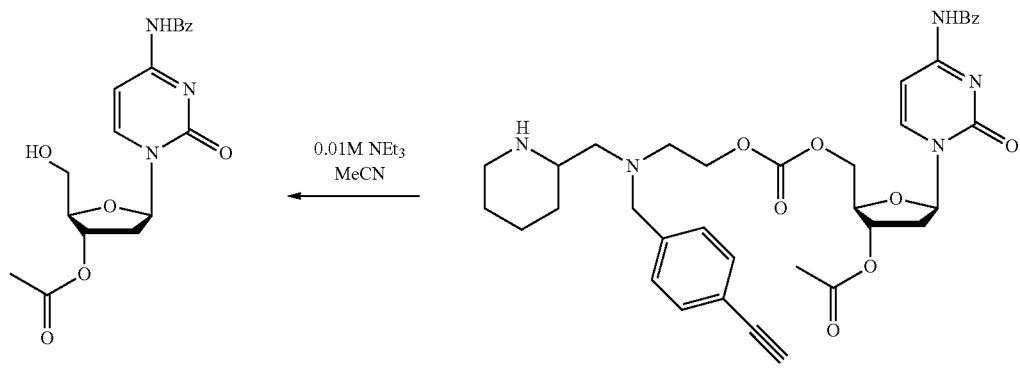

Example 19A: 2-((1R,3R,5S)-adamantan-1-yl)propan-2-yl 2-(((2-(((((2R,3S,5R)-3-acetoxy-5-(4-benzamido-2-oxopyrimidin-1(2H)-yl)tetrahydrofuran-2-yl)methoxy)carbonyl)oxy)ethyl)(4-ethynylbenzyl)amino)methyl)piperidine-1-carboxylate

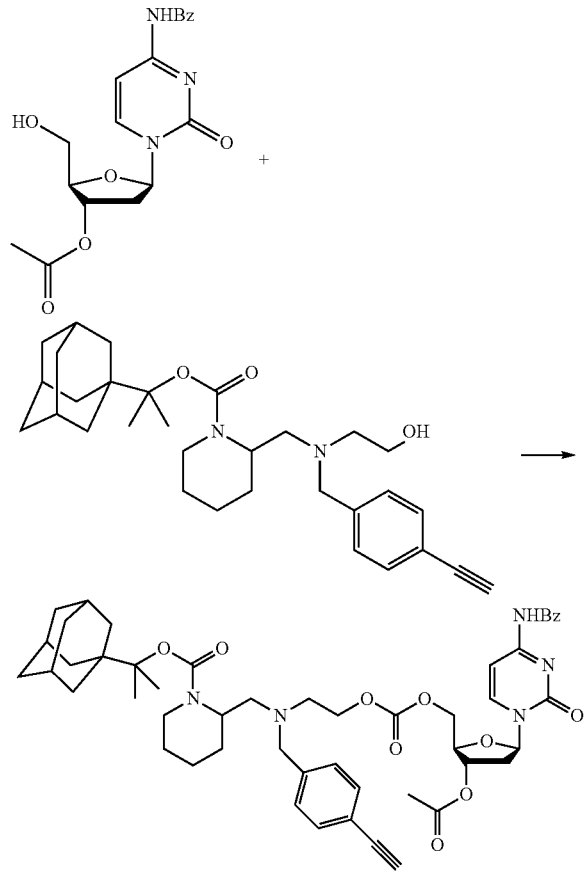

(2R,3S,5R)-5-(4-benzamido-2-oxopyrimidin-1(2H)-yl)-2-(hydroxymethyl)tetrahydrofuran-3-yl acetate (150 mg, 1.34 mmol, 1 equ) was dissolved in anhydrous acetonitrile (5 mL) after which CDI (78 mg, 1.61 mmol, 1.2 equ) was added, reaction mixture stirred for 24 hours at room temperature. After this time the CDI intermediate formation was complete by LC-MS. 2-((3R,5R,7R)-adamantan-1-yl)propan-2-yl 2-(((4-ethynylbenzyl)(2-hydroxyethyl)amino)methyl)piperidine-1-carboxylate (237 mg, 1.61 mmol, 1.2 equ) in anhydrous acetonitrile (5 mL) and DBU (72 uL, 1.61 mmol, 1.2 equ) were added and the reaction mixture was stirred for 4 hours. After this time the reaction was complete by LC-MS. EtOAc (20 mL) was added and washed with $H_2O$ (50 mL), saturated brine solution (50 mL), saturated $HNaCO_3$ solution (50 mL), dried over $Mg_2SO_4$ and the solvent removed under reduced pressure at 40° C. The crude product was purified by silica chromatography (0-100% Petroleum ether:DCM then 0-100% DCM:EtOAc) to give the product as a white solid (224 mg, 72%). LC-MS Method A (Short acidic); Rt=3.05 min, m/z 893 (MH$^+$). $^1$H NMR (CDCl$_3$, 400 MHz); 8.59 (1H, s), 8.02 (1H, m), 7.87 (2H, m), 7.61 (1H, t, J=7.2 Hz), 7.51 (2H, t, J=7.6 Hz), 7.38 (2H, d, J=8.0 Hz), 6.33 (1H, dd, J=5.6, 2.8 Hz), 5.52 (1H, m), 4.40 (2H, d, 2.8 Hz), 4.34 (2H, m), 4.25 (2H, m), 3.01 (1H, s), 2.86 (1H, m), 2.78 (1H, m), 2.49 (1H, m), 2.09 (3H, s), 1.98 (2H, s), 1.66 (8H, s), 1.57 (6H, s), 1.44 (11H, s), 1.23 (2H, s) 1.15 (1H, s), 0.88-0.77 (1H, m), 0.24 (2H, s)

Example 19B: (2R,3S,5R)-5-(4-benzamido-2-oxopyrimidin-1(2H)-yl)-2-((((2-((4-ethynylbenzyl)(piperidin-2-ylmethyl)amino)ethoxy)carbonyl)oxy)methyl)-tetrahydrofuran-3-yl Acetate

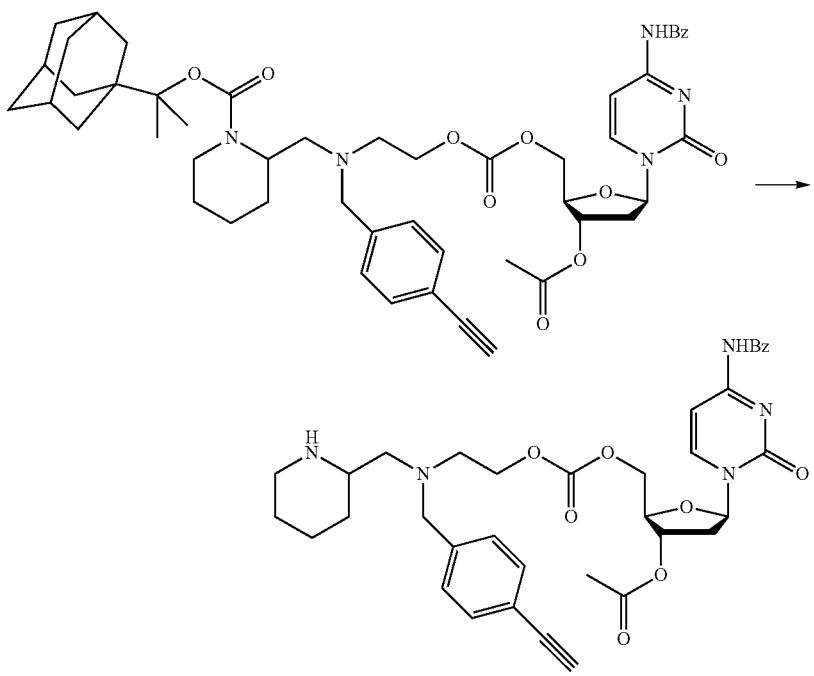

2-(((1R,3R,5S)-adamantan-1-yl)propan-2-yl 2-(((2-(((((2R,3S,5R)-3-acetoxy-5-(4-benzamido-2-oxopyrimidin-1(2H)-yl)tetrahydrofuran-2-yl)methoxy)carbonyl)oxy)ethyl)(4-ethynylbenzyl)amino)methyl)piperidine-1-carboxylate (50 mg, 0.056 mmol) was dissolved in 3% Dichloroacetic acid in MeCN (50 mL) and stirred at 90° C. for 40 minutes. After this time the reaction was complete by LC-MS. EtOAc (20 mL) was added and washed with $H_2O$ (2×50 mL), dried over $Mg_2SO_4$ and the solvent removed under reduced pressure at 40° C. The crude product was purified by silica chromatography (0-10% DCM:MeOH) to give the product as a white solid (25 mg, 67%). LC-MS Method A (Short acidic); Rt=1.71 min, m/z 672 (MH+). +).
$^1$H NMR (CDCl3, 400 MHz); 7.92 (2H, dd, J=7.2.18 Hz), 7.85 (1H, dd, J=8, 22 Hz), 7.59-7.34 (5H, m), 7.22 (1H, t, J=7.6 Hz), 6.00 (1H, m), 5.68 (1H, s), 5.37 (1H, m), 4.59-4.13 (5H, m), 3.74 (2 h, M), 3.21-3.09 (2H, m), 3.04 (1H, s), 2.83-2.52 (6H, m), 2.11 (3H, s), 1.91-1.66 (5H, s), 1.53 (1H, m), 1.23 (1H, s)

Example 19C: Kinetic Experiment: Thermally Controlled Deprotection of Unlocked 5'-Protected Bz-Cytosine of Example 19B

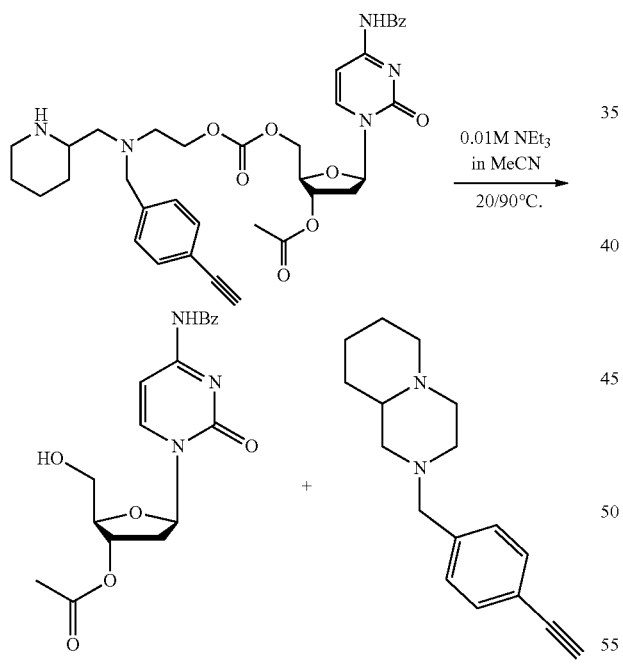

(2R,3S,5R)-5-(4-benzamido-2-oxopyrimidin-1(2H)-yl)-2-((((2-((4-ethynylbenzyl)(piperidin-2-ylmethyl)amino)ethoxy)carbonyl)oxy)methyl)tetrahydrofuran-3-yl acetate (2 mg) was dissolved in 0.01M $NEt_3$ in MeCN solution (4 mL). 300 uL aliquots were dispensed into maximum recovery LC-MS vials, sealed and heated to 90° C. in a hot water bath for the designated time. After this time the vials were chilled in an ice bath and analyses by LCMS (Method A) within 10 minutes. The results are presented in the following tables, and are represented graphically in FIG. 21.

| Temp/ °C. | Time/ min | Starting material/ 1.71 min MH+ 672 | Deprotection product/ 1.61 min MH+ 374 |
|---|---|---|---|
| 20 | 0 | 100 | 0 |
| 90 | 5 | 61 | 38.7 |
| 90 | 10 | 37 | 63 |
| 90 | 15 | 20 | 80 |
| 90 | 20 | 11 | 88.9 |
| 90 | 30 | 5.7 | 94.3 |
| 90 | 40 | 3.2 | 96.8 |
| 90 | 50 | 0 | 100 |
| 90 | 60 | 0 | 100 |
| 90 | 120 | 0 | 100 |
| 20 | 0 | 100 | 0 |
| 20 | 15 | 100 | 0 |
| 20 | 35 | 100 | 0 |
| 20 | 45 | 100 | 0 |
| 20 | 60 | 100 | 0 |
| 20 | 90 | 97.6 | 2.4 |
| 20 | 120 | 96.8 | 3.3 |
| 20 | 1200 | 76.3 | 23.7 |
| 20 | 1500 | 71.6 | 28.4 |
| 20 | 2580 | 57.1 | 42.9 |
| 20 | 2880 | 54 | 46 |
| 20 | 4080 | 42.8 | 57.2 |

Example 20

Synthesis of (2R,3S,5R)-2-(((tert-Butyldiphenylsilyl)oxy)methyl)-5-(5-methyl-2,4-dioxo-3,4-dihydropyrimidin-1(2H)-yl)tetrahydrofuran-3-yl (2-((4-ethynylbenzyl)(piperidin-2-ylmethyl)amino)ethyl) Carbonate Example 20A: (2R,3S,5R)-2-(((tert-Butyldiphenylsilyl)oxy)methyl)-5-(5-methyl-2,4-dioxo-3,4-dihydropyrimidin-1(2H)-yl)tetrahydrofuran-3-yl(2-(((1-(((1,1-dioxidobenzo[b]thiophen-2-yl)methyl)carbamoyl)piperidin-2-yl)methyl)(4-ethynylbenzyl)amino)ethyl) carbonate

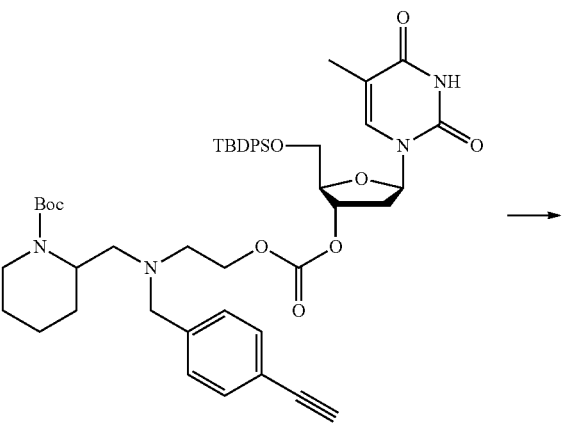

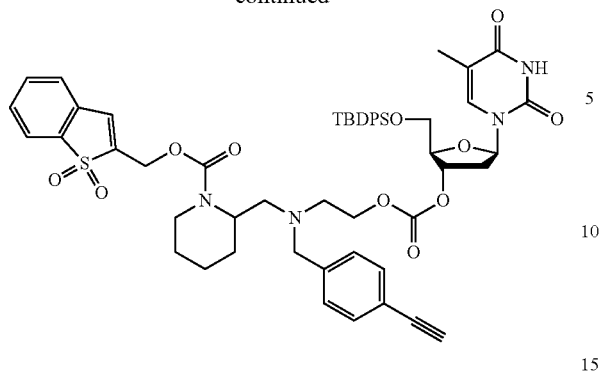

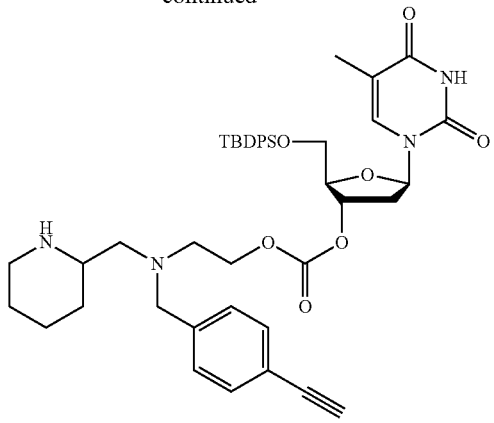

i) tert-Butyl 2-(((2-(((((2R,3S,5R)-2-(((tert-butyldiphenylsilyl)oxy)methyl)-5-(5-methyl-2,4-dioxo-3,4-dihydropyrimidin-1(2H)-yl)tetrahydrofuran-3-yl)oxy)carbonyl)oxy)ethyl)(4-ethynylbenzyl)amino)methyl)piperidine-1-carboxylate (compound of Example 10C) (1.88 g, 2.1 mmol) was dissolved in 1:1 TFA:DCM and the solution was stirred at rt for 2 h after which time the reaction was complete by LC-MS. The excess TFA and DCM were removed under reduced pressure and ethyl acetate (500 mL) and sat. aq. NaHCO₃ (300 mL) were added. The layers were separated and the organic layer was washed with sat. aq. NaHCO₃ (200 mL), dried (MgSO₄) and the solvent was removed under reduced pressure. ii) BsmocCl (660 mg, 2.52 mmol, 1.2 eq.) was added to a solution of the intermediate in DCM (500 mL) and Hunig's Base (0.75 mL, 4.2 mmol, 2 eq.), after 1 h; the reaction had gone to completion by LC-MS. Water was added and the layers were separated. The crude product was purified by silica chromatography (0-10% Methanol-DCM) to give a pale yellow foam, 1.9 g, 90%. LC-MS; Method A (Acidic); Rt=3.04, m/z 1001.5 (MH⁺).

Example 20B: (2R,3S,5R)-2-(((tert-Butyldiphenylsilyl)oxy)methyl)-5-(5-methyl-2,4-dioxo-3,4-dihydropyrimidin-1(2H)-yl)tetrahydrofuran-3-yl (2-((4-ethynylbenzyl)(piperidin-2-ylmethyl)amino)ethyl)carbonate

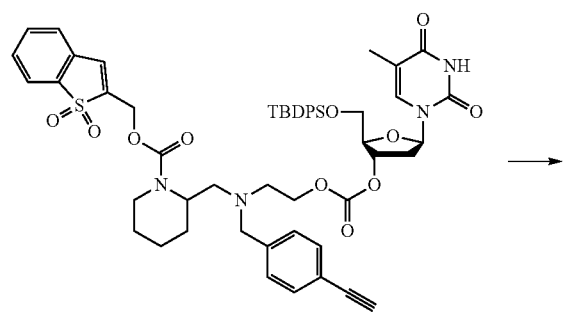

(2R,3S,5R)-2-(((tert-Butyldiphenylsilyl)oxy)methyl)-5-(5-methyl-2,4-dioxo-3,4-dihydropyrimidin-1(2H)-yl)tetrahydrofuran-3-yl(2-(((1-(((1,1-dioxidobenzo[b]thiophen-2-yl)methyl)carbamoyl)piperidin-2-yl)methyl)(4-ethynylbenzyl)amino)ethyl)carbonate(600 mg, 0.6 mmol) was dissolved in DCM (500 mL) and piperidine (0.3 mL, excess) was added. After 5 minutes at rt the reaction was complete by LC-MS. Water (50 mL) and DCM (100 mL) were added and the layers were separated. The solvent was removed and the residue was purified by silica chromatography, eluting with 0-10 MeOH-DCM. The solvent was carefully removed under reduced pressure at 25° C. and residue was then foamed with ether to give a pale yellow foam, 280 mg, 60%. LC-MS; Method A (Acidic); Rt=2.20, m/z 779 (MH⁺).

Examples 21-23

Time Course Studies on 3'-Protected 5'-O-TBDPS Thymidine Compound at Different Temperatures (Compounds of Examples IC, 20B and 4C, Respectively)

Time course studies on three different 3'-protected 5'-O-TBDPS thymidine compounds were carried out at different temperatures and different conditions, using the following protocols:

General Procedure—Reactions at Various High Temperatures

The compound to be tested was dissolved in the required solution at a concentration of 0.5 mg/mL at room temperature. This solution was divided (0.5-0.75 mL per vial) between enough LC-MS vials to measure the reaction course at the required number of time-points as well as one for the room temperature measurements. The vials for the heated experiments were immediately placed in a hot water bath set at either 40° C., 60° C. or 90° C. (±0.1° C.), such that the level of liquid in the vial was below the surface of the hot water. At each time-point in the experiment an LC-MS vial was removed and then immediately cooled in a brine ice-bath at a temperature of 3° C. The LC-MS experiment was then carried out within ten minutes of the reaction being quenched by cooling. The ratio of starting material to cleaved nucleoside was measured by integrating the corresponding peaks in the UV trace of the LC-MS.

General Procedure—Reactions at the Low Temperature

An LC-MS vial containing the same solution as used for the high-temperature experiment was placed in the pre-chilled auto sampler chamber of the LC-MS machine set at the low temperature, for example, 20±0.1° C. or 10±0.1° C. and the solution was analysed by LC-MS at suitable time-points.

Example 21

Time Course Experiments for Cleavage of the 3'-Protected 5' O-TBDPS-Thymidine (Compound of Example 1C) at 20° C., 40° C., 60° C. and 90° C. in 1:1 0.01 M PBS Buffer:Acetonitrile

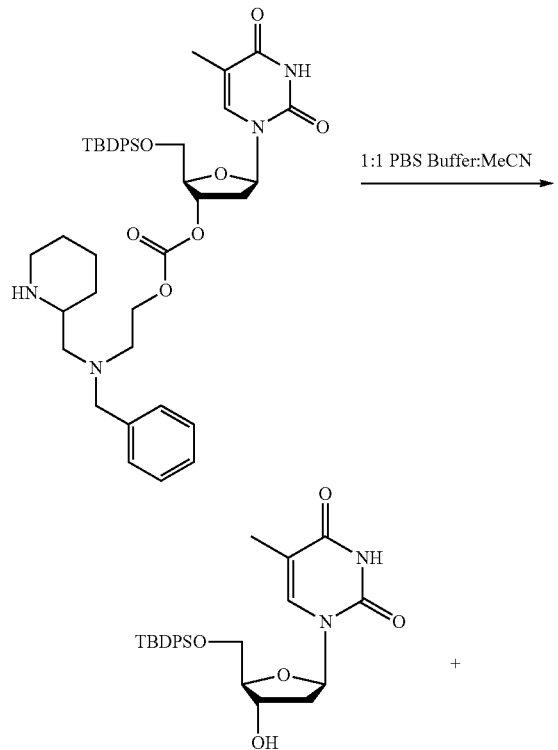

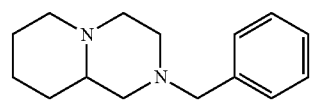

The results of this study are shown in the following table, and are represented graphically in FIG. 22.

| Time | % Starting Material at 90° C. | % Starting Material at 60° C. | % Starting Material at 40° C. | % Starting Material at 20° C. |
|---|---|---|---|---|
| 0 | 100 | 100 | 100 | 100 |
| 3 | 70.2 | | | |
| 6 | 45.65 | | | |
| 9 | 32.9 | | | |
| 12 | 18.92 | | | |
| 16 | 12.13 | | | |
| 20 | 6.32 | | | |
| 24 | 2.9 | | | |
| 30 | | 81.72 | | |
| 60 | | 68.01 | | |
| 90 | | 54.4 | | |
| 121 | | 44 | | |
| 150 | | 37.5 | | |
| 210 | | 27.5 | | |
| 240 | | 21.74 | | |
| 1020 | | | 73 | |
| 1260 | | | | 98.96 |
| 2540 | | | | 97.88 |
| 6990 | | | | 89.89 |

Example 22

Time Course Experiments for Cleavage of the 3'-Protected 5'O-TBDPS-Thymidine (Compound of Example 201B) at 20° C., 40° C., 60° C. and 90° C. in Different Solvents

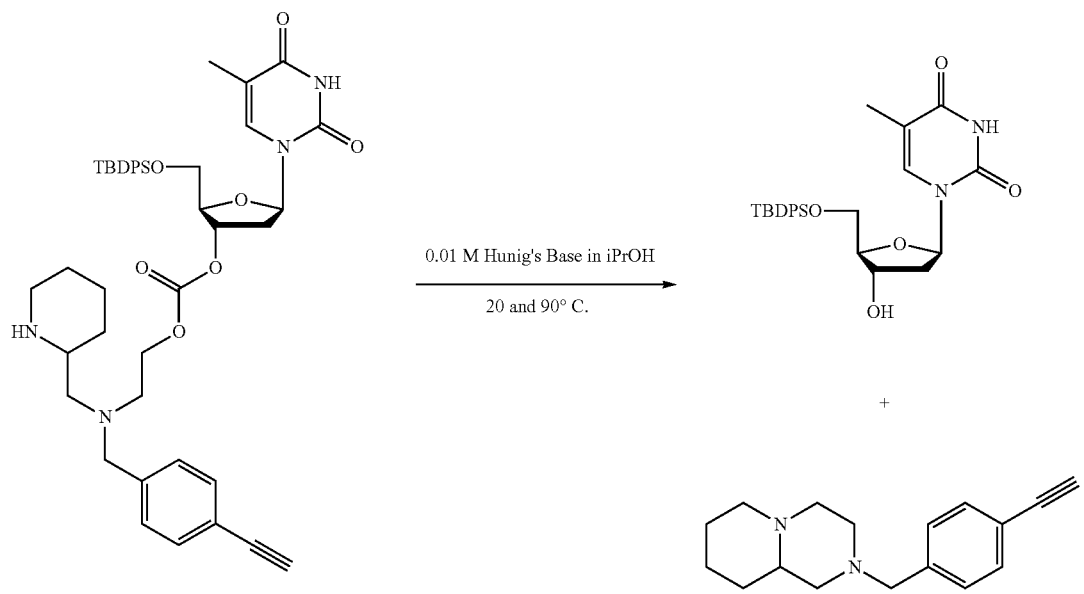

The results of this study are shown in the following table, and are represented graphically in FIG. 23.

| % Starting material in $^i$PrOH at 90° C. | % Starting material in 0.01M Hunig's Base/$^i$PrOH at 60° C. | % Starting material in iPrOH at 40° C. | % Starting material in 0.01M Hunig's Base/iPrOH at 20° C. |
|---|---|---|---|
| 100 | 100 | 100 | 100 |
| 73.4 | | | |
| 64.1 | | | |
| | 29.8 | | |
| 58.6 | | | |
| | 10.7 | | |
| 43.8 | | | |
| | 3.43 | | |
| | 2.4 | | |
| 26.7 | | | |
| | | | 97.2 |
| 15.14 | | | |
| | | 98.2 | |
| | | | 82.6 |
| | | 87.8 | |

Example 23

Time Course Experiments for Cleavage of the 3'-Protected 5' O-TBDPS-Thymidine (Compound of Example 4C) at 20° C., 40° C., 60° C. and 90° C. in 1:1 0.01 M PBS Buffer:Acetonitrile

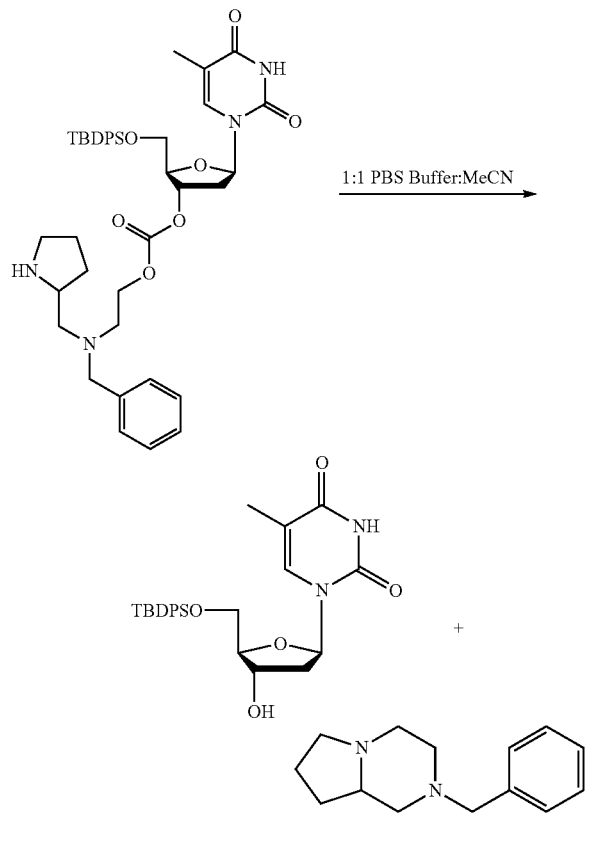

The results of this study are shown in the following table, and are represented graphically in FIG. 24.

| Time | % starting material (90° C.) | % starting material (60° C.) | % starting material (40° C.) | % starting material (20° C.) |
|---|---|---|---|---|
| 0 | 100 | 100 | 100 | 100 |
| 3 | 85.6 | | | |
| 6 | 63.3 | | | |
| 9 | 43.6 | | | |
| 15 | 27 | | | |
| 20 | 15.2 | | | |
| 35 | 3.7 | | | |
| 45 | 0 | 93.4 | | |
| 90 | | 87.31 | | |
| 220 | | 70 | | |
| 300 | | 62 | | |
| 420 | | 50.9 | | |
| 450 | | 48 | 97 | |
| 1380 | | | 91.1 | |
| 4020 | | | | 98.8 |
| 6900 | | | | 98.25 |
| 9780 | | | | 97.67 |
| 14250 | | | | 95.38 |

Example 24

Synthesis and Kinetic Experiments on 3'-Protected Bz-Cytosine

Example 24A: allyl 2-(((2-(((((2R,3S,5R)-5-(4-benzamido-2-oxopyrimidin-1(2H)-yl)-2-(((tert-butyldiphenylsilyl)oxy)methyl)tetrahydrofuran-3-yl)oxy)carbonyl)oxy) ethyl)(4-ethynylbenzyl)amino)methyl)piperidine-1-carboxylate

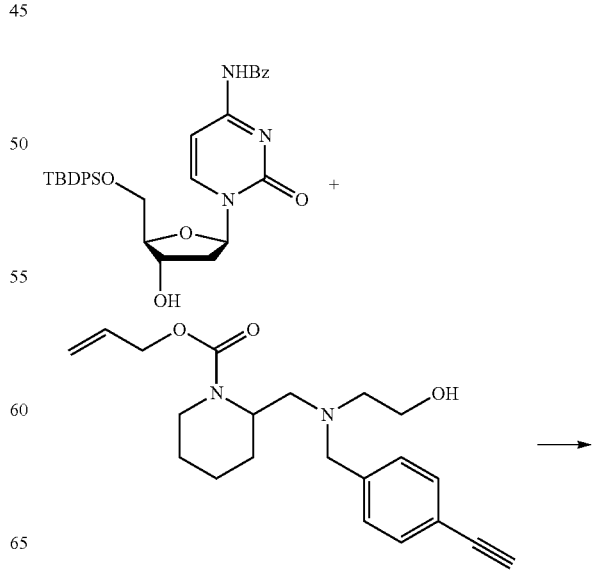

121

-continued

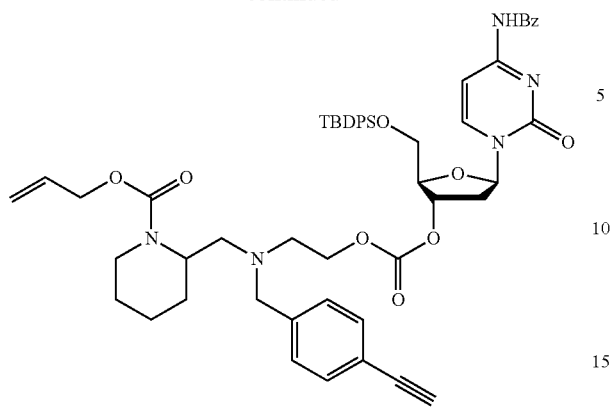

N-(1-(((2R,4S,5R)-5-(((tert-butyldiphenylsilyl)oxy) methyl)-4-hydroxytetrahydrofuran-2-yl)-2-oxo-1,2-dihydropyrimidin-4-yl)benzamide (400 mg, 0.70 mmol, 1 equ) was dissolved in anhydrous acetonitrile (15 mL) after which CDI (125 mg, 0.77 mmol, 1.1 equ) was added, reaction mixture stirred for 24 hours at room temperature. After this time the CDI intermediate formation was complete by LC-MS. 2 allyl 2-(((4-ethynylbenzyl)(2-hydroxyethyl) amino)methyl)piperidine-1-carboxylate (250 mg, 0.70 mmol, 1.0 equ) in anhydrous acetonitrile (5 mL) and DBU (115 uL, 0.77 mmol, 1.1 equ) were added and the reaction mixture was stirred for 2 hours. After this time the reaction was complete by LC-MS. The reaction mixture was diluted with EtOAc (20 mL), washed with H₂O (50 mL), saturated brine solution (50 mL), saturated HNaCO₃ solution (50 mL), dried over MgSO₄ and the solvent removed under reduced pressure at 40° C. The crude product was purified by silica chromatography 0-5% DCM:MeOH) to give the product as a white solid (210 mg, 31%). LC-MS Method A (Short acidic); Rt=3.20 min, m/z 853 (MH⁺), 85%.

Example 24B: (2R,3S,5R)-5-(4-benzamido-2-oxopyrimidin-1(2H)-yl)-2-(((tert-butyldiphenylsilyl) oxy)methyl) tetrahydrofuran-3-yl (2-((4-ethynylbenzyl)(piperidin-2-ylmethyl)amino)ethyl) carbonate

122

-continued

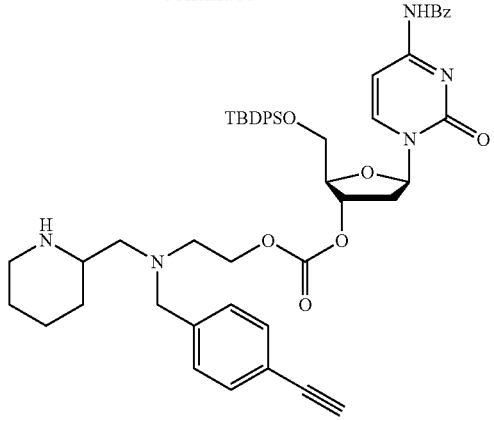

Allyl 2-(((2-(((((2R,3S,5R)-5-(4-benzamido-2-oxopyrimidin-1(2H)-yl)-2-(((tert-butyldiphenylsilyl)oxy)methyl) tetrahydrofuran-3-yl)oxy)carbonyl)oxy)ethyl)(4-ethynylbenzyl)amino)methyl)piperidine-1-carboxylate (150 mg, 0.157 mmol, 1 equ) and Dimedone (110 mg, 0.787 mmol, 5 equ) were dissolved in anhydrous THF (35 mL) and purged with N₂(g) for 10 minutes. Tetrakis(triphenylphosphine) palladium(0) (18 mg, 0.015 mmol, 0.1 equ) was added and stirred for 20 minutes at room temperature. After this time the reaction was complete by LC-MS. The reaction mixture was diluted with EtOAc (20 mL) washed with H₂O (20 mL), saturated HNaCO₃ solution (20 mL), saturated brine solution (20 mL), dried over MgSO₄ and the solvent removed under reduced pressure at 40° C. The crude product was purified by silica chromatography (0-20% DCM MeOH+2% NE₃) to give an off white solid (71 mg, 52%). LC-MS Method A (Acidic); Rt=2.38 min, m/z 869 (MH⁺) 91% (9% impurity characterised as N-(1-((2R,4S,5R)-5-(((tert-butyldiphenylsilyl)oxy)methyl)-4-hydroxytetrahydrofuran-2-yl)-2-oxo-1,2-dihydropyrimidin-4-yl)benzamide 2.68 min, MH+570 this indicates a degree of cyclisation during the purification process)

Example 24C: Kinetic Experiment—Deprotection by Intramolecular Cyclisation of (2R,3S,5R)-5-(4-benzamido-2-oxopyrimidin-1(2H)-yl)-2-(((tert-butyldiphenylsilyl)oxy)methyl)tetrahydrofuran-3-yl (2-((4-ethynylbenzyl)(piperidin-2-ylmethyl)amino) ethyl)carbonate

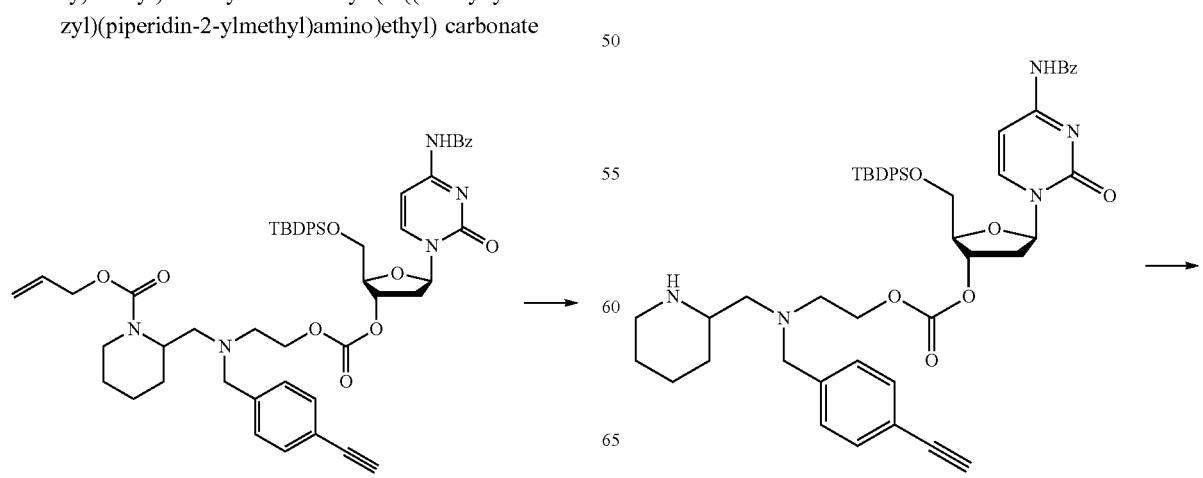

-continued

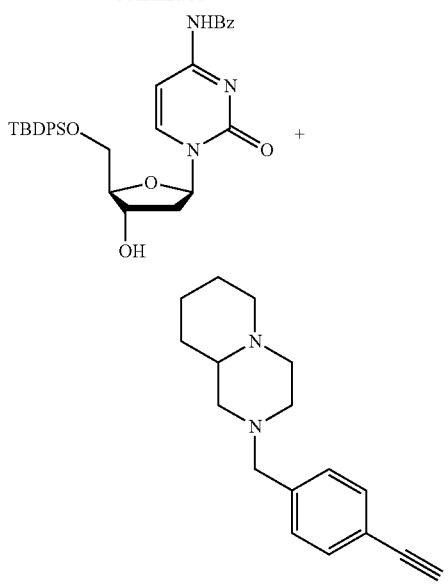

Compound of Example 24B (2 mg) was dissolved in 0.01M NEt₃ in MeCN solution (4 mL). 300 uL aliquots were dispensed into maximum recovery LC-MS vials, sealed and heated to 90° C. in a hot water bath for the designated time. After this time the vials were chilled in an ice bath and analysed by LCMS (Method A) within 10 minutes. The results of this study are shown in the following table, and are represented graphically in FIG. 25.

Note that both the data table and graph take into account the observed cyclisation from the previous step at time point 0.

| Temp/ °C. | Time/ min | Starting material/ 2.38 min MH+ 869 | Deprotection product/ 2.68 min, MH+ 570 |
|---|---|---|---|
| 20 | 0 | 90.6 | 9.4 |
| 90 | 2 | 72.4 | 27.6 |
| 90 | 5 | 52 | 48 |
| 90 | 10 | 25.2 | 74.8 |
| 90 | 15 | 11.5 | 88.5 |
| 90 | 20 | 4.7 | 95.3 |
| 90 | 30 | 1.2 | 98.8 |
| 90 | 45 | 0 | 100 |
| 90 | 60 | 0 | 100 |
| 20 | 0 | 90.6 | 9.4 |
| 20 | 60 | 88.8 | 11.2 |
| 20 | 120 | 87.4 | 12.6 |
| 20 | 240 | 84.3 | 15.7 |
| 20 | 360 | 81.8 | 18.2 |
| 20 | 1440 | 58.9 | 41.1 |

Further aspects and embodiments of the present invention are set out in the numbered clauses below:

1. A compound of formula (I), or an acid addition salt thereof:

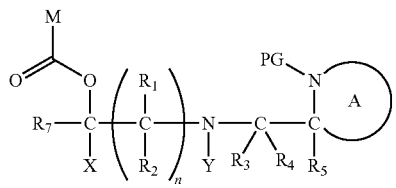

wherein:
M represents an organic fragment;
X represents hydrogen or hydrocarbyl;
Y represents hydrocarbyl or

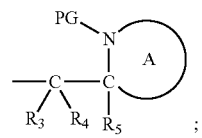

each of $R_1$, $R_2$, $R_3$, $R_4$, $R_5$ and $R_7$ are the same or different and each independently represents hydrogen or hydrocarbyl;
PG represents a cleavable protecting group for nitrogen;
n represents 0, 1, 2 or 3; and
ring A represents a nitrogen-containing heterocyclic group;
wherein at each occurrence, $R_1$, $R_2$, $R_3$, $R_4$, $R_5$, PG and A, may be the same or different.

2. A compound according to Clause 1 wherein at least one of the protecting groups PG is cleavable under a first reaction condition to produce a compound of formula (I*):

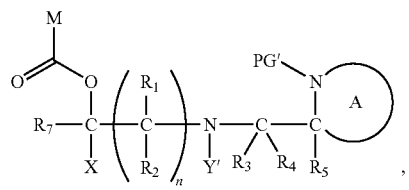

wherein the compound of Formula (I*) can undergo intramolecular cyclisation and cleavage with release of carbon dioxide under a second, different, reaction condition, to produce a compound of formula (II):

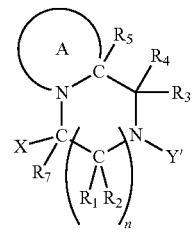

thereby releasing M or an organic compound comprising M;

wherein:
PG' is hydrogen or a cleavable protecting group for nitrogen, provided that at least one PG' is hydrogen;
Y' represents hydrocarbyl, or

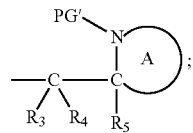

and
wherein X, $R_1$-$R_5$, $R_7$, A, M and n are as defined in Clause 1.

3. A compound according to Clause 1 or Clause 2, having the formula (IA):

(IA)
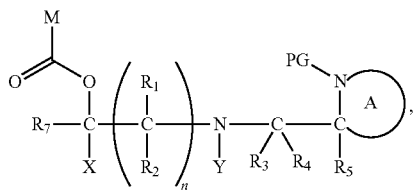

wherein:
Y represents hydrocarbyl; and
wherein X, $R_1$-$R_5$, $R_7$, PG, A, M and n are as defined in Clause 1.

4. A compound according to Clause 3, wherein the PG protecting group is cleavable under a first reaction condition to produce a compound of formula (IA*):

(IA*)
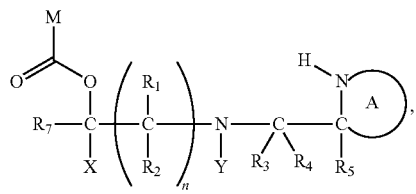

wherein:
Y represents hydrocarbyl; and
wherein X, $R_1$-$R_5$, $R_7$, A, M and n are as defined in Clause 1; wherein the compound of Formula (IA*) can undergo intramolecular cyclisation and cleavage with release of carbon dioxide under a second, different reaction condition, to produce a compound of formula (IIA):

(IIA)
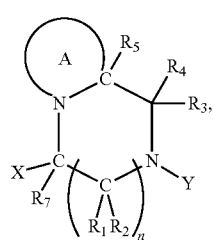

thereby releasing M or an organic compound comprising M.

5. A compound according to Clause 1 or Clause 2, having the formula (IB):

(IB)
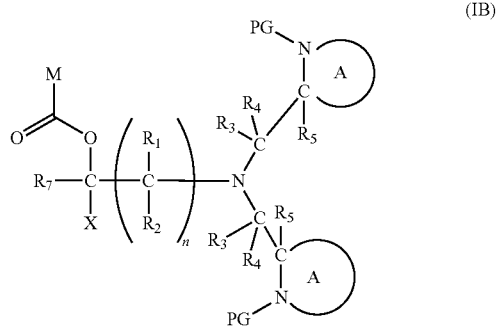

wherein X, $R_1$-$R_5$, $R_7$, PG, A, M and n are as defined in Clause 1.

6. A compound according to Clause 5 wherein $R_1$-$R_5$, PG and A at each occurrence in formula (IB), is the same.

7. A compound according to Clause 5 or Clause 6, wherein at least one of the protecting groups PG is cleavable under a first reaction condition to produce a compound of formula (IB*):

(IB*)
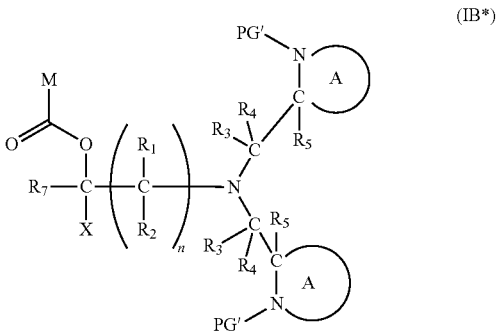

wherein
PG' is hydrogen or a cleavable protecting group for nitrogen, provided that at least one PG' is hydrogen; and
wherein X, $R_1$-$R_5$, $R_7$, A, M and n are as defined in Clause 1;
wherein the compound of Formula (IB*) can undergo intramolecular cyclisation and cleavage with release of carbon dioxide under a second, different reaction condition, to produce a compound of formula (IIB):

(IIB)
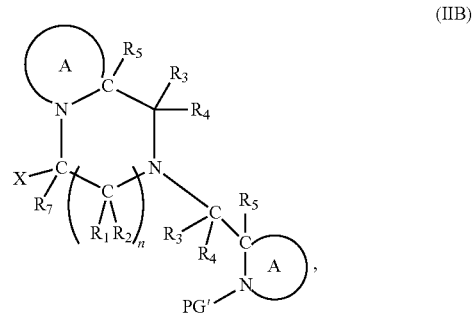

thereby releasing M or an organic compound comprising M.
8. A compound according to Clause 7 wherein PG' are both H.
9. A compound according to any preceding clause, wherein ring A represents a 4-12 membered mono-, bi- or tricyclic, preferably mono- or bicyclic nitrogen-containing heterocyclic group, and which may contain, in addition to the nitrogen, one or more other heteroatoms selected from N, O or S, preferably O or N.
10. A compound according to any preceding clause, wherein ring A represents a 4 to 8-membered monocyclic heterocyclic group.
11. A compound according to any preceding clause, wherein ring A represents a 5, 6, or 7-membered monocyclic heterocyclic group.
12. A compound according to any preceding clause, wherein ring A represents a heterocycle selected from: piperidyl, morpholinyl, pyrrolidinyl, thiomorpholinyl, and imidazolyl.
13. A compound according to any preceding clause wherein ring A represents piperidyl, pyrrolidinyl or imidazolyl.
14. A compound according to any preceding clause, wherein ring A represents piperidyl, or pyrrolidinyl.
15. A compound according to any preceding clause, wherein at each occurrence of —C($R_3$)($R_4$), one of $R_3$ or $R_4$ is hydrocarbyl, and the other is H, or wherein $R_3$ and $R_4$ at each occurrence, represents H.
16. A compound according to any preceding clause, wherein n is 0, 1 or 2; and preferably wherein n is 0 or 1.
17. A compound according to any preceding clause, wherein n is 1.
18. A compound according to any preceding clause wherein X is H or hydrocarbyl, wherein the hydrocarbyl is selected from the group consisting of alkyl, aryl or arylalkyl.
19. A compound according to Clause 18, wherein X is H or aryl, and more preferably wherein X is H or phenyl.
20. A compound according to any preceding clause wherein $R_7$ is H.
21. A compound according to any preceding clause wherein $R_1$ and $R_2$ are H.
22. A compound according to any preceding clause wherein $R_3$ and $R_4$ are H.
23. A compound according to any preceding clause, wherein $R_5$ is H.
24. A compound according to any preceding clause, wherein cleavage of at least one protecting group PG can be activated by pH, temperature, radiation, or by a chemical activating agent, or by a combination thereof.
25. A compound according to any preceding clause wherein the cleavage of at least one protecting group PG can be activated by pH, temperature, a chemical activation agent, or by a combination thereof.
26. A compound according to any preceding clause, wherein at least one protecting group PG is thermally cleavable in the presence of an activating agent.
27. A compound according to any preceding clause, wherein at least one protecting group PG is not thermally cleavable in the absence of an activating agent.
28. A compound according to preceding clause, wherein the activating agent is an acid or a base.
29. A compound according to any preceding clause, wherein at least one protecting group PG is thermally cleavable in the presence of an acid, and the intramolecular cyclisation and cleavage of the linker is effected by heating in the presence of a base.
30. A compound according to any of Clauses 1-29, wherein at least one protecting group PG is thermally cleavable in the presence of a base, and the intramolecular cyclisation and cleavage of the linker is effected by further heating.
31. A compound according to any of Clauses 1-30, wherein at least one protecting group PG is cleavable in the presence of an acid, and wherein PG is preferably selected from: tert-butyloxycarbonyl (Boc), trityl (Trt), benzyloxycarbonyl, α,α-dimethyl-3,5-dimethoxybenzyloxycarbonyl (Ddz), 2-(4-biphenyl)isopropoxycarbonyl (Bpoc), 2-nitrophenylsulfenyl (Nps), tosyl (Ts), and more preferably wherein the acid cleavable protecting group is selected from Boc and Trt.
32. A compound according to any of Clauses 1-29, and 32, wherein at least one protecting group PG is cleavable in the presence of a base, and wherein PG is preferably selected from: (1,1-dioxobenzo[b]thiophene-2-yl)methyloxycarbonyl (Bsmoc), 9-fluorenylmethoxycarbonyl (Fmoc), (1,1-dioxonaphtho[1,2-b]thiophene-2-yl)methyloxycarbonyl (α-Nsmoc), 2-(4-nitrophenylsulfonyl)ethoxycarbonyl (Nsc), 2,7-di-tert-butyl-Fmoc, 2-fluoro-Fmoc, 2-monoisooctyl-Fmoc (mio-Fmoc) and 2,7-diisooctyl-Fmoc (dio-Fmoc), 2—[phenyl(methyl)sulfonio]ethyloxycarbonyl tetrafluoroborate (Pms), ethanesulfonylethoxycarbonyl (Esc), 2-(4-sulfophenylsulfonyl)ethoxycarbonyl (Sps), acetyl (Ac), benzoyl (Bz), $CF_3C(=O)$— trifluoroacetamido, and preferably wherein the base cleavable protecting group is selected from Bsmoc, Fmoc, α-Nsmoc, mio-Fmoc, dio-Fmoc, and more preferably Bsmoc.
33. A compound according to any of Clauses 1-29, wherein PG is selected from the group consisting of Boc, Fmoc or Bsmoc.
34. A compound according to any of Clauses 1-23, wherein PG is Alloc.
35. A compound according to any preceding clause wherein at least one Y group is hydrocarbyl, preferably wherein at least one Y is alkyl, alkenyl, aryl, aralkyl, alkaryl, wherein said alkyl, alkenyl, aryl, aralkyl or alkaryl group is substituted with a terminal alkyne group.
36. A compound according to any preceding clause wherein at least one Y group is alkyl, alkenyl, aryl, aralkyl, alkaryl, which is substituted with a terminal alkynyl group, wherein the terminal alkyne group is a $C_2$ to Cr alkynyl group, more preferably a $C_2$ to $C_4$ alkynyl group, and most preferably ethynyl.
37. A compound according to any preceding clause wherein at least one Y group is aralkyl which is substituted with an alkynyl group and more preferably wherein one Y group is $CH_2$—$(C_6H_4)CH=CH$.
38. A compound according to any preceding clause wherein M is —W—$R_6$, wherein W represents —N($R_8$)—, —O—, —S—, —C($R_9$)($R_{10}$)— or —P($R_{11}$)($R_{12}$)($R_{13}$)—, and each $R_8$, $R_9$, $R_{10}$, $R_{11}$, $R_{12}$ and $R_{13}$ independently represents: hydrogen, alkyl, aryl, alkaryl or aralkyl; and $R_6$ represents an organic fragment.
39. A compound according to any of Clauses 2-37, wherein the organic compound comprising M is H—W—$R_6$.
40. A compound according to Clause 38 or Clause 39, wherein $R_8$ is alkyl, aryl, alkaryl or aralkyl, preferably wherein $R_8$ is alkyl or aryl, and more preferably wherein $R_8$ is alkyl.
41. A compound according to any of Clauses 38-40, wherein $R_9$ and $R_{10}$ each independently represents hydrogen, alkyl, aryl, alkaryl or aralkyl; preferably wherein $R_9$ and $R_{10}$ independently represents alkyl or aryl, more preferably wherein $R_9$ and $R_{10}$ independently represents H or alkyl and most preferably wherein $R_9$ and $R_{10}$ each represents H.

42. A compound according to any of Clauses 38-41, wherein $R_{11}$, $R_{12}$ and $R_{13}$ each independently represents alkyl, aryl, alkaryl or aralkyl, preferably wherein $R_{11}$, $R_{12}$ and $R_{13}$ each independently represents alkyl or aryl, and more preferably wherein $R_{11}$, $R_{12}$ and $R_{13}$ each independently represents alkyl.

43. A compound according to any of Clauses 38-42, wherein W represents —O—, —N($R_8$)— or —C($R_9$)($R_{10}$)—, preferably —O— or —C($R_9$)($R_{10}$)—.

44. A compound according to any of Clauses 38-43, wherein W represents O.

45. A compound according to any of Clauses 38-44, wherein $R_6$ is a residue of: a biological molecule, a drug, a therapeutic entity, a nucleotide, an oligonucleotide, a polynucleotide, an amino acid, a peptide, a peptide fragment, an antibody, an antibody conjugate, an engineered receptor such as an artificial T-cell receptor, a B-cell an antigen, a reporter molecule such as a dye or a dye conjugate, a chemotherapeutic sensitizer, a protein, a saccharide, an oligosaccharide, a polysaccharide.

46. A compound according to any of Clams 38-45, wherein $R_6$ is a residue of: an oligonucleotide, a polynucleotide, an amino acid, a peptide or peptide fragment, a protein, a saccharide, an oligosaccharide or a polysaccharide.

47. A compound according to any of Clauses 38-46, wherein $R_6$ is a residue of a nucleotide, an oligonucleotide or a polynucleotide, which is preferably attached via an ether bond at the 3' or 5' position of a nucleotide.

48. A compound according to Clause 1 or Clause 2, wherein:
M represents —W—$R_6$, wherein W represents —O— and $R_6$ represents an organic fragment which is covalently bound to W;
X represents hydrogen or phenyl;
Y represents hydrocarbyl, or the group

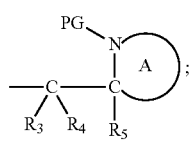

each of $R_1$, $R_2$, $R_3$, $R_4$ and $R_5$ represents hydrogen;
$R_7$ represents hydrogen or hydrocarbyl;
PG represents a cleavable protecting group for nitrogen;
n represents 0 or 1; and
ring A represents a nitrogen-containing heterocyclic group.

49. A compound according to Clause 48 wherein $R_6$ is as defined in any of Clauses 45-47.

50. A compound according to any of Clauses 48-49, wherein PG is as defined according to any of Clauses 25-34.

51. A compound according to any of Clauses 48-50, wherein n is 1.

52. A compound according to any of Clauses 48-51, wherein Y is benzyl.

53. A compound according to any of Clauses 48-51, wherein Y is:

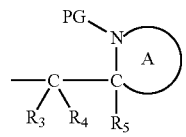

wherein each $R_3$, $R_4$ and $R_5$ represents hydrogen, both protecting groups PG are the same and both ring A are the same.

54. A compound according to any of Clauses 48-53, wherein ring A is as defined in any of Clauses 9-15, and preferably ring A represents piperidyl or pyrrolidinyl.

55. A composition comprising a compound according to any preceding clause, wherein the compound is covalently bound to a substrate, preferably via a linker group.

56. A composition according to Clause 55 wherein the compound is covalently bound to a substrate at one of $R_1$, $R_2$, $R_3$, $R_4$, $R_5$, $R_7$, X, Y or A.

57. A composition according to Clause 55 or Clause 56, wherein the compound is covalently bound to a substrate at $R_7$ or Y.

58. A composition according to Clause 57, wherein the compound is covalently bound to a substrate at Y:

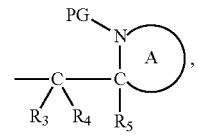, preferably via a linker group.

59. A composition according to any of Clauses 55-58, wherein the substrate is a solid phase or a solid support, an antibody, a metal surface, a conductive surface, a polymeric support, a pharmaceutically inert support, a chip, a resin, a sensor, a glass support, or a polystyrene support.

60. A composition according to Clause 59, wherein the substrate is a solid phase comprising particles selected from the group consisting of gold, colloidal metal, silicon, a polymer, a pharmaceutically inert support, solid resin, ceramic, glass or silica gel.

61. A composition according to any of Clauses 55-60, wherein the substrate is a solid support comprising particles selected from gold or silicon.

62. A cleavable protecting group or cleavable linker of formula (L-1):

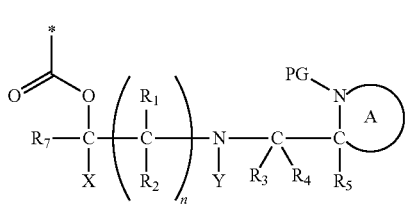

(L-1)

wherein:
* represents a point of attachment to an organic moiety to be protected or to be released from the cleavable linker or protecting group;
X represents hydrogen or hydrocarbyl;

Y represents hydrocarbyl or

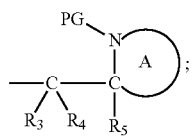

each of $R_1$, $R_2$, $R_3$, $R_4$, $R_5$ and $R_7$ are the same or different and each independently represents hydrogen or hydrocarbyl;
PG represents a cleavable protecting group for nitrogen;
n represents 0, 1, 2 or 3; and
ring A represents nitrogen-containing heterocyclic group; wherein at each occurrence $R_1$, $R_2$, $R_3$, $R_4$, $R_5$, PG and A may be the same or different.

63. A cleavable protecting group or cleavable linker according to Clause 62, wherein at least one of the protecting groups PG is cleavable under a first reaction condition to produce a deprotected linker, wherein the deprotected linker can undergo intramolecular cyclisation and cleavage with release of carbon dioxide under a second, different, reaction condition, to produce a compound of formula (II):

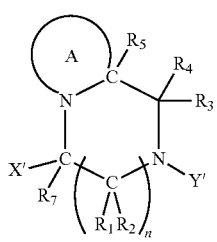

(II)

thereby releasing the organic moiety from the cleavable linker.

64. A cleavable protecting group or cleavable linker according to Clause 62 or Clause 63, wherein X is H or hydrocarbyl selected from the group consisting of alkyl, aryl or arylalkyl, preferably wherein X is aryl, and more preferably wherein X is phenyl.
65. A cleavable protecting group or cleavable linker according to any of Clauses 62-64, wherein Y is benzyl.
66. A cleavable protecting group or cleavable linker according to any of Clauses 62-64, wherein Y is:

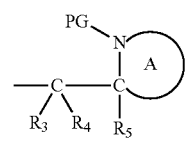

wherein each $R_3$, $R_4$ and $R_5$ represents hydrogen, both protecting groups PG are the same and both ring A are the same.
67. A cleavable protecting group or cleavable linker according to any of Clauses 62-66, wherein ring A represents piperidinyl or pyrrolidinyl.
68. A cleavable protecting group or cleavable linker according to Clauses 62-67, selected from the group consisting of: (L-IA) or (L-IB):

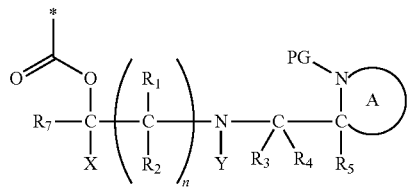

(L-IA)

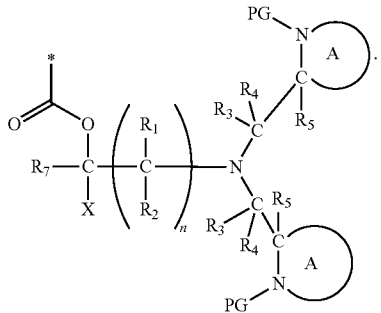

(L-IB)

69. A cleavable protecting group or cleavable linker according to Clause 68 wherein at least one of the protecting groups PG is cleavable under a first reaction condition to produce a deprotected linker, wherein the deprotected linker can undergo intramolecular cyclisation and cleavage with release of carbon dioxide under a second, different, reaction condition, to produce a corresponding compound of formula (IIA) and (IIB) respectively:

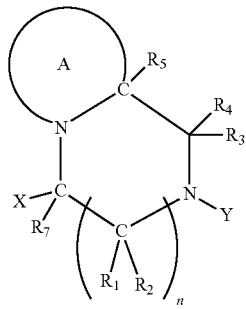

(IIA)

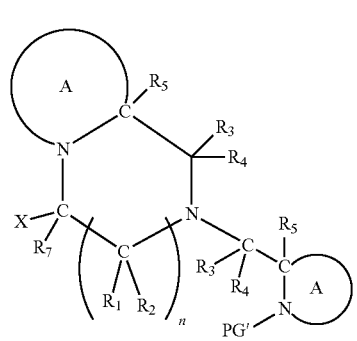

(IIB)

wherein PG' in (IIB) is hydrogen or a cleavable protecting group for nitrogen, thereby releasing the organic fragment M or an organic compound comprising M.

70. A cleavable protecting group or cleavable linker according to any of Clauses 62-69, wherein PG' in compound (IIB) is hydrogen.

71. A cleavable protecting group or cleavable linker according to any of Clauses 62-70, wherein ring A is as defined in any of Clauses 9-15.
72. A cleavable protecting group or cleavable linker according to any of Clauses 62-71, wherein $R_3$ and $R_4$, preferably at each occurrence, represents H.
73. A cleavable protecting group or cleavable linker according to any of Clauses 62-72, wherein n is 0, 1 or 2; and preferably wherein n is 0 or 1.
74. A cleavable protecting group or cleavable linker according to any of Clauses 62-73, wherein n is 1.
75. A cleavable protecting group or cleavable linker according to any of Clauses 62-74, wherein X is H or hydrocarbyl, wherein the hydrocarbyl is selected from the group consisting of alkyl, aryl or arylalkyl, preferably wherein X is aryl, and more preferably wherein X is phenyl.
76. A cleavable protecting group or cleavable linker according to any of Clauses 62-75, wherein PG is as defined in any of Clauses 25-34.
77. A cleavable protecting group or cleavable linker according to any of Clauses 62-76, wherein Y is as defined in any of Clauses 35-37.
78. A cleavable protecting group or cleavable linker according to any of Clauses 62-77, wherein $R_5$ is hydrogen.
79. A cleavable protecting group or cleavable linker according to any of Clauses 62-78, wherein X is: H or hydrocarbyl, wherein the hydrocarbyl is selected from the group consisting of alkyl, aryl or arylalkyl, preferably wherein X is aryl, and more preferably wherein X is phenyl.
80. A cleavable protecting group or cleavable linker according to any of Clauses 62-79, wherein $R_7$ is H.
81. A cleavable protecting group or cleavable linker according to any of Clauses 62-80, wherein $R_1$ and $R_2$ are H.
82. A cleavable protecting group or cleavable linker according to any of Clauses 62-81, wherein $R_3$ and $R_4$ are both hydrogen.
83. A cleavable protecting group according to any of Clauses 62-82.
84. A cleavable linker according to any of Clauses 62-83, which is covalently bound to a substrate at one of $R_1$, $R_2$, $R_3$, $R_4$, $R_5$, $R_7$, X, Y or A.
85. A cleavable linker according to Clause 84, which is covalently bonded to the substrate at $R_7$ or Y.
86. A cleavable linker according to Clause 84, which is covalently bonded to the substrate at $R_7$ when Y is:

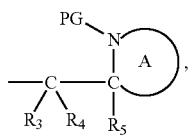

or wherein the cleavable linker is covalently bound to the substrate at Y when Y is hydrocarbyl.
87. A cleavable linker according to any of Clauses 84-86, wherein substrate is a solid phase or a solid support, a metal surface, a conductive surface, a polymeric support, a pharmaceutically inert support, a chip, a resin, a sensor, a glass support, polystyrene support.
88. A cleavable linker according to Clauses 84-87, wherein the substrate is a solid phase comprising particles selected from the group consisting of gold, colloidal metal, silicon, a polymer, a pharmaceutically inert support, solid resin, ceramic, glass, silica gel, preferably wherein the substrate is a solid support comprising particles selected from gold or silicon.
89. A process for the solid state synthesis of an organic compound comprising an organic fragment M, the process comprising:
   (d) synthesis of the organic compound on a solid substrate which is covalently bound to the cleavable linker of any of Clauses 62-88;
   (e) cleaving the organic fragment M from the cleavable linker and substrate to form the organic compound, and
   (f) optionally isolating the organic compound.
90. A process according to Clause 89, wherein step (b) comprises cleavage of at least one protecting group PG on the cleavable linker followed by intramolecular cyclisation with release of carbon dioxide, thereby releasing the organic compound from the substrate.
91. A process according to Clause 89 or Clause 90, wherein the organic compound has the formula H—W—$R_6$, wherein $R_6$ is as defined in any of Clauses 45-47.
92. A process according to any of Clauses 89-91, wherein the organic compound is a single-stranded oligonucleotide or a single-stranded polynucleotide.
93. A process according to any of Clauses 89-91, wherein the organic compound is a double-stranded oligonucleotide or a double-stranded polynucleotide.
94. A process according to Clause 93, wherein the process comprises a step of annealing a complementary oligonucleotide or a complementary polynucleotide before step (b), and optionally isolating the double stranded oligonucleotide or double stranded polynucleotide.
95. A process according to Clause 93, wherein the process comprises a step of annealing a complementary oligonucleotide or a complementary polynucleotide after step (b) or step (c), and optionally isolating the double stranded oligonucleotide or double stranded polynucleotide.
96. A process according to any of Clauses 89-95, wherein step (b) comprises:
   (i) heating in the presence of an activating agent to remove the protecting group;
   (ii) heating, optionally in the presence of an activating agent, to effect intramolecular cyclisation and cleavage of the linker and solid substrate from the compound.
97. A process according to Clause 96, wherein the activating agent in step (i) is an acid, and step (ii) comprises heating in the presence of a base.
98. A process according to Clause 96, wherein the activating agent in step (i) is a base, and step (ii) comprises heating.
99. A process according to Clause 96, wherein step (i) comprises heating to a first temperature in the presence of a base, and wherein the intramolecular cyclisation and cleavage in step (ii) is effected by heating to a second temperature, wherein the second temperature is higher than the first temperature.
100. A process according to any of Clauses 96-99, wherein the protecting group PG is selected from: tert-butyloxycarbonyl (Boc), trityl (Trt), benzyloxycarbonyl, α,α-dimethyl-3,5-dimethoxybenzyloxycarbonyl (Ddz), 2-(4-Biphenyl)isopropoxycarbonyl (Bpoc), 2-Nitrophenylsulfenyl (Nps), tosyl (Ts), and preferably wherein protecting group is selected from Boc, or Trt, and more preferably Boc, and wherein the activating agent in step (i) is an acid, preferably selected from trifluoroacetic acid.
101. A process according to any of Clauses 96-100, wherein the activating agent in step (ii) is a base, preferably wherein the base is selected from a basic buffer, preferably phosphate buffer, preferably a phosphate buffer having a pH of about 7.1 to about 8.5, more preferably a pH of about 7.2 to about 8.0, and most preferably a pH of about 7.2 to about 7.6.

102. A process according to any of Clauses 96-101, wherein the protecting group is selected from: (1,1-dioxobenzo[b]thiophene-2-yl)methyloxycarbonyl (Bsmoc), 9-fluorenylmethoxycarbonyl (Fmoc), (1,1-dioxonaphtho[1,2-b]thiophene-2-yl)methyloxycarbonyl (α-Nsmoc), 2-(4-nitrophenylsulfonyl)ethoxycarbonyl (Nsc), 2,7-di-tert-butyl-Fmoc, 2-fluoro-Fmoc, 2-monoisooctyl-Fmoc (mio-Fmoc) and 2,7-diisooctyl-Fmoc (dio-Fmoc), 2-[phenyl(methyl)sulfonio]ethyloxycarbonyl tetrafluoroborate (Pms), ethanesulfonylethoxycarbonyl (Esc), 2-(4-sulfophenylsulfonyl)ethoxycarbonyl (Sps), acetyl (Ac), benzoyl (Bz), $CF_3C(=O)$— trifluoroacetamido, and preferably wherein the protecting group is selected from Bsmoc, Fmoc, α-Nsmoc, mio-Fmoc, dio-Fmoc, and more preferably wherein the protecting group is Bsmoc, and wherein the activating agent in step (i) is a base, preferably selected from morpholine, piperidine.

103. A process according to any of Clauses 96-102, wherein the step (ii) is carried out in the presence of at least one polar solvent, preferably wherein the polar solvent comprises acetonitrile, or dimethylsulfoxide.

104. Use of a compound as defined in any of Clauses 1-54: for the controlled release of a therapeutic entity; as a diagnostic; or for the purification of proteins and peptides.

105. Use of a compound as defined in any of Clauses 1-54, or a composition as defined in any of Clauses 55-61, or a cleavable protecting group or a cleavable linker as defined in any of Clauses 62-88 in solid state synthesis, preferably in the solid state synthesis of saccharides, oligosaccharides, polysaccharides, peptides, proteins, oligonucleotides, or polynucleotides, preferably in the solid state synthesis of peptides, proteins, oligonucleotides, or polynucleotides.

106. Use according to Clause 105, in the solid state synthesis of oligonucleotides or polynucleotides.

107. A process for the preparation of one or more oligonucleotides or polynucleotides comprising:
    (i) providing a composition comprising a compound as defined in any of Clauses 1-54, wherein M represents —W—$R_6$, wherein $R_6$ represents a first optionally protected nucleotide, wherein the compound is covalently bound to a solid support; and
    (ii) conducting solid phase synthesis by the phosphoramidite method to produce the oligonucleotide or polynucleotide;
    (ii) cleaving the oligonucleotide or polynucleotide from the solid support.

108. A process according to Clause 107, comprising:
    (i) providing a composition comprising a compound as defined in any of Clauses 1-54, wherein M represents —W—$R_6$, wherein $R_6$ represents a first 5'-protected nucleotide, wherein the compound is covalently bound to a solid support;
    (ii) removing the 5'-protecting group from the 5'-protected nucleoside;
    (iii) coupling at the 5'—OH of the nucleoside with a nucleoside phosphoramidite monomer to form a support-bound phosphite triester;
    (iv) optionally capping the 5'-hydroxyl groups on the unreacted nucleoside phosphoramidite monomer by acetylation;
    (v) oxidising the phosphite triester to a phosphotriester;
    (vi) repeating steps (ii) to (v) in order to produce the oligonucleotide or polynucleotide;
    (vii) cleaving the oligonucleotide or polynucleotide from the solid support; and
    (viii) optionally isolating the oligonucleotide.

109. A process according to Clause 108, wherein the process comprises a step of annealing a complementary oligonucleotide or a complementary polynucleotide before step (vii), and optionally isolating the double stranded oligonucleotide or double stranded polynucleotide.

110. A process according to Clause 108, wherein the process comprises a step of annealing a complementary oligonucleotide or a complementary polynucleotide after step (vii) or step (viii), and optionally isolating the double stranded oligonucleotide or double stranded polynucleotide.

111. A process according to any of Clauses 108-110, wherein step (vii) comprises:
    (vii-a) heating in the presence of an activating agent to remove the protecting group PG from the cleavable linker; and
    (vii-b) heating, optionally in the presence of an activating agent, to effect intramolecular cyclisation and cleavage of the linker and solid substrate from the compound.

112. A process according to Clause 111, wherein the activating agent in step (vii-a) is an acid, and step (vii-b) comprises heating in the presence of a base.

113. A process according to Clause 111, wherein the activating agent in step (vii-a) is a base, and step (vii-b) comprises heating.

114. A process according to Clause 113, wherein step (vii-a) comprises heating to a first temperature in the presence of a base, and wherein the intramolecular cyclisation and cleavage in step (vii-b) is effected by heating to a second temperature, wherein the second temperature is higher than the first temperature.

115. A process according to Clause 112 or Clause 113, wherein the protecting group PG is selected from: tert-butyloxycarbonyl (Boc), trityl (Trt), benzyloxycarbonyl, and, α,α-dimethyl-3,5-dimethoxybenzyloxycarbonyl (Ddz), 2-(4-biphenyl)isopropoxycarbonyl (Bpoc), 2-nitrophenylsulfenyl (Nps), tosyl (Ts), and preferably wherein protecting group is selected from Boc, or Trt, and more preferably Boc, and wherein the activating agent in step (vii-a) is an acid, preferably selected from trifluoroacetic acid.

116. A process according to any of Clauses 111, 113 and 114, wherein the activating agent in step (vii-b) is a base, preferably wherein the base is selected from a basic buffer, preferably a buffer having a pH of about 7.1 to about 8.5, more preferably a pH of about 7.2 to about 8.0, and most preferably a pH of about 7.2 to about 7.6.

117. A process according to any of Clauses 111, 113, 115 and 116, wherein the protecting group PG is selected from: (1,1-dioxobenzo[b]thiophene-2-yl)methyloxycarbonyl (Bsmoc), 9-fluorenylmethoxycarbonyl (Fmoc), (1,1-dioxonaphtho[1,2-b]thiophene-2-yl)methyloxycarbonyl (α-Nsmoc), 2-(4-nitrophenylsulfonyl)ethoxycarbonyl (Nsc), 2,7-di-tert-butyl-Fmoc, 2-fluoro-Fmoc, 2-monoisooctyl-Fmoc (mio-Fmoc) and 2,7-diisooctyl-Fmoc (dio-Fmoc), 2—[phenyl(methyl)sulfonio]ethyloxycarbonyl tetrafluoroborate (Pms), ethanesulfonylethoxycarbonyl (Esc), 2-(4-sulfophenylsulfonyl)ethoxycarbonyl (Sps), acetyl (Ac), benzoyl (Bz), $CF_3C(=O)$— trifluoroacetamido, and preferably wherein the protecting group is selected from Bsmoc, Fmoc, α-Nsmoc, mio-Fmoc, dio-Fmoc, and more preferably wherein the protecting group is Bsmoc, and wherein the activating agent in step (vii-a) is a base, preferably selected from morpholine, and piperidine.

118. A process according to any of Clauses 111-117, wherein the step (vii-b) is carried out in the presence of at least one polar solvent, preferably wherein the polar solvent comprises acetonitrile and dimethylsulfoxide.

The invention claimed is:

1. A compound of formula (I), or an acid addition salt thereof:

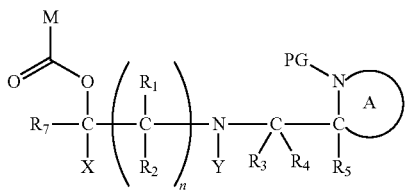
(I)

wherein: M is —W—R$_6$, wherein W is —O—, and R$_6$ is an organic fragment;

X is hydrogen or hydrocarbyl;

Y is hydrocarbyl or

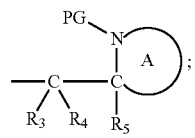
;

each of R$_1$, R$_2$, R$_3$, R$_4$, R$_5$ and R$_7$ are hydrogen;

PG is a cleavable protecting group for nitrogen;

n is (i) 0 or (ii) 1; and ring A is a 5, 6, or 7-membered nitrogen-containing monocyclic heterocyclic group;

wherein PG and A at each occurrence, is the same or different.

2. The compound according to claim 1, wherein at least one PG is cleavable under a first reaction condition to produce a compound of formula (I*):

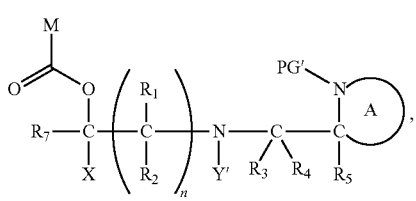
(I*)

wherein the compound of Formula (I*) undergoes intramolecular cyclisation and cleavage with release of carbon dioxide under a second, different, reaction condition, to produce a compound of formula (II):

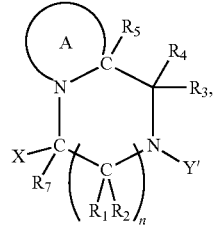
(II)

thereby releasing M or an organic compound comprising M;

wherein:

PG' is hydrogen or a cleavable protecting group for nitrogen, provided that at least one PG' is hydrogen;

Y' is hydrocarbyl, or

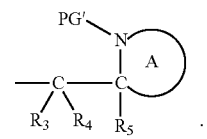
.

3. The compound according to claim 1, having the formula (IA):

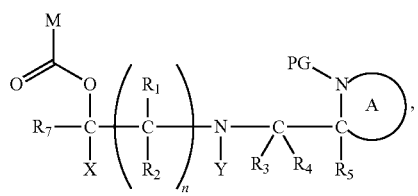
(IA)

wherein:

Y is hydrocarbyl;

optionally wherein PG is cleavable under a first reaction condition to produce a compound of formula (IA'):

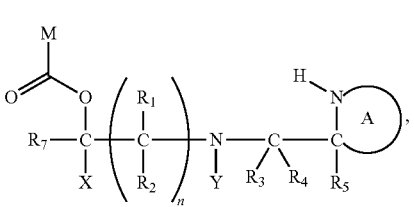
(IA*)

wherein the compound of Formula (IA*) undergoes intramolecular cyclisation and cleavage with release of carbon dioxide under a second, different, reaction condition, to produce a compound of formula (IIA):

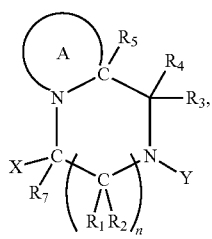

(IIA)

thereby releasing M or an organic compound comprising M.

4. The compound according to claim 1, having the formula (IB):

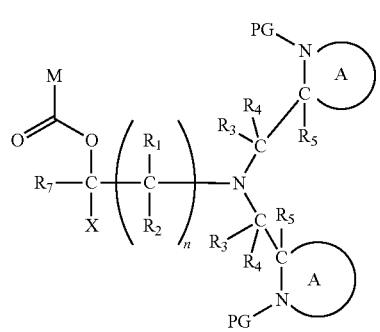

(IB)

optionally wherein PG and A at each occurrence in formula (IB), is the same.

5. The compound according to claim 4, wherein at least one PG is cleavable under a first reaction condition to produce a compound of formula (IB*):

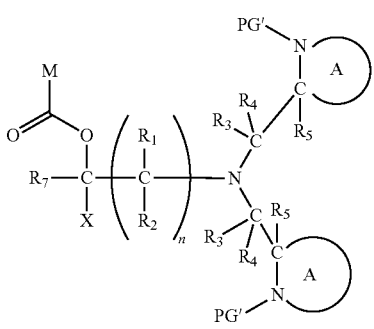

(IB*)

wherein

PG' is hydrogen or a cleavable protecting group for nitrogen, provided that at least one PG' is hydrogen; and wherein the compound of Formula (IB*) undergoes intramolecular cyclisation and cleavage with release of carbon dioxide under a second, different reaction condition, to produce a compound of formula (IIB):

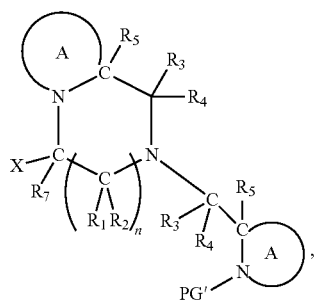

(IIB)

thereby releasing M or an organic compound comprising M; optionally wherein PG' are both H.

6. The compound according to claim 1, wherein ring A is a heterocycle that is piperidyl, morpholinyl, pyrrolidinyl, or thiomorpholinyl.

7. The compound according to claim 1, wherein X is H or hydrocarbyl, wherein the hydrocarbyl is alkyl, aryl or arylalkyl.

8. The compound according to claim 1, wherein the cleavage of at least one PG is activated by pH, temperature, a chemical activating agent, or by a combination thereof; optionally wherein at least one PG is (i) thermally cleavable in the presence of an activating agent; or (ii) not thermally cleavable in the absence of an activating agent.

9. The compound according to claim 8, wherein the chemical activating agent is an acid or a base.

10. The compound according to claim 1, wherein at least one PG is thermally cleavable in the presence of an acid, and the intramolecular cyclisation and cleavage of the linker is effected by heating in the presence of a base.

11. The compound according to claim 1, wherein at least one PG is cleavable in the presence of an acid, and wherein PG is optionally tert-butyloxycarbonyl (Boc), trityl (Trt), benzyloxycarbonyl, α,α-dimethyl-3,5-dimethoxybenzyloxycarbonyl (Ddz), 2-(4-biphenyl)isopropoxycarbonyl (Bpoc), 2-nitrophenylsulfenyl (Nps), or tosyl (Ts).

12. The compound according to claim 1, wherein PG is Alloc.

13. The compound according to claim 1, wherein at least one Y group is hydrocarbyl.

14. The compound according to claim 1, wherein at least one Y group is aralkyl which is substituted with an alkynyl group.

15. The compound according to claim 1, wherein $R_6$ is a residue of a nucleotide, an oligonucleotide or a polynucleotide, which is optionally attached via an ether bond at the 3' or 5' position of a nucleotide.

16. The compound according to claim 1, wherein:

M is —W—$R_6$,

W is —O—, $R_6$ is an organic fragment which is covalently bound W;

X is hydrogen or phenyl;

Y is hydrocarbyl, or the group

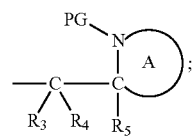

each of $R_1$, $R_2$, $R_3$, $R_4$ and $R_5$ is hydrogen;

$R_7$ is hydrogen;

PG is a cleavable protecting group for nitrogen;

n is (i) 0 or 1, or (ii) 1; and
ring A is a 5, 6, or 7-membered nitrogen-containing monocyclic heterocyclic group.

17. The compound according to claim 16, wherein $R_6$ is a residue of a nucleotide, an oligonucleotide or a polynucleotide, which is optionally attached via an ether bond at the 3' or 5' position of a nucleotide.

18. The compound according to claim 16, wherein at least one PG is: i) activated by pH, temperature, a chemical activating agent, or by a combination thereof, ii) thermally cleavable in the presence of an activating agent, or iii) not thermally cleavable in the absence of an activating agent.

19. The compound according to claim 16, wherein Y is (i) benzyl; or (ii)

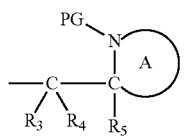

wherein each $R_3$, $R_4$ and $R_5$ is hydrogen, both protecting groups PG are the same and both ring A are the same.

20. The compound according to claim 16, wherein ring A is a heterocycle that is piperidyl, morpholinyl, pyrrolidinyl, or thiomorpholinyl.

21. The compound according to claim 16, wherein at least one PG thermally cleavable in the presence of an acid or base.

22. The compound according to claim 16, wherein at least one protecting group PG is thermally cleavable in the presence of an acid, and the intramolecular cyclisation and cleavage of the linker is effected by heating in the presence of a base.

23. The compound according to claim 16, wherein at least one protecting group PG is cleavable in the presence of an acid.

24. A composition comprising a compound according to claim 1, wherein the compound is (i) covalently bound to a substrate or (ii) covalently bound via a linker group to a substrate

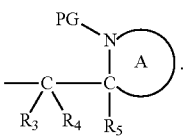

25. The composition according to claim 24, wherein the substrate is a solid support comprising particles that are gold or silicon.

26. A process for the preparation of one or more oligonucleotides or polynucleotides comprising:
(i) providing a composition comprising the compound claim 1, wherein M is —W—$R_6$, wherein $R_6$ is a first optionally protected nucleotide, wherein the compound is covalently bound to a solid support;
(ii) conducting solid phase synthesis by a phosphoramidite method to produce the oligonucleotide or polynucleotide; and
(iii) cleaving the oligonucleotide or polynucleotide from the solid support.

27. The process according to claim 26, comprising:
(i) providing a composition comprising the compound of claim 1, wherein the compound is covalently bound to a solid support;
(ii) removing the 5'-protecting group from the 5'-protected nucleoside;
(iii) coupling at the 5'-OH of the nucleoside with a nucleoside phosphoramidite monomer to form a support-bound phosphite triester;
(iv) optionally capping the 5'-hydroxyl groups on the unreacted nucleoside phosphoramidite monomer by acetylation;
(v) oxidising the phosphite triester to a phosphotriester;
(vi) repeating steps (ii) to (v) in order to produce the oligonucleotide or polynucleotide;
(vii) cleaving the oligonucleotide or polynucleotide from the solid support; and
(viii) optionally isolating the oligonucleotide; and
(ix) the process optionally further comprising:
a step of annealing a complementary oligonucleotide or a complementary polynucleotide before step (vii), and optionally isolating the double stranded oligonucleotide or double stranded polynucleotide; or
a step of annealing a complementary oligonucleotide or a complementary polynucleotide after step (vii) or step (viii), and optionally isolating the double stranded oligonucleotide or double stranded polynucleotide.

28. The process according to claim 27, wherein step (vii) comprises:
(vii-a) heating in the presence of an activating agent to remove PG from the cleavable linker; and
(vii-b) heating, optionally in the presence of an activating agent, to effect intramolecular cyclisation and cleavage of the linker and solid substrate from the compound.

29. The process according to claim 28, wherein (a) the activating agent in step (vii-a) is an acid, and step (vii-b) comprises heating in the presence of a base; or (b) the activating agent in step (vii-a) is an acid and after step (vii-a), the reaction mixture is neutralised, and step (vii-b) comprises heating to effect intramolecular cyclisation and cleavage of the linker and solid substrate from the compound.

30. The process according to claim 28, wherein the activating agent in step (vii-a) is a base, and step (vii-b) comprises heating; optionally wherein step (vii-a) comprises heating to a first temperature in the presence of a base, and wherein the intramolecular cyclisation and cleavage in step (vii-b) is effected by heating to a second temperature, wherein the second temperature is higher than the first temperature.

31. The process according to claim 28, wherein step (vii-a) or step (vii-b), or both step (vii-a) and step (vii-b), are carried out in a non-aqueous system, optionally wherein step (vii-a) or step (vii-b), or both steps (vii-a) and (vii-b), are carried out in an organic solvent, optionally wherein the organic solvent is acetonitrile, dimethylformamide, tetrahydrofuran, or dioxane.

32. The process according to claim 28, wherein the step (vii-b) is carried out in the presence of (i) least one polar solvent, or (ii) a polar solvent that comprises acetonitrile and dimethylsulfoxide.

* * * * *